(12) United States Patent
Schmidt et al.

(10) Patent No.: US 8,283,151 B2
(45) Date of Patent: Oct. 9, 2012

(54) ISOLATION, CLONING AND CHARACTERIZATION OF NEW ADENO-ASSOCIATED VIRUS (AAV) SEROTYPES

(75) Inventors: Michael Schmidt, Kensington, MD (US); John A. Chiorini, Kensington, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1007 days.

(21) Appl. No.: 11/912,803

(22) PCT Filed: May 1, 2006

(86) PCT No.: PCT/US2006/017157
§ 371 (c)(1),
(2), (4) Date: Jul. 8, 2008

(87) PCT Pub. No.: WO2006/119432
PCT Pub. Date: Nov. 9, 2006

(65) Prior Publication Data
US 2010/0129405 A1    May 27, 2010

Related U.S. Application Data

(60) Provisional application No. 60/676,604, filed on Apr. 29, 2005.

(51) Int. Cl.
*C12N 7/00*      (2006.01)
*C07K 2/00*      (2006.01)
*C07H 23/00*     (2006.01)
*C12Q 1/70*      (2006.01)

(52) U.S. Cl. .............. 435/235.1; 435/7.1; 435/320.1; 435/5; 530/300; 530/350; 530/387.1; 536/23.1; 536/23.72

(58) Field of Classification Search .......................... None
See application file for complete search history.

(56) References Cited

U.S. PATENT DOCUMENTS

| | | | |
|---|---|---|---|
| 6,110,456 | A | 8/2000 | During |
| 6,146,874 | A | 11/2000 | Zolotukhin et al. |
| 6,180,613 | B1 | 1/2001 | Kaplitt et al. |
| 6,221,349 | B1 | 4/2001 | Couto et al. |
| 6,309,634 | B1 | 10/2001 | Bankiewicz et al. |
| 6,391,858 | B2 | 5/2002 | Podsakoff et al. |
| 6,468,524 | B1 | 10/2002 | Chiorini et al. |
| 6,485,976 | B1 | 11/2002 | Nadler et al. |
| 6,855,314 | B1 | 2/2005 | Chiorini et al. |
| 6,984,517 | B1 | 1/2006 | Chiorini et al. |
| 7,056,502 | B2 | 6/2006 | Hilding |
| 7,282,199 | B2 | 10/2007 | Gao |
| 7,378,272 | B2 | 5/2008 | Meruelo |
| 7,419,817 | B2 | 9/2008 | Chiorini et al. |
| 7,479,554 | B2 | 1/2009 | Chiorini et al. |
| 2002/0076754 | A1 | 6/2002 | Sun et al. |
| 2002/0086847 | A1 | 7/2002 | Chain |
| 2003/0215422 | A1 | 11/2003 | Chiorini et al. |
| 2004/0086490 | A1 | 5/2004 | Chiorini et al. |

FOREIGN PATENT DOCUMENTS

| | | |
|---|---|---|
| DE | 44 36 664 | 7/1996 |
| EP | 1 310 571 | 5/2003 |
| WO | WO 93/24641 | 12/1993 |
| WO | WO 95/11997 | 5/1995 |
| WO | WO 96/00587 | 1/1996 |
| WO | WO 96/15777 | 5/1996 |
| WO | WO 96/18727 | 6/1996 |
| WO | WO 97/06272 | 2/1997 |
| WO | WO 98/11244 | 3/1998 |
| WO | WO 98/41240 | 9/1998 |
| WO | WO 98/45462 | 10/1998 |
| WO | WO 99/61601 | 12/1999 |
| WO | WO 00/26254 | 5/2000 |
| WO | WO 00/28061 | 5/2000 |
| WO | WO 01/70276 | 9/2001 |
| WO | WO 01/83692 | 11/2001 |
| WO | WO 03/042397 | 5/2003 |
| WO | WO 03/093479 | 11/2003 |
| WO | WO 2004/112727 | 12/2004 |
| WO | WO 2005/017101 | 2/2005 |
| WO | WO 2005/056807 | 6/2005 |
| WO | WO 2006/029196 | 3/2006 |

OTHER PUBLICATIONS

Gao et al. PNAS 2003, vol. 100, pp. 6081-6086.*
Alexander et al., "DNA-Damaging Agents Greatly Increase the Transduction of Nondividing Cells by Adeno-Associated Virus Vectors," Dec. 1994, *J. Virol.*, 68(12):8282-8287.
Alisky et al., "Transduction of Murine Cerebellar Neurons with Recombinant FIV and AAV5 Vectors," *Mol. Neurosci.*, Aug. 2000, 11(1221):2669-2673.
Alisky J.M. and Tolbert D.M., "Differential labeling of converging afferent pathways using biotinylated dextran amine and cholera toxin subunit B," 1994, *Journal of Neuroscience Methods*, 52:143-148.
Allen, J.M., Halbert, C.L. and Miller, A.D., "Improved adeno-associated virus vector production with transfection of a single helper adenovirus gene, E4orf6," 2000, *Mol Ther*, 1:88-95.
Amberg, N., A. H. Kidd, K. Edlund, J. Nilsson, P. Pring-Akerblom, and G. Wadell, "Adenovirus type 37 binds to cell surface sialic acid through a charge-dependent interaction," 2002, *Virology*, 302:33-43.
Atchison, R. W., B. C. Casto, and W. M. Hammon, "Adenovirus-Associated Defective Virus Particles," 1965, *Science*, 149:754-756.
Auricchio et al., "A Single-Step Affinity Column for Purification of Serotype-5 Based Adeno-Associated Viral Vectors," Oct. 2001, *Mol Ther* 4(4):372-374.
Bachmann, P.A., M.D. Hoggan, E. Kurstak, J.L. Melnick, H.G. Pereira, P. Tattersall, and C. Vago, "Parvoviridae: second report," 1979, *Interverology*, 11:248-254.

(Continued)

*Primary Examiner* — Mary E Mosher
*Assistant Examiner* — Myron Hill
(74) *Attorney, Agent, or Firm* — Sheridan Ross P.C.

(57) ABSTRACT

The present invention provides new adeno-associated virus (AAV) viruses and vectors, and particles derived therefrom. In addition, the present invention provides methods of delivering a nucleic acid to a cell using the AAV vectors and particles.

16 Claims, 16 Drawing Sheets

OTHER PUBLICATIONS

Bajocchi G, Feldman SH, Crystal RG, Mastrangeli A., "Direct in vivo gene transfer to ependymal cells in the central nervous system using recombinant adenovirus vectors," 1993, *Nat Genet*, 3:229-234.

Bantel-Schaal U, Delius H, Schmidt R, zur Hausen H., "Human adeno-associated virus type 5 is only distantly related to other known primate helper-dependent parvoviruses," 1999, *J Virol.*, 73(2):939-947.

Bantel-Schaal U, zur Hausen H., "Characterization of the DNA of a defective human parvovirus isolated from a genital site," 1984, *Virology*, 134(1):52-63, XP009028974.

Bantel-Schaal, U. and M. Stohr, "Influence of adeno-associated virus on adherence and growth properties of normal cells," 1992, *J. Virol.*, 66:773-779.

Bantel-Schaal, U., Hub, B. and Kartenbeck, J., "Endocytosis of adeno-associated virus type 5 leads to accumulation of virus particles in the Golgi compartment," 2002, *J Virol* 76:2340-2349.

Bartlett JS, Kleinschmidt J., Boucher RC, and Samulski RJ, "Targeted adeno-associated virus vector transduction of nonpermissive cells mediated by a bispecific F(ab'gamma)$_2$ antibody," 1999, *Nat Biotechnol*, 17:181-186.

Bartlett JS, Samulski RJ, McCown TJ., "Selective and rapid uptake of adeno-associated virus type 2 in brain," 1998, *Hum Gene Ther*, 9(8):1181-1186.

Bartlett, J.S., Wilcher, R. and Samulski, R.J., "Infectious entry pathway of adeno-associated virus and adeno-associated virus vectors," 2000, *J Virol*, 74:2777-2785.

Ben-Israel, H. and Kleinberger, T., "Adenovirus and cell cycle control," 2002, *Front Biosci*, 7:d1369-1395.

Bergelson, JM, Cunningham JA, Droguett G., Kurt-Jones EA, Krithivas A., Hong JS, Horwitz MS, Crowell RL, and Finberg RW, "Isolation of a common receptor for Coxsackie B viruses and adenoviruses 2 and 5," 1997, *Science*, 275:1320-1323.

Berns, K. I., "Parvoviridae: the viruses and their replication," *In* F. B. N., K. D. M., and H. P. M. (ed.), *Fields virology*, 3rd ed. Lippincott-Raven Publishers, Philadelphia, PA, p. 2173-2197.

Blacklow, et al., "Serologic Evidence for Human Infection With Adenovirus-Associated Viruses," 1968, *J NCI*, 40(2):319-327.

Blacklow, N.R., Hoggan, M.D. and Rowe, W.P. "Isolation of adenovirus-associated viruses from man," 1967, *Proc Natl Acad Sci U S A*, 58:1410-1415.

Bomsel M, Alfsen A, "Entry of viruses through the epithelial barrier: pathogenic trickery," 2003, *Nat Rev Mol Cell Biol*, 4:57-68.

Bomsel M, David V, "Mucosal gatekeepers: selecting HIV viruses for early infection," 2002, *Nat Med*, 8:114-116.

Bossis, I. and Chiorini, J.A., "Cloning of an Avian Adeno-Associated Virus (AAAV) and Generation of Recombinant AAAV Particles," 2003, *J Virol*, 77(12):6799-6810.

Burcin, M.M., O'Malley, B.W. and S.Y. Tsai, "A regulatory system for target gene expression," 1998, *Frontiers in Bioscience*, 3:c1-7.

Carter, B. J., B. A. Antoni, and D. F. Klessig, "Adenovirus containing a deletion of the early region 2A gene allows growth of adeno-associated virus with decreased efficiency," 1992, *Virology*, 191:473-476.

Carter, B. J., C. A. Laughlin, L. M. de la Maza, and M. Myers, "Adeno-associated virus autointerference," 1979, *Virology*, 92:449-462.

Casto, B. C., J. A. Armstrong, R. W. Atchison, and W. M. Hammon, "Studies on the relationship between adeno-associated virus type 1 (AAV-1) and adenoviruses. II. Inhibition of adenovirus plaques by AAV; its nature and specificity," 1967b, *Virology*, 33:452-458.

Casto, B. C., R. W. Atchison, and W. M. Hammon, "Studies on the relationship between adeno-associated virus type I (AAV-1) and adenoviruses. I. Replication of AAV-1 in certain cell cultures and its effect on helper adenovirus," 1967a, *Virology*, 32:52-59.

Chang, L.S. and Shenk, T., "The adenovirus DNA-binding protein stimulates the rate of transcription directed by adenovirus and adeno-associated virus promoters," 1990, *J Virol*, 64:2103-2109.

Chang, L.S., Y. Shi, and T. Shenk, "Adeno-associated virus P5 promoter contains an adenovirus E1A-inducible element and a binding site for the major late transcription factor,"1989, *J. Virol.*, 63:3479-3488.

Chao H et al., "Several Log Increase in Therapeutic Transgene Delivery by Disticnt Adeno-Associated Viral Serotype Vectors," 2000, *Molecular Therapy*, 2(6):619-623.

Chejanovsky, N. and B.J. Carter, "Mutagenesis of an AUG codon in the adeno-associated virus rep gene: effects on viral DNA replication," 1989b, *Virology*, 173:120-128.

Chejanovsky, N. and B.J. Carter, "Replication of a human parvovirus nonsense mutant in mammalian cells containing an inducible amber suppressor," 1989a, *Virology*, 171:239-247.

Chiorini et al. "Cloning of Adeno-Associated Virus Type 4 (AAV4) and Generation of Recombinant AAV4 Particles" *J. Virol.* 71(9):6823-6833, Sep. 1997.

Chiorini JA, Afione S, Kotin RM, "Adeno-associated virus (AAV) type 5 Rep protein cleaves a unique terminal resolution site compared with other AAV serotypes," 1999a May, *J Virol*, 73(5):4293-4298.

Chiorini JA, Kim F, Yang L, Kotin RM, "Cloning and characterization of adeno-associated virus type 5," 1999b, Feb., *J Virol.*, 73(2):1309-1319, XP-002125035.

Chiorini, J.A., C.M. Wendtner, E. Urcelay, B. Safer, M. Hallek, and R.M. Kotin, "High-efficiency transfer of the T cell co-stimulatory molecule B7-2 to lymphoid cells using high-titer recombinant adeno-associated virus vectors,"1995, *Human Gene Therapy*, 6:1531-1541.

Chiorini, J.A., L. Yang, B. Safer, and R.M. Kotin, "Determination of adeno-associated virus Rep68 and Rep78 binding sites by random sequence oligonucleotide selection," 1995, *J. Virol.*, 69:7334-7338.

Chiorini, J.A., M.D. Weitzman, R.A. Owens, E. Urcelay, B. Safer, and R.M. Kotin, "Biologically active Rep proteins of adeno-associated virus type 2 produced as fusion proteins in *Escherichia coli*," 1994a, J. Virol., 68:797-804.

Chiorini, J.A., S.M. Wiener, R.M. Kotin, R.A. Owens, SRM Kyöstiö, and B. Safer, "Sequence requirements for stable binding and function of Rep68 on the adeno-associated virus type 2 inverted terminal repeats,"1994b, *J. Virol.*, 68:7448-7457.

Clark et al., "Highly Purified Recombinant Adeno-Associated Virus Vectors are Biologically Active and Free of Detectable Helper and Wild-Type Viruses," 1999, *Hum. Gene Ther*. 10:1031-1039.

Cohen-Salmon et al., "Targeted ablation of connexin26 in the inner ear epithelial gap junction network causes hearing impairment and cell death," 2002, *Curr Biol*, 12:1106-1111.

Coria et al., "Isolation and identification of a bovine adenovirus type 3 with an adenovirus-associated virus", 1978, *American Journal of Veterinary Research*, 39(12):1904-1906, XP009050511.

Crystal RG, "Transfer of genes to humans: early lessons and obstacles to success," 1995, *Science*, 270(5235):404-410.

Database EMBL, Entry GGACTAA, GenBank Accession No. M61166, Mar. 27, 1991, XP002125220.

Davidson BL et al. "Recombinant Adeno-associated Virus Type 2, 4, and 5 Vectors: Transduction of Variant Cell Types and Regions in the Mammalian Central Nervous System" *Proc. Natl Acad Sci.* 97(7):3428-32, Mar. 2000.

Davidson BL, Doran SE, Shewach DS, Latta JM, Hartman JW, Roessler BJ., "Expression of *Escherichia coli beta*-galactosidase and rat HPRT in the CNS of *Macaca mulatta* following adenoviral mediated gene transfer,"1994, *Exp Neurol*, 125:258-267.

Deonarain MP, "Ligand-targeted receptor-mediated vectors for gene delivery," *Molecular Conjugate Vectors*, 1998, 8(1):53-69.

Derby, M. L., M. Sena-Esteves, et al., "Gene transfer into the mammalian inner ear using HSV-1 and vaccinia virus vectors," 1999, *Hear Res* 134(1-2):1-8.

Di Pasquale, et al., "AAV transcytosis through barrier epithelia and endothelium," *Mol Ther. 13*(3):506-16 (2005).

Di Pasquale, et al., "AAV transcytosis through barrier epithelia," Xth Parvovirus Workshop Program, Sep. 9, 2004 http://cme.ufl.edu/conf/parvovirus/program.shtml (2005).

Di Pasquale, et al., "AAV transytosis through barrier eoithelia and endothelium," 8th Annual Meeting American Socierty of Gene Therapy Jun. 1, 2005 http://www.asgt.org/am05/programm/fina1program.pdf.

Di Pasquale, G., and J. A. Chiorini, "PKA/PrKX activity is a modulator of AAV/adenovirus interaction," 2003, *EMBO J*, 22:1716-1724.

Di Pasquale, G., B. L. Davidson, et al., "Identification of PDGFR as a receptor for AAV-5 transduction," 2003, *Nat Med* 9(10):1306-1312.

Di Pasquale, G., Rzadzinska, A., Schneider, M.E., Bossis, I., Chiorini, J.A., Kachar, B., "A novel bovine virus efficiently transduces inner ear neuroepithelial cells," 2005, *Molecular Therapy*, Academic Press, 11(6):849-855, XP004908862.

Dixit, M., M.S. Webb, W.C. Smart, and S. Ohi,"Construction and expression of a recombinant adeno-associated virus that harbors a human *beta*-globin-encoding cDNA," 1991, *Gene* 104:253-257.

Doll RF, Crandall JE, Dyer CA, Aucoin JM, Smith FI., "Comparison of promoter strengths on gene delivery into mammalian brain cells using AAV vectors," 1996, *Gene Ther*, 3:437-447.

Drapkin, et al., "Targeting the urokinase plasminogen activator receptor enhances gene transfer to human airway epithelia," *The Journal of Clinical Investigation* 105(5):589-596 (2002).

Duan, D., Yue Y., Yan Z., McCray PB Jr, and Engelhardt JF., "Polarity influences the efficiency of recombinant adenoassociated virus infection in differentiated airway epithelia," 1998, *Hum Gene Ther*, 9:2761-2776.

During MJ, Leone P, "Adeno-associated virus vectors for gene therapy of neurodegenerative disorders," 1995-96, *Clin Neurosci*, 3(5):292-300, XP-002125034.

During MJ, Symes CW, Lawlor PA, Lin J, Dunning J, Fitzsimons HL, Poulsen D, Leone P, Xu R, Dicker BL, Lipski J, Young D, "An oral vaccine against NMDAR1 with efficacy in experimental stroke and epilepsy," 2000, *Science*, 287:1453-1460.

During MJ, Xu R, Young D, Kaplitt MG, Sherwin RS, Leone P., "Peroral gene therapy of lactose intolerance using an adeno-associated virus vector," 1998, *Nat Med*, 4(10):1131-1135.

Erles, K., Sebokova, P. and Schlehofer, J.R., "Update on the prevalence of serum antibodies (IgG and IgM) to adeno-associated virus (AAV)," 1999, *J Med Virol*, 59:406-411.

Fan D-S, Ogawa M, Fujimoto K-I, Ikeguchi K, Ogasawara Y, Urabe M, Nishizawa M, Nakano I, Yoshida M, Nagatsu I, Ichinose H, Nagatsu T, Kurtzman GJ, Ozawa K, "Behavioral recovery in 6-hydroxydopamine-lesioned rats by cotransduction of striatum with tyrosine hydroxylase and aromatic L-amino acid decarboxylase genes using two separate adeno-associated virus vectors," 1998, *Hum Gene Ther*, 9:2527-2535.

Fisher, KJ, Jooss K., Alston J., Yang Y., Haecker SE, High K., Pathak R., Raper SE, and Wilson JM, "Recombinant adeno-associated virus for muscle directed gene therapy," 1997, *Nat Med*, 3:306-312.

Fisher, R.E., H.D. Mayor, "The evolution of defective and autonomous parvoviruses," 1991, *J Theor Biol* 149:429-439.

Flannery et al., "Efficient Photoreceptor-targeted Gene Expression in vivo by Recombinant Adeno-Associated Virus," 1997, *Proc Natl Acad Sci USA*, 94:6916-6921.

Flotte TR, Solow R, Owens RA, Afione S, Zeitlin PL, Carter BJ, "Gene expression from adeno-associated virus vectors in airway epithelial cells," 1992, *Am J Respir Cell Mol Biol*, 7(3):349-356; XP000609213.

Flotte, et al., "A phase I study of an adeno-associated virus-CFTR gene vector in adult CF patients with mild lung disease," *Human Gene Therapy* 7:1145-1159 (1996).

Flotte, T.R., S.A. Afione, C. Conrad, S.A. McGrath, R. Solow, H. Oka, P.L. Zeitlin, W.B. Guggino, and B.J. Carter, "Stable in vivo expression of the cystic fibrosis transmembrane conductance regulator with an adeno-associated virus vector," 1993, *Proc. Natl. Acad. Sci.*, 90:10613-10617.

Flotte, T.R., S.A. Afione, R. Solow, M.L. Drumm, D. Markakis, W.B. Guggino, P.L. Zeitlin, and B.J. Carter, "Expression of the cystic fibrosis transmembrane conductance regulator from a novel adeno-associated virus promoter," 1993, *J Biol Chem*, 268:3781-3790.

Frolenkov GI, Belyantseva IA, Friedman TB, Griffith AJ, "Genetic insights into the morphogenesis of inner ear hair cells," 2004, *Nat Rev Genet*, 5:489-498.

Gao, G., L. H. Vandenberghe, M. R. Alvira, Y. Lu, R. Calcedo, X. Zhou, and J. M. Wilson, "Clades of Adeno-associated viruses are widely disseminated in human tissues," 2004, *J Virol*, 78:6381-6388.

Gao, G.P., Alvira, M.R., Wang, L., Calcedo, R., Johnston, J. and Wilson, J.M., "Novel adeno-associated viruses from rhesus monkeys as vectors for human gene therapy," 2002, *Proc Natl Acad Sci USA*, 99:11854-11859.

GenBank Accession No. AY186198.

Georg-Fries B, Biederlack S, Wolf J, zur Hausen H, "Analysis of proteins, helper dependence, and seroepidemiology of a new human parvovirus," 1984, *Virology*, 134(1):64-71, XP002027460.

Ghodsi A., Stein C., Derksen T., Martins I., Anderson RD, & Davidson BL, "Systemic hyperosmolality improves *beta*-glucuronidase distribution and pathology in murine MPS VII brain following intraventricular gene transfer," 1999, *Exp Neurol*, 160:109-116.

Ghodsi A., Stein, C., Derksen T., Yang, G., Anderson R.D., Davidson B.L., "Extensive *beta*-glucuronidase activity in murine central nervous system after adenovirus-mediated gene transfer to brain,"1998, *Hum Gene Ther*, 9:2331-2340.

Girod A., Ried M., Wobus C., Lahm H., Leike K., Kleinschmidt J., Deleage G., and Hallek M., "Genetic capsid modifications allow efficient re-targeting of adeno-associated virus type 2," 1999, *Nat Med*, 5:1052-1056.

Grimm D and Kern A, Rittner K Kleinschmidt JA, "Novel Tools for Production and Purification of Recombinant Adenoassociated Virus Vectors," 1998, *Human Gene Therapy*, 9:2745-2760.

Grimm, D. and M. A. Kay, "From virus evolution to vector revolution: use of naturally occurring serotypes of adeno-associated virus (AAV) as novel vectors for human gene therapy," 2003, *Curr Gene Ther*, 3(4)::281-304.

Guy J., Qi X., Muzyczka N., and Hauswirth WW, "Reporter expression persists 1 year after adeno-associated virus-mediated gene transfer to the optic nerve," 1999, *Arch Ophthalmol*, 117:929-937.

Halbert CL, Standaert TA, Aitken ML, Alexander IE, Russell DW, and Miller AD, "Transduction by adeno-associated virus vectors in the rabbit airway: efficiency, persistence, and readministration," 1997, *J.Virol.*, 71:5932-5941.

Halbert, C. L., J. M. Allen, and A. D. Miller, "Adeno-associated virus type 6 (AAV6) vectors mediate efficient transduction of airway epithelial cells in mouse lungs compared to that of AAV2 vectors," 2001, *J Virol*, 75:6615-6624.

He, D. Z., J. Zheng, et al., "Development of acetylcholine receptors in cultured outer hair cells," 2001, *Hear Res* 162(1-2):113-125.

Hehir K.M., Armentano D., Cardoza L.M., Choquette T.L., Berthelette P.B., White G.A., Couture L.A., Everton M.B., Keegan J., Martin J.M., Pratt D.A., Smith M.P., Smith A.E., Wadsworth S.C., "Molecular characterization of replication-competent variants of adenovirus vectors and genome modifications to prevent their occurrence," 1996, *J Virol*, 70(12):8459-8467.

Heister, T., Heid, I. Ackermann, M., Fraefel, C., "Herpes simplex virus type 1/adeno-associated virus hybrid vectors mediate site-specific integration at the adeno-associated virus preintegration site, AAVS1, on human chromosome 19," 2002 *J Virol*, 76(14):7163-7173.

Hermonat PL, Santin AD, De Greve J, De Rijcke M, Bishop BM, Han L, Mane M, Kokorina N, "Chromosomal latency and expression at map unit 96 of a wild-type plus adeno-associated virus (AAV)/Neo vector and identification of p81, a new AAV transcriptional promoter," Nov.-Dec. 1999, *J Hum Virol*, 2(6):359-368.

Hermonat, P.L., M.A. Labow, R. Wright, K.I. Berns, and N. Muzyczka, "Genetics of adeno-associated virus: isolation and preliminary characterization of adeno-associated virus type 2 mutants," 1984, *J. Virol.*, 51:329-339.

Hermonat, PL and N Muzyczka, "Use of adeno-associated virus as a mammalian DNA cloning vector: transduction of neomycin resistance into mammalian tissue culture cells," 1984, *Proc Natl Acad Sci USA*, 81:6466-6470.

Hisako et al., "Identification of adeno-associated virus contamination in cell and virus stocks by PCR", *Biotechniques*, Apr. 2004, vol. 36, No. 4, Apr. 2004, pp. 676-680.

Hoggan, M. D., N. R. Blacklow, and W. P. Rowe, "Studies of small DNA viruses found in various adenovirus preparations: physical, biological, and immunological characteristics," 1966, *Proc Natl Acad Sci USA*, 55:1467-1474.

Hoggan, M.D., "Adenovirus associated viruses," 1970, *Prog Med Virol*, 12:211-239.

Holt, J. R., "Viral-mediated gene transfer to study the molecular physiology of the Mammalian inner ear" 2002, *Audiol Neurootol*, 7(3):157-160.

Holt, J. R., D. C. Johns, et al., "Functional expression of exogenous proteins in mammalian sensory hair cells infected with adenoviral vectors," 1999, *J Neurophysiol*, 81(4):1881-1888.

Hsueh Y-P, Sheng M., "Regulated expression and subcellular localization of syndecan heparan sulfate proteoglycans and the syndecan-binding protein CASK/LIN-2 during rat brain development," 1999, *J Neurosci*, 19(17):7415-7425.

Hsueh Y-P, Yang F-C, Kharazia V, Naisbitt S, Cohen AR, Weinberg RJ, Sheng M, "Direct interaction of CASK/LIN-2 and syndecan heparan sulfate proteoglycan and their overlapping distribution in neuronal synapses," 1998, *J Cell Biol*, 142(1):139-151.

Hull, R. N., and J. R. Minner, "New viral agents recovered from tissue cultures of monkey kidney cells. II. Problems of isolation and identification," 1957, *Ann NY Acad Sci*, 67:413-423.

Hull, R. N., J. R. Minner, and C. C. Mascoli, "New viral agents recovered from tissue cultures of monkey kidney cells. III. Recovery of additional agents both from cultures of monkey tissues and directly from tissues and excreta," 1958, *Am J Hyg*, 68:31-44.

Hull, R. N., J. R. Minner, and J. W. Smith, "New viral agents recovered from tissue cultures of monkey kidney cells. I. Origin and properties of cytopathogenic agents S.V.1, S.V.2, S.V.4, S.V.5, S.V.6, S.V.11, S.V.12 and S.V.15," 1956, *Am J Hyg*, 63:204-215.

Hunter, L.A. and R.J. Samulski, "Colocalization of adeno-associated virus Rep and capsid proteins in the nuclei of infected cells," 1992, *J. Virol.*, 66:317-324.

Im DS, Muzyczka N, "Partial purification of adeno-associated virus Rep78, Rep52, and Rep40 and their biochemical characterization," Feb. 1992, *J Virol.*, 66(2):1119-1128, XP002125031.

Inglis VI, Jones MP, Tse AD, Easton AS, "Neutrophils both reduce and increase permeability in a cell culture model of the blood-brain barrier," 2004, *Brain Res*, 998(2):218-229.

Ito, M. and H.D. Mayor, "Hemagglutinin of type 4 adeno-associated satellite virus," 1968, *J. Immunol*, 100:61-68.

Jaksch, M., K.D. Gerbitz, and C. Kilger, "Screening for mitochondrial DNA (mtDNA) point mutations using nonradioactive single strand conformation polymorphism (SSCP) analysis," 1995 *Clin. Biochem.*, 28:503-509.

Janik, J.E., M.M. Huston, K. Cho, and J.A. Rose, "Efficient syntheses of adeno-associated virus structural proteins requires both adenovirus DNA binding protein and VA I RNA," 1989, *Virology* 168:320-329.

Janson, et al., "Gene therapy of canavan disease: AAV-2 vector for neurosurgical delivery of aspartoacylase gene (ASPA) to the human brain," *Hunan Gene Therapy* 13:1391-1412 (2202).

Jero J, Mhatre AN, Tseng CJ, Stern RE, Coling DE, Goldstein JA, Hong K, Zheng WW, Hogue AT, Lalwani AK., "Cochlear gene delivery through an intact round window membrane in mouse," 2001, *Hum Gene Ther*, 12(5):539-548.

Johansson CB, Momma S, Clarke DL, Risling M, Lendahl U, Frisen J, "Identification of a neural stem cell in the adult mammalian central nervous system," 1999, *Cell*, 96(1):25-34.

Kaludov et al., "Adeno-Associated Virus Serotype 4 (AAV4) and AAV5 Both Require Sialic Acid Binding for Hemagglutination and Efficient Transduction but Differ in Sialic Acid Linkage Specificity" 2001, *J. Virol.*, 75(15):6884-6893.

Kaludov et al., "Scalable Purification of Adeno-Associated Virus Type 2, 4 or 5 Using Ion-Exchange Chromatography," 2002, *Human Gene Therapy*, 13:1235-1243.

Kanzaki, S., K. Ogawa, et al., "Transgene expression in neonatal mouse inner ear explants mediated by first and advanced generation adenovirus vectors," 2002, *Hear Res*, 169(1-2):112-120.

Kaplitt, M.G., P. Leone, R.J. Samulski, X. Xiao, D.W. Pfaff, K.L. O'Malley, and J.M. During, "Long-term gene expression and phenotypic correction using adeno-associated virus vectors in the mammalian brain," 1994, *Nature Genetics*, 8:148-154.

Katano et al., "Identification of adeno-associated virus contamination in cell and virus stocks by PCR," Apr. 2004, *Biotechniques*, 36(4):676-680, XP001207105.

Kelsell, D.P., Dunlop, J., Stevens, H.P., Lench, N.J., Liang, J.N., Parry, G., Mueller, R.F., Leigh, I.M., "Connexin 26 mutations in hereditary non-syndromic sensorineural deafness," 1997, *Nature*, 387(6628):80-83.

Kern, A., K. Schmidt, C. Leder, O. J. Muller, C. E. Wobus, K. Bellinger, C. W. Von der Lieth, J. A. King, and J. A. Kleinschmidt, "Identification of a heparin-binding motif on adeno-associated virus type 2 capsids," 2003, *J Virol*, 77:11072-11081.

Klein RL, Meyer EM, Peel AL, Zolotukhin S, Meyers C, Muzyczka N, King MA., "Neuron-specific transduction in the rat septohippocampal or nigrostriatal pathway by recombinant adeno-associated virus vectors," 1998, *Exp Neurol*, 150:183-194.

Kondo M., Finkbeiner WE, and Widdicombe JH., "Simple technique for culture of highly differentiated cells from dog tracheal epithelium," 1991, *Am.J.Physiol*, 261:L106-L117.

Kotin et al., "Organization of adeno-associated virus DNA in latently infected Detroit 6 cells." Virology 170(2):460-7 (1989).

Kotin, R.M., M. Siniscalco, R.J. Samulski, X. Zhu, L. Hunter, C.A. Laughlin, S. McLaughlin, N. Muzyczka, M. Rocchi, and K.I. Berns, "Site-specific integration by adeno-associated virus," 1990, *Proc. Natl. Acad. Sci. USA*, 87:2211-2215.

Kovacs P, Pinter M, Csaba G, "Effect of glucosphingolipid synthesis inhibitor (PPMP and PDMP) treatment on *Tetrahymena pyriformis*: data on the evolution of the signaling system," 2000, *Cell Biochem Funct*, 18(4):269-280.

Kyo S, Nakamura M, Kiyono T, Maida Y, Kanaya T, Tanaka M, Yatabe N, Inoue M, "Successful immortalization of endometrial glandular cells with normal structural and functional characteristics," 2003, *Am J Pathol*, 163(6):2259-2269.

Kyostio SR, Owens RA, Weitzman MD, Antoni BA, Chejanovsky N, Carter BJ, "Analysis of adeno-associated virus (AAV) wild-type and mutant Rep proteins for their abilities to negatively regulate AAV $p_5$ and $p_{19}$ mRNA levels," 1994, *J Virol*, 68(5):2947-2957, XP-002125032.

Laughlin, C.A., M.W. Myers, D.L. Risin, B.J. Carter, "Defective-interfering particles of the human parvovirus adeno-associated virus," 1979, *Virology*, 94:162-174.

Laughlin, C.A., N. Jones, and B.J. Carter, "Effect of deletions in adenovirus early region 1 genes upon replication of adeno-associated virus," 1982, *J. Virol*, 41:868-876.

Lee K, Kim YG, Jo EC, "Shuttle PCR-based cloning of the infectious adeno-associated virus type 5 genome," 2003, *J Virol Methods*, 111(2):75-84.

Li Duan, M., T. Bordet, et al., "Adenoviral and adeno-associated viral vector mediated gene transfer in the guinea pig cochlea," 2002, *Neuroreport*, 13(10)1295-1299.

Li J, Samulski RJ, Xiao X, "Role for Highly Regulated *rep* Gene Expression in Adeno-Associated Virus Vector Production," *J Virol*, 1997, 71(7):5236-5243.

Liang Y, Annan RS, Carr SA, Popp S, Mevissen M, Margolis RK, Margolis RU., "Mammalian homologues of the *Drosophila* slit protein are ligands of the heparan sulfate proteoglycan glypican-1 in brain," 1999, *J Biol Chem*, 274(25):17885-17892.

Lo WD, Qu G, Sferra TJ, Clark R, Chen R, Johnson PR., "Adeno-associated virus-mediated gene transfer to the brain: duration and modulation of expression," 1999, *Hum Gene Ther*, 10:201-213.

Luchsinger, E., Strobbe, R., Dekegel, D. and Wellemans, G., "Use of B-IV zonal rotor centrifugation as a simple tool for the separation of adeno-associated X 7 virus (AAVX 7) from helper adenoviruses," 1971, *Arch Gesamte Virusforsch*, 33:251-258.

Luchsinger, E., Strobbe, R., Wellemans, G., Dekegel, D. and Sprecher-Goldberger, S., "Haemagglutinating adeno-associated virus (AAV) in association with bovine adenovirus type 1," 1970, *Brief report. Arch Gesamte Virusforsch*, 31:390-392.

Luebke, A. E., J. D. Steiger, et al., "A modified adenovirus can transfect cochlear hair cells in vivo without compromising cochlear function," 2001, *Gene Ther*, 8(10):789-794.

Luebke, A. E., P. K. Foster, et al., "Cochlear function and transgene expression in the guinea pig cochlea, using adenovirus- and adeno-associated virus-directed gene transfer," 2001, *Hum Gene Ther*, 12:773-781.

Maeda Y, Ikeda U, Ogasawara Y, Urabe M, Takizawa T, Saito T, Colosi P, Kurtzman G, Shimada K, Ozawa K, "Gene transfer into vascular cells using adeno-associated virus (AAV) vectors," 1997, *Cardiovasc Res*, 35(3):514-521, XP-002125030.

Mandel RJ, Rendahl KG, Spratt SK, Snyder RO, Cohen LK, Leff SE., "Characterization of intrastriatal recombinant adeno-associated virus-mediated gene transfer of human tyrosine hydroxylase and human GTP-cyclohydrolase I in a rat model of Parkinson's disease," 1998, *J Neurosci*, 18(11):4271-4284.

McCarty, D.M., J. Pereira, I. Zolotukhin, X. Zhou, J.H. Ryan, and N. Muzyczka, "Identification of linear DNA sequences that specifically bind the adeno-associated virus Rep protein," 1994, *J. Virol.*, 68:4988-4997.

McCown TJ, Xiao X, Li J, Breese GR, Samulski RJ, "Differential and Persistent Expression Patterns of CNS Gene Transfer by an Adeno-Associated Virus (AAV) Vector," 1996, *Brain Res*, 713:99-107.

McPherson, R. A., L. J. Rosenthal, and J. A. Rose, "Human cytomegalovirus completely helps adeno-associated virus replication," 1985, *Virology*, 147:217-222.

Mendelson, E., J.P. Trempe, and B.J. Carter "Identification of the trans-acting Rep proteins of adeno-associated virus by antibodies to a synthetic oligopeptide," 1986, *J. Virol.*, 60:823-832.

Meyers, C., Mane, M., Kokorina, N., Alam, S. and Hermonat, P.L., "Ubiquitous human adeno-associated virus type 2 autonomously replicates in differentiating keratinocytes of a normal skin model," 2000, *Virology*, 272:338-346.

Mitrani E, Ziv T, Thomsen G, Shimoni Y, Melton Da, Bril A, "Activin can induce the formation of axial structures and is expressed in the hypoblast of the chick," 1990, *Cell*, 63(3):495-501.

Mizukami, H., N.S. Young, and K.E. Brown, "Adeno-associated virus type 2 binds to a 150-kilodalton cell membrane glycoprotein," 1996, *Virology*, 217:124-130.

Mori, S., L. Wang, T. Takeuchi, and T. Kanda, "Two novel adeno-associated viruses from cynomolgus monkey: pseudotyping characterization of capsid protein," 2004, *Virology*, 330:375-383.

Mouw, M.B. and Pintel, D.J., "Adeno-associated virus RNAs appear in a temporal order and their splicing is stimulated during coinfection with adenovirus," 2000, *J Virol*, 74:9878-9888.

Muramatsu et al. "Nucleotide Sequencing and Generation of an Infectious Clone of Adeno-Associated Virus 3" *Virology* 221:208-217, 1996.

Muster et al. "Physical Mapping of Adeno-Associated Virus Serotype 4 DNA" *J. Virol.* 35(3):653-661, Sep. 1980.

Muzyczka, N, "Use of adeno-associated virus as a general transduction vector for mammalian cells," 1992, *Curr Top Microbiol Immunol*, 158:97-129.

Myrup, A.C., Mohanty, S.B. and Hetrick, F.M., "Isolation and characterization of adeno-associated viruses from bovine adenovirus types 1 and 2," 1976, *Am J Vet Res*, 37(8):907-910.

Naz, S., Griffith A.J., Riazuddin, S., Hampton, L.L., Battey, J.F. Jr, Khan, S.N., Riazuddin, S., Wilcox, E.R., Friedman, T.B., "Mutations of *ESPN* cause autosomal recessive deafness and vestibular dysfunction," 2004, *J Med Genet*, 41(8):591-595.

No D, Yao TP, Evans RM., "Ecdysone-inducible gene expression in mammalian cells and transgenic mice," 1996, *Proc Natl Acad Sci USA*, 93(8):3346-3351.

Ogston, P., K. Raj, and P. Beard, "Productive replication of adeno-associated virus can occur in human papillomavirus type 16 (HPV-16) episome containing keratinocytes and is augmented by the HPV-16 E2 protein," 2000, *J Virol*, 74:3494-3504.

Opie et al., "Identification of amino acid residues in the capsid proteins of adeno-associated virus type 2 that contribute to heparan sulfate proteoglycan binding," 2003, *J Virol*, 77:6995-7006.

O'Riordan et al., "Scaleable Chromatographic Purification Process for Recombinant Adeno-Associated Virus (rAAV)," 2000, *J Gene Med*, 2:444-454.

Parks, W.P., J.L. Melnick, R. Rongey, and H.D. Mayor, "Physical assay and growth cycle studies of a defective adeno-satellite virus," 1967, *J. Virol.*, 1:171-180.

Podsakoff, G., K.K. Jr Wong, and S. Chatterjee, "Efficient gene transfer into nondividing cells by adeno-associated virus-based vectors," 1994, *J. Virol.*, 68:5656-5666.

Polishchuk R, Di Pentima A, Lippincott-Schwartz J, "Delivery of raft-associated, GPI-anchored proteins to the apical surface of polarized MDCK cells by a transcytotic pathway," 2004, *Nat Cell Biol*, 6(4):297-307.

Prasad KM, Zhou C, Trempe JP, "Characterization of the Rep78/adeno-associated virus complex," 1997, *Virology*, 229(1):183-192, XP-002125033.

Qing K, Mah C, Hansen J, Zhou S, Dwarki V, Srivastava A., "Human fibroblast growth factor receptor 1 is a co-receptor for infection by adeno-associated virus 2," 1999, *Nat Med*, 5(1):71-77.

Qiu J, Brown KE., "Integrin *alphaVbeta*5 is not involved in adeno-associated virus type 2 (AAV2) infection," 1999, *Virology*, 264(2):436-440.

Rabinowitz et al., "Cross-Packaging of a Single Adeno-Associated Virus (AAV) Type 2 Vector Genome into Multiple AAV Serotypes Enables Transduction with Broad Specificity," 2002, *J Virol*, 76(2):791-801, XP002247245.

Rabinowitz JE, Bowles DE, Faust SM, Ledford JG, Cunningham SE, Samulski RJ., "Cross-dressing the virion: the transcapsidation of adeno-associated virus serotypes functionally defines subgroups," 2004, *J Virol*, 78(9):4421-4432.

Reddy, V. S., P. Natarajan, B. Okerberg, K. Li, K. V. Damodaran, R. T. Morton, C. L. Brooks, 3rd, and J. E. Johnson, "Virus Particle Explorer (VIPER), a website for virus capsid structures and their computational analyses," 2001, *J Virol*, 75:11943-11947.

Rich DP, Couture LA, Cardoza LM, Guiggio LM, Armentano D., Espino PC, Hehir K., Welsh MJ, Smith AE, and Gregory RJ, "Development and analysis of recombinant adenoviruses for gene therapy of cystic fibrosis," 1993, *Hum. Gene Ther.*, 4:461-476.

Richardson, W. D., and H. Westphal, "Requirement for either early region 1a or early region 1b adenovirus gene products in the helper effect for adeno-associated virus," 1984, *J Virol*, 51:404-410.

Rose, J.A., M.D. Hoggan, F. Koczot, and A.J. Shatkin, "Genetic relatedness studies with adenovirus-associated viruses," 1968, *J. Virol.*, 2:999-1005.

Rosenfeld et al., "Adeno-associated viral vector gene transfer into leptomeningeal xenografts," 1997, *J Neuro-Oncology*, 34(2):139-144.

Russell et al., "Adeno-Associated Virus Vectors Preferentially Transduce Cells in S Phase," 1994, *Proc. Natl. Acad. Sci. USA*, 91:8915-8919.

Rutledge EA, Halbert CL, and Russell DW, "Infectious Clones and Vectors Derived from Adeno-Associated Virus (AAV) Serotypes other Than AAV Type 2," 1998, *J. Virol.*, 72(1):309-319.

Ryan, J.H., S. Zolotukhin, and N. Muzyczka, "Sequence requirements for binding of Rep68 to the adeno-associated virus terminal repeats," 1996, *J. Virol.*, 70:1542-1553.

Rzadzinska, A. K., M. E. Schneider, et al., "An actin molecular treadmill and myosins maintain stereocilia functional architecture and self-renewal," 2004, *J Cell Biol*, 164(6):887-897.

Saffer, L. D., R. Gu, et al., "An RT-PCR analysis of mRNA for growth factor receptors in damaged and control sensory epithelia of rat utricles," 1996, *Hear Res*, 94(1-2):14-23.

Salo R. and Mayor H. "Structural Polypeptides of Parvoviruses" *Virology* 78:340-345, 1977.

Samulski RJ, Chang LS, Shenk T, "Helper-free stocks of recombinant adeno-associated viruses: normal integration does not require viral gene expression," 1989, *J Virol.*, 63(9):3822-3828, XP000283071.

Samulski, R. J., and T. Shenk, "Adenovirus E1B 55-$M_r$ polypeptide facilitates timely cytoplasmic accumulation of adeno-associated virus mRNAs," 1988, *J Virol*, 62:206-210.

Samulski, R.J., K.I. Berns, M. Tan, and N. Muzyczka, "Cloning of adeno-associated virus into pBR322: rescue of intact virus from the recombinant plasmid in human cells," 1982, *Proc Nat Acad Sci USA*, 79:2077-2081.

Sanes JR, JLR Rubenstein, and JF Nicolas, "Use of a recombinant retrovirus to study post-implantation cell lineage in mouse embryos," 1986, *EMBO J*, 5:3133-3142.

Sanlioglu, S., Benson, P.K., Yang, J., Atkinson, E.M., Reynolds, T. and Engelhardt, J.F., "Endocytosis and nuclear trafficking of adeno-associated virus type 2 are controlled by rac1 and phosphatidylinositol-3 kinase activation," 2000, *J Virol*, 74:9184-9196.

Schinkel AH, "P-Glycoprotein, a gatekeeper in the blood-brain barrier,"1999, *Adv Drug Deliv Rev*, 36:179-194.

Schlehofer Jr, Heilbronn R, Georg-Fries B, zur Hausen H, "Inhibition of initiator-induced SV40 gene amplification in SV40-transformed Chinese hamster cells by infection with a defective parvovirus," 1983, *Int J Cancer*, 32(5):591-595, XP009010321.

Schlehofer, J. R., M. Ehrbar, and H. zur Hausen, "Vaccinia virus, herpes simplex virus, and carcinogens induce DNA amplification in a human cell line and support replication of a helpervirus dependent parvovirus," 1986, *Virology*, 152:110-117.
Schmidt et al., "Cloning and characterization of a bovine adeno-associated virus," 2004, *Journal of Virology*, 78(12):6509-6516, XP00233552.
Schmidt M, Grot E, Cervenka P, Wainer S, Buck C, Chiorini JA, "Identification and characterization of novel adeno-associated virus isolates in ATCC virus stocks," 2006, *J Virol*, 80(10):5082-5085.
Schneider, M. E., I. A. Belyantseva, et al., "Rapid renewal of auditory hair bundles," 2002, *Nature*, 418(6900):837-838.
Schwede, T., J. Kopp, N. Guex, and M. C. Peitsch, "Swiss-Model: An automated protein homology-modeling server," 2003, *Nucleic Acids Res*, 31:3381-3385.
Seiler MP, Miller AD, Zabner J, Halbert CL, "Adeno-associated virus types 5 and 6 use distinct receptors for cell entry," 2006, *Hum Gene Ther*, 17:10-19.
Seiler, M. P., C. L. Halbert, J. A. Chiorini, A. D. Miller, and J. Zabner, "AAV5 and AAV6 Mediate Gene Transfer to Human Airway Epthelia Via Different Receptors," 2002, *Mol Ther*, 5:S40.
Senapathy, P., J.D. Tratschin, and B.J. Carter, "Replication of adeno-associated virus DNA. Complementation of naturally occurring rep-mutants by a wild-type genome or an ori- mutant and correction of terminal palindrome deletions," 1984, *J Mol Biol* 179:1-20.
Shou, J., J. L. Zheng, et al., "Robust generation of new hair cells in the mature mammalian inner ear by adenoviral expression of *Hath1*," 2003, *Mol Cell Neurosci*, 23(2):169-179.
Smith, R. H., S. A. Afione, et al., "Transposase-mediated construction of an integrated adeno-associated virus type 5 helper plasmid," 2002, *Biotechniques*, 33(1):204-206,208,210-211.
Snyder RO, Miao CH, Patijn GA, Spratt SK, Danos O., Nagy D., Gown AM, Winther B., Meuse L., Cohen LK, Thompson AR, and Kay MA, "Persistent and therapeutic concentrations of human factor IX in mice after hepatic gene transfer of recombinant AAV vectors," 1997, *Nat.Genet.*, 16:270-276.
Sobkowicz, H. M., J. M. Loftus, et al., "Tissue culture of the organ of Corti," 1993, *Acta Otolaryngol Suppl*, 502:3-36.
Srivastava et al. "Nucleotide Sequence and Organization of the Adeno-Associated Virus 2 Genome" *J. Virol.* 45(2):555-564, Feb. 1983.
Staecker H, Li D, O'Malley BW Jr, Van De Water TR., "Gene expression in the mammalian cochlea: a study of multiple vector systems," 2001, *Acta Otolaryngol*, 121(2):157-163.
Stracker, T. H., G. D. Cassell, P. Ward, Y. M. Loo, B. van Breukelen, S. D. Carrington-Lawrence, R. K. Hamatake, P. C. van der Vliet, S. K. Weller, T. Melendy, and M. D. Weitzman, "The Rep protein of adeno-associated virus type 2 interacts with single-stranded DNA-binding proteins that enhance viral replication," 2004, *J Virol*, 78:441-453.
Summerford C, Bartlett JS, Samulski RJ., "*AlphaVbeta5* integrin: a co-receptor for adeno-associated virus type 2 infection," 1999, *Nat Med*, 5(1):78-82.
Summerford, C. and R. J. Samulski, "Membrane-associated heparan sulfate proteoglycan is a receptor for adeno-associated virus type 2 virions," 1998, *J Virol*, 72(2):1438-1445.
Superti, F., M. L. Marziano, A. Tinari, and G. Donelli, "Effect of polyions on the infectivity of SA-11 rotavirus in LCC-MK2 cells," 1993, *Comp Immunol Microbiol Infect Dis*, 16:55-62.
Suzuki, H., Y. Katori, et al., "Carbohydrate distribution in the living utricular macula of the guinea pig detected by lectins," 1995, *Hear Res*, 87(1-2):32-40.
Teramoto, S., Bartlett JS, McCarty DXX, Samulski RJ, and Boucher RC, "Factors influencing adeno-associated virus-mediated gene transfer to human cystic fibrosis airway epithelial cells: comparison with adenovirus vectors," 1998, *J Virol*, 72:8904-8912.
Thomas CE, Storm TA, Huang Z, Kay MA, "Rapid uncoating of vector genomes is the key to efficient liver transduction with pseudotyped adeno-associated virus vectors," 2004, *J Virol*, 78(6):3110-3122.
Tratschin, J. D., M. H. West, T. Sandbank, and B. J. Carter, "A human parvovirus, adeno-associated virus, as a eucaryotic vector: transient expression and encapsidation of the procaryotic gene for chloramphenicol acetyltransferase," 1984, *Mol Cell Biol*, 4:2072-2081.
Tratschin, J.D., I.L. Miller, and B.J. Carter, "Genetic analysis of adeno-associated virus: properties of deletion mutants constructed in vitro and evidence for an adeno-associated virus replication function," 1984, *J. Virol.*, 51:611-619.
Trempe, J.P. and B.J. Carter, "Regulation of adeno-associated virus gene expression in 293 cells: control of mRNA abundance and translation," 1988, *J. Virol.*, 62:68-74.
Trempe, J.P., E. Mendelson, and B.J. Carter, "Characterization of adeno-associated virus rep proteins in human cells by antibodies raised against rep expressed in *Escherichia coli*," 1987, *Virology*, 161:18-28.
Tuma PL and Hubbard AL, "Transcytosis: crossing cellular barriers," 2003, *Physiol Rev*, 83(3):871-932.
Voutetakis A, Kok MR, Zheng C, Bossis I, Wang J, Cotrim AP, Marracino N, Goldsmith CM, Chiorini JA, Loh YP, Nieman LK, Baum BJ, "Reengineered salivary glands are stable endogenous bioreactors for systemic gene therapeutics," 2004, *Proc Natl Aced Sci USA*, 101(9):3053-3058.
Walsh, C.E., J.M. Liu, X. Xiao, N.S. Young, A.W. Nienhuis, and R.J. Samulski, "Regulated high level expression of a human gamma-globin gene introduced into erythroid cells by an adeno-associated virus vector," 1992, *Proc Natl Acad Sci USA*, 89:7257-7261.
Walters, R.W., Yi, S.M., Keshavjee, S., Brown, K.E., Welsh, M.J., Chiorini, J.A. and Zabner, J., "Binding of adeno-associated virus type 5 to 2,3-linked sialic acid is required for gene transfer," 2001, *J Biol Chem*, 276:20610-20616.
Walters, RW, Duan D., Engelhardt JF, and Welsh MJ., "Incorporation of adeno-associated virus in a calcium phosphate coprecipitate improves gene transfer to airway epithelia in vitro and in vivo," 2000, *J. Virol.*, 74:535-540.
Walters, RW, Grunst T., Bergelson JM, Finberg RW, Welsh MJ, and Zabner J., "Basolateral localization of fiber receptors limits adenovirus infection from the apical surface of airway epithelia," 1999, *J. Biol. Chem.*, 274:10219-10226.
Walz, C., A. Deprez, T. Dupressoir, M. Durst, M. Rabreau, and J. R. Schlehofer, "Interaction of human papillomavirus type 16 and adeno associated virus type 2 co-infecting human cervical epithelium," 1997, *J Gen Virol*, 78(Pt 6):1441-1452.
Wang G., Davidson BL, Melchert P., Slepushkin VA, van Es HH, Bodner M., Jolly DJ, and McCray PB Jr., "Influence of cell polarity on retrovirus-mediated gene transfer to differentiated human airway epithelia," 1998, *Journal of Virology*, 72:9818-9826.
Wang, X. S., and A. Srivastava, "Rescue and autonomous replication of adeno-associated virus type 2 genomes containing Rep-binding site mutations in the viral p5 promoter," 1998, *J Virol*, 72:4811-4818.
Ward, P., F. B. Dean, M. E. O'Donnell, and K. I. Berns, "Role of the adenovirus DNA-binding protein in in vitro adeno-associated virus DNA replication," 1998, *J Virol*, 72:420-427.
Weindler, F. W., and R. Heilbronn, "A subset of herpes simplex virus replication genes provides helper functions for productive adeno-associated virus replication," 1991, *J Virol*, 65:2476-2483.
Winocour, E., M.F. Callaham, and E. Huberman, "Perturbation of the cell cycle by adeno-associated virus," 1988, *Virology*, 167:393-399.
Xiao et al., "Efficient Long-Term Gene Transfer into Muscle Tissue of Immunocompetent Mice by Adeno-Associated Virus Vector," 1996, *J. Virol.*, 70(11):8098-8108.
Xiao Xm Li J, Samulski RJ, "Production of High-Titer Recombinant Adeno-Associated Virus Vectors in the Absence of Helper Adenovirus," 1997, *J Virol*, 72(3):2224-2232.
Xiao, W., N. Chirmule, S. C. Berta, B. McCullough, G. Gao, and J. M. Wilson, "Gene therapy vectors based on adeno-associated virus type 1," 1999, *J Virol*, 73:3994-4003.
Xie Q. and Chapman MS, "Canine parvovirus capsid structure, analyzed at 2.9 Å resolution," 1996, *J Mol Biol*, 264:497-520.
Yakobson, B., Hrynko, T.A., Peak, M.J. and Winocour, E., "Replication of adeno-associated virus in cells irradiated with UV light at 254 nm," 1989, *J Virol*, 63:1023-1030.

Yalkinoglu, A.O., Heilbronn, R., Burkle, A., Schlehofer, J.R. and zur Hausen, H., "DNA amplification of adeno-associated virus as a response to cellular genotoxic stress," 1988, *Cancer Res*, 48:3123-3129.

Yamano, S., Huang, L.Y., Ding, C., Chiorini, J.A., Goldsmith, C.M., Wellner, R.B., Golding, B., Kotin, R.M., Scott, D.E. and Baum, B.J., "Recombinant adeno-associated virus serotype 2 vectors mediate stable interleukin 10 secretion from salivary glands into the bloodstream," 2002, *Hum Gene Ther*, 13:287-298.

Yamaya, M., Finkbeiner WE, Chun SY, and Widdicombe JH, "Differentiated structure and function of cultures from human tracheal epithelium," 1992, *Am.J.Physiol*, 262:L713-L724.

Zabner J, Seiler M, Walters R, Kotin RM, Fulgeras W, Davidson BL, Chiorini JA, "Adeno-associated virus type 5 (AAV5) but not AAV2 binds to the apical surfaces of airway epithelia and facilitates gene transfer," 2000, *J Virol.*, 74(8):3852-3858, XP002197205.

Zabner, J., Zeiher BG, Friedman E, and Welsh MJ, "Adenovirus-mediated gene transfer to ciliated airway epithelia requires prolonged incubation time," 1996, *J.Virol.*, 70:6994-7003.

Zhang JR, Mostov KE, Lamm ME, Nanno M, Shimida S, Ohwaki M, Tuomanen E, "The polymeric, immunoglobulin receptor translocates pneumococci across human nasopharyngeal epithelial cells," 2000, *Cell*, 102(6):827-837.

Zhu ZB, Makhija SK, Lu B, Wang M, Rivera AA, Preuss M, Zhou F, Siegal GP, Alvarez RD, Curiel DT, "Transport across a polarized monolayer of Caco-2 cells by transferrin receptor-mediated adenovirus transcytosis," 2004, *Virol*, 325:116-128.

Zolotukhin et al., "Recombinant Adeno-Associated Virus Purification using Novel Methods Improves Infectious Titer and Yield," 1999, *Gene Ther*, 6:973-985.

* cited by examiner

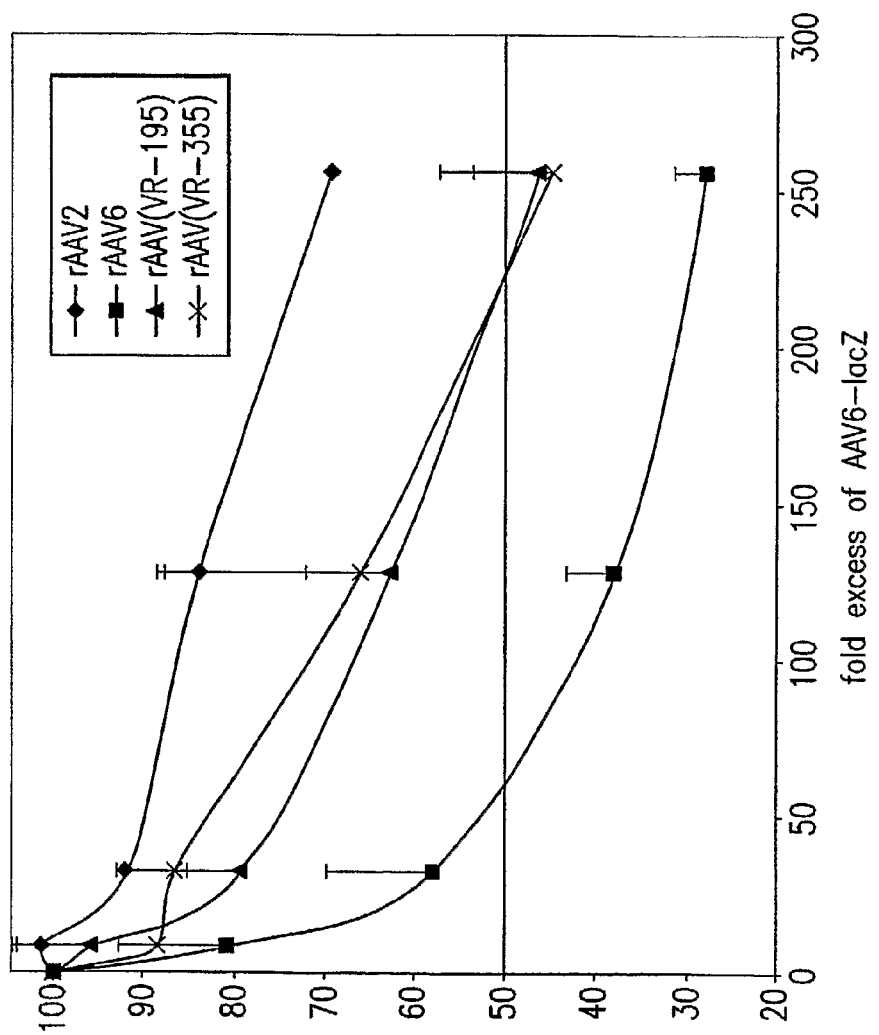

ISOLATION, CLONING AND CHARACTERIZATION OF NEW ADENO-ASSOCIATED VIRUS (AAV) SEROTYPES

CROSS-REFERENCE TO RELATED APPLICATIONS

This application claims benefit to International Patent Application No. PCT/US06/017157, filed May 2, 2006, which claims priority to U.S. Provisional Application No. 60/676,604, filed Apr. 29, 2005, both of which are hereby incorporated by reference in its their entirety.

BACKGROUND OF THE INVENTION

Adeno-associated virus (AAV) is a member of the Parvoviridae, a virus family characterized by a single stranded linear DNA genome and a small icosahedral shaped capsid measuring about 20 nm in diameter. AAV was first described as a contamination of tissue culture grown simian virus 15, a simian adenovirus and was found dependent on adenovirus for measurable replication. This lead to its name, adeno-associated virus, and its classification in the genus *Dependovirus* (reviewed in Hoggan et al., 1970). AAV is a common contaminant of adenovirus samples and has been isolated from human virus samples (AAV2, AAV3, AAV5), from samples of simian virus-15 infected cells (AAV1, AAV4) as well as from stocks of avian (AAAV) (Bossis and Chiorini, 2003), bovine, canine and ovine adenovirus and laboratory adenovirus type 5 stock (AAV6). DNA spanning the entire rep-cap ORFs of AAV7 and AAV8 was amplified by PCR from heart tissue of rhesus monkeys (Gao et al., 2002). With the exception of AAVs 1 and 6, all cloned AAV isolates appear to be serologically distinct. Nine isolates have been cloned, and recombinant viral stocks have been generated from each isolated virus.

AAV appears to commonly infect humans. 50%-80% of adults in North America are seropositive for AAV. A steep rise in antibody response against AAV 1-3 was observed in the age group between 1-10 years (Blacklow et al., 1968). AAV 2 and 3 were readily isolated from anal and throat specimens from children (Blacklow et al., 1967) whereas isolation from adults was not observed. It appears that AAV spreads primarily in the young population (Hoggan, 1970). Prevalence of antibodies against AAV was found to be similar in Europe, Brazil and Japan, which suggests a global spread of AAV (Erles et al., 1999). Infection with AAV appears to be benign in man and laboratory animals. Currently, no disease has been associated with AAV infections.

AAV2 is the best characterized adeno-associated virus and will be discussed as an AAV prototype. The AAV2 genome consists of a linear single stranded DNA of 4,780 nucleotides. Both polarities of DNA are encapsulated by AAV with equal efficiency. The AAV2 genome contains 2 open reading frames (ORF) named rep and cap. The rep ORF encodes the non-structural proteins that are essential for viral DNA replication, packaging and AAV integration. The cap ORF encodes the capsid proteins. The rep ORF is transcribed from promoters at map units P5 and P19. The rep transcripts contain an intron close to the 3' end of the rep ORF and can be alternatively spliced. The rep ORF is therefore expressed as 4 partially overlapping proteins, which were termed according to their molecular weight Rep78, 68, 52 and 40. The cap ORF is expressed from a single promoter at P40. By alternative splicing and utilization of an alternative ACG start codon, cap is expressed into the capsid proteins VP1-3 which range in size from 65-86 kDa. VP3 is the most abundant capsid protein and constitutes 80% of the AAV2 capsid. All viral transcripts terminate at a polyA signal at map unit 96.

During a productive AAV2 infection, unspliced mRNAs from the p5 promoter encoding Rep78 are the first detectable viral transcripts. In the course of infection, expression from P5, P19 and P40 increase to 1:3:18 levels respectively. The levels of spliced transcripts increased to 50% for P5, P19 products and 90% of P40 expressed RNA (Mouw and Pintel, 2000).

The AAV2 genome is terminated on both sides by inverted terminal repeats (ITRs) of 145 nucleotides (nt). 125 nt of the ITR constitute a palindrome which contains 2 internal palindromes of 21 nt each. The ITR can fold back on itself to generate a T-shaped hairpin with only 7 non-paired bases. The stem of the ITR contains a Rep binding site (RBS) and a sequence that is site and strand specifically cleaved by Rep—the terminal resolution site (TRS). The ITR is essential for AAV2 genome replication, integration and contains the packaging signals.

The single-stranded AAV2 genome is packaged into a non-enveloped icosahedral shaped capsid of about 20-25 nm diameter. The virion consists of 26% DNA and 74% protein and has a density of 1.41 g/cm$^3$. AAV2 particles are extremely stable and can withstand heating to 60° C. for 1 hour, extreme ph, and extraction with organic solvents.

Rep proteins are involved in almost every step of AAV2 replication including AAV2 genome replication, integration, and packaging. Rep78 and Rep68 possess ATPase, 3'-5' helicase, ligase and nicking activities and bind specifically to DNA. Rep52 and Rep40 appear to be involved in the encapsidation process and encode ATPase and 3'-5' helicase activities. Mutational analysis suggests a domain structure for Rep78. The N-terminal 225 aa are involved in DNA binding, DNA nicking and ligation. Rep78 and Rep68 recognize a GCTC repeat motif in the ITR as well as in a linear truncated form of the ITR (Chiorini et al., 1994) with similar efficiencies. Rep78 and Rep68 possess a sequence and strand specific endonuclease activity, which cleaves the ITR at the terminal resolution site (TRS). Rep endonuclease activity is dependent on nucleoside triphosphate hydrolysis and presence of metal cations. Rep 78 and 68 can also bind and cleave single stranded DNA in a NTP independent matter. In addition, Rep78 catalyzes rejoining of single stranded DNA substrates originating from the AAV2 origin of replication—i.e., sequences containing a rep binding and terminal resolution element.

The central region of AAV2 Rep78, which represents the N-terminus of Rep52 and Rep40, contains the ATPase and helicase activities as well as nuclear localization signals. The helicase activity unwinds DNA-DNA and DNA-RNA duplexes, but not RNA-RNA. The ATPase activity is constitutive and independent of a DNA substrate. The C-terminus of Rep78 contains a potential zinc-finger domain and can inhibit the cellular serine/threonine kinase activity of PKA as well as its homolog PRKX by pseudosubstrate inhibition. Rep68 which is translated from a spliced mRNA that encodes the N-terminal 529 amino acids (aa) of Rep78 fused to 7 aa unique for Rep68, doesn't inhibit either PKA or PRKX. In addition to these biochemical activities, Rep can affect intracellular conditions by protein-protein interactions. Rep78 binds to a variety of cellular proteins including transcription factors like SP-1, high-mobility-group non-histone protein 1 (HMG-1) and the oncosuppressor p53. Overexpression of Rep results in pleiotrophic effects. Rep78 disrupts cell cycle progression and inhibits transformation by cellular and viral oncogenes. In susceptible cell lines, overexpression of Rep resulted in apoptosis and cell death. Several of Rep78 activities contribute to cytotoxicity, including its constitutive ATPase activity, interference with cellular gene expression and protein interactions.

The first step of an AAV infection is binding to the cell surface. Receptors and coreceptors for AAV2 include heparan sulfate proteoglycan, fibroblast growth factor receptor-1, and $\alpha_v\beta_5$ integrins whereas N-linked 2,3-linked sialic acid is required for AAV5 binding and transduction (Walters et al., 2001). In HeLa cells, fluorescently labeled AAV2 particles appear to enter the cell via receptor-mediated endocytosis in clathrin coated pits. More than 60% of bound virus was internalized within 10 min after infection. Labeled AAV particles are observed to have escaped from the endosome, been trafficked via the cytoplasm to the cell nucleus and accumulated perinuclear, before entering the nucleus, probably via nuclear pore complex (NPC). AAV2 particles have been detected in the nucleus, suggesting that uncoating takes place in the nucleus (Bartlett et al., 2000; Sanlioglu et al., 2000). AAV5 is internalized in HeLa cells predominantly by clathrin coated vesicles, but to a lesser degree also in noncoated pits. AAV particles can also be trafficked intercellularly via the Golgi apparatus (Bantel-Schaal et al., 2002). At least partial uncoating of AAV5 was suggested to take place before entering the nucleus since intact AAV5 particles could not be detected in the nucleus (Bantel-Schaal et al., 2002) After uncoating, the single stranded genome is converted into duplex DNA either by leading strand synthesis or annealing of input DNA of opposite polarity. AAV replication takes place within the nucleus.

During a co-infection with a helper virus such as Adenovirus, herpes simplex virus or cytomegalovirus, AAV is capable of an efficient productive replication. The helper functions provided by Adenovirus have been studied in great detail. In human embryonic kidney 293 cells, which constitutively express the Adenovirus E1A and E1B genes, the early Adenovirus gene products of E2A, E4 and VA were found sufficient to allow replication of recombinant AAV. Allen et al. reported that efficient production of rAAV is possible in 293 cells transfected with only an E4orf6 expression plasmid (Allen et al., 2000). E1A stimulates S phase entry and induces unscheduled DNA synthesis by inactivating the pRB checkpoint at the G1/S border by interaction with pRB family proteins which results in the release of E2F (reviewed in (Ben-Israel and Kleinberger, 2002). This leads to either induction or activation of enzymes involved in nucleotide synthesis and DNA replication. Since unscheduled DNA synthesis is a strong apoptotic signal, anti-apoptotic functions are required. E1B-19k is a Bcl-2 homolog and E1B-55k is a p53 antagonist. Both proteins have anti-apoptotic functions. E4orf6 forms a complex with E1B-55k and results in degradation of p53. It is also reported to cause S-phase arrest (Ben-Israel and Kleinberger, 2002). E2A encodes a single strand DNA binding protein, which appears to be non-essential for DNA replication but effects gene expression (Chang and Shenk, 1990) (Fields 39, 40). The VA transcription unit affects AAV2 RNA stability and translation (Janik et al., 1989). E1A has a more direct effect on AAV2 gene expression. The cellular transcription factor YY-1 binds and inhibits the viral P5 promoter. E1A relieves this transcriptional block. None of the late Ad gene products have been found to be essential for AAV2 replication. The main function of the helper virus appears to be the generation of a cellular environment with active DNA replication machinery and blocked pro-apoptotic functions that allows high-level AAV replication rather than a direct involvement in AAV replication.

While AAV is usually dependent on a helper virus for efficient replication, low level AAV replication was observed under conditions of genotoxic stress (Yakinoglu et al., 1988; Yakobson et al., 1989). AAV DNA replication and particle formation was also observed in differentiating keratinocytes in the absence of helper virus infection (Meyers et al., 2000). This demonstrates that AAV is not defective per se but rather depends on the helper virus to establish the favorable cellular condition and to provide factors for efficient replication The ability of AAV vectors to infect dividing and non-dividing cells, establish long-term transgene expression, and the lack of pathogenicity has made them attractive for use in gene therapy applications. Lack of cross competition in binding experiments suggests that each AAV serotype may have a distinct mechanism of cell entry. Comparison of the cap ORFs from different serotypes has identified blocks of conserved and divergent sequence, with most of the latter residing on the exterior of the virion, thus explaining the altered tissue tropism among serotypes (19-21, 48, 56). Vectors based on new AAV serotypes may have different host range and different immunological properties, thus allowing for more efficient transduction in certain cell types. In addition, characterization of new serotypes will aid in identifying viral elements required for altered tissue tropism.

BRIEF SUMMARY OF THE INVENTION

Provided herein are adeno-associated viruses (AAV) and vectors derived therefrom. Thus, the present invention relates to AAV vectors for and methods of delivering nucleic acids to cells of subjects.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 5 shows neuraminidase treatment blocks rAAV6, rAAV(VR-195), and rAAV(VR-355) transduction and cell binding.

FIG. 8 shows AAV6 competition. COS cells were transduced with a constant amount of rAAV6, rAAV(VR-195) or rAAV(VR-355) expressing GFP after 60 min pre-incubation with increasing titers of rAAV6-lacZ. Forty-eight hour post-inoculation, transduction was analyzed by flow cytometry. Values are means from three experiments; error bars represent standard deviations.

DETAILED DESCRIPTION OF THE INVENTION

Figure 1:
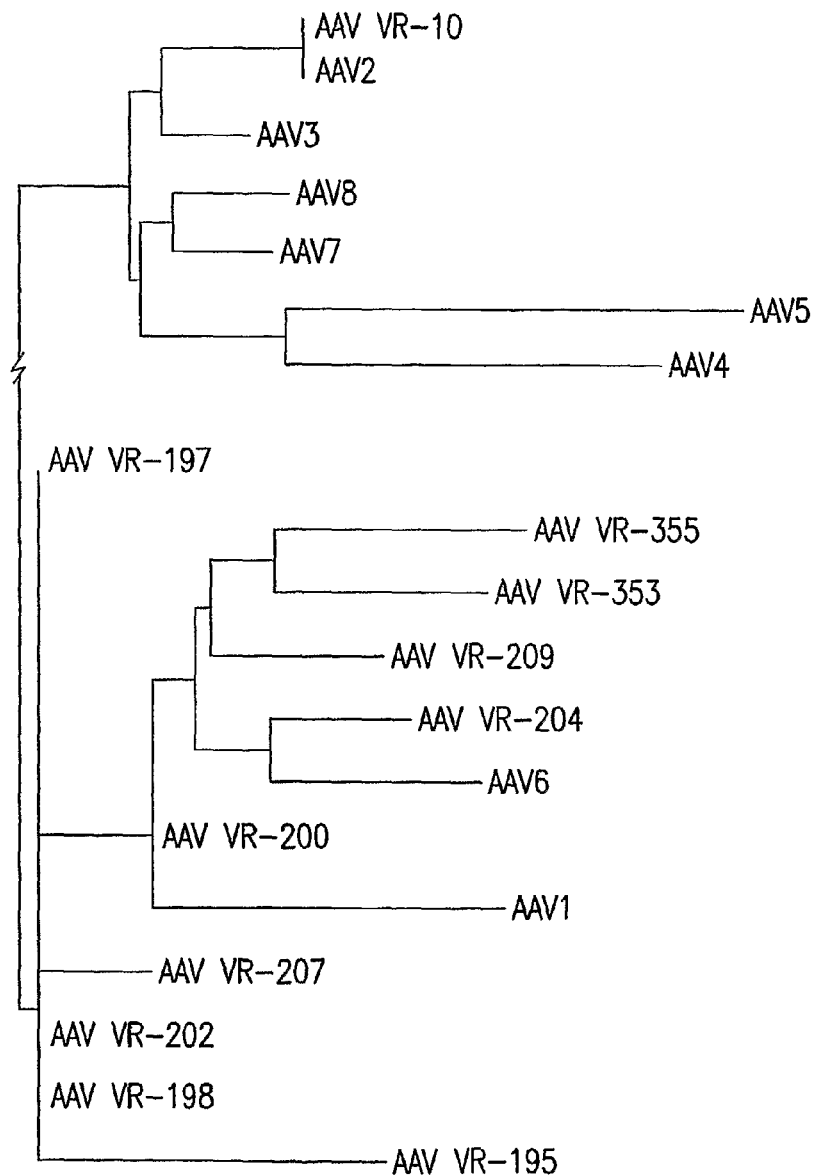
FIG. 1 shows evolutionary relationship among human, non-human primate AAVs, and AAV contaminants detected in adenovirus stocks. The phylogenetic tree is based on merged ClustalW alignments of VP1 sequences. VR numbers are identifiers of the ATCC virus collection.

The disclosed method and compositions may be understood more readily by reference to the following detailed description of particular embodiments and the Example included therein and to the Figures and their previous and following description.

It is to be understood that the disclosed methods and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a vector is disclosed and discussed and a number of modifications that can be made to a number of molecules including the promoters and ITRs are discussed, then each and every combination and permutation of the promoters and ITRs, and the modifications that are possible, are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a", "an", and "the" include plural reference unless the context clearly dictates otherwise. Thus, for example, reference to "a vector" includes a plurality of such vectors, reference to "the vector" is a reference to one or more vectors and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

Provided herein are new recombinant adeno-associated viruses (AAVs) designated AAV-X1, AAV-X1b, AAV-X5, AAV-X19, AAV-X21, AAV-X22, AAV-X23, AAV-X24, AAV-X25, and AAV-X26. The term AAVX is used herein to refer generally to the new AAVs disclosed herein. Thus, AAVX can refer to one or more or all of AAV-X1, AAV-X1b, AAV-X5, AAV-X19, AAV-X21, AAV-X22, AAV-X23, AAV-X24, AAV-X25, or AAV-X26. The application provides the isolation, subcloning, and sequencing of the disclosed AAVXs. These viruses have one or more of the characteristics described below. In one embodiment, the compositions provided herein do not include wild-type AAV. The methods provided herein can use either wild-type AAV or recombinant AAV-based delivery. Thus, in one embodiment, the methods provided herein do not use wild-type AAV.

Provided herein are recombinant AAV-X1, AAV-X1b, AAV-X5, AAV-X19, AAV-X21, AAV-X22, AAV-X23, AAV-X24, AAV-X25, and AAV-X26 particles, recombinant AAV-X1, AAV-X1b, AAV-X5, AAV-X19, AAV-X21, AAV-X22, AAV-X23, AAV-X24, AAV-X25, and AAV-X26 vectors and recombinant AAV-X1, AAV-X1b, AAV-X5, AAV-X19, AAV-X21, AAV-X22, AAV-X23, AAV-X24, AAV-X25, and AAV-X26 virions. As used herein, "recombinant" refers to nucleic acids, vectors, polypeptides, or proteins that have been generated using DNA recombination (cloning) methods and are distinguishable from native or wild-type nucleic acids, vectors, polypeptides, or proteins. An AAVX particle is a viral particle comprising an AAVX capsid protein. A recombinant AAVX vector is a nucleic acid construct that comprises at least one unique, isolated nucleic acid of AAVX. The recombinant AAVX vector can further comprise at least one non-AAVX nucleic acid. As used herein, a "virion" refers to an infectious virus particle, and "infectious" refers to the ability of a virion to deliver genetic material to a cell. Thus, a recombinant AAVX virion is a particle containing a recombinant AAVX vector, wherein the particle can be either an AAVX particle as described herein or a non-AAVX particle. Alternatively, a recombinant AAVX virion can be an AAVX particle containing a recombinant vector, wherein the vector can be either an AAVX vector as described herein or a non-AAVX vector. An AAVX particle can further be an "empty particle", wherein the particle does not contain a nucleic acid, vector or plasmid, and is therefore not infectious. These vectors, particles, virions, nucleic acids and polypeptides are described below.

Provided herein are nucleotide sequences of AAVX genomes and vectors and particles derived therefrom. Specifically provided is an AAVX nucleic acid vector. Thus, provided is a nucleic acid vector, comprising an AAVX-specific nucleic acid or a nucleic acid encoding an AAVX-specific protein. The AAVX-specific nucleic acid can be a pair of AAVX inverted terminal repeats (ITRs) or an AAVX promoter. The nucleic acid encoding an AAVX-specific protein can be an AAVX capsid protein or an AAVX Rep protein. Thus, the provided AAVX nucleic acid vector need only have an AAVX ITR, an AAVX promoter, an AAVX Rep or an AAVX capsid to be an AAVX nucleic acid vector.

The AAV ITR functions as an origin of replication for packaging of recombinant AAV particles. The minimum sequence necessary for this activity is the TRS site where Rep cleaves in order to replicate the virus. Minor modifications in an ITR are contemplated and are those that will not interfere with the hairpin structure formed by the ITR as described herein and known in the art. Furthermore, to be considered within the term it must retain the Rep binding site described herein. For example, the D− region of the AAV2 ITR, a single stranded region of the ITR (the D+ region is the reverse complement of the D− region), inboard of the TRS site, has been shown to bind a factor, which, depending on its phosphorylation state, correlates with the conversion of the AAV2 from a single stranded genome to a transcriptionally active form that allows for expression of the viral DNA. For example, this region is conserved between AAV2, AAV3, AAV4, and AAV6 but is divergent in AAV5 and BAAV. Further, as disclosed herein, the TRS signal (e.g., aa 176-181 of SEQ ID NO:40) and Rep Binding site (e.g., aa 195-210 of SEQ ID NO:40) is conserved between AAV2 and AAV-X26.

In one aspect, the AAVX nucleic acid vector comprises an AAVX ITR. Thus, the AAVX nucleic acid vector can comprise an AAV-X1, AAV-X1b, AAV-X5, AAV-X19, AAV-X21, AAV-X22, AAV-X23, AAV-X24, AAV-X25, or AAV-X26 ITR. In another aspect, the AAVX nucleic acid vector comprises an ITR from any AAV serotype. Thus, the AAVX nucleic acid vector can comprise an AAV1, AAV2, AAV3, AAV4, AAV5, AAV6, AAV7, AAV8, AAV9, AAV10, AAV11, AAAV, or BAAV ITR.

In one aspect, the AAVX nucleic acid vector comprises an AAVX promoter. Thus, the promoter can be an AAVX p5, p19 or p40 promoter. Thus, the promoter can be an AAV-X1 p5 promoter, an AAV-X1b p5 promoter, an AAV-X5 p5 promoter, an AAV-X19 p5 promoter, n AAV-X21 p5 promoter, an AAV-X22 p5 promoter, an AAV-X23 p5 promoter, an AAV-X24 p5 promoter, an AAV-X25 p5 promoter, or an AAV-X26 p5 promoter.

In another aspect, the promoter can be a promoter from any of the AAV serotypes. Thus, the promoter can be an AAV1 p5 promoter, an AAV2 p5 promoter, an AAV3 p5 promoter, an AAV4 p5 promoter, AAV5 p5 promoter, an AAV6 p5 promoter, an AAAV p5 promoter, a BAAV p5 promoter, or an AAVX p5 promoter.

Furthermore, smaller fragments of an AAV p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated.

In yet another aspect, the promoter of the AAVX nucleic acid vector can be any desired promoter, selected by known considerations, such as the level of expression of a nucleic acid functionally linked to the promoter and the cell type in which the vector is to be used. That is, the promoter can be tissue/cell-specific. Promoters can be prokaryotic, eukaryotic, fungal, nuclear, mitochondrial, viral or plant promoters. Promoters can be exogenous or endogenous to the cell type being transduced by the vector. Promoters can include, for example, bacterial promoters, or known strong promoters such as SV40 or the inducible metallothionein promoter. Additionally, chimeric regulatory promoters for targeted gene expression can be utilized. Examples of these regulatory systems, which are known in the art, include the tetracycline based regulatory system which utilizes the tet transactivator protein (tTA), a chimeric protein containing the VP16 activation domain fused to the tet repressor of *Escherichia coli*, the IPTG based regulatory system, the CID based regulatory system, and the Ecdysone based regulatory system (No, D., et al., Proc Natl Acad Sci USA. 93(8):3346-3351 (1996)). Other promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc.

In one aspect, the AAVX nucleic acid vector comprises a nucleic acid encoding an AAVX Rep protein. Thus, the Rep protein can be an AAV-X1 Rep protein, an AAV-X1b Rep protein, an AAV-X5 Rep protein, an AAV-X19 Rep protein, n AAV-X21 Rep protein, an AAV-X22 Rep protein, an AAV-X23 Rep protein, an AAV-X24 Rep protein, an AAV-X25 Rep protein, or an AAV-X26 Rep protein. In another aspect, the AAVX nucleic acid vector comprises a nucleic acid encoding a Rep protein from any AAV serotype. Thus, the AAVX nucleic acid vector can comprise a nucleic acid encoding an AAV1 Rep protein, an AAV2 Rep protein, an AAV3 Rep protein, an AAV4 Rep protein, an AAV5 Rep protein, an AAV6 Rep protein, an AAV7 Rep protein, an AAV8 Rep protein, an AAV9 Rep protein, an AAV10 Rep protein, an AAV11 Rep protein, an AAAV Rep protein, or an BAAV Rep protein. For all AAV serotypes, the AAV Rep proteins can be selected from a group consisting of Rep78, Rep68, Rep52 and Rep40.

The AAV-X1 Rep protein of an AAV-X1 nucleic acid vector can be encoded by a nucleic acid sequence comprising nucleotides 1-743, 744, 745, 746, 747, 748, 749, 750, 751, 752, 752, 754, 755, 756, 757, 758, 759, 760, 761, 762, or 763 of SEQ ID NO:1. The AAV-X1 Rep protein can be encoded by a nucleic acid sequence of SEQ ID NO:48. The AAV-X1 Rep protein can comprise the amino acid sequence of SEQ ID NO:49. The AAV-X1b Rep protein of an AAV-X1b nucleic acid vector can be encoded by a nucleic acid sequence comprising nucleotides 1-2016, 2017, 2018, 2019; 2020, 2021, 2022, 23 2024, 2025, 2026, 2027, 2028, 2029, 2030, 2031, 2032, 2033, 2034, 2035, or 2036 of SEQ ID NO:2. The AAV-X5 Rep protein of an AAV-X5 nucleic acid vector can be encoded by a nucleic acid sequence comprising nucleotides 1-1926, 1927, 1928, 1929, 1930, 1931, 1932, 1933, 1934, 1935, 1936, 1937, 1938, 1939, 1940, 1941, 1942, 1943, 1944, 1945, or 1946 of SEQ ID NO3. The AAV-X19 Rep protein of an AAV-X19 nucleic acid vector can be encoded by a nucleic acid sequence comprising nucleotides 1-743, 744, 745, 746, 747, 748, 749, 750, 751, 752, 752, 754, 755, 756, 757, 758, 759, 760, 761, 762, or 763 of SEQ ID NO:4. The AAV-X21 Rep protein of an AAV-X21 nucleic acid vector can be encoded by a nucleic acid sequence comprising nucleotides 1-752, 753, 754, 755, 756, 757, 758, 759.760, 761, 762, 763, 764, 765, 766, 767, 768, 769, 770, 771, or 772 of SEQ ID NO:5. The AAV-X22 Rep protein of an AAV-X22 nucleic acid vector can be encoded by a nucleic acid sequence comprising nucleotides 1-748, 749, 750, 751, 752, 753, 754, 755, 756, 757, 758, 759, 760, 761, 762, 763, 764, 765, 766, 767, or 768 of SEQ ID NO:6. The AAV-X23 Rep protein of an AAV-X23 nucleic acid vector can be encoded by a nucleic acid sequence comprising nucleotides 1-746, 747, 748, 749, 750, 751, 752, 753, 754, 755, 756, 757, 758, 759, 760, 761, 762, 763, 764, 765, or 766 of SEQ ID NO:7. The AAV-X24 Rep protein of an AAV-X24 nucleic acid vector can be encoded by a nucleic acid sequence comprising nucleotides 1-752, 753, 754, 755, 756, 757, 758, 759, 760, 761, 762, 763, 764, 765, 766, 767, 768, 769, 770, 771, or 772 of SEQ ID NO:8. The AAV-X25 Rep protein of an AAV-X25 nucleic acid vector can be encoded by the a nucleic acid sequence comprising nucleotides 1-974, 975, 976, 977, 978, 979, 980, 981, 982, 983, 984, 985, 986, 987, 988, 989, 990, 991, 992, 993, or 994 of SEQ ID NO:9. The AAV-X25 Rep protein can be encoded by a nucleic acid sequence of SEQ ID NO:50. The AAV-X25 Rep protein can comprise the amino acid sequence of SEQ ID NO:51. The AAV-X26 Rep protein of an AAV-X26 nucleic acid vector can be encoded by the a nucleic acid sequence comprising nucleotides 1-789, 790, 791, 792, 793, 794, 795, 796, 797, 798, 799, 800, 801, 802, 803, 804, 805, 806, 807, 808, or 809 of SEQ ID NO:10. The AAV-X26 Rep protein can be encoded by a nucleic acid sequence of SEQ ID NO:52. The AAV-X26 Rep protein can comprise the amino acid sequence of SEQ ID NO:53.

In one aspect, the AAVX nucleic acid vector comprises a nucleic acid encoding an AAVX capsid protein. Thus, the capsid protein can be an AAV-X1 capsid protein, an AAV-X1b capsid protein, an AAV-X5 capsid protein, an AAV-X19 capsid protein, n AAV-X21 capsid protein, an AAV-X22 capsid protein, an AAV-X23 capsid protein, an AAV-X24 capsid protein, an AAV-X25 capsid protein, or an AAV-X26 capsid protein. In another aspect, the AAVX nucleic acid vector comprises a nucleic acid encoding a capsid protein from any AAV serotype. Thus, the AAVX nucleic acid vector can comprise a nucleic acid encoding an AAV 1 capsid protein, an AAV2 capsid protein, an AAV3 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV 11 capsid protein, an AAAV capsid protein, or an BAAV capsid protein. For all AAV serotypes, the AAV capsid proteins can be selected from a group consisting of VP1, VP2 and VP3.

As an example, the AAV-X1 VP1 capsid protein of an AAV-X1 particle can have the amino acid sequence of SEQ ID NO:21. The AAV-X1b VP1 capsid protein of an AAV-X1b particle can have the amino acid sequence of SEQ ID NOS: 22. The AAV-X5 VP1 capsid protein of an AAV-X5 particle can have the amino acid sequence of SEQ ID NO:23. The AAV-X19 VP1 capsid protein of an AAV-X19 particle can have the amino acid sequence of SEQ ID NO:24. The AAV-X21 VP1 capsid protein of an AAV-X21 particle can have the amino acid sequence of SEQ ID NO:25. The AAV-X22 VP1 capsid protein of an AAV-X22 particle can have the amino acid sequence of SEQ ID NO:26. The AAV-X23 VP1 capsid protein of an AAV-X23 particle can have the amino acid sequence of SEQ ID NO:27. The AAV-X24 VP1 capsid protein of an AAV-X24 particle can have the amino acid sequence of SEQ ID NO:28. The AAV-X25 capsid protein of an AAV-X25 particle can have the amino acid sequence of SEQ ID NO:29. The AAV-X26 capsid protein of an AAV-X26 particle can have the amino acid sequence of SEQ ID NO:30.

The AAV-X1 VP1 capsid protein of an AAV-X1 particle can be encoded by the nucleic acid sequence of SEQ ID NO:11. The AAV-X1b VP1 capsid protein of an AAV-X1b particle can be encoded by the nucleic acid sequence of SEQ ID NO:12. The AAV-X5 VP1 capsid protein of an AAV-X5 particle can be encoded by the nucleic acid sequence of SEQ ID NO:13. The AAV-X19 VP1 capsid protein of an AAV-X19 particle can be encoded by the nucleic acid sequence of SEQ ID NO:14. The AAV-X21 VP1 capsid protein of an AAV-X21 particle can be encoded by the nucleic acid sequence of SEQ ID NO:15. The AAV-X22 VP1 capsid protein of an AAV-X22 particle can be encoded by the nucleic acid sequence of SEQ ID NO:16. The AAV-X23 VP1 capsid protein of an AAV-X23 particle can be encoded by the nucleic acid sequence of SEQ ID NOS:17. The AAV-X24 VP 1 capsid protein of an AAV-X24 particle can be encoded by the nucleic acid sequence of SEQ ID NO:18. The AAV-X25 VP1 capsid protein of an AAV-X25 particle can be encoded by the nucleic acid sequence of SEQ ID NO:19. The AAV-X26 VP1 capsid protein of an AAV-X26 particle can be encoded by the nucleic acid sequence of SEQ ID NO:20.

It should be recognized that any errors in any of the nucleotide sequences disclosed herein can be corrected, for example, by using the hybridization procedure described below with various probes derived from the described sequences such that the coding sequence can be re-isolated and re-sequenced. Rapid screening for point mutations can also be achieved with the use of polymerase chain reaction-single strand conformation polymorphism (PCR-SSCP). The corresponding amino acid sequence can then be corrected accordingly. Also, since the disclosed AAV serotypes AAV-X1, AAV-X1b, AAV-X5, AAV-X19, AAV-X21, AAV-X22, AAV-X23, AAV-X24, AAV-X25, and AAV-X26 are disclosed herein to be present in defined ATCC cultures, the whole virus sequence is provided by reference to the deposit.

The AAVX-derived vector provided herein can further comprise an exogenous nucleic acid functionally linked to the promoter. By "exogenous" nucleic acid is meant any nucleic acid that is not normally found in wild-type AAVX that can be inserted into a vector for transfer into a cell, tissue or organism. The exogenous nucleic acid can be a nucleic acid not normally found in the target cell, or it can be an extra copy or copies of a nucleic acid normally found in the target cell. The terms "exogenous" and "heterologous" are used herein interchangeably.

By "functionally linked" is meant that the promoter can promote expression of the exogenous nucleic acid, as is known in the art, and can include the appropriate orientation of the promoter relative to the exogenous nucleic acid. Furthermore, the exogenous nucleic acid preferably has all appropriate sequences for expression of the nucleic acid. The nucleic acid can include, for example, expression control sequences, such as an enhancer, and necessary information processing sites, such as ribosome binding sites, RNA splice sites, polyadenylation sites, and transcriptional terminator sequences.

The exogenous nucleic acid can encode beneficial proteins or polypeptides that replace missing or defective proteins required by the cell or subject into which the vector is transferred or can encode a cytotoxic polypeptide that can be directed, e.g., to cancer cells or other cells whose death would be beneficial to the subject. The exogenous nucleic acid can also encode antisense RNAs that can bind to, and thereby inactivate, mRNAs made by the subject that encode harmful proteins. The exogenous nucleic acid can also encode ribozymes that can effect the sequence-specific inhibition of gene expression by the cleavage of mRNAs. In one aspect, antisense polynucleotides can be produced from an exogenous expression cassette in an AAV5 vector construct where the expression cassette contains a sequence that promotes cell-type specific expression (Wirak et al., *EMBO* 10:289 (1991)). For general methods relating to antisense polynucleotides, see *Antisense RNA and DNA*, D. A. Melton, Ed., Cold Spring Harbor Laboratory, Cold Spring Harbor, N.Y. (1988).

Examples of exogenous nucleic acids which can be administered to a cell or subject as part of the present AAVX vector can include, but are not limited to the following: nucleic acids encoding secretory and nonsecretory proteins, nucleic acids encoding therapeutic agents, such as tumor necrosis factors (TNF), such as TNF-α; interferons, such as interferon-α, interferon-β, and interferon-γ, interleukins, such as IL-1, IL-1β, and ILs-2 through -14; GM-CSF; adenosine deaminase; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; anti-HIV decoy tar elements; and antisense sequences which inhibit viral replication, such as antisense sequences which inhibit replication of hepatitis B or hepatitis non-A, non-B virus. The nucleic acid is chosen considering several factors, including the cell to be transfected. Where the target cell is a blood cell, for example, particularly useful nucleic acids to use are those which allow the blood cells to exert a therapeutic effect, such as a gene encoding a clotting factor for use in treatment of hemophilia. Another target cell is the lung airway cell, which can be used to administer nucleic acids, such as those coding for the cystic fibrosis transmembrane receptor, which could provide a gene therapeutic treatment for cystic fibrosis. Other target cells include muscle cells where useful nucleic acids, such as those encoding cytokines and growth factors, can be transduced and the protein the nucleic acid encodes can be expressed and secreted to exert its effects on other cells, tissues and organs, such as the liver. Furthermore, the nucleic acid can encode more than one gene product, limited only, if the nucleic acid is to be packaged in a capsid, by the size of nucleic acid that can be packaged.

Furthermore, suitable nucleic acids can include those that, when transferred into a primary cell, such as a blood cell, cause the transferred cell to target a site in the body where that cell's presence would be beneficial. For example, blood cells such as TIL cells can be modified, such as by transfer into the cell of a Fab portion of a monoclonal antibody, to recognize a selected antigen. Another example would be to introduce a nucleic acid that would target a therapeutic blood cell to tumor cells. Nucleic acids useful in treating cancer cells include those encoding chemotactic factors which cause an inflammatory response at a specific site, thereby having a therapeutic effect.

Cells, particularly blood cells, muscle cells, airway epithelial cells, brain cells and endothelial cells having such nucleic acids transferred into them can be useful in a variety of diseases, syndromes and conditions. For example, suitable nucleic acids include nucleic acids encoding soluble CD4 used in the treatment of AIDS and α-antitrypsin, used in the treatment of emphysema caused by α-antitrypsin deficiency. Other diseases, syndromes and conditions in which such cells can be useful include, for example, adenosine deaminase deficiency, sickle cell deficiency, brain disorders such as Alzheimer's disease, thalassemia, hemophilia, diabetes, phenylketonuria, growth disorders and heart diseases, such as those caused by alterations in cholesterol metabolism, and defects of the immune system.

Other cells in which a gene of interest can be expressed include, but are not limited to, fibroblasts, neurons, retinal cells, kidney cells, lung cells, bone marrow stem cells, hematopoietic stem cells, retinal cells and neurons. The cells in which the gene of interest can be expressed can be dividing cells such as MDCK cells, BHK cells, HeLa cells, 3T3 cells, CV1 cells, COS7 cells, HOS cells and 293 cells. The cells can also be embryonic stem cells of mouse, rhesus, human, bovine or sheep origin, as well as stem cells of neural, hematopoietic, muscle, cardiac, immune or other origin. Non-dividing cells can also be contacted with a particle provided herein to express a gene of interest. Such cells include, but are not limited to hematopoietic stem cells and embryonic stem cells that have been rendered non-dividing.

As another example, hepatocytes can be transfected with the present vectors having useful nucleic acids to treat liver disease. For example, a nucleic acid encoding OTC can be used to transfect hepatocytes (ex vivo and returned to the liver or in vivo) to treat congenital hyperammonemia, caused by an inherited deficiency in OTC. Another example is to use a nucleic acid encoding LDL to target hepatocytes ex vivo or in vivo to treat inherited LDL receptor deficiency. Such transfected hepatocytes can also be used to treat acquired infectious diseases, such as diseases resulting from a viral infection. For example, transduced hepatocyte precursors can be used to treat viral hepatitis, such as hepatitis B and non-A, non-B hepatitis, for example by transducing the hepatocyte precursor with a nucleic acid encoding an antisense RNA that inhibits viral replication. Another example includes transferring a vector provided herein having a nucleic acid encoding a protein, such as γ-interferon, which can confer resistance to the hepatitis virus.

For a procedure using transfected hepatocytes or hepatocyte precursors, hepatocyte precursors having a vector provided herein transferred in can be grown in tissue culture, removed from the tissue culture vessel, and introduced to the body, such as by a surgical method. In this example, the tissue would be placed directly into the liver, or into the body cavity in proximity to the liver, as in a transplant or graft. Alternatively, the cells can simply be directly injected into the liver, into the portal circulatory system, or into the spleen, from which the cells can be transported to the liver via the circulatory system. Furthermore, the cells can be attached to a support, such as microcarrier beads, which can then be introduced, such as by injection, into the peritoneal cavity. Once the cells are in the liver, by whatever means, the cells can then express the nucleic acid and/or differentiate into mature hepatocytes which can express the nucleic acid.

The provided viral particles can be administered to cells, as described herein, with a Multiplicity of Infection (MOI) of 10. The MOI is the ratio of infectious virus particles to the number of cells being infected. Thus, an MOI of 0.1 results in the average inoculation of 1 virus particle for every 10 cells. The general theory behind MOI is to introduce one infectious virus particle to every host cell that is present in the culture. However, more than one virus may infect the same cell which leaves a percentage of cells uninfected. This occurrence can be reduced by using a higher MOI to ensure that every cell is infected. The provided viral particles can therefore be administered to cells, as described herein, with a MOI of 0.01 to 100, such as for example 1, 2, 3, 4, 5, 6, 7, 8, 9, 10, 11, 12, 13, 14, 15, 16, 17, 18, 19, 20, 30, 40, 50, 60, 70, 80, 90, 100.

The AAVX-derived vector can include any normally occurring AAVX nucleic acid sequences. The AAVX-derived vector can also include sequences that are at least 80%, 81%, 82%, 83%, 84%, 85%, 86%, 87%, 89%, 90%, 91%, 92%, 93%, 94%, 95%, 96%, 97%, 98%, 98.5%, 99%, 99.5% or 99.9% identical to the AAVX nucleic acids set forth herein. Examples of vector constructs are provided below.

The present AAVX vector or AAVX particle or recombinant AAVX virion can utilize any unique nucleic acid fragment of the AAVX disclosed herein, including the AAVX nucleic acids set forth in SEQ ID NOS:1-20. A unique fragment consists of a sequence that is not present anywhere else on a genome. A fragment is a subpart of the reference sequence, and thus is identical in sequence to the region of the parent nucleic acid of which it is a fragment. To be unique, the fragment must be of sufficient size to distinguish it from other known sequences, which is most readily determined by comparing any nucleic acid fragment to the nucleotide sequences of nucleic acids in computer databases, such as GenBank. Such comparative searches are standard in the art. Typically, a unique fragment useful as a primer or probe will be at least about 8 or 10, preferable at least 20 or 25 nucleotides in length, depending upon the specific nucleotide content of the sequence. Additionally, fragments can be, for example, at least about 30, 40, 50, 75, 100, 200 or 500 nucleotides in length and can encode polypeptides or be probes. The nucleic acid can be single or double stranded, depending upon the purpose for which it is intended. Where desired, the nucleic acid can be RNA.

It is understood that as discussed herein the use of the terms "homology" and "identity" mean the same thing as similarity. Thus, for example, if the use of the word homology is used to refer to two non-natural sequences, it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of homology to specific known sequences. In general, variants of nucleic acids and polypeptides herein disclosed typically have at least, about 80%, 81%, 82%, 83%, 84%, 85%, 86%, 87%, 89%, 90%, 91%, 92%, 93%, 94%, 95%, 96%, 97%, 98%, 98.5%, 99%, 99.5% or 99.9% homology to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/b12seq/b12.html), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Further provided herein is an AAVX capsid protein that can combine with other capsid proteins to form an AAVX particle to contain the disclosed vectors. Also provided herein is an AAVX particle, comprising an AAVX capsid protein. The capsid protein can be selected from a group consisting of VP1, VP2 and VP3.

The AAV-X1 VP1 capsid protein of an AAV-X1 particle can have the amino acid sequence of SEQ ID NO:21. The AAV-X1b VP1 capsid protein of an AAV-X1b particle can have the amino acid sequence of SEQ ID NO:22. The AAV-X5 VP1 capsid protein of an AAV-X5 particle can have the amino acid sequence of SEQ ID NO:23. The AAV-X19 VP1 capsid protein of an AAV-X19 particle can have the amino acid sequence of SEQ ID NO:24. The AAV-X21 VP1 capsid protein of an AAV-X21 particle can have the amino acid sequence of SEQ ID NO:25. The AAV-X22 VP1 capsid protein of an AAV-X22 particle can have the amino acid sequence of SEQ ID NO:26. The AAV-X23 VP1 capsid protein of an AAV-X23 particle can have the amino acid sequence of SEQ ID NO:27. The AAV-X24 VP1 capsid protein of an AAV-X24 particle can have the amino acid sequence of SEQ ID NO:28. The AAV-X25 capsid protein of an AAV-X25 particle can have the amino acid sequence of SEQ ID NO:29. The AAV-X26 capsid protein of an AAV-X26 particle can have the amino acid sequence of SEQ ID NO:30.

The AAV-X1 VP1 capsid protein of an AAV-X1 particle can be encoded by the nucleic acid sequence of SEQ ID NO:11. The AAV-X1b VP1 capsid protein of an AAV-X1b particle can be encoded by the nucleic acid sequence of SEQ ID NO:12. The AAV-X5 VP1 capsid protein of an AAV-X5 particle can be encoded by the nucleic acid sequence of SEQ ID NO:13. The AAV-X19 VP1 capsid protein of an AAV-X19 particle can be encoded by the nucleic acid sequence of SEQ ID NO:14. The AAV-X21 VP1 capsid protein of an AAV-X21 particle can be encoded by the nucleic acid sequence of SEQ ID NO:15. The AAV-X22 VP1 capsid protein of an AAV-X22 particle can be encoded by the nucleic acid sequence of SEQ ID NO:16. The AAV-X23 VP1 capsid protein of an AAV-X23 particle can be encoded by the nucleic acid sequence of SEQ ID NO:17. The AAV-X24 VP1 capsid protein of an AAV-X24 particle can be encoded by the nucleic acid sequence of SEQ ID NO:18. The AAV-X25 VP1 capsid protein of an AAV-X25 particle can be encoded by the nucleic acid sequence of SEQ ID NO:19. The AAV-X26 VP1 capsid protein of an AAV-X26 particle can be encoded by the nucleic acid sequence of SEQ ID NO:20.

For example, provided is an AAVX particle, comprising all three AAVX capsid proteins, i.e., VP1, VP2 and VP3. Also provided is an AAVX particle, comprising each AAVX capsid protein individually or in combination. Also provided is an AAVX particle comprising VP1 and VP3 capsid proteins, i.e., lacking any VP2 capsid proteins. Thus, an AAVX particle comprising an AAVX capsid protein comprises at least one AAVX capsid protein (VP1, VP2 or VP3) or a functional fragment thereof. One of skill in the art understands that it is the non-conserved amino acids that are contributing to the properties of AAVX that make it distinct from the other serotypes. Provided therefore is a capsid protein comprising a mutation, deletion or substitution in the conserved regions, including, for example, a substitution with a homologous region from another AAV serotype., An AAVX particle comprising an AAVX capsid protein can be utilized to deliver a nucleic acid vector to a cell, tissue or subject. For example, the herein described AAVX vectors can be encapsidated in an AAVX capsid-derived particle and utilized in a gene delivery method. Furthermore, other viral nucleic acids can be encapsidated in the AAVX particle and utilized in such delivery methods. For example, an AAV1-11, AAAV, or BAAV vector (e.g. AAV1-11, AAAV, BAAV or AAVX ITR and nucleic acid of interest) can be encapsidated in an AAVX particle and administered. Furthermore, an AAVX chimeric capsid incorporating AAV1-11, AAAV, BAAV or AAVX capsid sequences and a different AAVX capsid sequences can be generated, by standard cloning methods, selecting regions from the known sequences of each protein as desired. For example, particularly antigenic regions of the AAVX capsid protein can be replaced with the corresponding region of the AAV2 capsid protein. In addition to chimeric capsids incorporating AAV2 capsid sequences, chimeric capsids incorporating AAV1, 3-8, AAAV, BAAV or AAVX capsid sequences can be generated, by standard cloning methods, selecting regions from the known sequences of each protein as desired. Alternatively a chimeric capsid can be made by the addition of a plasmid that expresses AAV1-11, AAAV, BAAV or AAVX capsid proteins at a ratio with the AAVX capsid expression plasmid that allows only a few capsid proteins to be incorporated into the AAVX particle. Thus, for example, a chimeric particle may be constructed that contains 6 AAV2 capsid proteins and 54 AAVX capsid proteins if the complete capsid contains 60 capsid proteins. Methods for generating chimeric AAVs are known in the art and can be found in Rabinowitz J E, et al. J. Virol. 2004 May; 78(9):4421-32, herein incorporated by reference for these methods. Examples of chimeric capsids would be to combine the VP1, 2, 3 proteins of AAVX and the VP1, 2, 3 proteins of AAV5 such that a new tropism would arise. The capsids can also be modified to alter their specific tropism by genetically altering the capsid to encode a specific ligand to a cell surface receptor.

Alternatively, the capsid can be chemically modified by conjugating a ligand to a cell surface receptor. By genetically or chemically altering the capsids, the tropism can be modified to direct AAVX to a particular cell or population of cells. The capsids can also be altered immunologically by conjugating the capsid to an antibody that recognizes a specific protein on the target cell or population of cells.

Provided are three regions in the capsid of AAVX that are on the virus surface and could tolerate substitution. These three regions in AAV-X1, AAV-X1b, AAV-X19, AAV-X21, AAV-X22, AAV-X23, AAV-X24, and AAV-X25 are aa 261-271, aa 450-476, and aa 546-559. These three regions in AAV-X5 are aa 259-268, aa 448-473, and aa 543-554. These three regions in AAV-X26 are aa 260-274, aa 445-477, and aa 550-565. Thus, provided is an AAVX VP1 capsid, comprising amino acid substitutions in aa 261-271, aa 450-476, or aa 546-559 of SEQ ID NOS:21, 22, 24, 25, 26, 27, 28, or 29. Thus, also provided is an AAVX VP1 capsid, comprising amino acid substitutions in aa 259-268, aa 448-473, and aa 543-554 of SEQ ID NO:23. Thus, also provided is an AAVX VP1 capsid, comprising amino acid substitutions in aa 260-274, aa 445-477, and aa 550-565 of SEQ ID NO:30.

Other regions of the AAVX capsid could also accommodate the substitution of amino acids that would allow for epitope presentation on the surface of the virus. All of these regions would have surface exposure and the ability to support a substitution of sequence to insert the epitope while still allowing for capsid assembly. The substitutions can include non-AAVX epitopes and non-AAVX ligands.

Because of the symmetry of the AAV particles, a substitution in one subunit of the capsid will appear multiple times on the capsid surface. For example the capsid is made of approximately 50 VP3 proteins, 5 VP1 and 5 VP2. Therefore an epitope incorporated in the VP3 protein could be expressed 55 times on the surface of each particle increasing the likelihood of the epitope forming a stable interaction with its target. In some cases this may be too high of a ligand density for functional binding or this high density of epitope may interfere with capsid formation. The epitope density could be lowered by introducing another plasmid into the packaging system for production of recombinant particles and the ratio between the packaging plasmid with the modified VP3 protein and the wt VP3 protein altered to balance the epitope density on the virus surface. Thus, the ratio between the modified VP3 and the wt VP3 can be 0:50 to 50:0, including, for example, 1:49, 2:48, 3:47, 4:46, 5:45, 6:44, 7:43, 8:42, 9:41, 10:40, 11:39, 12:38, 13:37, 14:36, 15:35, 16:34, 17:33, 18:32, 19:31, 20:30, 21:29, 22:28, 23:27, 24:27, 25:25, 26:24, 27:23, 28:22, 29:21, 30:20, 31:19, 32:18, 33:17, 34:16, 35:15, 36:14, 37:13, 38:12, 39:11, 40:10, 41:9, 42:8, 43:7, 44:6, 45:5, 46:4, 47:3, 48:2, or 49:1.

Epitopes could be incorporated into the virus capsid for the purpose of 1) altering the tropism of the virus 2) blocking an immune response directed at the virus 3) developing a host immune response to the epitope for the purpose of vaccination.

Examples of epitopes that could be added to AAVX capsids include but are not limited to LH receptor binding epitope RGD integrin binding epitope CD13 binding epitope NGRAHA SEQ ID NO:35

The Retanefpolyprotein vaccine candidate for HIV-1 single chain antibody fragments directed against tumor cells

Endothelial cell binding epitope SIGYPLP SEQ ID NO:36 serpin receptor ligand, KFNKPFVFLI SEQ ID NO:37 protective B-cell epitope hemagglutinin (HA) 91-108 from influenza HA NDV B-cell immunodominant epitope (IDE) spanning residues 447 to 455

Major immunogenic epitope for parvovirus B19 (NISLDN-PLENPSSLFDLVARIK SEQ ID NO:38) that can elicit protective antibody titers.

The capsids can also be assembled into empty particles by expression in mammalian, bacterial, fungal or insect cells. For example, AAV2 particles are known to be made from VP3 and VP2 capsid proteins in baculovirus. The same basic protocol can produce an empty AAVX particle comprising AAVX capsid proteins and also full particles. The empty AAVX particles can be used to deliver, for example, antigens, drugs, proteins, or metals to cells or cells in a subject. Antigens can be directly incorporated into the capsid of an empty AAVX particle. An antigen can further be coupled via an antibody-antigen complex to the empty particle. Also disclosed is the coupling of drugs, proteins, or metals on the inside of the empty particles.

The herein described recombinant AAVX nucleic acid derived vector can be encapsidated in a viral particle. The viral particle can be a parvovirus particle. The parvovirus particle can be a dependovirus particle. The viral particle can be an AAV particle. In particular, the recombinant AAVX nucleic acid derived vector can be encapsidated in an AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 particle, a particle comprising a portion of any of these capsids, or a chimeric capsid particle as described above, by standard methods using the appropriate capsid proteins in the encapsidation process, as long as the nucleic acid vector fits within the size limitation of the particle utilized. The encapsidation process itself is standard in the art. The AAVX replication machinery, i.e. the rep initiator proteins and other functions required for replication, can be utilized to produce the AAVX genome that can be packaged in an AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 virion.

The recombinant AAVX virion containing a vector can also be produced by recombinant methods utilizing multiple plasmids. In one example, the AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 rep nucleic acid would be cloned into one plasmid, the AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 ITR nucleic acid would be cloned into another plasmid and the AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 capsid nucleic acid would be cloned on another plasmid. These plasmids would then be introduced into cells. The cells that were efficiently transduced by all three plasmids, would exhibit specific integration as well as the ability to produce AAVX recombinant virus. Additionally, two plasmids could be used where the AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 rep nucleic acid would be cloned into one plasmid and the AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 ITR and AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 capsid would be cloned into another plasmid. These plasmids would then be introduced into cells. The cells that were efficiently transduced by both plasmids, would exhibit specific integration as well as the ability to produce AAVX recombinant virus.

An AAV-X1, AAV-X1b, AAV-X19, AAV-X21, AAV-X22, AAV-X23, AAV-X24, or AAV-X25 capsid can have about 98%, 98.5%, 99%, 99.1%, 99.2%, 99.3%, 99.4%, 99.5%, 99.6%, 99.7%, 99.8%, or 99.9% homology to the polypeptide having the amino acid sequence encoded by nucleotides in SEQ ID NOS:11, 12, 14, 15, 16, 17, 18, or 19, respectively. An AAV-X5 capsid can have about 93%, 94%, 95%, 96%, 97%, 98%, 98.5%, or 99% homology to the polypeptide having the amino acid sequence encoded by nucleotides in SEQ ID NO:13. An AAV-X26 capsid can have about 83%, 84%, 85%, 86%, 87%, 88%, 89%, 90%, 91%, 92%, 93%, 94%, 95%, 96%, 97%, 98%, 98.5%, or 99% homology to the polypeptide having the amino acid sequence encoded by nucleotides in SEQ ID NO:20.

An AAV-X1, AAV-X1b, AAV-X19, AAV-X21, AAV-X22, AAV-X23, AAV-X24, or AAV-X25 capsid protein can have about 98%, 98.5%, 99%, 99.1%, 99.2%, 99.3%, 99.4%, 99.5%, 99.6%, 99.7%, 99.8%, or 99.9% homology to the protein having the amino acid sequence encoded by the nucleotides set forth in SEQ ID NOS:21, 22, 24, 25, 26, 27, 28, or 29, respectively. An AAV-X5 capsid protein can have about 93%, 94%, 95%, 96%, 97%, 98%, 98.5%, or 99% homology to the protein having the amino acid sequence encoded by the nucleotides set forth in SEQ ID NO:23. An AAV-X26 capsid protein can have about 83%, 84%, 85%, 86%, 87%, 88%, 89%, 90%, 91%, 92%, 93%, 94%, 95%, 96%, 97%, 98%, 98.5%, or 99% homology to the protein having the amino acid sequence encoded by the nucleotides set forth in SEQ ID NO:30.

The percent homology used to identify proteins herein, can be based on a nucleotide-by-nucleotide comparison or more preferable is based on a computerized algorithm as described herein. Variations in the amino acid sequence of the AAVX capsid protein are contemplated herein, as long as the resulting particle comprising an AAVX capsid protein remains antigenically or immunologically distinct from AAV1-11, AAAV, or BAAV capsid, as can be routinely determined by standard methods. Specifically, for example, ELISA and Western blots can be used to determine whether a viral particle is antigenically or immunologically distinct from AAV2 or the other serotypes. Furthermore, the AAVX particle preferably retains tissue tropism distinction from other AAVs, such as that exemplified in the examples herein. An AAVX chimeric particle comprising at least one AAVX coat protein may have a different tissue tropism from that of an AAVX particle consisting only of AAVX coat proteins, but is still distinct from the tropism of an AAV2 particle.

Provided herein is a recombinant AAVX virion, comprising an AAVX particle containing, i.e., encapsidating, a vector comprising a pair of AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X22, AAV-X23, AAV-X24, AAV-X25, or AAV-X26 inverted terminal repeats. The recombinant vector can further comprise an AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26 Rep-encoding nucleic acid. The vector encapsidated in the particle can further comprise an exogenous nucleic acid inserted between the inverted terminal repeats.

Further contemplated are chimeric recombinant ITRs that contain a rep binding site and a TRS site recognized by that Rep protein. By "Rep protein" is meant one or more of the Rep proteins, Rep 40, Rep 78, Rep 52, Rep 68. Alternatively, "Rep protein" could be all four of the Rep proteins described herein.

Examples of the combinations of ITR, Rep protein and Capsids that will produce recombinant virus include but are not limited to:
AAVX ITR+AAVX Rep+AAVX Cap=virus
AAV5 ITR+AAVX Rep+AAVX Cap=virus
AAV5 ITR+AAVX Rep+AAV1 Cap=virus
AAV5 ITR+AAVX Rep+AAV2 Cap=virus
AAV5 ITR+AAVX Rep+AAV3 Cap=virus
AAV5 ITR+AAVX Rep+AAV4 Cap=virus
AAV5 ITR+AAVX Rep+AAV5 Cap=virus
AAV5 ITR+AAVX Rep+AAV6 Cap=virus
AAV5 ITR+AAVX Rep+AAV7 Cap=virus
AAV5 ITR+AAVX Rep+AAV8 Cap=virus
AAV5 ITR+AAVX Rep+AAV9 Cap=virus
AAV5 ITR+AAVX Rep+AAV10 Cap=virus
AAV5 ITR+AAVX Rep+AAV11 Cap=virus
AAV5 ITR+AAVX Rep+AAAV Cap=virus
AAV5 ITR+AAVX Rep+BAAV Cap=virus
AAVX ITR+AAV5 Rep+AAVX Cap=virus
AAVX ITR+AAV5 Rep+AAV1 Cap=virus
AAVX ITR+AAV5 Rep+AAV2 Cap=virus
AAVX ITR+AAV5 Rep+AAV3 Cap=virus
AAVX ITR+AAV5 Rep+AAV4 Cap=virus
AAVX ITR+AAV5 Rep+AAV5 Cap=virus
AAVX ITR+AAV5 Rep+AAV6 Cap=virus
AAVX ITR+AAV5 Rep+AAV7 Cap=virus
AAVX ITR+AAV5 Rep+AAV8 Cap=virus
AAVX ITR+AAV5 Rep+AAV9 Cap=virus
AAVX ITR+AAV5 Rep+AAV10 Cap=virus
AAVX ITR+AAV5 Rep+AAV11 Cap=virus
AAVX ITR+AAV5 Rep+AAAV Cap=virus
AAVX ITR+AAV5 Rep+BAAV Cap=virus
AAV1 ITR+AAV1 Rep+AAVX Cap=virus
AAV2 ITR+AAV2 Rep+AAVX Cap=virus
AAV3 ITR+AAV3 Rep+AAVX Cap=virus
AAV4 ITR+AAV4 Rep+AAVX Cap=virus
AAV5 ITR+AAV5 Rep+AAVX Cap=virus
AAV6 ITR+AAV6 Rep+AAVX Cap=virus
AAV7 ITR+AAV7 Rep+AAVX Cap=virus
AAV8 ITR+AAV8 Rep+AAVX Cap=virus
AAV9 ITR+AAV9 Rep+AAVX Cap=virus
AAV10 ITR+AAV10 Rep+AAVX Cap=virus
AAV11 ITR+AAV11 Rep+AAVX Cap=virus
AAAV ITR+AAAV Rep+AAVX Cap=virus
BAAV ITR+BAAV Rep+AAVX Cap=virus
[Note that AAVX can be AAV-X1, AAV-X1b, AAV-X5, AAV-X19, AAV-X21, AAV-X22, AAV-X23, AAV-X24, AAV-X25, or AAV-X26]

One of skill in the art would know how to employ standard techniques to obtain the sequences from any of AAV1-11, AAAV, BAAV or AAVX in order to combine them with AAVX sequences. Examples of AAVX sequences that can be utilized in these constructs can be found herein. Examples of AAV1 sequences that can be utilized in these constructs can be found in GenBank under Accession No. AF063497 and these sequences are hereby incorporated in their entireties by this reference. Examples of AAV2 sequences that can be utilized in these constructs can be found in GenBank under Accession No. AF043303 and these sequences are hereby incorporated in their entireties by this reference. Examples of AAV3 sequences that can be utilized in these constructs can be found in GenBank under Accession No. NC_001729 and these sequences are hereby incorporated in their entireties by this reference. Examples of AAV4 sequences that can be utilized in these constructs can be found in GenBank under Accession No. U89790 and these sequences are hereby incorporated in their entireties by this reference. Examples of AAV5 sequences that can be utilized in these constructs can be found in GenBank under Accession No. AF085716 and these sequences are hereby incorporated in their entireties by this reference. Examples of AAV6 sequences that can be utilized in these constructs can be found in GenBank under Accession No. NC_001862 and AF028704 and these sequences are hereby incorporated in their entireties by this reference. Examples of AAV7 sequences that can be utilized in these constructs can be found in GenBank under Accession No. AF513851 and these sequences are hereby incorporated in their entireties by this reference. Examples of AAV8 sequences that can be utilized in these constructs can be found in GenBank under Accession No. AF513852 and these sequences are hereby incorporated in their entireties by this reference. Examples of AAV9 sequences that can be utilized in these constructs can be found in GenBank under Accession No. AY530579 and these sequences are hereby incorporated in their entireties by this reference. Examples of AAV10 sequences that can be utilized in these constructs can be found in GenBank under Accession No. AY631965 and these sequences are hereby incorporated in their entireties by this reference. Examples of AAV11 sequences that can be utilized in these constructs can be found in GenBank under Accession No. AY631966 and these sequences are hereby incorporated in their entireties by this reference. Examples of AAAV sequences that can be utilized in these constructs can be found in GenBank under Accession No. AY186198 and these sequences are hereby incorporated in their entireties by this reference. Examples of BAAV sequences that can be utilized in these constructs can be found in GenBank Accession No. AY388617 and these sequences are hereby incorporated in their entireties by this reference.

In any of the constructs described herein, inclusion of a promoter is preferred. As used in the constructs herein, unless otherwise specified, Cap (capsid) refers to any of VP1, VP2, VP3, combinations thereof, functional fragments of any of VP1, VP2 or VP3, or chimeric capsids as described herein. The ITRs of the constructs described herein, can be chimeric recombinant ITRs as described elsewhere in the application.

Conjugates of recombinant or wild-type AAVX virions and nucleic acids or proteins can be used to deliver those molecules to a cell. For example, the purified AAVX can be used as a vehicle for delivering DNA bound to the exterior of the virus. Examples of this are to conjugate the DNA to the virion by a bridge using poly-L-lysine or other charged molecule. Also contemplated are virosomes that contain AAVX structural proteins (AAVX capsid proteins), lipids such as DOTAP, and nucleic acids that are complexed via charge interaction to introduce DNA into cells.

Also provided herein are AAVX capsid proteins (e.g. VP1, VP2 or VP3 or combinations thereof), or AAVX particles consisting of AAVX capsid proteins, wherein the capsid proteins or particles do not contain AAV nucleic acid, vector or plasmid, and are therefore not infectious. These capsid proteins and "empty particles" can comprise other substances such as biologically active molecules (e.g., small molecules, polypeptides, or non-AAV nucleic acids). The substances can be conjugated to the capsid proteins or comprise a fusion protein with an AAVX capsid polypeptide. Alternatively, the substance can be incorporated within an AAVX empty particle. AAVX capsid proteins and empty particles can be used to deliver the substance to a target cell using the targeting ability of the capsid protein to achieve the desired tissue tropism. In addition, the empty particles can function to protect the substance from depredation or immune response.

Also provided herein are conjugates that utilize the AAVX capsid or a unique region of the AAVX capsid protein (e.g. VP1, VP2 or VP3 or combinations thereof) to introduce DNA into cells. For example, the AAVX VP1 protein or fragment thereof, can be conjugated to a DNA on a plasmid that is conjugated to a lipid. Cells can be infected using the targeting ability of the VP 1 capsid protein to achieve the desired tissue tropism, specific to the AAVX. AAVX VP2 and VP3 proteins can also be utilized to introduce DNA or other molecules into cells. By further incorporating the Rep protein and the AAV TRS into the DNA-containing conjugate, cells can be transduced and targeted integration can be achieved. For example, if AAVX specific targeted integration is desired, a conjugate composed of the AAVX VP1 capsid, AAVX Rep or a fragment of AAVX Rep, AAVX TRS, the Rep binding site, the exogenous DNA of interest, and a lipid, can be utilized to achieve AAVX specific tropism and AAVX specific targeted integration in the genome.

Further provided herein are chimeric viruses where AAVX vectors can be encapsidated by herpes simplex virus (HSV) (Heister, T., et al. J. Virol. 2002 July; 76(14):7163-73), incorporated herein for its teaching of HSV/AAV hybrid vectors), baculovirus or other viruses to achieve a desired tropism associated with another virus. For example, the AAVX ITRs could be encapsidated by HSV and cells could be infected. Post-infection, the ITRs of AAVX could be acted on by AAVX Rep provided in the system or in a separate vehicle to rescue AAVX from the genome. Therefore, the cellular tropism of HSV can be combined with AAVX Rep mediated targeted integration. Other viruses that could be utilized to construct chimeric viruses include lentivirus, retrovirus, pseudotyped retroviral vectors and adenoviral vectors.

Provided herein are isolated nucleic acids of AAV-X1, AAV-X1b, AAV-X5, AAV-X19, AAV-X21, AAV-X22, AAV-X23, AAV-X24, AAV-X25, and AAV-X26. For example, provided is an isolated nucleic acid comprising the nucleotide sequence set forth in SEQ ID NO:1 (AAV-X1 partial genome). Also provided is an isolated nucleic acid comprising the nucleotide sequence set forth in SEQ ID NO:2 (AAV-X1b partial genome). Also provided is an isolated nucleic acid comprising the nucleotide sequence set forth in SEQ ID NO:3 (AAV-X5 partial genome). Also provided is an isolated nucleic acid comprising the nucleotide sequence set forth in SEQ ID NO:4 (AAV-X19 partial genome). Also provided is an isolated nucleic acid comprising the nucleotide sequence set forth in SEQ ID NO:5 (AAV-X21 partial genome). Also provided is an isolated nucleic acid comprising the nucleotide sequence set forth in SEQ ID NO:6 (AAV-X22 partial genome). Also provided is an isolated nucleic acid comprising the nucleotide sequence set forth in SEQ ID NO:7 (AAV-X23 partial genome). Also provided is an isolated nucleic acid comprising the nucleotide sequence set forth in SEQ ID NO:8 (AAV-X24 partial genome). Also provided is an isolated nucleic acid comprising the nucleotide sequence set forth in SEQ ID NO:9 (AAV-X25 partial genome). Also provided is an isolated nucleic acid comprising the nucleotide sequence set forth in SEQ ID NO:10 (AAV-X26 partial genome).

This nucleic acid, or unique portions thereof, can be inserted into vectors, such as plasmids, yeast artificial chromosomes, or other viral vector (particle), if desired, by standard cloning methods. Also provided is an isolated nucleic acid consisting essentially of the nucleotide sequence set forth in SEQ ID NOs:1-10.

The phrase "consisting essentially of" is used herein to refer to a composition that comprises the essential characteristics of the identified composition. By "essential" is meant the characteristics that contribute to the structure or function of the disclosed molecule. Thus, any substitution, deletion or addition to the provided composition that does not significantly alter the defining characteristics of the composition are considered therein.

For example, if an amino acid sequence X is disclosed, then a provided polypeptide consisting essentially of the amino acid sequence X includes, for example, conservative amino acid substitutions (as described below) that do not significantly alter the essential characteristics of the polypeptide, e.g., secondary/tertiary structure or function of the protein. The provided polypeptide can further constitute a fusion protein or otherwise have additional N-terminal, C-terminal, or intermediate amino acid sequences, e.g., linkers or tags. "Linker", as used herein, is an amino acid sequences or insertion that can be used to connect or separate two distinct polypeptides or polypeptide fragments, wherein the linker does not otherwise contribute to the essential function of the composition. A polypeptide provided herein, can have an amino acid linker comprising, for example, the amino acids GLS, ALS, or LLA. A "tag", as used herein, refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

As another example, if a nucleic acid X is disclosed, then a provided nucleic acid consisting essentially of nucleic acid sequence X, includes, for example, nucleotide substitutions that do not alter the amino acid sequence of the encoded polypeptide, i.e., due to degeneracy. If sequence X comprises introns and exons, then the provided nucleic acid can further be the cDNA sequence that lacks the introns but comprises the exons of sequence X. To the extent that specific genes within a genome are identified herein, it is further understood that the disclosure of a nucleic acid consisting essentially of the genome sequence would include fragments of the genome such as isolated sequences comprising a gene or genes within the genome.

Other characteristics of nucleic acid or amino acid sequences that are not herein considered essential include, for example, junk DNA between genes or any identifiable sequence unit, e.g., promoters, enhancers, transmembrane domains, poly-adenylation sequences, signal sequences, etc., that when substituted or removed would be presumed by one skilled in the art to not significantly alter the essential characteristics of the disclosed sequence.

Thus, the nucleotides of SEQ ID NOS:1-10 can have minor modifications and still be contemplated herein. For example, modifications that do not alter the amino acid encoded by any given codon (such as by modification of the third, "wobble," position in a codon) can readily be made, and such alterations are known in the art. Furthermore, modifications that cause a resulting neutral (conserved) amino acid substitution of a similar amino acid can be made in a coding region of the genome. Additionally, modifications as described herein for the AAVX components, such as the ITRs, the p5 promoter, etc. are contemplated herein. Furthermore, modifications to regions of SEQ ID NOS:1-10, other than in the ITR, TRS, Rep binding site and hairpin, are likely to be tolerated without serious impact on the function of the nucleic acid as a recombinant vector.

As used herein, the term "isolated" refers to a nucleic acid separated or significantly free from at least some of the other components of the naturally occurring organism, for example, the cell structural components or viral components commonly found associated with nucleic acids in the environment of the virus and/or other nucleic acids. The isolation of the native nucleic acids can be accomplished, for example, by techniques such as cell lysis followed by phenol plus chloroform extraction, followed by ethanol precipitation of the nucleic acids. The nucleic acids provided herein can be isolated from cells according to any of many methods well known in the art.

As used herein, the term "nucleic acid" refers to single- or multiple-stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the genes discussed herein or may include alternative codons which encode the same amino acid as those provided herein, including that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

Additionally provided is an isolated nucleic acid that selectively hybridizes with any nucleic acid disclosed herein, including the AAV-X1, AAV-X1b, AAV-X5, AAV-X19, AAV-X21, AAV-X22, AAV-X23, AAV-X24, AAV-X25, or AAV-X26 genome (SEQ ID NOS:1-10) and any unique fragment thereof, including the Rep and capsid encoding sequences, promoters and ITRs. Specifically, the nucleic acid can selectively or specifically hybridize to an isolated nucleic acid consisting of the nucleotide sequence set forth in SEQ ID NO:1, 2, 3, 4, 5, 6, 7, 8, 9, or 10. By "selectively hybridizes" as used herein is meant a nucleic acid that hybridizes to one of the disclosed nucleic acids under sufficient stringency conditions without significant hybridization to a nucleic acid encoding an unrelated protein, and particularly, without detectably hybridizing to nucleic acids of other AAVs. Thus, a nucleic acid that selectively hybridizes with a nucleic acid provided herein will not selectively hybridize under stringent conditions with a nucleic acid encoding a different protein or the corresponding protein from a different serotype of the virus, and vice versa. A "specifically hybridizing" nucleic acid is one that hybridizes under stringent conditions to only a nucleic acid found in AAVX. Therefore, nucleic acids for use, for example, as primers and probes to detect or amplify the target nucleic acids are contemplated herein. Nucleic acid fragments that selectively hybridize to any given nucleic acid can be used, e.g., as primers and or probes for further hybridization or for amplification methods (e.g., polymerase chain reaction (PCR), ligase chain reaction (LCR)). Additionally, for example, a primer or probe can be designed that selectively hybridizes with both AAVX and a gene of interest carried within the AAVX vector (i.e., a chimeric nucleic acid).

Stringency of hybridization is controlled by both temperature and salt concentration of either or both of the hybridization and washing steps. Typically, the stringency of hybridization to achieve selective hybridization involves hybridization in high ionic strength solution (6×SSC or 6×SSPE) at a temperature that is about 12-25° C. below the $T_m$ (the melting temperature at which half of the molecules dissociate from their hybridization partners) followed by washing at a combination of temperature and salt concentration chosen so that the washing temperature is about 5° C. to 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual,* 2nd Ed., Cold Spring Harbor Laboratory, Cold Spring Harbor, N.Y., 1989; Kunkel et al. *Methods Enzymol.* 1987:154:367, 1987). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

A nucleic acid that selectively hybridizes to any portion of the AAVX genome is contemplated herein. Therefore, a nucleic acid that selectively hybridizes to AAVX can be of longer length than the AAVX genome, it can be about the same length as the AAVX genome or it can be shorter than the AAVX genome. The length of the nucleic acid is limited on the shorter end of the size range only by its specificity for hybridization to AAVX, i.e., once it is too short, typically less than about 5 to 7 nucleotides in length, it will no longer bind specifically to AAVX, but rather will hybridize to numerous background nucleic acids. Additionally contemplated herein is a nucleic acid that has a portion that specifically hybridizes to AAVX and a portion that specifically hybridizes to a gene of interest inserted within AAVX.

Provided is an isolated nucleic acid comprising an AAVX p5 promoter. Provided is an isolated nucleic acid comprising an AAVX p19 promoter. Provided is an isolated nucleic acid comprising an AAVX p40 promoter. Provided is an isolated nucleic acid comprising an AAVX ITR. Further provided is an isolated nucleic acid encoding an AAVX Rep protein. The AAVX Rep proteins are encoded by open reading frame (ORF) 1 of the AAVX genome. Examples of the AAV Rep proteins include Rep78, Rep68, Rep52 and Rep40. However, it is contemplated that the Rep nucleic acid can encode any one, two, three, or four of the four Rep proteins, in any order.

Furthermore, minor modifications are contemplated in the nucleic acid, such as silent mutations in the coding sequences, mutations that make neutral or conservative changes in the encoded amino acid sequence, and mutations in regulatory regions that do not disrupt the expression of the gene. Examples of other minor modifications are known in the art. Further modifications can be made in the nucleic acid, such as to disrupt or alter expression of one or more of the Rep proteins in order to, for example, determine the effect of such a disruption; such as to mutate one or more of the Rep proteins to determine the resulting effect, etc.

Further provided is an isolated nucleic acid encoding an AAVX Capsid protein. Furthermore, provided is a nucleic acid encoding each of the three AAVX capsid proteins, VP1, VP2, and VP3. Thus, provided is an isolated nucleic acid encoding AAVX VP1, a nucleic acid encoding AAVX VP2, and an isolated nucleic acid encoding AAVX VP3. Thus, provided is an isolated nucleic acid encoding the amino acid sequence set forth in SEQ ID NO:21 (AAV-X1 VP1). Thus, provided is an isolated nucleic acid encoding the amino acid sequence set forth in SEQ ID NO:22 (AAV-X1b VP1). Thus, provided is an isolated nucleic acid encoding the amino acid sequence set forth in SEQ ID NO:23 (AAV-X5 VP1). Thus, provided is an isolated nucleic acid encoding the amino acid sequence set forth in SEQ ID NO:24 (AAV-X19 VP1). Thus, provided is an isolated nucleic acid encoding the amino acid sequence set forth in SEQ ID NO:25 (AAV-X21 VP1). Thus, provided is an isolated nucleic acid encoding the amino acid sequence set forth in SEQ ID NO:26 (AAV-X22 VP1). Thus, provided is an isolated nucleic acid encoding the amino acid sequence set forth in SEQ ID NO:27 (AAV-X23 VP1). Thus, provided is an isolated nucleic acid encoding the amino acid sequence set forth in SEQ ID NO:28 (AAV-X24 VP1). Thus, provided is an isolated nucleic acid encoding the amino acid sequence set forth in SEQ ID NO:29 (AAV-X25 VP1). Thus, provided is an isolated nucleic acid encoding the amino acid sequence set forth in SEQ ID NO:30 (AAV-X26 VP1).

Also specifically provided is an isolated nucleic acid comprising SEQ ID NO:11 (AAV-X1 VP1). Also specifically provided is an isolated nucleic acid comprising SEQ ID NO:12 (AAV-X1b VP1). Also specifically provided is an isolated nucleic acid comprising SEQ ID NO:13 (AAV-X5 VP1). Also specifically provided is an isolated nucleic acid comprising SEQ ID NO:14 (AAV-X19 VP1). Also specifically provided is an isolated nucleic acid comprising SEQ ID NO:15 (AAV-X21 VP1). Also specifically provided is an isolated nucleic acid comprising SEQ ID NO:16 (AAV-X22 VP1). Also specifically provided is an isolated nucleic acid comprising SEQ ID NO:17 (AAV-X23 VP1). Also specifically provided is an isolated nucleic acid comprising SEQ ID NO:18 (AAV-X24 VP1). Also specifically provided is an isolated nucleic acid comprising SEQ ID NO:19 (AAV-X25 VP1). Also specifically provided is an isolated nucleic acid comprising SEQ ID NO:20 (AAV-X26 VP1).

Minor modifications in the nucleotide sequences encoding the capsid, or coat, proteins are contemplated, as described above for other AAVX nucleic acids. However, in general, a modified nucleic acid encoding a capsid protein will have at least about 80%, 81%, 82%, 83%, 84%, 85%, 86%, 87%, 89%, 90%, 91%, 92%, 93%, 94%, 95%, 96%, 97%, 98%, 98.5%, 99%, 99.5% or 99.9% or 100% homology to the capsid nucleic sequences described herein e.g., SEQ ID NOS: 11-20, and the capsid polypeptide encoded therein will have overall about 80%, 81%, 82%, 83%, 84%, 85%, 86%, 87%, 89%, 90%, 91%, 92%, 93%, 94%, 95%, 96%, 97%, 98%, 98.5%, 99%, 99.5% or 99.9% or 100% homology with the amino acid sequence described herein, e.g., SEQ ID NOS: 21-30. Isolated nucleic acids that selectively hybridize with the nucleic acids of SEQ ID NOS:11-20 under the conditions described above are also provided.

Also provided is a cell containing one or more of the herein described nucleic acids, such as the AAVX genome, AAVX ORF1 and ORF2, each AAVX Rep protein gene, or each AAVX capsid protein gene. Such a cell can be any desired cell and can be selected based upon the use intended. For example, cells can include bacterial cells, yeast cells, insect cells, human HeLa cells and simian Cos cells as well as other human and mammalian cells and cell lines. Primary cultures as well as established cultures and cell lines can be used. Nucleic acids provided herein can be delivered into cells by any selected means, in particular depending upon the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art. Additionally, if the nucleic acids are in a viral particle, the cells can simply be transduced with the virion by standard means known in the art for AAV transduction. Small amounts of the recombinant AAVX virus can be made to infect cells and produce more of itself.

Provided herein are purified AAVX polypeptides. The term "polypeptide" as used herein refers to a polymer of amino acids and includes full-length proteins and fragments thereof. Thus, "protein," polypeptide," and "peptide" are often used interchangeably herein. Substitutions can be selected by known parameters to be neutral (see, e.g., Robinson W E Jr, and Mitchell W M., AIDS 4:S151-S162 (1990)). As will be appreciated by those skilled in the art, also provided herein are those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The location of any modifications to the polypeptide will often determine its impact on function. Particularly, alterations in regions nonessential to protein function will be tolerated with fewer effects on function. Elsewhere in the application regions of the AAVX proteins are described to provide guidance as to where substitutions, additions or deletions can be made to minimize the likelihood of disturbing the function of the variant.

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions
Original Residue Exemplary Conservative
Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity can result from selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Generally, a conservative substitution is a substitution of an amino acid residue for another amino acid residue having similar biochemical properties. Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

For example, a conservative substitution in an AAVX VP1 peptide (such as a peptides encoded by SEQ ID NOS:21-30) does not substantially affect the ability of VP1 peptide to confer the unique tropism of the AAVX particle. A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Examples of amino acids which can be substituted for an original amino acid in a protein and which are regarded as conservative substitutions include, but are not limited to: Ser for Ala; Lys for Arg; Gln or H is for Asn; Glu for Asp; Ser for Cys; Asn for Gln; Asp for Glu; Pro for Gly; Asn or Gln for H is; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988) and in standard textbooks of genetics and molecular biology.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86 [1983]), acetylation of the N-terminal amine and, in some instances, amidation of the C-terminal carboxyl.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-CH═CH— (cis and trans), —COCH2-, —CH(OH)CH2-, and —CHH2SO (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-1249 (1986) (—CH H2-S); Hann J. Chem. Soc Perkin Trans. I 307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appin, EP 45665 CA (1982): 97:39405 (1982) (—CH(OH)CH2-); Holladay et al. Tetrahedron. Lett 24:4401-4404 (1983) (—C(OH)CH2-); and Hruby Life Sci 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

A polypeptide provided herein can be readily obtained by any of several means. For example, the polypeptide of interest can be synthesized chemically by standard methods. Additionally, the coding regions of the genes can be recombinantly expressed and the resulting polypeptide isolated by standard methods. Furthermore, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from a cell expressing the nucleic acid encoding the polypeptide by selective hybridization with the antibody. This protein can be purified to the extent desired by standard methods of protein purification (see, e.g., Sambrook et al., *Molecular Cloning: A Laboratory Manual*, 2nd Ed., Cold Spring Harbor Laboratory, Cold Spring Harbor, N.Y., 1989).

An antigenic or immunoreactive fragment of the provided compositions and methods is typically an amino acid sequence of at least about 5 consecutive amino acids, and it can be derived from the AAVX polypeptide amino acid sequence. An antigenic AAVX fragment is any fragment unique to the AAVX protein, as described herein, against which an AAVX-specific antibody can be raised, by standard methods. Thus, the resulting antibody-antigen reaction should be specific for AAVX.

By "unique fragment thereof" is meant any smaller polypeptide fragment encoded by an AAVX rep gene that is of sufficient length to be found only in the Rep polypeptide. Substitutions and modifications of the amino acid sequence can be made as described herein and, further, can include protein processing modifications, such as glycosylation, to the polypeptide. Typically, to be unique, a polypeptide fragment provided herein will be at least about 5 amino acids in length; however, unique fragments can be 6, 7, 8, 9, 10, 20, 30, 40, 50, 60, 70, 80, 90, 100 or more amino acids in length. A unique polypeptide will typically comprise such a unique fragment; however, a unique polypeptide can also be determined by its overall homology. A unique polypeptide can be 6, 7, 8, 9, 10, 20, 30, 40, 50, 60, 70, 80, 90, 100 or more amino acids in length. Uniqueness of a polypeptide fragment can readily be determined by standard methods such as searches of computer databases of known peptide or nucleic acid sequences or by hybridization studies to the nucleic acid encoding the protein or to the protein itself, as known in the art. The uniqueness of a polypeptide fragment can also be determined immunologically as well as functionally. Uniqueness can be simply determined in an amino acid-by-amino acid comparison of the polypeptides.

Provided is an isolated AAVX Rep protein. An AAVX Rep polypeptide is encoded by ORF1 of AAVX. Also provided is each individual AAVX Rep protein. Provided is an isolated polypeptide, comprising AAVX Rep 52, or a unique fragment thereof. Provided is an isolated polypeptide, comprising AAV Rep 78, or a unique fragment thereof.

Further provided is an isolated AAVX Capsid protein or a unique fragment thereof. AAVX capsid protein is encoded by ORF 2 of AAVX. Further provided are the individual AAVX capsid proteins, VP1, VP2 and VP3 or unique fragments thereof. Thus, provided is an isolated polypeptide having the amino acid sequence set forth in SEQ ID NO:21 (AAV-X1 VP1). Also provided is an isolated polypeptide having the amino acid sequence set forth in SEQ ID NO:22 (AAV-X1b VP1). Also provided is an isolated polypeptide having the amino acid sequence set forth in SEQ ID NO:23 (AAV-X5 VP1). Also provided is an isolated polypeptide having the amino acid sequence set forth in SEQ ID NO:24 (AAV-X19 VP1). Also provided is an isolated polypeptide having the amino acid sequence set forth in SEQ ID NO:25 (AAV-X21 VP1). Also provided is an isolated polypeptide having the amino acid sequence set forth in SEQ ID NO:26 (AAV-X22 VP1). Also provided is an isolated polypeptide having the amino acid sequence set forth in SEQ ID NO:27 (AAV-X23 VP1). Also provided is an isolated polypeptide having the amino acid sequence set forth in SEQ ID NO:28 (AAV-X24 VP1). Also provided is an isolated polypeptide having the amino acid sequence set forth in SEQ ID NO:29 (AAV-X25 VP1). Also provided is an isolated polypeptide having the amino acid sequence set forth in SEQ ID NO:30 (AAV-X26 VP1). Further provided is an isolated polypeptide consisting essentially of the amino acid sequence set forth in SEQ ID NO:21, 22, 23, 24, 25, 26, 27, 28, 29, or 30.

By "unique fragment thereof" is meant any smaller polypeptide fragment encoded by any AAVX capsid gene that is of sufficient length to be found only in the AAVX capsid protein. Substitutions and modifications of the amino acid sequence can be made as described above and, further, can include protein processing modifications, such as glycosylation, to the polypeptide. However, an AAVX Capsid polypeptide including all three coat proteins will have greater than about 80%, 81%, 82%, 83%, 84%, 85%, 86%, 87%, 89%, 90%, 91%, 92%, 93%, 94%, 95%, 96%, 97%, 98%, 98.5%, 99%, 99.5% or 99.9% overall homology to the polypeptide encoded by the nucleotides set forth in SEQ ID NOS:21-30.

Also provided herein are isolated AAV-X1, AAV-X1b, AAV-X5, AAV-X19, AAV-X21, AAV-X22, AAV-X23, AAV-X24, AAV-X25, and AAV-X26 viruses. In one aspect, the isolated viruses can be used to produce antibodies specific for each AAVX. Thus, provided is an isolated antibody that specifically binds an AAVX-specific protein. The isolated viruses can be used to detect antibodies specific for each AAVX.

Thus, provided is an isolated antibody that specifically binds an AAVX Rep protein, or a unique epitope thereof. Thus, also provided is an isolated antibody that specifically bind AAVX Rep 52 or AAVX Rep 78, or a unique fragment thereof. Additionally provided is an isolated antibody that specifically binds any of the AAVX capsid proteins (VP1, VP2 or VP3), a unique epitope thereof, or the polypeptide comprising all three AAVX coat proteins. Also provided is an isolated antibody that specifically binds the AAVX capsid protein having the amino acid sequence set forth in SEQ ID NO:21 (AAV-X1 VP1), or that specifically binds a unique fragment thereof. Also provided is an isolated antibody that specifically binds the AAVX capsid protein having the amino acid sequence set forth in SEQ ID NO:22 (AAV-X1b VP1), or that specifically binds a unique fragment thereof. Also provided is an isolated antibody that specifically binds the AAVX capsid protein having the amino acid sequence set forth in SEQ ID NO:23 (AAV-X5 VP1), or that specifically binds a unique fragment thereof. Also provided is an isolated antibody that specifically binds the AAVX capsid protein having the amino acid sequence set forth in SEQ ID NO:24 (AAV-X19 VP1), or that specifically binds a unique fragment thereof. Also provided is an isolated antibody that specifically binds the AAVX capsid protein having the amino acid sequence set forth in SEQ ID NO:25 (AAV-X21 VP1), or that specifically binds a unique fragment thereof. Also provided is an isolated antibody that specifically binds the AAVX capsid protein having the amino acid sequence set forth in SEQ ID NO:26 (AAV-X22 VP1), or that specifically binds a unique fragment thereof. Also provided is an isolated antibody that specifically binds the AAVX capsid protein having the amino acid sequence set forth in SEQ ID NO:27 (AAV-X23 VP1), or that specifically binds a unique fragment thereof. Also provided is an isolated antibody that specifically binds the AAVX capsid protein having the amino acid sequence set forth in SEQ ID NO:28 (AAV-X24 VP1), or that specifically binds a unique fragment thereof. Also provided is an isolated antibody that specifically binds the AAVX capsid protein having the amino acid sequence set forth in SEQ ID NO:29 (AAV-X25 VP1), or that specifically binds a unique fragment thereof. Also provided is an isolated antibody that specifically binds the AAVX capsid protein having the amino acid sequence set forth in SEQ ID NO:30 (AAV-X26 VP1), or that specifically binds a unique fragment thereof. Again, any given antibody can recognize and bind one of a number of possible epitopes present in the polypeptide; thus only a unique portion of a polypeptide (having the epitope) needs to be present in an assay to determine if the antibody specifically binds the polypeptide.

The antibody can be a component of a composition that comprises an antibody that specifically binds the AAVX protein. The composition can further comprise, e.g., serum, serum-free medium, or a pharmaceutically acceptable carrier such as physiological saline, etc.

By "an antibody that specifically binds" an AAVX polypeptide or protein is meant an antibody that selectively binds to an epitope on any portion of the AAVX peptide such that the antibody binds specifically to the corresponding AAVX polypeptide without significant background. Specific binding by an antibody further means that the antibody can be used to selectively remove the target polypeptide from a sample comprising the polypeptide or and can readily be determined by radioimmunoassay (RIA), bioassay, or enzyme-linked immunosorbant (ELISA) technology. An ELISA method effective for the detection of the specific antibody-antigen binding can, for example, be as follows: (1) bind the antibody to a substrate; (2) contact the bound antibody with a sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

An antibody can include antibody fragments such as Fab fragments which retain the binding activity. Antibodies can be made as described in, e.g., Harlow and Lane, *Antibodies: A Laboratory Manual*, Cold Spring Harbor Laboratory, Cold Spring Harbor, N.Y. (1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. Individual hybridomas are then propagated as individual clones serving as a source for a particular monoclonal antibody.

Additionally provided is a method of screening a cell for infectivity by AAVX, comprising contacting the cell with AAVX and detecting the presence of AAVX in the cells. AAVX particles can be detected using any standard physical or biochemical methods. For example, physical methods that can be used for this detection include DNA based methods such as 1) polymerase chain reaction (PCR) for viral DNA or RNA or 2) direct hybridization with labeled probes, and immunological methods such as by 3) antibody directed against the viral structural or non-structural proteins. Catalytic methods of viral detection include, but are not limited to, detection of site and strand specific DNA nicking activity of Rep proteins or replication of an AAV origin-containing substrate. Reporter genes can also be utilized to detect cells that transduce AAVX. For example, β-gal, green fluorescent protein or luciferase can be inserted into a recombinant AAVX. The cell can then be contacted with the recombinant AAVX, either in vitro or in vivo and a colorimetric assay could detect a color change in the cells that would indicate transduction of AAVX in the cell. Additional detection methods are outlined in Fields, *Virology*, Raven Press, New York, N.Y. 1996.

Provided is a method of screening a cell for infectivity by AAVX, wherein the presence of AAVX in the cells is determined by nucleic acid hybridization methods, a nucleic acid probe for such detection can comprise, for example, a unique fragment of any of the AAVX nucleic acids provided herein. The uniqueness of any nucleic acid probe can readily be determined as described herein. Additionally, the presence of AAVX in cells can be determined by fluorescence, antibodies to gene products, focus forming assays, plaque lifts, Western blots and chromogenic assays. The nucleic acid can be, for example, the nucleic acid whose nucleotide sequence is set forth in SEQ ID NOS:1, 2, 3, 4, 5, 6, 7, 8, 9, 10, 11, 12, 13, 14, 15, 16, 17, 18, 19, or 20 or a unique fragment thereof.

Provided is a method of determining the suitability of an AAVX vector for administration to a subject comprising contacting an antibody-containing sample from the subject with an antigenic fragment of an isolated AAVX Rep or Capsid protein, and detecting an antibody-antigen reaction in the sample, the presence of a neutralizing reaction indicating the AAVX vector to be unsuitable for use in the subject. Further provided is a method of determining the presence in a subject of an AAVX-specific antibody comprising contacting an antibody-containing sample from the subject with an antigenic fragment of an isolated AAVX Rep or Capsid protein and detecting an antibody-antigen reaction in the sample, the presence of a reaction indicating the presence of an AAVX-specific antibody in the subject. The present methods of determining the suitability of an AAVX vector for administration to a subject or the presence of an AAVX-specific antibody in a subject can comprise contacting an antibody-containing sample from the subject with a unique antigenic or immunogenic fragment of an AAVX Rep protein (e.g. Rep 52, Rep 78) and detecting an antibody-antigen reaction in the sample, the presence of a reaction indicating the presence of an AAVX-specific antibody and therefore the AAVX vector to be unsuitable for use in the subject. The AAVX Rep proteins are provided herein, and their antigenic fragments are routinely determined. The AAVX capsid protein can be used to select an antigenic or immunogenic fragment, for example from the amino acid sequence set forth in SEQ ID NO:21 (AAV-X1 VP1), the amino acid sequence set forth in SEQ ID NO:22 (AAV-X1b VP1), the amino acid sequence set forth in SEQ ID NO:23 (AAV-X5 VP1), the amino acid sequence set forth in SEQ ID NO:24 (AAV-X19 VP1), the amino acid sequence set forth in SEQ ID NO:25 (AAV-X21 VP1), the amino acid sequence set forth in SEQ ID NO:26 (AAV-X22 VP1), the amino acid sequence set forth in SEQ ID NO:27 (AAV-X23 VP1, the amino acid sequence set forth in SEQ ID NO:28 (AAV-X24 VP1), the amino acid sequence set forth in SEQ ID NO:29 (AAV-X25 VP1), or the amino acid sequence set forth in SEQ ID NO:30 (AAV-X26 VP1)

Alternatively, or additionally, an antigenic or immunogenic fragment of an isolated AAVX Rep protein can be utilized in this determination method. Any given antibody can recognize and bind one of a number of possible epitopes present in the polypeptide; thus only a unique portion of a polypeptide (having the epitope) may need to be present in an assay to determine if the antibody specifically binds the polypeptide.

The AAVX polypeptide fragments can be analyzed to determine their antigenicity, immunogenicity and/or specificity. Briefly, various concentrations of a putative immunogenically specific fragment are prepared and administered to a subject and the immunological response (e.g., the production of antibodies or cell mediated immunity) of an animal to each concentration is determined. The amounts of antigen administered depend on the subject, e.g. a human, rabbit or a guinea pig, the condition of the subject, the size of the subject, etc. Thereafter an animal so inoculated with the antigen can be exposed to the AAVX viral particle or AAVX protein to test the immunoreactivity or the antigenicity of the specific immunogenic fragment. The specificity of a putative antigenic or immunogenic fragment can be ascertained by testing sera, other fluids or lymphocytes from the inoculated animal for cross reactivity with other closely related viruses, such as AAV1-11, AAAV, or BAAV.

By the "suitability of an AAVX vector for administration to a subject" is meant a determination of whether the AAVX vector will elicit a neutralizing immune response upon administration to a particular subject. A vector that does not elicit a significant immune response is a potentially suitable vector, whereas a vector that elicits a significant, neutralizing immune response (e.g. at least 90%) is thus likely to be unsuitable for use in that subject. Significance of any detectable immune response is a standard parameter understood by the skilled artisan in the field. For example, one can incubate the subject's serum with the virus, then determine whether that virus retains its ability to transduce cells in culture. If such virus cannot transduce cells in culture, the vector likely has elicited a significant immune response.

Alternatively, or additionally, one skilled in the art could determine whether or not AAVX administration would be suitable for a particular cell type of a subject. For example, the artisan could culture muscle cells in vitro and transduce the cells with AAVX in the presence or absence of the subject's serum. If there is a reduction in transduction efficiency, this could indicate the presence of a neutralizing antibody or other factors that may inhibit transduction. Normally, greater than 90% inhibition would have to be observed in order to rule out the use of AAVX as a vector. However, this limitation could be overcome by treating the subject with an immunosuppressant that could block the factors inhibiting transduction.

As will be recognized by those skilled in the art, numerous types of immunoassays are available for use in the present methods to detect binding between an antibody and an AAVX polypeptide as provided herein. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988). For example, enzyme immunoassays such as immunofluorescence assays (IFA), enzyme linked immunosorbent assays (ELISA) and immunoblotting can be readily adapted to accomplish the detection of the antibody. An ELISA method effective for the detection of the antibody bound to the antigen can, for example, be as follows: (1) bind the antigen to a substrate; (2) contact the bound antigen with a fluid or tissue sample containing the antibody; (3) contact the above with a secondary antibody specific for the antigen and bound to a detectable moiety (e.g., horseradish peroxidase enzyme or alkaline phosphatase enzyme); (4) contact the above with the substrate for the enzyme; (5) contact the above with a color reagent; (6) observe color change.

The antibody-containing sample of this method can comprise any biological sample which would contain the antibody or a cell containing the antibody, such as blood, plasma, serum, bone marrow, saliva and urine.

Also provided is a method of producing the AAVX virus by transducing a cell with the nucleic acid encoding the virus.

The present method further provides a method of delivering an exogenous nucleic acid to a cell comprising administering to the cell an AAVX particle containing a vector comprising the nucleic acid inserted between a pair of AAV inverted terminal repeats, thereby delivering the nucleic acid to the cell.

The AAV ITRs in the vector for the herein described delivery methods can be AAVX ITRs. Furthermore, the AAV ITRs in the vector for the herein described nucleic acid delivery methods can also comprise AAV1, AAV2, AAV3, AAV4, AAV5, AAV6, AAV7, AAV8, AAV9, AAV10, AAV11, AAAV, or BAAV inverted terminal repeats.

Also provided is a method of delivering an exogenous nucleic acid to a subject comprising administering to a cell of or from the subject an AAVX particle containing a vector comprising the nucleic acid inserted between a pair of AAV inverted terminal repeats, and returning the cell to the subject, thereby delivering the nucleic acid to the subject. The AAV ITRs can be any AAV ITRs, including AAVX ITRs, AAV5 ITRs and AAV2 ITRs. For example, in an ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transduce the cells. Cells can then be transplanted back into the subject's body, again by means standard for the cell type and tissue (e.g., in general, U.S. Pat. No. 5,399,346; for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transduction by the virus, by known detection means and as described herein. Cells for ex vivo transduction followed by transplantation into a subject can be selected from those listed above, or can be any other selected cell. Preferably, a selected cell type is examined for its capability to be transfected by AAVX. Preferably, the selected cell will be a cell readily transduced with AAVX particles; however, depending upon the application, even cells with relatively low transduction efficiencies can be useful, particularly if the cell is from a tissue or organ in which even production of a small amount of the protein or antisense RNA encoded by the vector will be beneficial to the subject.

Further provided is a method of delivering an exogenous nucleic acid to a cell in a subject comprising administering to the subject an AAVX particle containing a vector comprising the nucleic acid inserted between a pair of AAV inverted terminal repeats, thereby delivering the nucleic acid to a cell in the subject. Administration can be an ex vivo administration directly to a cell removed from a subject, such as any of the cells listed above, followed by replacement of the cell back into the subject, or administration can be in vivo administration to a cell in the subject. For ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transfect the cells. Cells can then be transplanted back into the subject's body, again by means standard for the cell type and tissue (e.g., for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transfection by the virus, by known detection means and as described herein.

Further provided is a method of delivering a nucleic acid to a cell in a subject having neutralizing antibodies to AAV1, AAV2, AAV3, AAV4, AAV5, AAV6, AAV7, AAV8, AAV9, AAV10, AAV11, AAAV, or BAAV comprising administering to the subject an AAVX particle containing a vector comprising the nucleic acid, thereby delivering the nucleic acid to a cell in the subject. A subject that has neutralizing antibodies to AAV1, AAV2, AAV3, AAV4, AAV5, AAV6, AAV7, AAV8, AAV9, AAV10, AAV11, AAAV, or BAAV can readily be determined by any of several known means, such as contacting AAV 1, AAV2, AAV3, AAV4, AAV5, AAV6, AAV7, AAV8, AAV9, AAV10, AAV11, AAAV, or BAAV protein(s) with an antibody-containing sample, such as blood, from a subject and detecting an antigen-antibody reaction in the sample. Delivery of the AAV1, AAV2, AAV3, AAV4, AAV5, AAV6, AAV7, AAV8, AAV9, AAV10, AAV11, AAAV, or BAAV particle can be by either ex vivo or in vivo administration as herein described. Thus, a subject who might have an adverse immunogenic reaction to a vector administered in an AAV1, AAV2, AAV3, AAV4, AAV5, AAV6, AAV7, AAV8, AAV9, AAV10, AAV11, AAAV, or BAAV viral particle can have a desired nucleic acid delivered using an AAVX particle. This delivery system can be particularly useful for subjects who have received therapy utilizing AAV1, AAV2, AAV3, AAV4, AAV5, AAV6, AAV7, AAV8, AAV9, AAV10, AAV11, AAAV, or BAAV particles in the past and have developed antibodies to AAV1, AAV2, AAV3, AAV4, AAV5, AAV6, AAV7, AAV8, AAV9, AAV10, AAV11, AAAV, or BAAV. An AAVX regimen can now be substituted to deliver the desired nucleic acid.

In any of the methods of delivering exogenous nucleic acids to a cell or subject described herein, the AAVX-conjugated nucleic acid or AAVX particle-conjugated nucleic acids described herein can be used.

In vivo administration to a human subject or an animal model can be by any of many standard means for administering viruses, depending upon the target organ, tissue or cell. Virus particles can be administered orally, parenterally (e.g., intravenously), by intramuscular injection, intrarectally, by direct tissue or organ injection, by intraperitoneal injection, topically, transdermally, via aerosol delivery, via the mucosa or the like. Viral nucleic acids (non-encapsidated) can also be administered, e.g., as a complex with cationic liposomes, or encapsulated in anionic liposomes. The present compositions can include various amounts of the selected viral particle or non-encapsidated viral nucleic acid in combination with a pharmaceutically acceptable carrier and, in addition, if desired, may include other medicinal agents, pharmaceutical agents, carriers, adjuvants, diluents, etc. Parental administration, if used, is generally characterized by injection.

Injectables can be prepared in conventional forms, either as liquid solutions or suspensions, solid forms suitable for solution or suspension in liquid prior to injection, or as emulsions. Dosages will depend upon the mode of administration, the disease or condition to be treated, and the individual subject's condition, but will be that dosage typical for and used in administration of other AAV vectors, such as AAV2 vectors. Often a single dose can be sufficient; however, the dose can be repeated if desirable. Administration methods for gene delivery to the cochlea are routine and are described in Jero, J. et al. (Gene Ther. 2001 Mar. 20; 12(5):539-48) and Staecker H, et al. (Acta Otolaryngol. 2001 January; 121(2):157-63), both references herein incorporated by reference for these methods.

Administration methods can be used to treat brain disorders such as Parkinson's disease, Alzheimer's disease, and demyelination disease. Other diseases that can be treated by these methods include metabolic disorders such as musculoskeletal diseases, cardiovascular disease, cancer, and autoimmune disorders.

Administration of this recombinant AAVX virion to the cell can be accomplished by any means, including simply contacting the particle, optionally contained in a desired liquid such as tissue culture medium, or a buffered saline solution, with the cells. The virion can be allowed to remain in contact with the cells for any desired length of time, and typically the virion is administered and allowed to remain indefinitely. For such in vitro methods, the virion can be administered to the cell by standard viral transduction methods, as known in the art and as exemplified herein. Titers of virus to administer can vary, particularly depending upon the cell type, but will be typical of that used for AAV transduction in general which is well known in the art. Additionally the titers used to transduce the particular cells in the present examples can be utilized.

The cells that can be transduced by the present recombinant AAVX virion can include any desired cell, such as the following cells and cells derived from the following tissues, human as well as other mammalian tissues, such as primate, horse, sheep, goat, pig, dog, rat, and mouse and avian species: Adipocytes, Adenocyte, Adrenal cortex, Amnion, Aorta, Ascites, Astrocyte, Bladder, Bone, Bone marrow, Brain, Breast, Bronchus, Cardiac muscle, Cecum, Cervix, Chorion, Cochlear, Colon, Conjunctiva, Connective tissue, Cornea, Dermis, Duodenum, Embryonic stem cells, Endometrium, Endothelium, Endothelial cells, Epithelial tissue, Epithelial cells, Epidermis, Esophagus, Eye, Fascia, Fibroblasts, Foreskin, Gastric, Glial cells, Glioblast, Gonad, Hepatic cells, Histocyte, Hair cells in the inner ear, auditory (organ of Corti) sensory epithelia, vestibular sensory epithelia, Ileum, Intestine, small Intestine, Jejunum, Keratinocytes, Kidney, Larynx, Leukocytes, Lipocyte, Liver, Lung, Lymph node, Lymphoblast, Lymphocytes, Macrophages, Mammary alveolar nodule, Mammary gland, Mastocyte, Maxilla, Melanocytes, Mesenchymal, Monocytes, Mouth, Myelin, Myoblasts Nervous tissue, Neuroblast, Neurons, Neuroglia, Osteoblasts, Osteogenic cells, Ovary, Palate, Pancreas, Papilloma, Peritoneum, Pituicytes, Pharynx, Placenta, Plasma cells, Pleura, Prostate, Rectum, Salivary gland, Skeletal muscle, Skin, Smooth muscle, Somatic, Spleen, Squamous, Stem cells, Stomach, Submandibular gland, Submaxillary gland, Synoviocytes, Testis, Thymus, Thyroid, Trabeculae, Trachea, Turbinate, Umbilical cord, Ureter, Uterus, and vestibular hair cells.

For example, provided herein is a method of transducing a cancer cell (e.g., lung cancer cell, non-small cell lung cancer cell), colon cell, CNS derived cell, ovarian cell, prostate cell, breast derived cell, cervical cord cell, kidney cell, salivary gland cell, or muscle cell using an AAV particle disclosed herein.

Also provided herein is a method of delivering a nucleic acid to a cancer cell (e.g., lung cancer cell, non-small cell lung cancer cell), colon cell, CNS derived cell, ovarian cell, prostate cell, breast derived cell, cervical cord cell, kidney cell, salivary gland cell, or muscle cell comprising administering to the cell an AAV-X1, AAV-X1b, AAV-X5, AAV-X19, AAV-X21, AAV-X22, AAV-X23, AAV-X24, AAV-X25, or AAV-X26 particle containing a vector comprising the nucleic acid inserted between a pair of AAV inverted terminal repeats, thereby delivering the nucleic acid to the cell.

The cell of the provided methods can be an inner ear epithelial cell. Thus, the cell of the provided method can be an inner ear hair cell. The cell of the provided methods can be an inner or outer hair cell of the organ of Corti or a vestibular hair cell. The cell of the provided methods can be an inner ear supporting cell such as Hensen's, phalangal, interdental, or vestibular supporting cells.

The cell of the provided method can be an airway epithelial cell. The cell of the provided method can be a columnar, goblet or basal cell.

The cell of the provided method can be a cell of the submandibular gland. The cell of the provided method can be a ductal or acinar cell.

Provided are recombinant vectors based on AAVX. Such vectors may be useful for transducing erythroid progenitor cells or cells resistant to transduction by other serotypes of AAV. These vectors may also be useful for transducing cells with a nucleic acid of interest in order to produce cell lines that could be used to screen for agents that interact with the gene product of the nucleic acid of interest. In addition to transduction of other cell types, transduction of erythroid cells would be useful for the treatment of cancer and genetic diseases which can be corrected by bone marrow transplants using matched donors. Some examples of this type of treatment include, but are not limited to, the introduction of a therapeutic gene such as genes encoding interferons, interleukins, tumor necrosis factors, adenosine deaminase, cellular growth factors such as lymphokines, blood coagulation factors such as factor VIII and IX, cholesterol metabolism uptake and transport protein such as EpoE and LDL receptor, and antisense sequences to inhibit viral replication of, for example, hepatitis or HIV.

Provided is a vector, comprising the AAVX virus as well as AAVX viral particles. While AAVX is similar to AAV1-11, the viruses are found herein to be physically and genetically distinct. These differences endow AAVX with some unique advantages, which better suit it as a vector for gene therapy.

Furthermore, as shown herein, AAVX capsid protein is distinct from AAV1, AAV2, AAV3, AAV4, AAV5, AAV6, AAV7, AAV8, AAV9, AAV10, AAV11, AAAV, or BAAV capsid proteins and exhibits different tissue tropism. AAV1, AAV2, AAV3, AAV4, AAV5, AAV6, AAV7, AAV8, AAV9, AAV10, AAV11, AAAV, BAAV, and AAVX likely utilize distinct cellular receptors. AAV1, AAV2, AAV3, AAV4, AAV5, AAV6, AAV7, AAV8, AAV9, AAV10, AAV11, AAAV, BAAV, and AAVX are serologically distinct and humans are not reported to have neutralizing antibodies to AAVX, thus in a gene therapy or gene transfer application, AAVX would allow for transduction of a patient who already possess neutralizing antibodies to AAV1, AAV2, AAV3, AAV4, AAV5, AAV6, AAV7, AAV8, AAV9, AAV10, AAV11, AAAV, or BAAV either as a result of natural immunological defense or from prior exposure to AAV1, AAV2, AAV3, AAV4, AAV5, AAV6, AAV7, AAV8, AAV9, AAV10, AAV11, AAAV, or BAAV vectors.

Figure 11A:
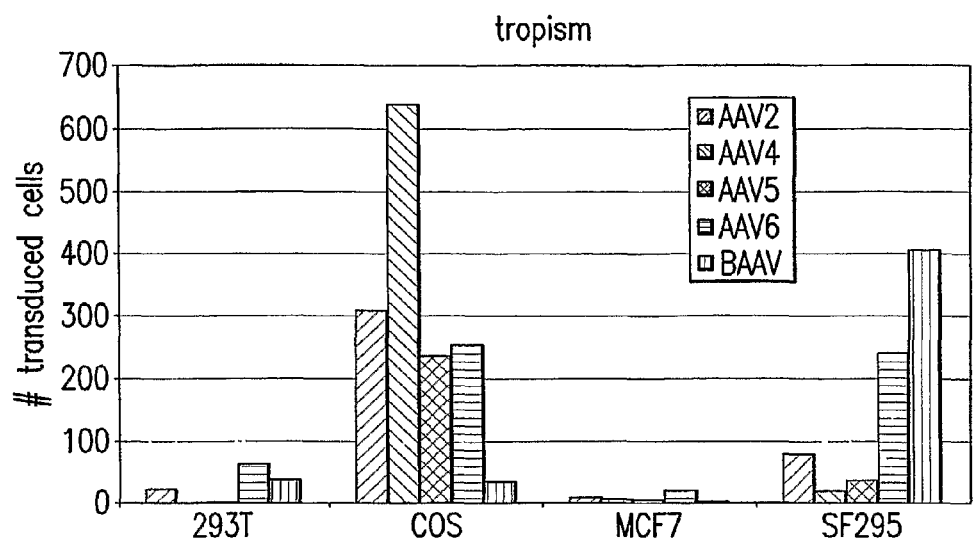
FIG. 11 shows transduction efficiency of rAAVs in cell lines. Cells were transduced with various rAAV serotypes encoding GFP. Two days after inoculation, cells were analyzed for GFP expression by flow cytometry. The transduction profiles of AAV-X1, AAV-X5, AAV-X25 and AAV-X26 were different from that of known AAVs.
Figure 11B:
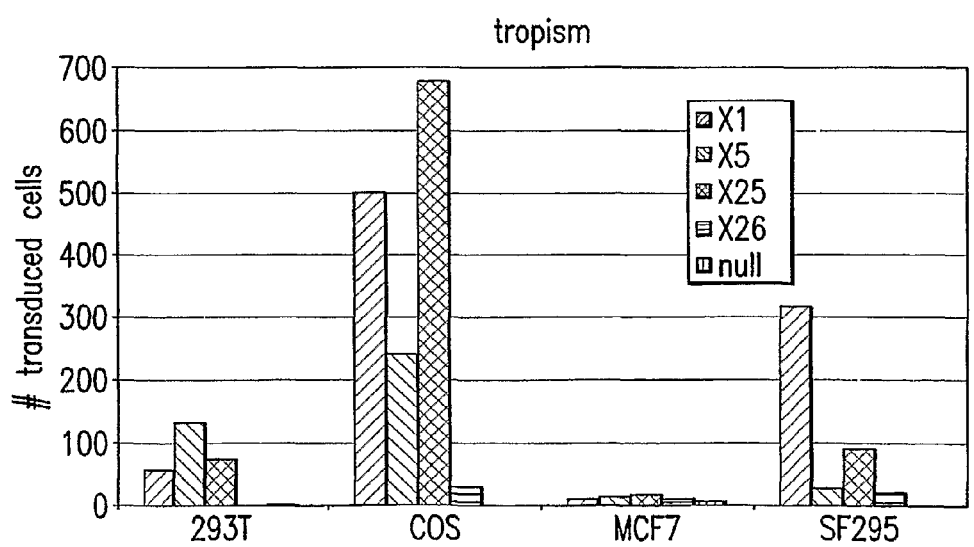

Each of the herein disclosed AAVX vectors, or vectors comprising AAVX capsid proteins, can have unique or distinct tissue tropism. As shown in FIG. 11, transduction profiles of AAV-X1, AAV-X5, AAV-X25 and AAV-X26 were different from that of known AAVs. AAVX1 and AAVX25 utilize α 2-3 link sialic acid as a cell attachment factor, whereas AAVX26 does not utilize sialic acid in the transduction process. Further, AAV12 (AAVX26) can be used to transduce cells lacking cell surface heparan sulfate or glycosphingolipids. Instead, mannosamine can be part of the AAV12 receptor or attachment.

As disclosed herein, cells that can be transduced by AAV12 include, but are not limited to, non-small cell lung cancer cells (e.g., NSCLC), (e.g., A549, EKVX, NCI-H226), colon cells (e.g., HCT-15), CNS derived cells (e.g., SF-268 and SF295), ovarian cells (e.g., IGROV1), prostate cells (e.g., PC-3), breast derived cells (e.g., T-47D), kidney cells (e.g., 293T), salivary glands (e.g., ductal cells), muscle cells.

Further, many of the AAV contaminated simian adenoviruses were originally isolated from pooled primary kidney cell cultures (Hull et al. 1957, 1956, 1958) originally established as part of a vaccine development program (VR-195, VR-197, VR-198, VR-200, VR-202, VR-209 and VR-353), but also from rectal swabs (VR-204), cervical cord (VR-355) and CNS cultures (VR-207) demonstrating that the tropism of the AAVs isolated from these adenovirus stocks include cells of kidney, cervical cord and CNS origin.

Thus, provided herein is a method of transducing a cancer cell (e.g., lung cancer cell, non-small cell lung cancer cell), colon cell, CNS derived cell, ovarian cell, prostate cell, breast derived cell, cervical cord cell, kidney cell, salivary gland cell, or muscle cell using an AAV particle disclosed herein.

Thus, provided herein is a method of delivering a nucleic acid to a cancer cell (e.g., lung cancer cell, non-small cell lung cancer cell) comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a colon cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a CNS derived cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to an ovarian cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a prostate cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a breast derived cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a cervical cord cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a kidney cell comprising administering to the cell an AAV-X1, AAV-X1b, AAV-X5, AAV-X19, AAV-X21, AAV-X22, AAV-X23, AAV-X24, AAV-X25, or AAV-X26 particle containing a vector comprising the nucleic acid inserted between a pair of AAV inverted terminal repeats, thereby delivering the nucleic acid to the cell.

Thus, provided herein is a method of delivering a nucleic acid to a salivary gland cell comprising administering to the cell an AAV12 particle containing a vector comprising the nucleic acid inserted between a pair of AAV inverted terminal repeats, thereby delivering the nucleic acid to the cell.

Thus, provided herein is a method of delivering a nucleic acid to a muscle cell comprising administering to the cell an AAV12 particle containing a vector comprising the nucleic acid inserted between a pair of AAV inverted terminal repeats, thereby delivering the nucleic acid to the cell.

Vector System

Provided herein is a vector system for producing infectious virus particles having a characteristic of AAVX. As used herein, a "vector system" is a combination of one or more vectors that, when added to an appropriate cell system, can produce a recombinant AAVX virion, as provided herein. Thus, the provided vector system comprises at least one vector comprising a nucleic acid selected from the group consisting of a pair of AAV ITRs, a nucleic acid encoding an AAV capsid protein, and a nucleic acid encoding an AAV Rep protein. In addition, it is understood that an AAV vector system comprises at least one adenovirus helper plasmid.

The vector system can comprise one or more unique AAV vectors. Thus, the vector system can comprise, for example, 1, 2, 3, 4, 5, or 6 unique AAV vectors. In a three-vector system, the first AAV vector can comprise a nucleic acid encoding an AAV capsid protein, the second AAV vector can comprise a nucleic acid encoding an AAV Rep protein, and the third AAV vector can comprise a pair of AAV ITRs (Table 3). It is understood that Rep and Cap sequences can be efficiently combined in the same vector. Thus, in an example of a two-vector vector system, the first AAV vector can comprise a nucleic acid encoding an AAV capsid protein and a nucleic acid encoding an AAV Rep protein and the second AAV vector can comprise a pair of AAV ITRs (Table 3). It is understood that at least one AAV vector in the provided AAVX vector system comprises an AAVX capsid, Rep or ITR (Table 3).

Thus, provided is an AAV vector system, wherein the first vector can comprise a nucleic acid encoding an AAVX capsid protein and the second vector can comprise a pair of AAV ITRs. The AAV ITRs of the second vector can be a pair of AAV1 ITRs. The AAV inverted terminal repeats can be a pair of AAV2 ITRs. The AAV ITRs can be a pair of AAV3 ITRs. The AAV ITRs can be a pair of AAV4 ITRs. The AAV ITRs can be a pair of AAV5 ITRs. The AAV ITRs can be a pair of AAV6 ITRs. The AAV ITRs can be a pair of AAV7 ITRs. The AAV ITRs can be a pair of AAV8 ITRs. The AAV ITRs can be a pair of AAV9 ITRs. The AAV ITRs can be a pair of AAV 10 ITRs. The AAV ITRs can be a pair of AAV 11 ITRs. The AAV ITRs can be a pair of AAAV ITRs. The AAV ITRs can be a pair of BAAV ITRs. The AAV ITRs can be a pair of AAVX ITRs.

Also provided is an AAV vector system, wherein the first vector can comprise a nucleic acid encoding an AAV capsid protein and the second vector can comprise a pair of AAVX ITRs. The capsid protein can be an AAV1 capsid protein. The capsid protein can be an AAV2 capsid protein. The capsid protein can be an AAV3 capsid protein. The capsid protein can be an AAV4 capsid protein. The capsid protein can be an AAV5 capsid protein. The capsid protein can be an AAV6 capsid protein. The capsid protein can be an AAAV Rep protein. The capsid protein can be a BAAV Rep protein. The capsid protein can be an AAVX Rep protein.

In either of the above vector systems, the first vector or a third vector can further comprise a nucleic acid encoding an AAV Rep protein. The AAV Rep protein can be AAV1 Rep protein. The AAV Rep protein can be AAV2 Rep protein. The AAV Rep protein can be AAV3 Rep protein. The AAV Rep protein can be AAV4 Rep protein. The AAV Rep protein can be AAV5 Rep protein. The AAV Rep protein can be AAV6 Rep protein. The AAV Rep protein can be AAV7 Rep protein. The AAV Rep protein can be AAV8 Rep protein. The AAV Rep protein can be AAV9 Rep protein. The AAV Rep protein can be AAV10 Rep protein. The AAV Rep protein can be AAV11 Rep protein. The AAV Rep protein can be AAAV Rep protein. The AAV Rep protein can be BAAV Rep protein. The AAV Rep protein can be AAVX Rep protein.

Also provided is an AAV vector system, wherein the first vector can comprise a nucleic acid encoding an AAVX Rep protein and the second vector can comprise a pair of AAV ITRs. The AAV ITRs of the second vector can be a pair of AAV1 ITRs. The AAV inverted terminal repeats can be a pair of AAV2 ITRs. The AAV ITRs can be a pair of AAV3 ITRs. The AAV ITRs can be a pair of AAV4 ITRs. The AAV ITRs can be a pair of AAV5 ITRs. The AAV ITRs can be a pair of AAV6 ITRs. The AAV ITRs can be a pair of AAV7 ITRs. The AAV ITRs can be a pair of AAV8 ITRs. The AAV ITRs can be a pair of AAV9 ITRs. The AAV ITRs can be a pair of AAV10 ITRs. The AAV ITRs can be a pair of AAV 11 ITRs. The AAV ITRs can be a pair of AAAV ITRs. The AAV ITRs can be a pair of BAAV ITRs. The AAV ITRs can be a pair of AAVX ITRs.

The first vector or a third vector can further comprise a nucleic acid encoding an AAV Capsid protein. The capsid protein can be an AAV1 capsid protein. The capsid protein can be an AAV2 capsid protein. The capsid protein can be an AAV3 capsid protein. The capsid protein can be an AAV4 capsid protein. The capsid protein can be an AAV5 capsid protein. The capsid protein can be an AAV6 capsid protein. The capsid protein can be an AAAV Rep protein. The capsid protein can be a BAAV Rep protein. The capsid protein can be an AAVX Rep protein.

TABLE 3

AAVX Vector Systems

| First Vector | Second Vector | Third Vector |
|---|---|---|
| AAVX capsid + AAV Rep | AAV ITR | — |
| AAV capsid + AAV Rep | AAVX ITR | — |
| AAV capsid + AAVX Rep | AAV ITR | — |
| AAVX capsid | AAV ITR | AAV Rep |
| AAV capsid | AAVX ITR | AAV Rep |
| AAV capsid | AAV ITR | AAVX Rep |

"AAV" includes: AAV1, AAV2, AAV3, AAV4, AAV5, AAV6, AAV7, AAV8, AAV9, AAV10, AAV11, AAAV, BAAV, AAV-X1, AAV-X1b, AAV-X5, AAV-X19, AAV-X21, AAV-X22, AAV-X23, AAV-X24, AAV-X25, or AAV-X26.
"AAVX" includes: AAV-X1, AAV-X1b, AAV-X5, AAV-X19, AAV-X21, AAV-X22, AAV-X23, AAV-X24, AAV-X25, or AAV-X26.

In either of the above vector systems, the second vector comprising a pair of AAV ITRs can further comprise a promoter between the ITRs. The promoter can be AAV2 p5 promoter. The promoter can be AAV5 p5 promoter. The promoter can be AAVX p5 promoter. Furthermore, smaller fragments of p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated. The promoter can be the AAVX p19 promoter. The promoter can be the AAVX p40 promoter. The promoter can be a promoter of any of the AAV serotypes. The promoter can be a constitutive promoter. Thus, the promoter can be CMV. The promoter can be RSV. The promoter can be LTR. The promoter can be eF1. The promoter can be beta actin promoter. The promoter can be a tissue specific promoter. The promoter can be an inducible promoter. The promoter can further be functionally linked to an exogenous nucleic acid.

Further provided is any of the disclosed vectors of the vector systems encapsidated into an AAV particle. The AAV particle can be an AAV1 virus particle comprising at least one AAV1 capsid protein. The AAV particle can be an AAV2 virus particle comprising at least one AAV2 capsid protein. The AAV particle can be an AAV3 virus particle comprising at least one AAV3 capsid protein. The AAV particle can be an AAV4 virus particle comprising at least one AAV4 capsid protein. The AAV particle can be an AAV5 virus particle comprising at least one AAV5 capsid protein. The AAV particle can be an AAV6 virus particle comprising at least one AAV6 capsid protein. The AAV particle can be an AAV7 virus particle comprising at least one AAV7 capsid protein. The AAV particle can be an AAV8 virus particle comprising at least one AAV8 capsid protein. The AAV particle can be an AAV9 virus particle comprising at least one AAV9 capsid protein. The AAV particle can be an AAV10 virus particle comprising at least one AAV10 capsid protein. The AAV particle can be an AAV 11 virus particle comprising at least one AAV 11 capsid protein. The AAV particle can be an AAAV virus particle comprising at least one AAAV capsid protein. The AAV particle can be a BAAV virus particle comprising at least one BAAV capsid protein. The AAV particle can be an AAVX virus particle comprising at least one AAVX capsid protein. The AAV particle can be a chimeric capsid virus particle (described above) comprising a capsid protein from more than one serotype of AAV.

EXAMPLES

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Example 1

Identification and Characterization of Novel AAV Isolates in ATCC Virus Stocks

Materials and Methods

Cell culture and virus propagation: 293T and COS cells were maintained in DMEM, supplemented with 10% FBS, 2 mM L-glutamine, 100 U/ml penicillin, and 0.1 mg/ml streptomycin or RPMI with 5% FBS. SF295, MCF7, EKVX, Igrov1, CAKI, Ovcar 5 cells were cultured in RPMI supplemented with 5% FBS, 2 mM L-glutamine, 100 U/ml penicillin, and 0.1 mg/ml streptomycin. Cells were maintained at 37° C. in a 5% $CO_2$ humidified atmosphere.

Screening for novel AAVs: 109 virus samples, obtained from the ATCC (American Type Culture Collection) as lysate of infected cells, were analyzed for the presence of AAV DNA by PCR as described earlier (Katano, H., et al. 2004. Biotechniques 36:676-80). Briefly, low molecular weight DNA was purified with High Pure Viral Nucleic Acid Kit (Roche). These DNA samples were assayed for AAV contamination by PCR using the GC Rich PCR Kit (Roche). This method detects the presence of AAV DNA by PCR using degenerative PCR primers, which were shown to amplify a fragment containing sequences of the rep and vp ORF of all known AAV serotypes. PCR using DNA isolated from ATCC VR-195, VR-197, VR-198, VR-200, VR-202, VR-204, VR-207, VR-209, VR-353, VR-355, VR-942, VR-943 as template resulted in the generation of a 1.4 kb amplification product, which was subsequently cloned using the TOPO TA Cloning KIT (Invitrogen) and sequenced with an ABI Prism 3100 Genetic Analyzer (ABI) and FS dye-terminator chemistry (ABI). The obtained sequences showed homology to AAV6 rep ORF and cap ORF but were not identical to any known AAV.

Viral DNA isolation, cloning and sequencing: The rep and cap ORF of the new AAVs was PCR amplified and subcloned. Viral DNA that was isolated from VR-195, VR-197, VR-198, VR-200, VR-202, VR-204, VR-207, VR-209, VR-353, VR-355, VR-942, VR-943 was PCR amplified with primers:

```
AAV1-4 225(+):
GCGACAKTTTGCGACACCAYGTGG    (SEQ ID NO: 31)
and

UNI-NC:
CCANNNGGAATCGCAATGCCAAT,    (SEQ ID NO: 32)
or

UNIC:
ATGNTNATNTGGTGGGAGGAGGG    (SEQ ID NO: 33)
and

AAV1-4 polyA4400(-):
CGAATNAAMCGGTTTATTGATTAAC,    (SEQ ID NO: 34)
or

AAV 4500 (+):
CAATAAACCGkkTnATTCGTkTCAGT    (SEQ ID NO: 38)
and

AAV 450 (-):
ACANNWGAGTCAGAAATKCCNGGCAG    (SEQ ID NO: 39)
```

(N can be A, C, G, or T; K can be G or T; Y can be C or T; M can be A or C)

to amplify the Rep ORF, capsid ORF, and ITR(3'-AAVX terminus, ITR and 3'-terminus of circular or concatermerized AAVs), respectively. The PCR products were subcloned using the TOPO TA Cloning KIT (Invitrogen) and at least three clones of each isolate were sequenced with an ABI Prism 3100 Genetic Analyzer (ABI) and FS dye-terminator chemistry (ABI). The obtained sequences showed homology to AAV1 and AAV6 but were not identical to any known AAV. As shown in Table 5, there are three naming conventions used herein. For example, the newly identified AAVs were named according to the ATCC adenovirus strains from which they were discovered (e.g., AAV(VR-943)). Also, each unique AAV isolate was assigned a temporary identifier (e.g., AAV-X26). Finally, . . . (e.g., AAV-12).

Identical AAV sequences were detected in VR-195, VR-197, VR-198 and VR-202 and named AAV-X1. VR-195 also contained a homolog of AAV-X1 termed AAV-X1b.

AAV detected in VR-200 was named AAV-X19. AAV detected in VR-204 was named AAV-X21. AAV detected in VR-207 was named AAV-X22. AAV detected in VR-209 was named AAV-X23. AAV detected in VR-353 was named AAV-X24. AAV detected in VR-355 was named AAV-X25. AAV detected in VR-942 was named AAV-X5. AAV detected in VR-943 was named AAV-X26. (Table 5).

Sequence analysis: DNA and protein sequence alignments were performed using the Clustal W multiple sequence alignment tool of the Biology Workbench web based software (SDSC), MacVector 7 (Oxford Molecular). The sequences amplified from ATCC virus stocks were compared to sequences in GenBank using BLAST (Basic Local Alignment Search Tool at http://www.ncbi.nlm.nih.gov/BLAST/). DNA alignments were performed using the ClustalW multiple sequence alignment tool of the Biology Workbench web based software at http://seqtool.sdsc.edu (SDSC) and MacVector 7 (Accelrys, Burlington, Mass.). Divergent amino acids in VP1 were mapped on the capsid by superimposing the VP1 sequence onto a pseudoatomic structure for AAV-6. The AAV6 crystal structure was predicted by remodeling the AAV2 capsid structure, obtained from the Virus Particle Explorer, at the Swiss-Model server with the AAV6 capsid sequence.

AAV-X17 partial ITR sequence was 98% identical to corresponding AAV2 ITR sequence. AAV-X22 partial ITR sequence was 99% identical to corresponding AAV2 ITR sequence. AAV-X25 partial ITR sequence was 96% identical to corresponding AAV1 ITR sequence. AAV-X26 was only about 80% identical to corresponding AAV2 ITR sequence. However, the TRS signal (e.g., aa 176-181 of SEQ ID NO:40) and Rep Binding site (e.g., aa 195-210 of SEQ ID NO:40) were conserved in AAV-X26 ITR as compared to the AAV2 ITR.

Generation of recombinant virus: Recombinant AAV-X1, AAV-X1b, AAV-X19, AAV-X21, AAV-X22, AAV-X23, AAV-X24, AAV-X25, AAV-X5, and AAV-X26 were generated by transfecting 293 T cells with AAV2 vector plasmid (AAV2-NLS-GFP) consisting of an GFP expression cassette flanked by AAV-2 ITRs and AAV-X1, AAV-X1b, AAV-X19, AAV-X21, AAV-X22, AAV-X23, AAV-X24, AAV-X25, AAV-X5, or AAV-X26 packaging (subcloned UNI-C/AAV1-4 polyA4400 (−) PCR fragment), an AAV-2 like Rep expression plasmid, AAV-X26_Rep, (subcloned AAV-X26 Rep ORF, AAV1-4 225 (+) and UNI-NC PCR fragment), and Ad helper plasmids, 449B, which provided the essential adenovirus functions that are required for AAV replication (Smith, R. H., et al. (2002). Biotechniques 33(1): 204-6, 208, 210-1). Two confluent T175 flasks of 293T cells were harvested, resuspended in 100 ml DMEM 10% FCS, seeded in five 150 mm plates and incubated at 37° C., 5% $CO_2$ until cells are 80% confluent (typically 48 h). Cells were transfected with 15 µg pAAV2-NLS-GFP, 10 µg AAV-X1, AAV-X1b, AAV-X19, AAV-X21, AAV-X22, AAV-X23, AAV-X24, AAV-X25, AAV-X5, or AAV-X26 packaging plasmid, 5 µg AAV-X26 Rep and 30 µg p449B. 48 h after transfection, cells were harvested, washed with PBS and resuspended in 11 ml TD buffer (0.14 M NaCl, 5.0 mM KCl, 0.7 mM $K_2HPO_4$, 25.0 mM Tris, pH7.4. Cells were lyzed by 3 freeze thaw cycles and incubated for 30 minutes at 37° C. after adding benzonase to a final concentration of 20 U/ml sodium deoxycholate (final concentration of 0.5%). After adding 0.55 g/ml CsCl, the lysate was fractionated using density gradient centrifugation in a SW41 rotor for 48 h at 38,000 rpm. The gradients were harvested in 0.5 ml aliquots. Aliquots were assayed for infectivity and DNase-resistant genome copy titers of the vector preparations were determined by quantitative real-time PCR using the TAQMAN system (Applied Biosystems, Inc. (ABI), Foster City, Calif.) with probes specific to the CMV promoter.

Recombinant virus was successfully generated using each of the AAVX packaging plasmids with AAV2 ITR vector plasmids and AAV-X26 rep plasmids. Recombinant virus was also successfully generated using Rep plasmids derived from each of the AAVX viruses in combination with AAV2 ITR vector plasmids. There is therefore sufficient homology between AAVX and AAV2 Rep and ITR sequences that they can be used interchangeably in the herein provided vectors and vector systems.

Neutralization assay: Exponentially growing COS cells were plated at a density of 5×103/well in a flat-bottom 96-well plate. Twenty-four hours after seeding, cells were incubated for 60 min with 2×106 rAAV particles that were pre-incubated with serial dilutions of pooled human IgGs (Immune Globuline Intravenous, 10%, Gamunex, BAYER, Leverkusen, Germany). Twenty-four hours after infection, cells were analyzed for GFP expression with the Guava PCA-96 (Guava Technologies, Hayward, Calif.) fluorescent cell counter. GFP expression was used as a surrogate marker for transduction efficiency.

Determination of tissue tropism: Transduction efficiency of recombinant AAV-X1, AAV-X1b, AAV-X19, AAV-X21, AAV-X22, AAV-X23, AAV-X24, AAV-X25, AAV-X5, or AAV-X26 vector containing an expression cassette for GFP was analyzed in cancer cell lines. Cells were infected with dilutions ranging from $10^6$ to $10^9$ particles/well. 24-48 h after infection, cells were analyzed for GFP expression by flow cytometry.

Neuraminidase treatment: To analyze if sialic acid is required for transduction of AAV-X1 and AAV-X25, neuraminidases were used to digest cell surface sialic acid before infection. Cos cells were seeded at 5,000 cells/well in a 96 well plate. 24 h after seeding, cells were incubated for 60 min with a broad spectrum neuraminidase from *Arthrobacter ureafaciens* (0.05-1 U/ml) or a 2-3 linkage specific neuraminidase from *S. pneumoniae* (0.04-0.2 U/ml) (Calbiochem, La Jolla, Calif.). Cells were washed and transduced with a multiplicity of infection (MOI) of 500 with recombinant AAV6, AAV-X1 or AAV-X25 particles expressing GFP. Cells were analyzed for GFP expression by flow cytometry with the Guava PCA-96 (Guava Technologies) 24 h after transduction.

Binding assay: COS cells were seeded at 5000 cells/well in a 96-well plate. Forty-eight hours after seeding, cells were incubated for 60 min at 37° C. with neuraminidases from *A. ureafaciens* (0.1 U/ml), *S. pneumoniae* (0.08 U/ml) (Calbiochem) or mock. Cells were then chilled for 30 min at 4° C. and then incubated for 60 min at 4° C. with 5×$10^7$ recombinant AAV6, AAV(VR-195), or AAV(VR-355) particles expressing GFP. Cells were then washed twice with cold medium and phosphate buffered saline (PBS) and lysed in 50 μl PCRnGo buffer (Pierce). Copy numbers of cell-associated vector genomes in the cell lysates were determined by quantitative real-time PCR using the TAQMAN system (Applied Biosystems) with probes specific to the CMV promoter.

Lectin competition: COS cells were seeded at 5,000-10,000 cells/well in a 96 well plate. 16-24 h after seeding, cells were precubated for 30 min at 4° C. with 100 μg/ml of either ConA, MalII, LCA, ECL, WGA, UEA I, DBA, PNA, SBA, GSL I, PSA, LCA, PHA-E, PHA-L, SJA, succinylated WGA. Subsequently, cells were washed and transduced for 60 min at 4° C. with 3000 transducing units or $10^8$ recombinant AAV-2, AAV-4, AAV-5, AAV-6, BAAV, AAV-X1, AAV-X5, AAV-X25 or AAV-X26 particles expressing GFP in 50 μl medium supplemented with lectins (100 μg/ml). 24 h after transduction, cells were analyzed for GFP expression by flow cytometry.

Sugar competition: COS cells were seeded at 5,000 cells/well in a 96 well plate. 24 h after seeding, cells were precubated for 30 min at 4° C. before being transduced for 60 min at 4° C. with $10^8$ recombinant AAV-2, AAV-4, AAV-5, AAV-6, BAAV, AAV-X1, AAV-X5, AAV-X25 or AAV-X26 particles expressing GFP in 50 μl medium supplemented with various sugars (see FIG. 9). 24 h after transduction, cells were analyzed for GFP expression by flow cytometry.

Heparin competition assay: COS cells were plated at a density of 5×$10^3$/well in a flat-bottom 96-well plate. After 24 h, $10^7$ particles rAAV6-NLS-GFP, rAAV(VR-195)-NLS-GFP and rAAV(VR-355)-NLSGFP were preincubated for 1 h at room temperature in medium containing 0 to 2000 μg/ml heparin (Sigma, St. Louis, Mo.). Cells were then transduced for 1 h at 37° C. with this preincubation mixture, washed with medium and incubated for 24 h. GFP expression was detected with a fluorescent cell counter (Guava Technologies).

NaCl competition assay: COS cells were seeded at 5,000 cells/well in a 96 well plate. 24 h after seeding, were transduced for 60 min at 37° C. with MOI of 500 or $10^8$ recombinant AAV-2, AAV-4, AAV-5, AAV-6, BAAV, AAV-X1, AAV-X5, AAV-X25 or AAV-X26 particles expressing GFP in 50 μl medium supplemented with NaCl to 150 mM, 300 mM, and 450 mM final NaCl concentration. 24 h after transduction, cells were analyzed for GFP expression by flow cytometry/fluorescent cell counter (Guava Technologies).

Viral cross-competition: COS cells were plated at a density of 5×$10^3$/well in a flat-bottom 96-well plate. After 24 h, cells were preincubated for 1 h at 37° C. with increasing titers of rAAV6-lacZ, an AAV6 derived vector expressing a nuclear localized β-galactosidase, ranging from 0 to 2.6×$10^9$ particles/well. The cells were then washed with medium and transduced for 45 min with 2×$10^6$ particles of rAAV2-NLS-GFP, rAAV6-NLS-GFP, rAAV(VR-195)-NLS-GFP, or rAAV(VR-355)-NLS-GFP. GFP expression was analyzed 48 h after transduction by flow cytometry.

Results

Identification of AAV contaminations in ATCC virus isolates: Viral stocks, supplied by the ATCC were analyzed for the presence of AAV DNA by a PCR based assay as described earlier (Katano, H., et al. 2004). PCR primers in this study were designed to bind to highly conserved regions in the rep and cap ORFs resulting in amplification of a 1.5 kb fragment spanning from nucleotide 1437 to 2904 relative to the AAV-2 genome. This method is highly sensitive and can detect as few as 10 copies of viral DNA/μL of sample (Katano, H., et al. 2004). AAV DNA was detected in 13/137 samples analyzed (Table 4). AAV contaminations were detected in 26% of adenovirus isolates. Interestingly, no AAV was detected in herpesvirus, retrovirus, coronavirus, orthomyxovirus, poxvirus, or reovirus stocks. Many of the AAV contaminated simian adenoviruses were originally isolated from pooled primary kidney cell cultures (Hull, R. N., et al. 1957; Hull, R. N., et al. 1958; Hull, R. N., et al. 1956) originally established as part of a vaccine development program (VR-195, VR-197, VR-198, VR-200, VR-202, VR-209, and VR-353), but also from rectal swabs (VR-204), cervical cord (VR-355), and CNS cultures (VR-207). AAV was also detected in stocks of human adenovirus type 9 (VR-10) as well as in bovine adenovirus type 1 (VR-313) and type 2 (VR-314). Ten of theses isolates have high similarity to AAV1 and AAV6 (>98%), while AAV-X5 isolated from VR-942 and AAV-X26 isolated from VR-943 showed highest homology in the capsid protein VP-1 to AAV-3B (93%) and AAV-11 (83%) respectively.

Construction of packaging plasmids and generation of recombinant virus: The entire coding region for Rep and Cap of the AAV contaminations detected in VR-195 and VR-355 termed AAV(VR-195) and AAV(VR-355), respectively, as well as the capsid ORF under control of the viral P40 promoter from the adenovirus isolates VR-10, VR-195, VR-197, VR-198, VR-200, VR-202, VR-209, VR-353, VR-204, VR-355, and VR-207 were PCR amplified and subcloned to generate packaging plasmids.

TABLE 4

Screening of viral samples for the presence of AAV

| Family | # tested | # AAV positive | frequency (%) |
|---|---|---|---|
| Adenovirida | 53 | 13 | 26% |
| primate Adenovirida | 16 | 13 | 81% |
| Herpesviridae | 43 | 0 | 0 |
| Coronaviridae | 9 | 0 | 0 |
| Retrovirida | 15 | 0 | 0 |
| Reoviridae | 4 | 0 | 0 |
| Orthomyxovirida | 4 | 0 | 0 |

Recombinant AAV was produced by cotransfecting plasmids encoding the capsid of the novel AAVs, an AAV type 2 Rep expression plasmid, an AAV-2 vector plasmid, encoding a nuclear localized GFP together with an adenovirus helper plasmid. Recombinant viruses were then assayed for transduction activity. Capsid plasmids encoding functional VP proteins were sequenced on both strands. Several clones of each isolate were analyzed. GenBank accession numbers are as follows: AAV(VR-195): DQ180604 (SEQ ID NO:1) and AAV(VR-355): DQ180605 (SEQ ID NO:9).

The evolutionary relationship among mammalian AAVs and the AAV contaminants detected in human and non-human primate adenovirus stocks was analyzed by ClustalW alignments of VP1 amino acid sequences and plotted as a rooted phylogenetic tree (FIG. 1). All AAVs detected in simian adenovirus stocks displayed at least 96% homology on the DNA level and 98% identity in the capsid amino acid sequence to either AAV1, AAV6, or to each other. The amino acid sequence of VP1 encoded by AAV contaminants in VR-197, VR-198, and VR-202 were identical to each other but distinct from AAV1 and AAV6. The VP1 sequence of the only positive human adenovirus stock, VR-10 (adenovirus type 9), was greater than 99.9% identical to AAV2.

AAV-X1(97%, 99%), AAV-X1B (96%, 98%), AAV-X19 (97%, 99%), AAV-X21(97%, 99%), AAV-X22 (97%, 99%), AAV-X23(97%, 98%), AAV-X24(97%, 97%), and AAV-X25 (97%, 98%) share 96-99% sequence identity to AAV6 or AAV1 at the DNA level (based on a 3 kb partial genome fragment) (see FIG. 1). Numbers in brackets indicate identities to AAV6 and AAV1. The amino acid sequence of AAV-X5 capsid protein shows highest homology to AAV-3B (93%), and AAV-X26 capsid protein shows highest homology to AAV-11 (83%). AAV-X5 and AAV-X26 DNA sequences show highest homology to AAV-3 (88%) and AAV-11 (79%) respectively (based on a 3 kb partial genome fragment) (see FIG. 1).

Mapping of sequence variation: AAV contaminations, which were greater than 98% identical to AAV6 in the amino acid sequence of the capsid protein VP1, were detected in 10 adenovirus isolates. AAV-X5 isolated from VR-942 and AAV-X26 isolated from VR-943 showed homology (sequence similarity) in the capsid protein VP1 to AAV-3B (93%) and AAV-11 (83%), respectively, and only low homology to AAV6 (87% and 61%, respectively). AAV-X5 and AAV-X26 are therefore very different from the other new AAVs disclosed herein. The capsid protein VP1 of AAV(VR-195) and AAV(VR-355) differs in 7 or 6 amino acids, respectively, from that of AAV6 (Table 5). To identify the location of the amino acids that are unique for AAV(VR-195) and AAV(VR-355) within the capsid, we superimposed the AAV(VR-195) and AAV(VR-355) VP1 sequence onto a pseudoatomic structure for AAV-6. Divergent regions in the capsid proteins are located on exposed surface loops at the threefold axis of symmetry, an area of the capsid that has been associated with receptor binding (Kern, A., et al. 2003; Opie, S. R., et al. 2003). AAV(VR-195) specific amino acids of three different VP3 subunits were clustered in close proximity. AAV(VR-355) specific changes relative to AAV6 were similarly organized. Since the amino acid changes among AAV(VR-195), AAV(VR-355), and AAV6 are surface exposed, we hypothesized they may effect antigenicity or cell tropism.

TABLE 5

Novel AAVs were isolated from ATCC adenovirus samples

| Name | A.K.A. | Isolated from | Classification | Family |
|---|---|---|---|---|
| AAV-X1, AAV-X1b | AAV(VR-195) | VR-195 | Simian virus 1 | Adenovirida |
| AAV-X1 | AAV(VR-197) | VR-197 | Simian virus 15 | Adenovirida |
| AAV-X1 | AAV(VR-198) | VR-198 | Simian virus 17 | Adenovirida |
| AAV-X19 | AAV(VR-200) | VR-200 | Simian virus 23 | Adenovirida |
| AAV-X1 | AAV(VR-202) | VR-202 | Simian virus 27 | Adenovirida |
| AAV-X21 | AAV(VR-204) | VR-204 | Simian virus 31 | Adenovirida |
| AAV-X22 | AAV(VR-207) | VR-207 | Simian virus 34 | Adenovirida |
| AAV-X23 | AAV(VR-209) | VR-209 | Simian virus 37 | Adenovirida |
| AAV-X24 | AAV(VR-353) | VR-353 | Simian virus 39 | Adenovirida |
| AAV-X25 | AAV(VR-355) | VR-355 | Simian virus 38 | Adenovirida |
| AAV-X5 | AAV(VR-942) | VR-942 | Simian adenovirus 17 | Adenovirida |
| AAV-X26 | AAV(VR-943) AAV-12 | VR-943 | Simian adenovirus 18 | Adenovirida |

TABLE 6

Comparison of the amino acid sequence of VP1

| | 162 | 198 | 327 | 386 | 418 | 495 | 514 | 531 | 584 | 590 |
|---|---|---|---|---|---|---|---|---|---|---|
| AAV6 | T | V | *N* | *Q* | D | D | R | K | L | D |
| AAV(VR-195) | T | V | S | *Q* | E | G | H | E | F | H |
| AAV(VR-355) | S | L | *N* | K | E | D | R | E | F | D |

Numbers on top indicate the amino acid in AAV6 VP1, where either AAV(VR-195) or AAV(VR-355) diverges from AAV6.
Bold are basic amino acids:
Outlined are acidic;
Italic are polar or slightly acidic;
Underlined are aromatic.

Figure 2:
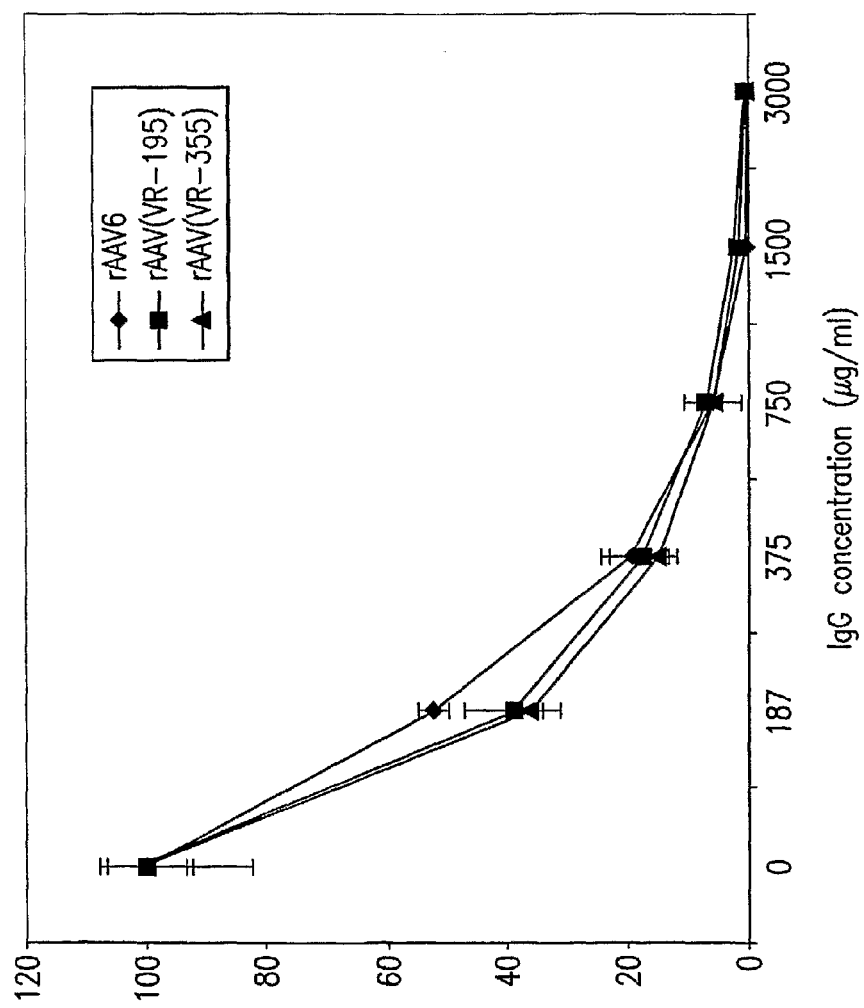
FIG. 2 shows rAAV6, rAAV(VR-195), and rAAV(VR-355) are neutralized by pooled human IgGs. COS cells were transduced with a pre-incubation mixture consisting of rAAV-6, rAAV(VR-195), and rAAV(VR-355) expressing GFP and human IgGs at the indicated concentrations. Twenty-four hours post-inoculation, transduction was analyzed by flow cytometry and graphed as percent transduction of the untreated control. Values are means from three experiments; error bars represent standard deviations.

Immunological characterization: To test for a difference in the immunological response to the isolates, IgGs purified from pooled human serum were assayed to determine if they contained neutralizing antibodies against the recombinant AAVs and whether a difference in the neutralization activity against either AAV6, AAV(VR-195) or AAV(VR-355) existed (FIG. 2). In this assay, all three viruses displayed similar sensitivity to neutralization with the purified pooled IgGs. Thus, the changes in the capsid of AAV(VR-195) or AAV(VR-355) compared to AAV6 and do not appear to alter their sensitivity to neutralization by human serum.

Figure 3:
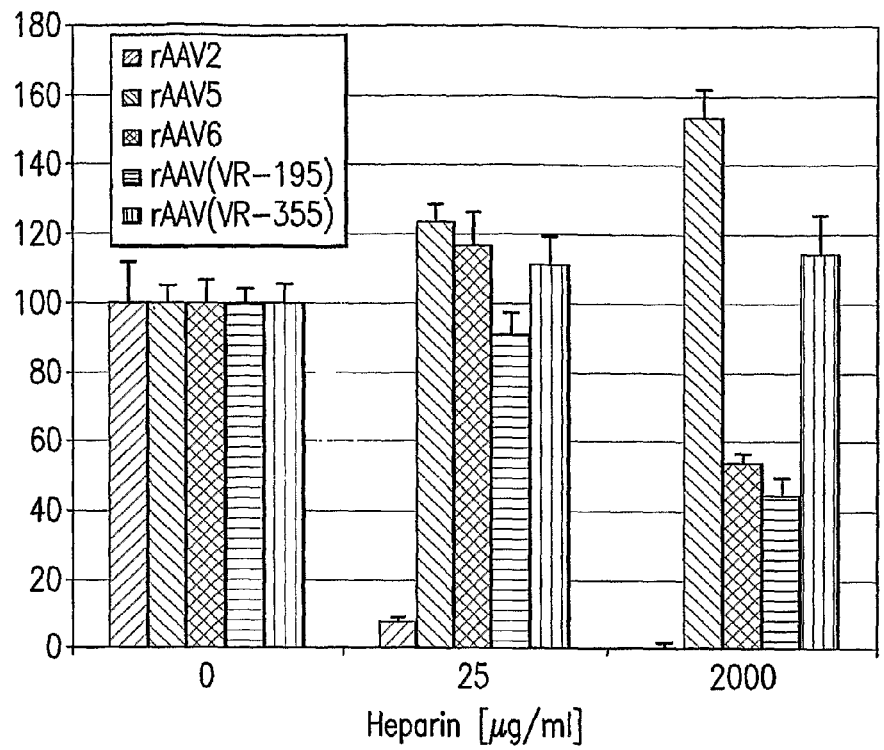
FIG. 3 shows inhibitory effect of heparin on of COS cell transduction. COS cells were transduced with a pre-incubation mixture consisting out of rAAV2, rAAV5, rAAV6, rAAV (VR-195), and rAAV(VR-355) expressing GFP and heparin at the indicated concentrations. 24 h post-inoculation, transduction was analyzed by flow cytometry. Values are means from three experiments; error bars represent standard deviations.

Heparin competition: Heparan sulfate, a ubiquitous cell surface glycosaminoglycan, is an attachment receptor for AAV2 (Summerford, C., et al. 1998). AAV2 transduction can be inhibited by heparin, a heparan sulfate analog. Like AAV2, AAV6 can be purified using a heparin affinity column; however, transduction is not inhibited by a low heparin concentration, indicating that heparan sulfate does not act as an AAV6 receptor (Halbert, C. L., et al. 2001). To investigate the role of heparan sulfate in AAV(VR-195) or AAV(VR-355) transduction, competition transduction experiments were performed with increasing amounts of heparin. At low concentrations of heparin (25 µg/ml), AAV2 was the only rAAV that was inhibited (FIG. 3). However, at 2000 µg/ml, approximately 50% inhibition of AAV6 and AAV(VR-195) was observed. No inhibition was observed with either AAV(VR-355) or AAV5. Therefore, heparan sulfate does not appear to be a co-receptor for either AAV(VR-195) or AAV(VR-355).

Figure 4:
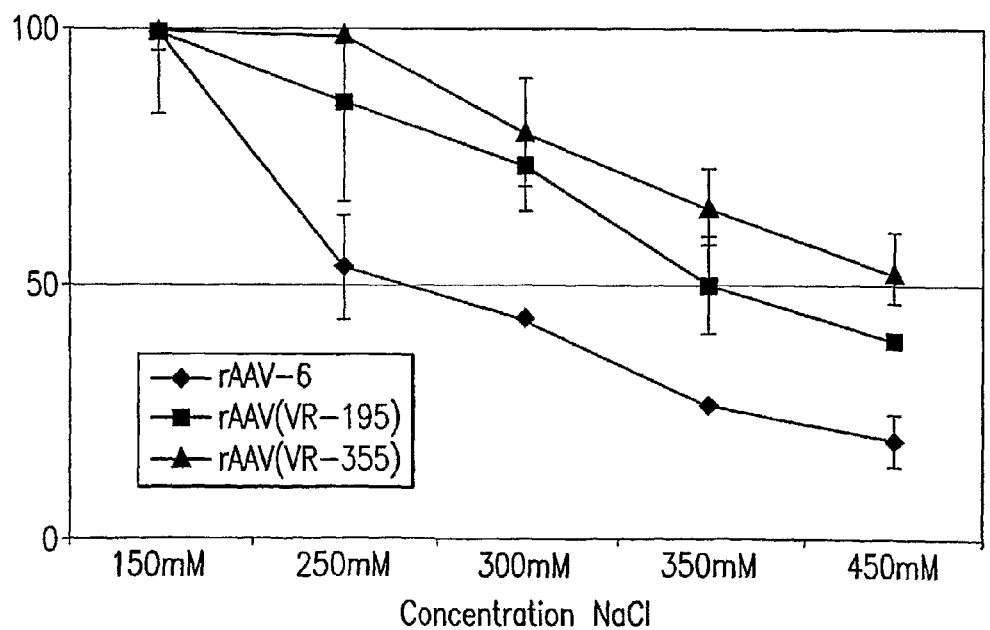
FIG. 4 shows charge-dependency of AAV6, rAAV(VR-195), and rAAV(VR-355) transduction of COS cells. COS cells were transduced with rAAV6, rAAV(VR-195), and rAAV(VR-355) in medium containing the indicated concentrations of NaCl. Twenty-four hour postinoculation, transduction was analyzed by flow cytometry. Values are means from three experiments; error bars represent standard deviations

AAV6 and AAV(VR-195) transduction is charge sensitive: Heparin is a highly charged molecule. The observed inhibition of AAV6 and AAV(VR-195) at high concentrations of heparin could be caused by a charge driven interaction between the viruses and heparin rather than a specific interaction. Increasing the ionic strength in the medium during transduction can minimize charge dependent interactions (Amberg, N., et al. 2002). Salt ions can bind to charged groups on the cell surface and virus capsid, thereby reducing these electrostatic interactions. To analyze if AAV6, AAV(VR-195), and AAV(VR-355) transduction is charge dependent, the ionic strength was increased during transduction by adjusting the NaCl concentration in the tissue culture medium from 150 mM up to 450 mM. Transduction of rAAV-6, rAAV(VR-195), and rAAV(VR-355) was inhibited to different amounts by increasing concentrations of NaCl (FIG. 4). While 250 mM NaCl was sufficient to inhibit rAAV6 by 50%, higher NaCl concentrations were required to inhibit AAV(VR-195) and AAV(VR-355) with IC50 of 350 mM and 450 mM respectively. The relative dependence on charge follows the inhibition of these viruses by heparin and indicates that the inhibition of AAV6 and AAV(VR-195) by heparin is charge dependent.

Figure 5A:
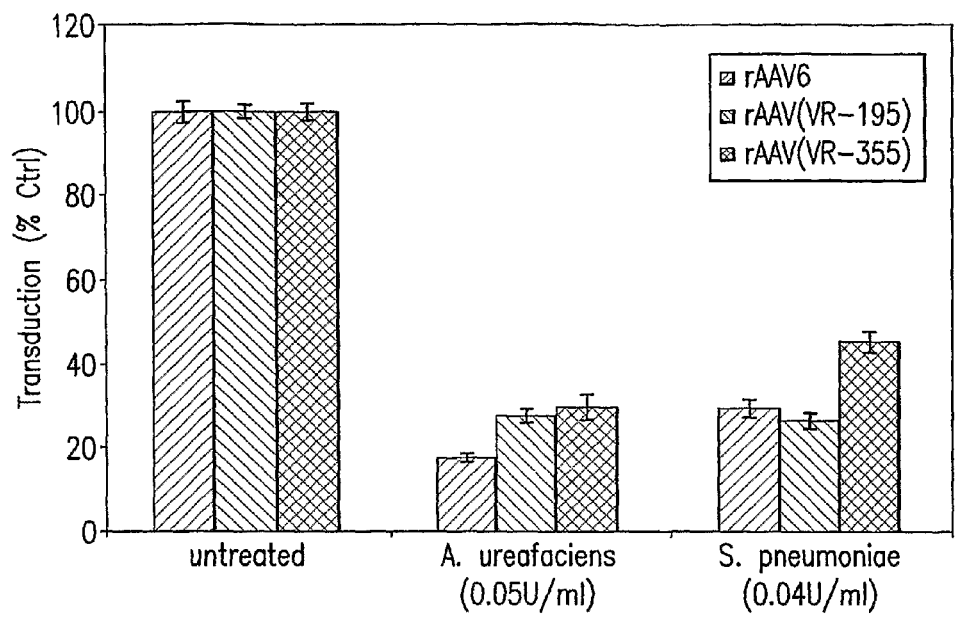
FIG. 5A shows gene transfer mediated by rAAV6, rAAV(VR-195), and rAAV(VR-355) expressing GFP in COS cells, following neuraminidase pretreatment.
Figure 5B:
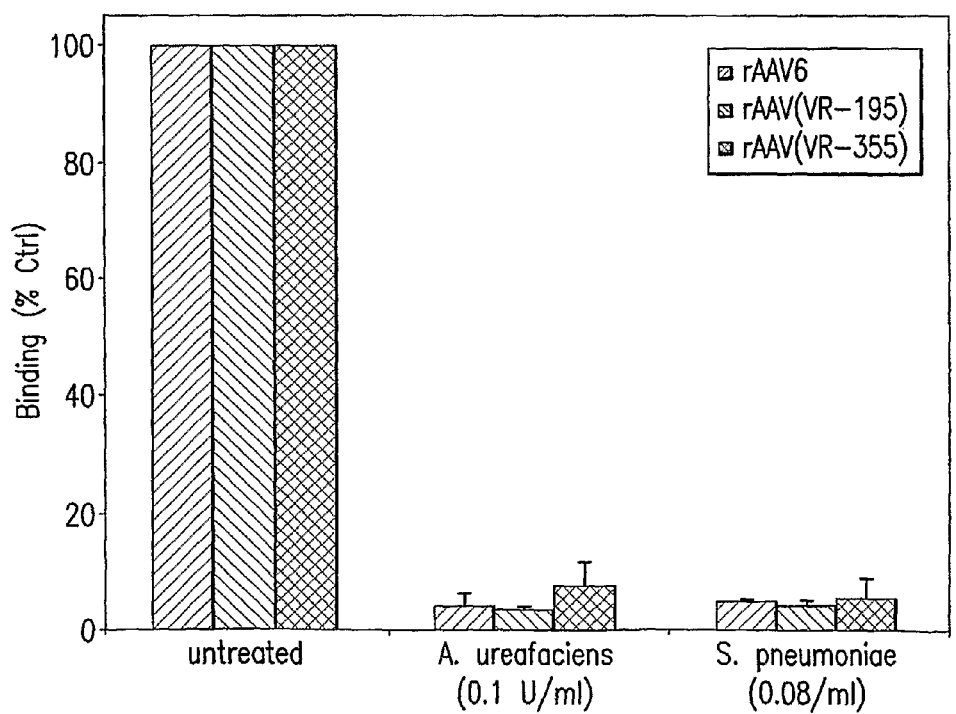
FIG. 5B shows binding. Values are means from three experiments; error bars represent standard deviations

Effect of neuraminidase treatment on rAAV transduction and virus binding: Dependent parvoviruses are also reported to use sialic acid as a co-receptor for binding and transduction (Kaludov, N., et al. 2001; Seiler, M. P., et al. 2002; Walters, R. W., et al. 2001). To analyze if sialic acid is required for transduction with AAV(VR-195) and AAV(VR-355) vectors, the effect of the removal of cell surface sialic acids was studied by neuraminidase treatment on transduction (FIG. 5A) and virus binding (FIG. 5B). Treating COS cells with a broad-spectrum neuraminidase from *A. ureafaciens* inhibited rAAV6, rAAV(VR-195), and rAAV(VR-355) transduction 3-5 fold. Neuraminidase isolated from *S. pneumoniae* will only remove α 2-3 linked sialic acid. Treatment of the cells with this enzyme again inhibited transduction with all three rAAVs. Removal of cell surface sialic acids with neuraminidases from *A. ureafaciens* or *S. pneumoniae* also resulted in a greater than 90% reduction in cell binding of rAAV6, rAAV(VR-195) and rAAV(VR-355), indicating that these viruses utilize α 2-3 link sialic acid as an cell attachment factor.

Figure 6:
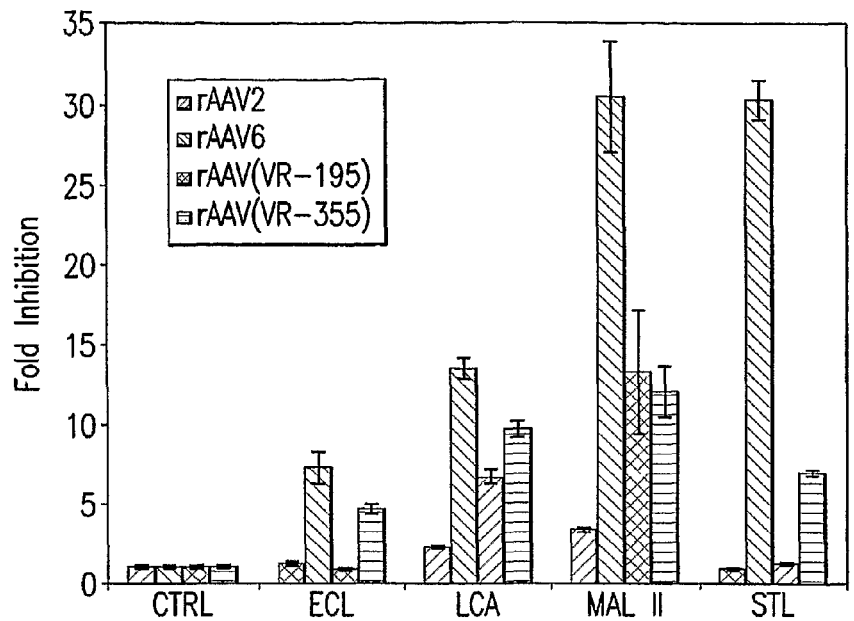
FIG. 6 shows effects of lectins on rAAV6, rAAV(VR-195), and rAAV(VR-355) transduction of COS cells. After pre-incubation with ECL, LCA, MalII or STL, COS cells were transduced with rAAV-6, rAAV(VR-195), and rAAV(VR-355) expressing GFP in the presence of the indicated lectin. Twenty-four hour post-inoculation, transduction was analyzed by flow cytometry. Values are means from two experiments done in duplicate; error bars represent standard deviations.

AAV6, AAV(VR-195), and AAV(VR-355) can be distinguished based upon lectin competition: Lectins are proteins that recognize and bind oligosaccharides conjugated to proteins and lipids and can be used to block virus binding (Summerford, C., et al. 1998). MalII, a lectin that recognizes α 2-3 linked sialic acid, inhibited transduction of rAAV-6, rAAV(VR-195), and rAAV(VR-355) (FIG. 6).

Many glycoproteins contain a core oligosaccharide structure which includes α-linked mannose. To study, if these "high-mannose" proteins play a role in AAV-X1 or AAV-X25 transduction, these proteins were blocked with ConA, a lectin that recognizes α-linked mannose. AAV-6, AAV-X1 or AAV-X25 were blocked equally by ConA, indicating that proteins with a mannose core are involved in binding and/or uptake. Lens Culinaris Agglutinin (LCA) recognizes α-linked mannose together with neighboring oligosachharides. It is less broad specific than ConA. LCA inhibited all recombinant viruses tested and had an approximately twofold higher inhibitory potential on rAAV6 than on rAAV(VR-195) or rAAV(VR355). ECL is a lectin specific toward galactose residues and had the highest binding activity toward galactosyl (β-1,4) N-acetylglucosamine. ECL blocked AAV-X1 mediated transduction less specific than AAV-6 or AAV-X25. While ECL, which recognizes α-mannose in conjugation with galactosyl (β-1,4) N-acetylglucosamine, did not inhibit rAAV(VR-195), it reduced rAAV6 and rAAV(VR-355) transduction 7 and 5-fold, respectively. STL, which recognizes Nacetylglucosamine, did not inhibit rAAV(VR-195), but reduced rAAV6 and rAAV(VR-355) transduction 30 and 12-fold, respectively. These results indicate that while all three viruses bind terminal α 2-3 linked sialic acid, the amino acid changes on the capsid surface affected the cell binding activity of each isolate.

These differences observed between AAV-6, AAV-X1 and AAV-X25 in lectin competition experiments and NaCl competition indicates utilization of different receptors or differences in receptor interaction that can result in a different cell tropism of vectors based on these isolates. The transduction efficiency of AAV-6, AAV-X1 and AAV-X25 based vectors were therefore analyzed in human cancer cell lines (FIG. 9). Each recombinant virus has a unique transduction profile indicating that they bind to different receptors or interact differently with a common receptor.

AAV-X5 isolated from VR-942 and AAV-X26 isolated from VR-943 showed homology (sequence similarity) in the capsid protein VP1 to AAV-3B (93%) and AAV-11 (83%), respectively, and only low homology to AAV6 (87% and 61%, respectively). AAV-X5 and AAV-X26 are therefore very different from the other new AAVs disclosed herein. To study the attachment factors that are involved in AAV-X5 and AAV-X26 mediated transduction, competition with various carbohydrates was analyzed (FIG. 10). Heparin is a known attachment factor/receptor for AAV2 and addition of Heparin and homolog sugars to the medium during transduction resulted in an inhibition of AAV-2 mediated gene transfer. Heparin had no effect on AAV-X5 and AAV-X26 mediated gene transfer demonstrating that extracellular heparin can not block AAV-X5 and AAV-X26 mediated gene transfer. Heparin and related carbohydrates do not appear to have receptor function for these viruses.

Figure 7:
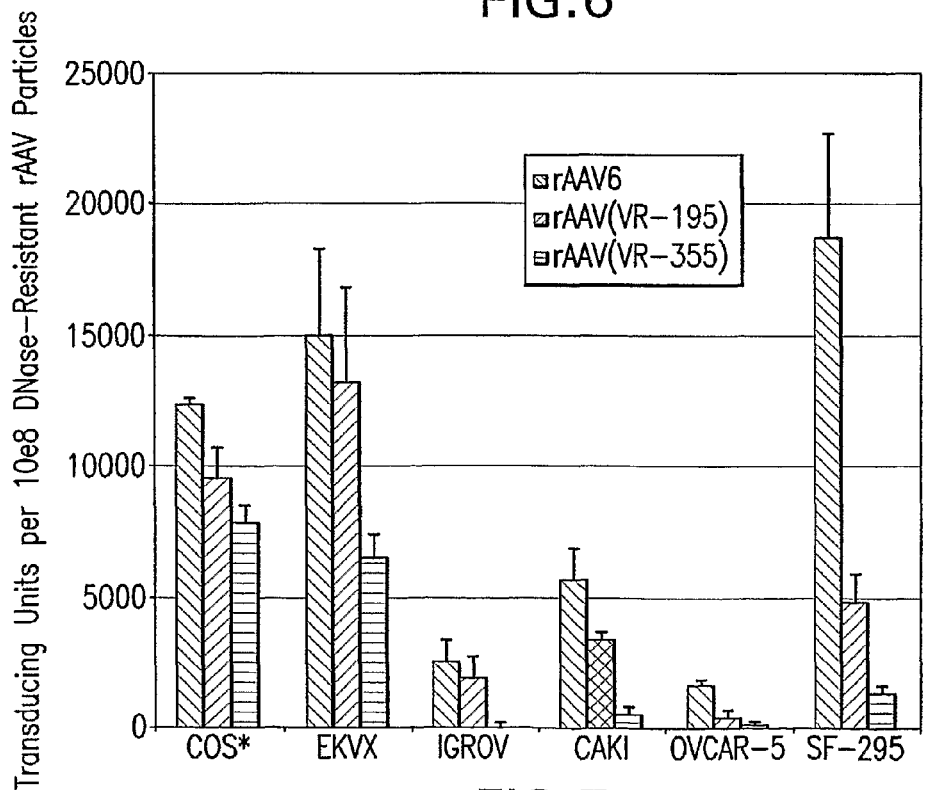
FIG. 7 shows transduction efficiency in human cancer cell lines. The indicated cell lines were transduced with $1 \times 10^8$ particles of rAAV6, rAAV(VR-195), and rAAV(VR-355) expressing a nuclear localized GFP. Twenty-four hour post-inoculation, transduction was analyzed by flow cytometry. Values are means from three experiments; error bars represent standard deviations. * COS cells transduction is given as transducing units/$2 \times 10^7$ particles.
Figure 9A:
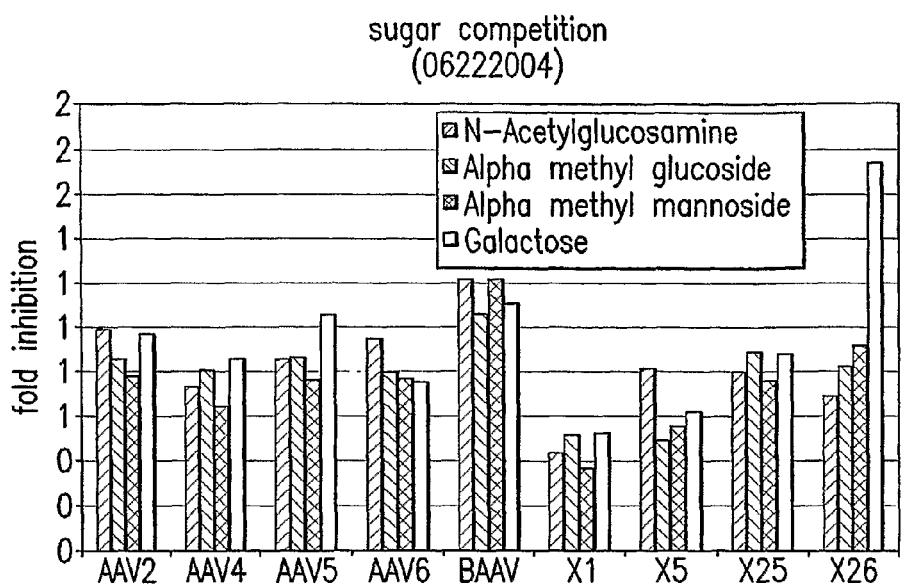
FIG. 9 shows effects of sugars on rAAV mediated transduction. Cos cells were transduced with GFP encoding rAAVs that were pre-incubated with various sugar monomers and polymers. 24 h post-inoculation, transduction was analyzed by flow cytometry. Heparin is the attachment factor for AAV2 that mediates initial binding of AAV2 to the cell. Extracellular heparin binds to the virus and blocks the attachment of the virus to the cell. None of the sugars tested blocked transduction of AAV-X1, AAV-X5, AAV-X25 or AAV-X26.
Figure 9B:
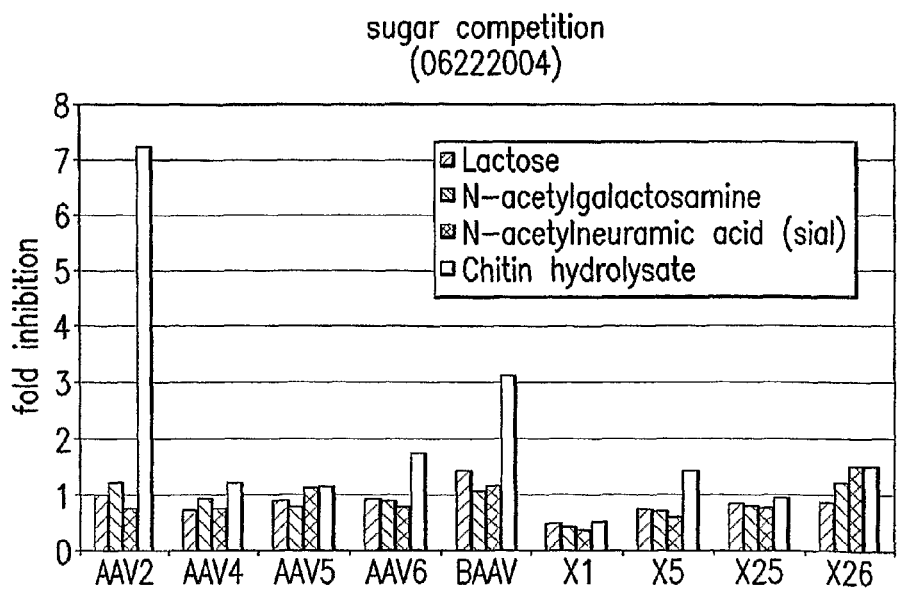
Figure 9C:
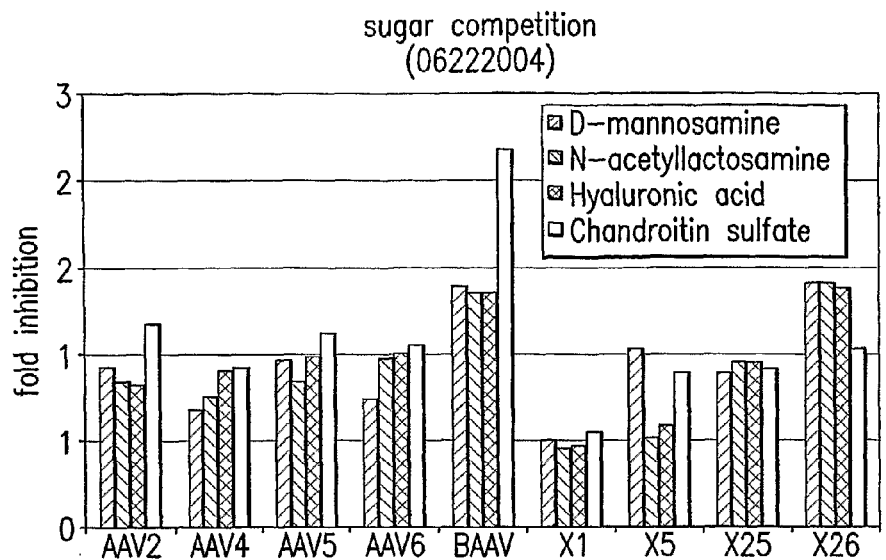
Figure 9D:
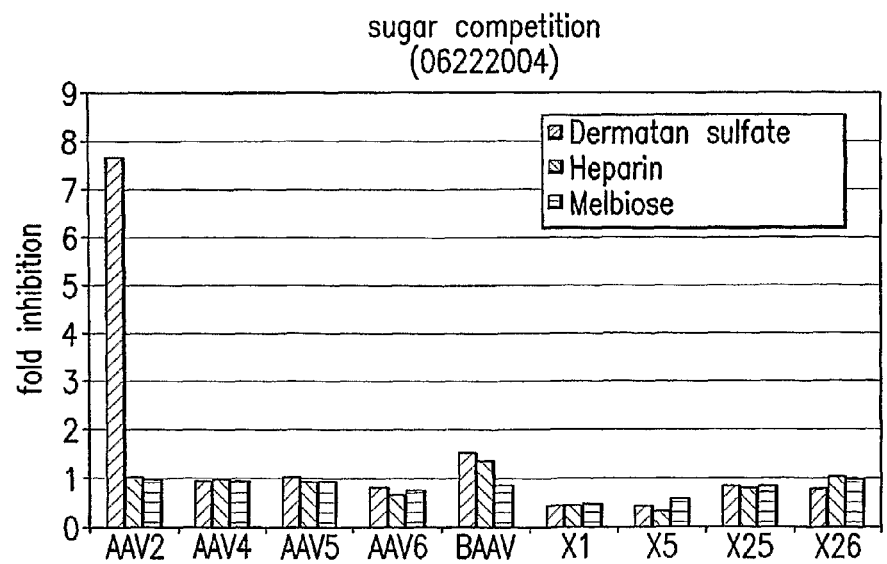
Figure 10A:
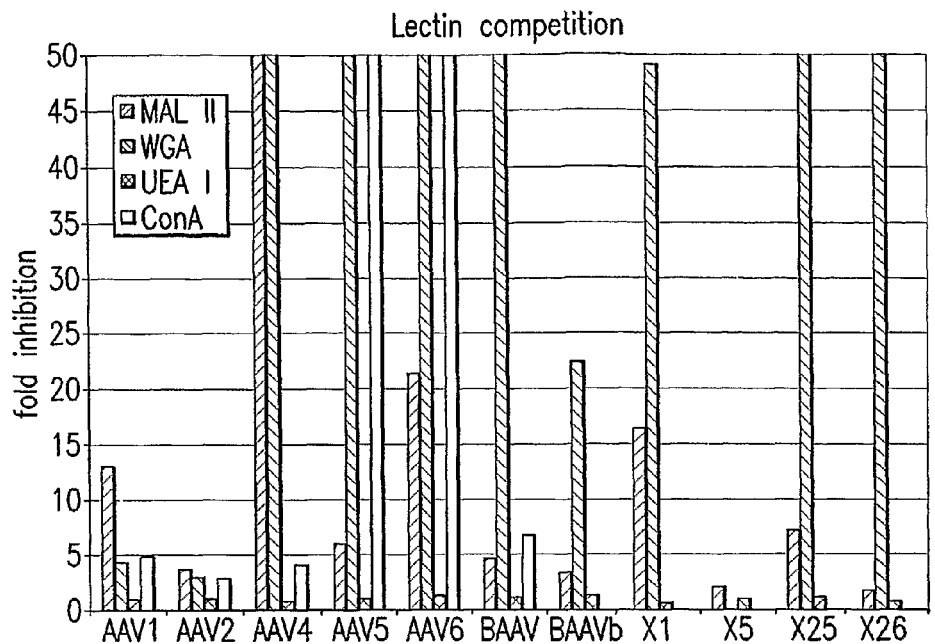
FIG. 10 shows effects of lectins on rAAV transduction of COS cells. After pre-incubation with various lectins, COS cells were transduced with rAAV-6, AAV-X1 and AAV-X25 expressing GFP in the presence of the indicated lectin. 24 h post-inoculation, transduction was analyzed by flow cytometry. All AAVs have a distinct profile on the lectin panel.
Figure 10B:
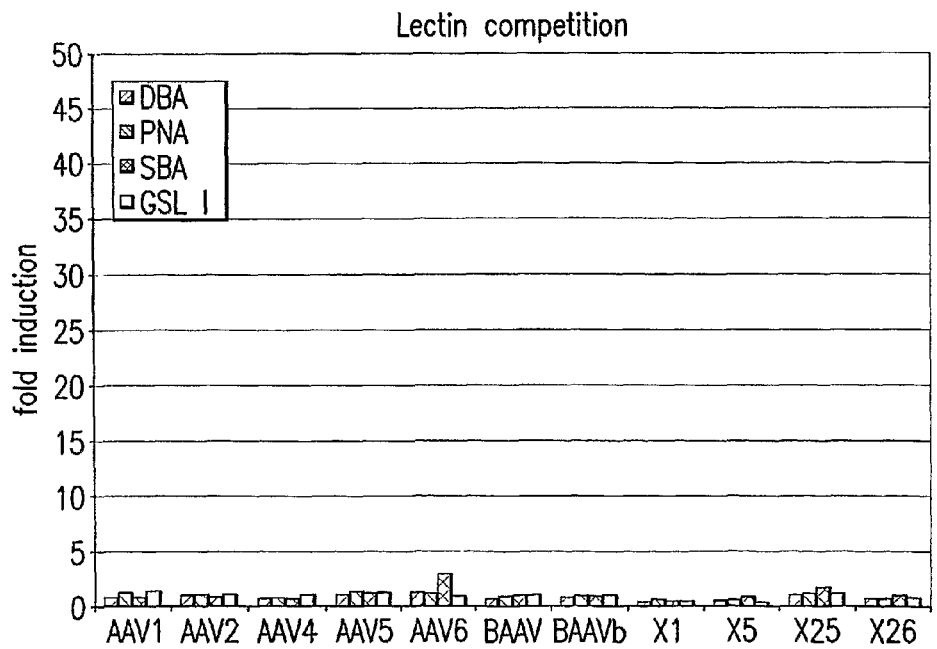
Figure 10C:
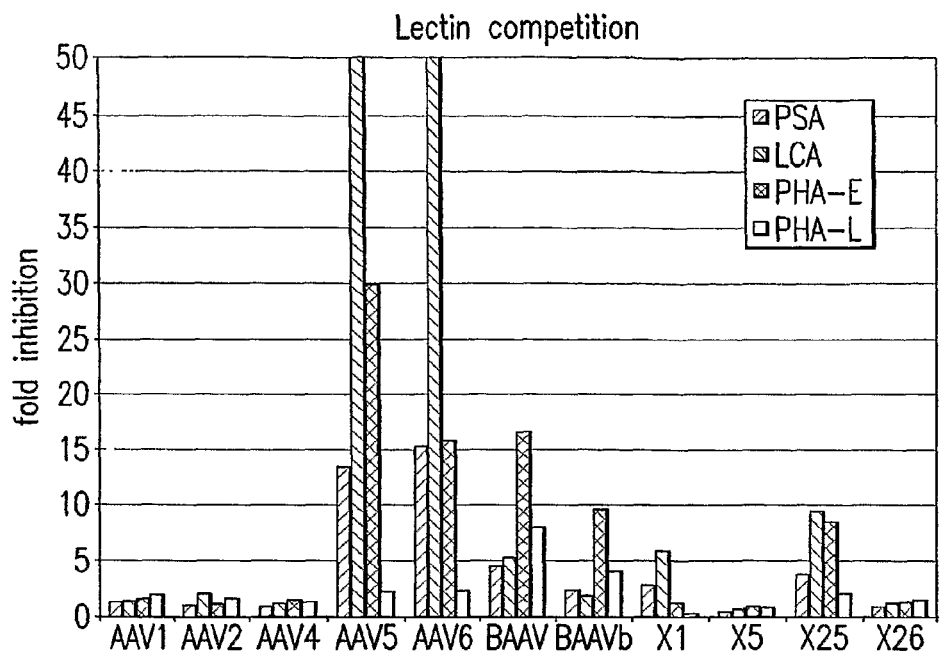
Figure 10D:
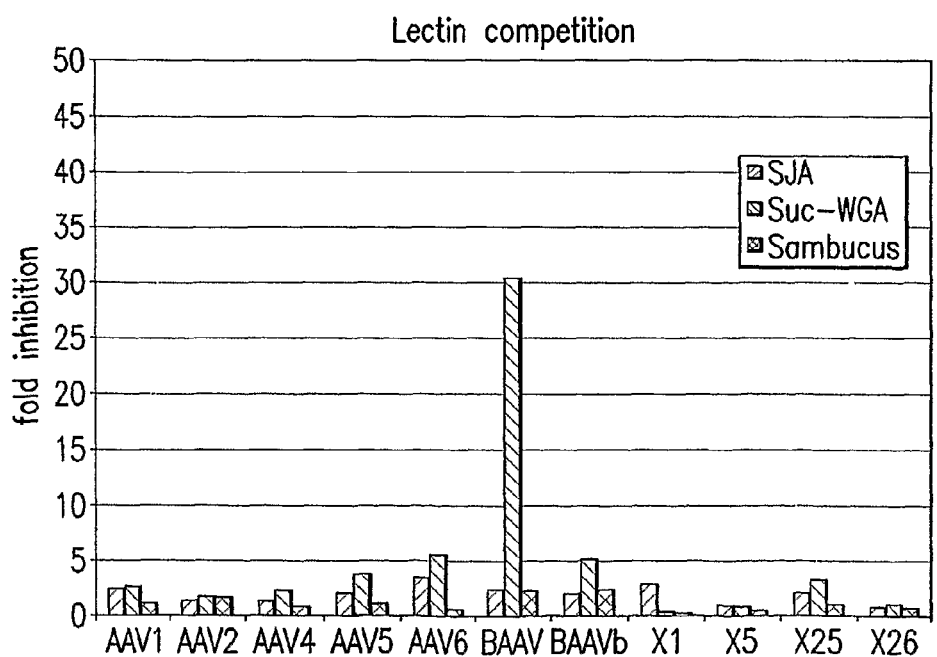

AAV-X5 and AAV-X26 therefore utilize unique uptake pathways/receptors that are different from all other AAVs analyzed thus far. Transduction efficiencies in four cancer cell lines were therefore examined (FIG. 11). AAV-X5 and AAV- X26 have unique transduction properties and tropism. Thus, the application range and potential use of recombinant vectors based on AAV-X5 and AAV-X26 are unique and different from other AAVs described thus far.

rAAV6, rAAV(VR-195), and rAAV(VR-355) differ in their cell tropism: As a result of the few sequence changes on the surface of the rAAV(VR-195) and rAAV(VR-355) capsid, each virus appears to exhibit different biological characteristics from each other and from rAAV6. To analyze if this difference also results in a change in tropism or transduction activity, six human cancer cell lines and African green monkey kidney cells, COS, were transduced with recombinant vectors based on rAAV6, rAAV(VR-195), and rAAV(VR-355) (FIG. 7). AAV6 and AAV(VR-195) transduced COS cells, the non-small cell lung cancer cell line EKVX, ovarian IGROV1, and renal CAKI cells with similar efficiency. However, the transduction rates of AAV(VR-195) on ovarian Ovcar5 cells and the CNS derived SF295 cell line were approximately 4 times lower compared to AAV6. AAV(VR-355) demonstrated efficient gene transfer in COS and EKVX cells, but transduction of Igrov1, CAKI, Ovcar5 and SF295 was 10 to 17-fold lower than for AAV6. The different transduction efficiencies of rAAV6, rAAV(VR-195), and rAAV(VR-355) indicate that each isolate may have a distinct cell tropism which could be the result of utilization distinct receptors for attachment or internalization or have different affinities for a common receptor.

rAAV6 competition: rAAV6, rAAV(VR-195), and rAAV(VR-355) require 2-3 linked sialic acid for cell attachment and transduction but differ in their charge dependency, sensitivity to lectin competition, and transduction activity on a panel of cells. To investigate if these viruses use distinct receptors, competition experiments were used to assay for change in transduction between AAV6 and the other isolates. COS cells were pre-incubated with increasing doses of rAAV6-lacZ followed by transduction with identical particle titers of either rAAV2, rAAV6, rAAV(VR-195), or rAAV (VR-355) expressing GFP. Changes in GFP expression were detected by flow cytometry (FIG. 8). rAAV6-LacZ competition had the greatest effect on rAAV6-NLS-GFP transduction. Fifty percent inhibition of rAAV6-NLS-GFP transduction was observed at approximately 60-fold excess of the competitor, whereas a 220-fold excess was required for the same level of inhibition of rAAV(VR-195) or rAAV(VR-355). Fifty percent inhibition of rAAV2-NLS-GFP transduction required greater than 250-fold particle excess. The stronger inhibition of rAAV6-NLS-GFP by rAAV6-lacZ compared with rAAV(VR-195) or rAAV(VR-355) suggests, that while rAAV6, rAAV(VR-195) and rAAV(VR-355) share a common attachment factor and potentially a common receptors, differences in the attachment factor and receptor interaction exist.

Example 2

Identification and Characterization of AAV12

Materials And Methods

Cells culture and virus: African green monkey kidney COS cells, obtained from the American Type Culture Collection (ATCC) (Manassas, Va.), were cultured in RPMI-1640 medium (Biosource, Camarillo, Calif.), supplemented with 5% fetal bovine serum (Hyclone, Logan, Utah), 2 mM L-glutamine, 100 U of penicillin/ml, and 0.1 mg of streptomycin/ml (Invitrogen, Carlsbad, Calif.). Cells were maintained at 37° C. under a 5% $CO_2$ humidified atmosphere. Simian Virus 18 isolate, VR-943, was obtained from the ATCC as crude lysate of virus-infected cells.

Subcloning of the AAV12 rep and cap gene: The complete coding region of AAV12 rep and cap were PCR amplified and subcloned. DNA was isolated from lysate of Simian Virus 18 infected cells with the QIAprep Spin Miniprep kit (Qiagen, Valencia, Calif.). The rep open reading frame (ORF) was PCR amplified from this DNA with the primers AAV225(+):GC-GACAKTTTGCGACACCAYGTGG (SEQ ID NO:44) and UNI-NC: CCANNNGGAATCGCAATGCCAAT (SEQ ID NO:45). AAV12 cap was amplified with the primers UNI-C: 5'-ATGNTNATNTGGTGGGAGGAGGG-3' (SEQ ID NO:46) and AAV1-4 polyA4400(−):5'-CGAATNAAMCG-GTTTATTGATTAAC-3' (SEQ ID NO:47). The PCR fragments were subcloned using the TOPO TA Cloning KIT (Invitrogen) resulting in the plasmids pAAV12-Rep and pAAV12-Cap. Three clones, that were capable of generating recombinant virus, were sequenced with an ABI Prism 3100 Genetic Analyzer (Applied Biosystems, Foster City, Calif.) and FS dye-terminator chemistry (Applied Biosystems).

Sequence analysis: The sequences of AAV12 rep and cap were compared to sequences in GenBank using BLAST. DNA alignments were performed using the ClustalW multiple sequence alignment tool of the Biology Workbench web based software at http://seqtool.sdsc.edu (SDSC) and MacVector 7 (Accelrys, Burlington, Mass.).

Generation of recombinant virus: AAV12 (AAVX26) vectors, expressing a nuclear localized green fluorescent protein (GFP), rAAV12GFP, were produced as described above. Briefly, 293T cells were cotransfected with pAAV2-NLS-GFP, pAAV12Rep and pAAV12Cap and the Ad helper plasmids 449B. Recombinant particles were purified by CsCl gradient centrifugation. DNase-resistant genome copy numbers of the vector stocks were determined by quantitative real-time PCR using the TAQMAN system (Applied Biosystems) with probes specific to the CMV promoter. AAV12-Epo expressing human erythropoietin was generated accordingly by packaging pAAVhEPO with pAAV12Rep and pAAV12Cap.

Digestion of cell surface sialic acid: Exponentially growing COS cells were plated at a density of $5\times10^3$/well in a flat-bottom 96-well plate. Twenty-four hours after seeding, cells were incubated for 30 min with 0.1 and 1 mU of the broad-spectrum neuraminidase from *Vibrio cholerae* (Calbiochem, La Jolla, Calif.). Cells were then washed with medium and transduced with $1\times10^7$ particles of rAAV2-GFP, rAAV4-GFP, rAAV5-GFP or rAAV12-GFP. GFP expression, which serves as a surrogate marker for transduction, was detected twenty-four hours later with a fluorescent cell counter (Guava PCA-96, Guava Technologies, Hayward, Calif.).

Heparin competition assay: COS cells were plated at a density of $5\times10^3$/well in a flat-bottom 96-well plate one day prior to transduction. $2\times10^7$ particles rAAV2-GFP, rAAV12-GFP were preincubated for 1 h at room temperature in medium supplemented with either heparin, mannose or mannosamine (Sigma, St. Louis, Mo.). This pre-incubation mixture was then added and left on the cells for 1 h at 37° C. Cells were then washed with medium and incubated for one day before GFP expression was detected with a fluorescent cell counter (Guava Technologies).

Protease treatment: COS cells were cultured in a 15-cm diameter culture dish until cells were 80% confluent. Cells were then washed twice with PBS, scraped, resuspended in 10 ml PBS and incubated with 0.05% trypsin (Biosource), or mock (untreated control) for 15 min at 37° C. Cells were then washed twice with medium and seeded at a density of 10,000 cells/well in a 96-well dish. After 1 h culture at 37° C., cells were transduced with 2×10⁷ particles rAAV2-GFP, rAAV12-GFP. Transduction efficiency was determined 24 h later by GFP expression detection with a fluorescent cell counter (Guava Technologies).

Inhibition of glycolipid synthesis: COS cells were plated at a density of 5×10³/well in a flat-bottom 96-well plate. Eight hours after seeding, cells were incubated for 40 h with the glucosylceramide synthase inhibitors DL-threo-1-Phenyl-2-palmitoylamino-3-morpholino-1-propanol (PPMP) (Sigma, St. Louis, Mo.). Cells were then washed with medium and transduced with 2×10⁸ particles of rAAV2-GFP, rAAV12-GFP and rBAAV-GFP for 1 h. GFP expression was analyzed 48 h after transduction by detection with a fluorescent cell counter (Guava Technologies).

Neutralization assay: COS cells were seeded at a density of 5×10³/well in a 96-well plate 1 day before inoculation. 2×10⁷ rAAV2-GFP, rAAV6-GFP and rAAV12-GFP particles that were pre-incubated with serial dilutions of pooled human IgGs (Immune Globuline Intravenous, 10%, Gamunex, BAYER, Leverkusen, Germany) in medium for 1 h at room temperature. Cells were then inoculated with this mixture for 1 h at 37° C. and then washed with medium. Twenty-four hours after transduction, cells were analyzed for GFP expression by flow cytometry (Guava Technologies).

Animal experiments: Male Balb/c mice were obtained from the Division of Cancer Treatment, NCI, Bethesda, Md. Mice were administered 10⁹ particles (suspended in 100 µl of 0.9% NaCl) of either AAV2-hEPO (n=3) or AAV12-hEPO (n=2) by retrograde ductal delivery to both submandibular glands (SG). Two additional groups (n=3 and n=2, respectively) received an equal dose of 10⁹ particles (suspended in 100 µl of 0.9% NaCl) in both their tibialis anterior (two injection sites per muscle). A further group (n=3) of naïve mice (administered with 50 µl of 0.9% NaCl to each SG) was included. Mild anesthesia was induced to all participating animals with 1 µl/g body weight of a 60 mg/ml ketamine (Phoenix Scientific, St. Joseph, Mo.) and 8 mg/ml xylazine (Phoenix Scientific) solution given intramuscularly. Blood samples were obtained by orbital bleeding at distinct time points. Hematocrits (Hcts) were determined using microhematocrit capillary tubes (Fisher Scientific, Pittsburgh, Pa.). Secretion of hEPO in mouse serum was determined by an ELISA using commercial assay kits (R&D systems, MN, USA). The lower limit of detection was 0.6 mU/ml. Assays were performed according to the manufacturer's instructions.

Results

Identification of AAV contaminations in ATCC virus isolates: AAV sequences were detected in a Simian Adenovirus 18 strain C676 stock, VR-943, which was isolated from a Vervet monkey (*Cercopithecus aethiops*). The entire rep and cap coding region of the AAV contamination in VR-943, termed AAV12, has been PCR amplified and subcloned (FIG. 1). Since the rep and cap encoding PCR fragments also contain viral promoter elements, these plasmids could be used as packaging constructs for the generation of recombinant virus. Vectors based on AAV12 were produced by cotransfecting an AAV-2 vector plasmid, encoding a nuclear localized GFP flanked by AAV2 inverted terminal repeats (ITRs), and plasmids encoding AAV12 rep and cap together with an adenovirus helper plasmid. Recombinant viruses were then assayed for transduction activity by inoculating COS cells and assaying for GFP expression by flow cytometry. Three clones, which were capable of generating recombinant virus were sequenced.

Phylogenetic analysis: The evolutionary relationship among mammalian AAVs and AAV12 was analyzed by Clustal W alignments of genomic, Rep78 and VP1 sequences and plotted as a rooted phylogenetic tree (FIG. 1). The DNA sequence of AAV12 showed highest homology with AAV 11 and AAV4, 83% and 81% respectively, whereas lowest similarity was observed with AAV5 (63%). The Rep78 amino acid sequence of AAV12 demonstrated high homology to AAV13, AAV4, AAV10 and AAV11 with 89% or 88% identity. For the capsid protein VP1, highest homology was observed with AAV11 and AAV4, 84% and 78% respectively, whereas AAV5 VP1 displayed lowest similarity with 53%.

Figure 12:
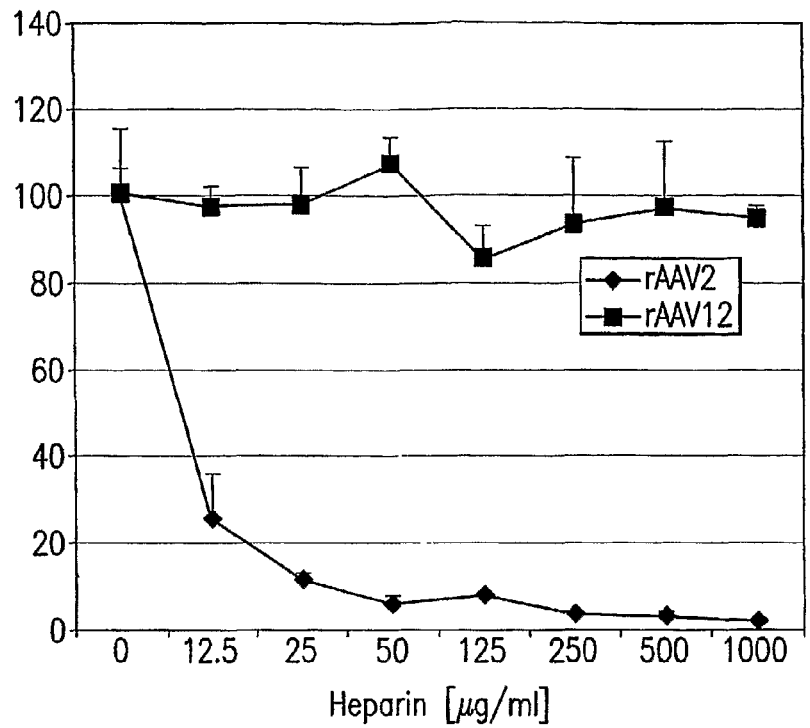
FIG. 12 shows rAAV12 COS cell transduction is not inhibited by heparin. COS cells were transduced with a pre-incubation mixture consisting out of rAAV2-GFP, or rAAV12-GFP expressing GFP and heparin at the indicated concentrations. 24 h post-inoculation, transduction was analyzed by flow cytometry. Values are means from three experiments; error bars represent standard deviations.

Heparin competition: Heparan sulfate, a cell surface glycosaminoglycan, which is expressed by virtually all cells, is an attachment receptor for AAV2 (Summerford, C., et al. 1998). AAV2 transduction can be inhibited by heparin, a heparan sulfate analog. Thus, analysis was conducted to determine whether AAV 12 uses heparan sulfate as a receptor by heparin competition experiments. COS cells were transduced with rAAV12 in the presence of increasing amounts of heparin. rAAV2 served as a control. rAAV2 transduction was inhibited to 75% at a concentration of 12.5 µg/ml heparin, whereas no inhibition of rAAV12 was observed at a 80 hold higher heparin concentration of 1000 µg/ml (FIG. 12). Since heparin has no inhibitory potential towards AAV12 transduction, heparan sulfate appears not to be involved in AAV12 transduction.

Figure 13:
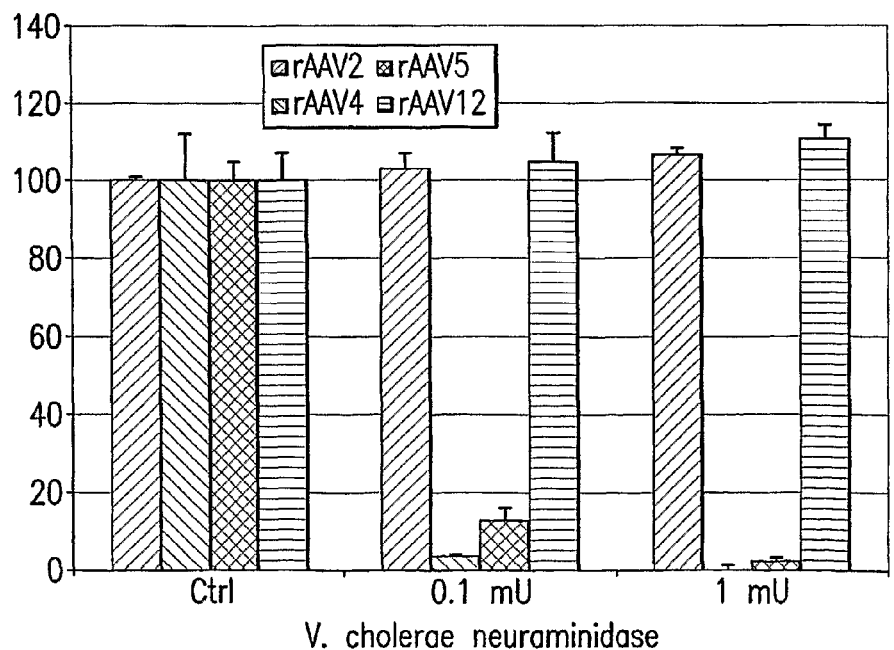
FIG. 13 shows rAAV12 transduction is independent of cell surface sialic acid. COS cells were pretreated with the *V. cholera* neuraminidase to remove exposed sialic acids groups before the cells were transduced with rAAV2, rAAV4, rAAV5 and rAAV12-GFP. Gene transfer was determined by flow cytometry. Values are means from three experiments; error bars represent standard deviations.
Figure 14A:
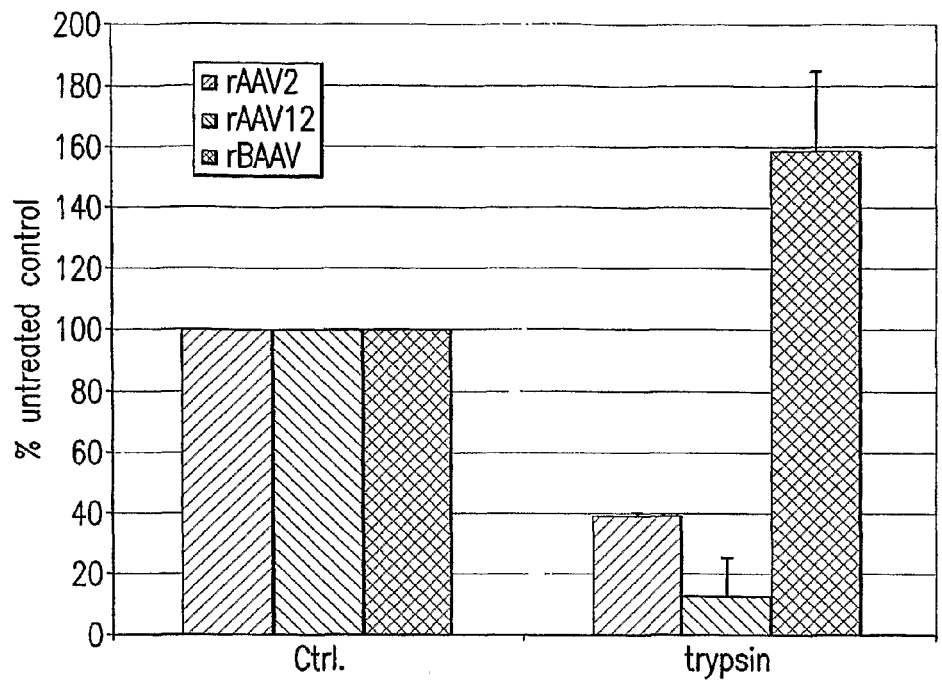
FIG. 14 shows rAAV12 transduction is protease sensitive and does not require glycosphingolipids. COS cells were proteolytically digested with trypsin (A) or treated with the glycosphingolipids synthesis inhibitors PPMP (B) prior to transduction with rAAV2-GFP, rAAV12-GFP and rBAAV-GFP. Gene transfer in these cells was compared to untreated cultures. Values are means from three experiments; error bars represent standard deviations.
Figure 14B:
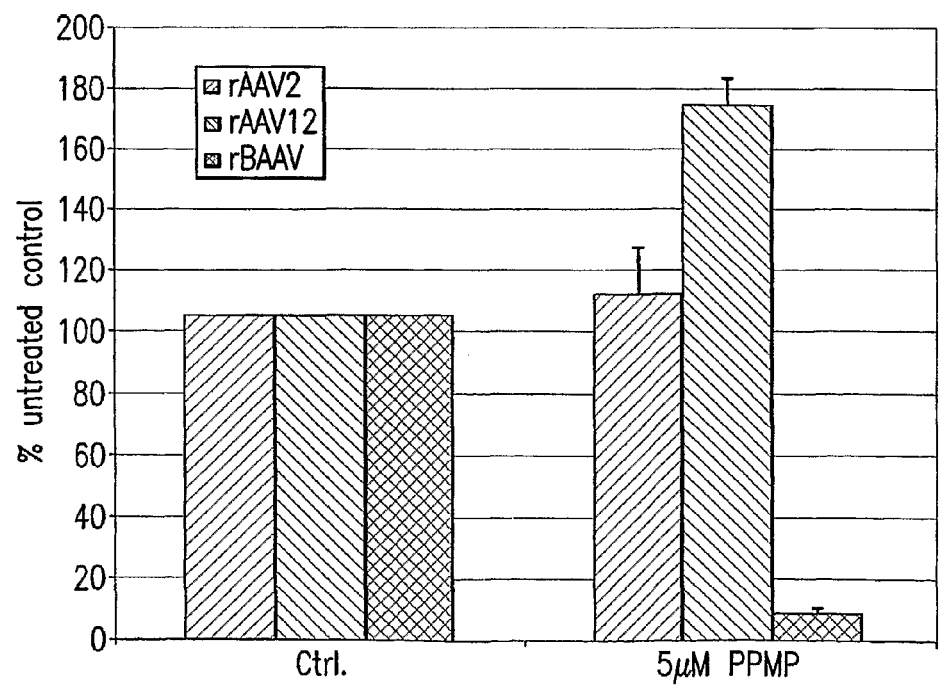
Figure 15:
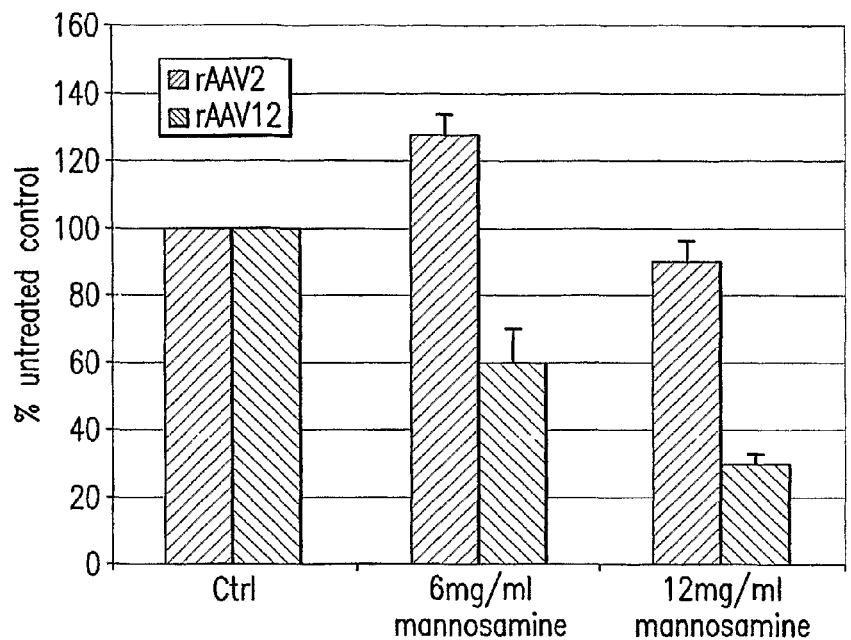
FIG. 15 shows extracellular mannosamine inhibits rAAV12 transduction. COS cells were transduced with a pre-incubation mixture of rAAV2-GFP, or rAAV12-GFP and mannosamine at the indicated concentrations. 24 h post-inoculation, transduction was analyzed by flow cytometry. Values are means from three experiments; error bars represent standard deviations.
Figure 16:
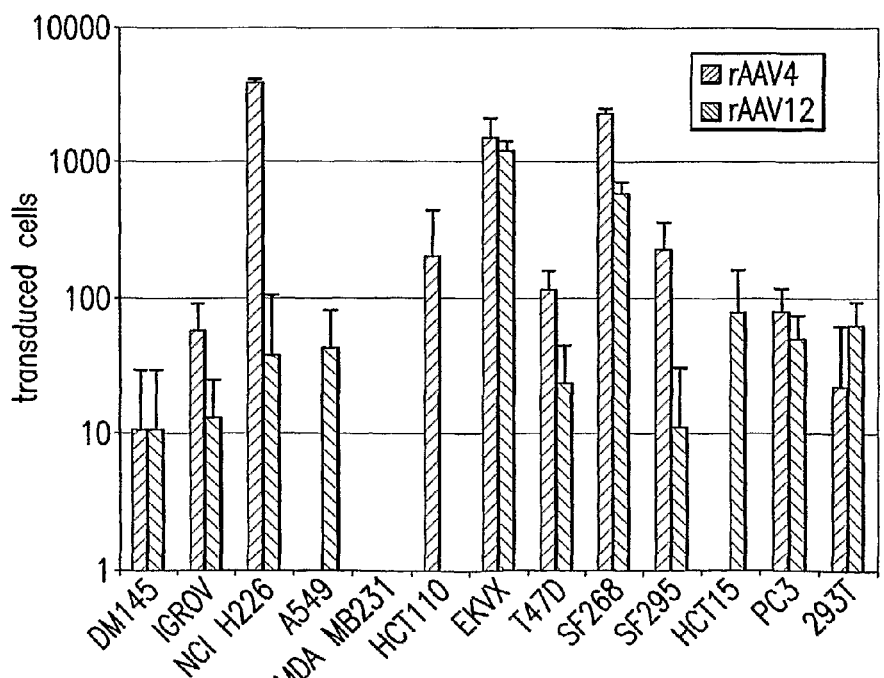
FIG. 16 shows rAAV12 has a broad tropism. Transduction efficiency of rAAV12 was compared to rAAV4 in 13 human cancer cell lines. Cells were transduced with particles of either rAAV12-GFP or rAAV4-GFP. Transduction was analyzed by flow cytometry 28 h after virus inoculation. Values are means from three experiments; error bars represent standard deviations.

Effect of neuraminidase treatment on rAAV12 transduction: Sialic acids, a family of monosaccharides based on N-acetylneuramic acid, are commonly found on the outermost end of glykans and glycolipids. Sialic acids have been identified to serve as receptors for several viruses, including influenza virus, AAV4, AAV5 AAV6 and AAV(VR-355). To analyze, if AAV 12 transduction is sialic acid dependent, the effect of the removal of cell surface sialic acids was studied by neuraminidase treatment on gene transfer (FIG. 13). Enzymatic digestion of COS cells with a broad spectrum neuraminidase from *Vibrio cholera* inhibited rAAV4 and rAAV5 transduction dose-dependently and blocked gene transfer up to 99% and 97% respectively. AAV12 transduction was unaffected by the enzymatic removal of cell surface sialic acids, indicating that AAV12 does not utilize sialic acid in the transduction process.

rAAV12 transduction is protease sensitive and does not require glycosphingolipids (GSLs): rBAAV cell entry and transduction depend on gangliosides, glycosphingolipids with sialic acid groups, and are resistant to protease treatment of the cell. To analyze if the rAAV12 receptor is a protein and if glycolipids are involved in the transduction process, the effect of proteolytically digesting cell surface proteins prior to transduction was studied (FIG. 14A). The dependency of rAAV12 transduction on GSLs was studied by incubating cells with DL-threo-1-Phenyl-2-palmitoylamino-3-morpholino-1-propanol (PPMP), a glucosylceramide synthase inhibitors, which act to deplete GSLs from the cell membrane prior to transduction (FIG. 14B). As shown in FIG. 14, AAV12 transduction is protease sensitive, but AAV12 can transduce cells lacking glycosphingolipids.

rAAV12 is inhibited by extracellular mannosamine: Since rAAV12 transduction does not depend on either heparin or sialic acid, a broad panel of carbohydrates was screened for the ability to interfere with rAAV12 transduction to identify components that might be involved in the rAAV 12 cell interaction. In this assay, mannosamine was identified as compound with inhibitory function against rAAV12. Pre-incubation of rAAV12 with mannosamine prior to transduction resulted in a dose-dependent inhibition of rAAV12 transduction (FIG. 15), while no specific inhibition of rAAV2 was observed. This result indicates that mannosamine could be part of the rAAV12 receptor or attachment factor.

rAAV12 has a broad tropism in human cancer cell lines: All studied AAVs utilize either sialic acid or heparin as cellular receptor or attachment factor. In contrast, rAAV12 trasduced cells independently of heparin and sialic acid but was inhibited by mannosamine, indicating that rAAV12 interacts in a unique way with the cell. To analyze if unique cell interaction results in a unique tropism, the transduction efficiency of rAAV12 was studied in 13 human cancer cell lines and compared it to rAAV4, a virus that shows 78% homology to rAAV12 in the capsid protein VP1 (FIG. 16). rAAV12 and rAAV4 demonstrated both a broad tropism with overall similar transduction efficiencies, but both viruses had a unique transduction profile. While only rAAV4 transduced HCT10 cells, rAAV12 gene transfer was specific for A549 and HCT15 cells.

Figure 17:
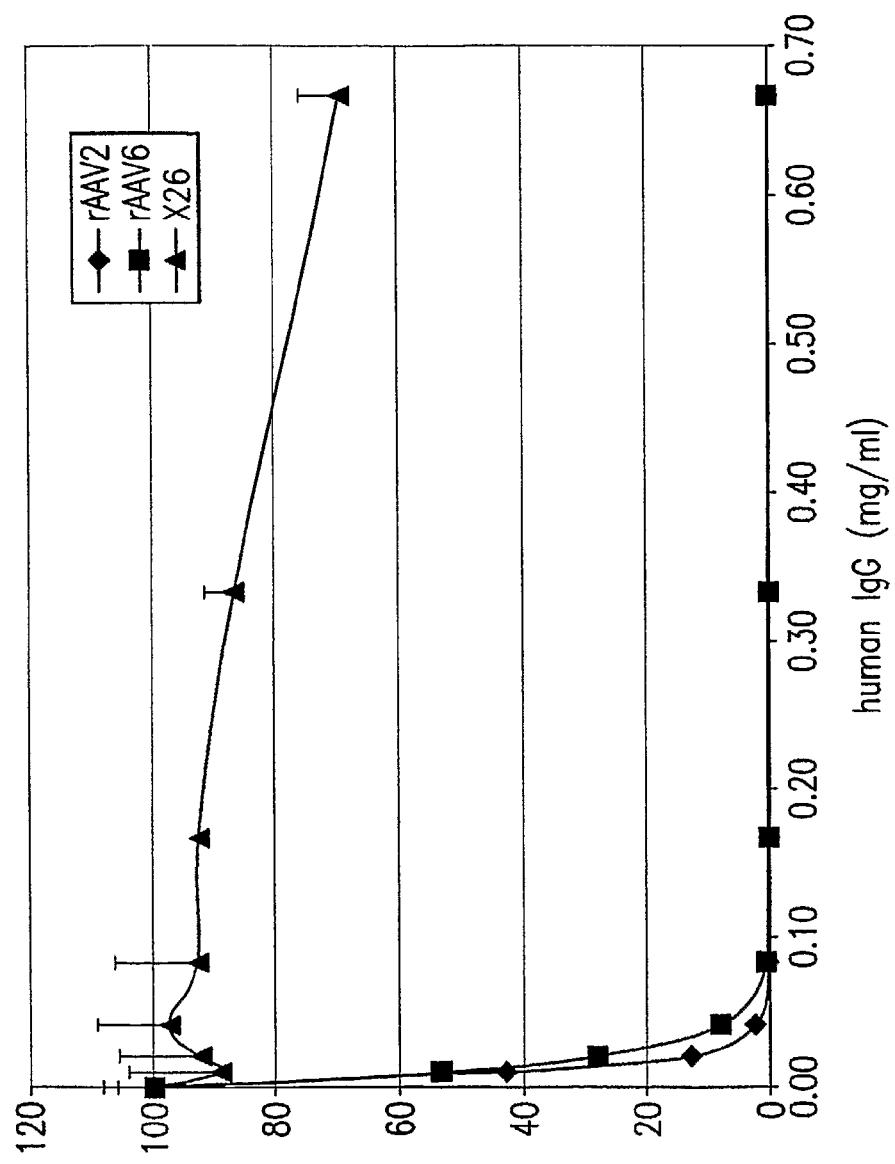
FIG. 17 shows rAAV12 is highly resistant to neutralization by human IgGs. rAAV2-GFP, rAAV6-GFP and rAAV12-GFP were incubated with pooled human IgGs prior to transduction of COS cells. 24 h post-inoculation, transduction was analyzed by flow cytometry. Transduction efficiencies relative to an untreated control were plotted. Values are means from three experiments; error bars represent standard deviations.
Figure 18A:
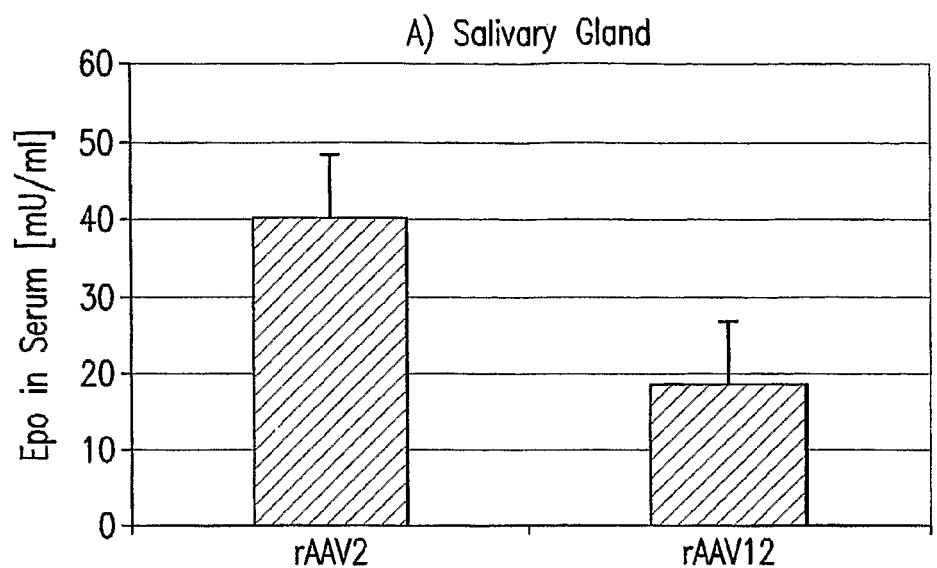
FIG. 18 shows rAAV12 transduces salivary glands and skeletal muscles in vivo. Male Balb/c mice were administered $10^9$ particles of either AAV2-hEPO or AAV12-hEPO by retrograde ductal delivery to both submandibular glands or in both their tibialis anterior (two injection sites per muscle). Secretion of hEPO in mouse serum was determined 4 weeks after transduction by an ELISA test. Error bars represent standard deviations.
Figure 18B:
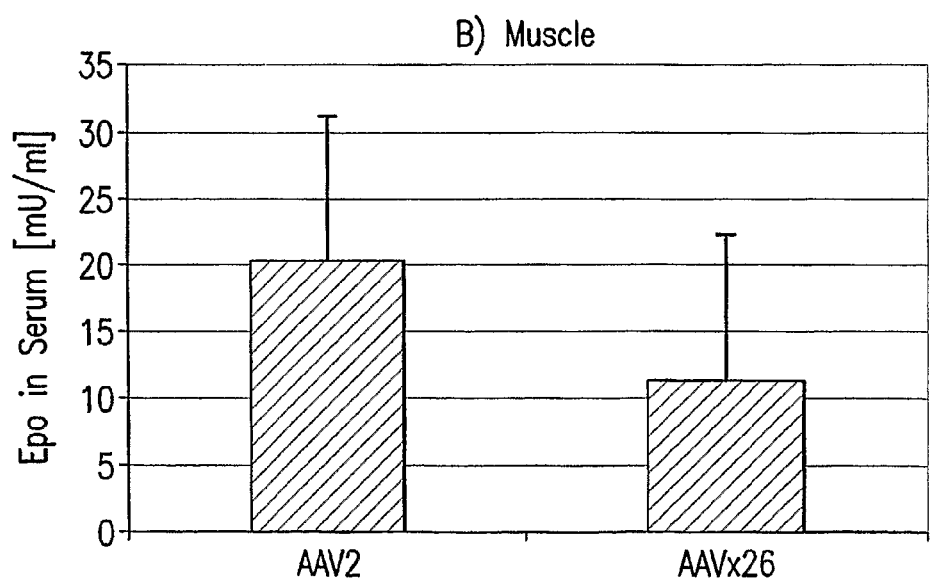

Immunological characterization of rAAV12: Infections with AAV2 are very common and approximately 80% of the human population are seropositive. Neutralization of human AAV serotypes, such as AAV2, AAV3 and AAV5, as well as the simian AAV6 by human serum have been reported. This pre-existing immunity against these AAVs might limit their usability as vectors for gene therapy. To test if rAAV 12 is antigentically distinct from rAAV2 and rAAV6, assays were conducted to determine if IgGs, purified from pooled human serum, contain neutralizing antibodies against the recombinant AAVs and whether there was a difference in the neutralization activity against either rAAV2, AAV6, or rAAV12 (FIG. 17). In this assay the human rAAV2 and simian rAAV6 displayed similar sensitivity to neutralization with the purified pooled IgGs and transduction was inhibited to 50% at a concentration of 0.01 mg/ml IgGs. In contrast, rAAV12 was highly resistant to neutralization by pooled human IgGs, and even at the highest concentration of 0.67 mg/ml, a concentration where 100% inhibition of rAAV2 and rAAV6 was observed, rAAV 12 transduction was only reduced by 30%.

rAAV12 transduces salivary glands and skeletal muscles in vivo: rAAV 12 transduced salivary glands and skeletal muscles with similar efficiency as rAAV2 (FIG. 18).

REFERENCES

Allen, J. M., Halbert, C. L. and Miller, A. D.: Improved adeno-associated virus vector production with transfection of a single helper adenovirus gene, E4orf6. Mol Ther 1 (2000) 88-95.

Amberg, N., A. H. Kidd, K. Edlund, J. Nilsson, P. Pring-Akerblom, and G. Wadell. 2002. Adenovirus type 37 binds to cell surface sialic acid through a charge-dependent interaction. Virology 302:33-43.

Atchison, R. W., B. C. Casto, and W. M. Hammon. 1965. Adenovirus-Associated Defective Virus Particles. Science 149:754-6.

Bartlett, J. S., Wilcher, R. and Samulski, R. J.: Infectious entry pathway of adeno-associated virus and adeno-associated virus vectors. J Virol 74 (2000) 2777-85.

Ben-Israel, H. and Kleinberger, T.: Adenovirus and cell cycle control. Front Biosci 7 (2002) D1369-95.

Berns, K. I. 1996. Parvoviridae: the viruses and their replication, p. 2173-2197. In F. B. N., K. D. M., and H. P. M. (ed.), Fields virology, 3rd ed. Lippincott-Raven Publishers, Philadelphia, Pa.

Blacklow, N. R., Hoggan, M. D. and Rowe, W. P.: Isolation of adenovirus-associated viruses from man. Proc Natl Acad Sci USA 58 (1967) 1410-5.

Blacklow, N. R., Hoggan, M. D. and Rowe, W. P.: Serologic evidence for human infection with adenovirus-associated viruses. J Natl Cancer Inst 40 (1968) 319-27.

Bossis, I. and Chiorini, J. A.: Cloning of an Avian Adeno-Associated Virus (AAAV) and Generation of Recombinant AAAV Particles. J Virol 77 (2003) 6799-810.

Carter, B. J., B. A. Antoni, and D. F. Klessig. 1992. Adenovirus containing a deletion of the early region 2A gene allows growth of adeno-associated virus with decreased efficiency. Virology 191:473-6.

Carter, B. J., C. A. Laughlin, L. M. de la Maza, and M. Myers. 1979. Adenoassociated virus autointerference. Virology 92:449-62.

Casto, B. C., J. A. Armstrong, R. W. Atchison, and W. M. Hammon. 1967. Studies on the relationship between adeno-associated virus type 1 (AAV-1) and adenoviruses. II. Inhibition of adenovirus plaques by AAV; its nature and specificity. Virology 33:452-8.

Casto, B. C., R. W. Atchison, and W. M. Hammon. 1967. Studies on the relationship between adeno-associated virus type I (AAV-1) and adenoviruses. I. Replication of AAV-1 in certain cell cultures and its effect on helper adenovirus. Virology 32:52-9.

Chang, L. S, and Shenk, T.: The adenovirus DNA-binding protein stimulates the rate of transcription directed by adenovirus and adeno-associated virus promoters. J Virol 64 (1990) 2103-9.

Chiorini, J. A., F. Kim, et al. (1999). "Cloning and characterization of adeno-associated virus type 5." J Virol 73(2): 1309-19.

Chiorini, J. A., L. Yang, Y. Liu, B. Safer, and R. M. Kotin. 1997. Cloning of adeno-associated virus type 4 (AAV4) and generation of recombinant AAV4 particles. J Virol 71:6823-33.

Chiorini, J. A., Wiener, S. M., Owens, R. A., Kyostio, S. R., Kotin, R. M. and Safer, B.: Sequence requirements for stable binding and function of Rep68 on the adeno-associated virus type 2 inverted terminal repeats. J Virol 68 (1994) 7448-57.

Davidson, B. L., C. S. Stein, et al. (2000). "Recombinant adeno-associated virus type 2, 4, and 5 vectors: transduction of variant cell types and regions in the mammalian central nervous system." Proc Natl Acad Sci USA 97(7): 3428-32.

Derby, M. L., M. Sena-Esteves, et al. (1999). "Gene transfer into the mammalian inner ear using HSV-1 and vaccinia virus vectors." Hear Res 134(1-2): 1-8.

Di Pasquale, G., and J. A. Chiorini. 2003. PKA/PrKX activity is a modulator of AAV/adenovirus interaction. EMBO J. 22:1716-24.

Di Pasquale, G., B. L. Davidson, et al. (2003). "Identification of PDGFR as a receptor for AAV5 transduction." Nat Med 9(10): 1306-12.

Di Pasquale, G., Rzadzinska, A., Schneider, M. E., Bossis, I., Chiorini, J. A., Kachar, B., A novel bovine virus efficiently transduces inner ear neuroepithelial cells, Manuscript submitted.

Erles, K., Sebokova, P. and Schlehofer, J. R.: Update on the prevalence of serum antibodies (IgG and IgM) to adeno-associated virus (AAV). J Med Virol 59 (1999) 406-11.

Gao, G., L. H. Vandenberghe, M. R. Alvira, Y. Lu, R. Calcedo, X. Zhou, and J. M. Wilson. 2004. Clades of Adeno-associated viruses are widely disseminated in human tissues. J Virol 78:6381-8.

Gao, G. P., Alvira, M. R., Wang, L., Calcedo, R., Johnston, J. and Wilson, J. M.: Novel adeno-associated viruses from rhesus monkeys as vectors for human gene therapy. Proc Natl Acad Sci USA 99 (2002) 11854-9.

Georg-Fries, B., S. Biederlack, J. Wolf, and H. zur Hausen. 1984. Analysis of proteins, helper dependence, and seroepidemiology of a new human parvovirus. Virology 134:64-71.

Grimm, D. and M. A. Kay (2003). "From virus evolution to vector revolution: use of naturally occurring serotypes of adeno-associated virus (AAV) as novel vectors for human gene therapy." Curr Gene Ther 3(4): 281-304.

Halbert, C. L., J. M. Allen, and A. D. Miller. 2001. Adeno-associated virus type 6 (AAV6) vectors mediate efficient transduction of airway epithelial cells in mouse lungs compared to that of AAV2 vectors. J Virol 75:6615-24.

He, D. Z., J. Zheng, et al. (2001). "Development of acetylcholine receptors in cultured outer hair cells." Hear Res 162(1-2): 113-25.

Heister, T., Heid, I. Ackermann, M., Fraefel, C. Herpes simplex virus type 1/adeno-associated virus hybrid vectors mediate site-specific integration at the adeno-associated virus preintegration site, AAVS1, on human chromosome 19. J. Virol. 2002 July; 76(14):7163-73.

Hoggan, M. D. 1970. Adenovirus associated viruses. Prog Med Virol 12:211-39.

Hoggan, M. D., N. R. Blacklow, and W. P. Rowe. 1966. Studies of small DNA viruses found in various adenovirus preparations: physical, biological, and immunological characteristics. Proc Natl Acad Sci USA 55:1467-74.

Holt, J. R. (2002). "Viral-mediated gene transfer to study the molecular physiology of the Mammalian inner ear." Audiol Neurootol 7(3): 157-60.

Holt, J. R., D. C. Johns, et al. (1999). "Functional expression of exogenous proteins in mammalian sensory hair cells infected with adenoviral vectors." J Neurophysiol 81(4): 1881-8.

Hull, R. N., and J. R. Minner. 1957. New viral agents recovered from tissue cultures of monkey kidney cells. II. Problems of isolation, and identification. Ann N Y Acad Sci 67:413-23.

Hull, R. N., J. R. Minner, and C. C. Mascoli. 1958. New viral agents recovered from tissue cultures of monkey kidney cells. III. Recovery of additional agents both from cultures of monkey tissues and directly from tissues and excreta. Am J Hyg 68:31-44.

Hull, R. N., J. R. Minner, and J. W. Smith. 1956. New viral agents recovered from tissue cultures of monkey kidney cells. I. Origin and properties of cytopathogenic agents S.V.1, S.V.2, S.V.4, S.V.5, S.V.6, S.V.11, S.V.12 and S.V.15. Am J Hyg 63:204-15.

Janik, J. E., Huston, M. M., Cho, K. and Rose, J. A.: Efficient synthesis of adeno-associated virus structural proteins requires both adenovirus DNA binding protein and VA I RNA. Virology 168 (1989) 320-9.

Jero J, Mhatre A N, Tseng C J, Stem R E, Coling D E, Goldstein J A, Hong K, Zheng W W, Hogue A T, Lalwani A K. Cochlear gene delivery through an intact round window membrane in mouse. Hum Gene Ther. 2001 Mar. 20; 12(5):539-48.

Kaludov, N., K. E. Brown, et al. (2001). "Adeno-associated virus serotype 4 (AAV4) and AAV5 both require sialic acid binding for hemagglutination and efficient transduction but differ in sialic acid linkage specificity." J Virol 75(15): 6884-93.

Kanzaki, S., K. Ogawa, et al. (2002). "Transgene expression in neonatal mouse inner ear explants mediated by first and advanced generation adenovirus vectors." Hear Res 169(1-2): 112-20.

Katano H, Afione S, Schmidt M, Chiorini J A. Identification of adeno-associated virus contamination in cell and virus stocks by PCR. Biotechniques. 2004 April; 36(4):676-80.

Kelsell, D. P., Dunlop, J., Stevens, H. P., Lench, N. J., Liang, J. N., Parry, G., Mueller, R. F., Leigh, I. M. Connexin 26 mutations in hereditary non-syndromic sensorineural deafness. Nature. 1997 May 1; 387(6628):80-3

Kern, A., K. Schmidt, C. Leder, O. J. Muller, C. E. Wobus, K. Bettinger, C. W. Von der Lieth, J. A. King, and J. A. Kleinschmidt. 2003. Identification of a heparin-binding motif on adeno-associated virus type 2 capsids. J Virol 77:11072-81.

Li Duan, M., T. Bordet, et al. (2002). "Adenoviral and adeno-associated viral vector mediated gene transfer in the guinea pig cochlea." Neuroreport 13(10): 1295-9.

Luchsinger, E., Strobbe, R., Dekegel, D. and Wellemans, G.: Use of B-IV zonal rotor centrifugation as a simple tool for the separation of adeno-associated X 7 virus (AAVX 7) from helper adenoviruses. Arch Gesamte Virusforsch 33 (1971) 251-8.

Luchsinger, E., Strobbe, R., Wellemans, G., Dekegel, D. and Sprecher-Goldberger, S.: Haemagglutinating adeno-associated virus (AAV) in association with bovine adenovirus type 1. Brief report. Arch Gesamte Virusforsch 31 (1970) 390-2.

Luebke, A. E., J. D. Steiger, et al. (2001). "A modified adenovirus can transfect cochlear hair cells in vivo without compromising cochlear function." Gene Ther 8(10): 789-94.

Luebke, A. E., P. K. Foster, et al. (2001). "Cochlear function and transgene expression in the guinea pig cochlea, using adenovirus- and adeno-associated virus-directed gene transfer." Hum Gene Ther 12(7): 773-81.

McPherson, R. A., L. J. Rosenthal, and J. A. Rose. 1985. Human cytomegalovirus completely helps adeno-associated virus replication. Virology 147:217-22.

Meyers, C., M. Mane, N. Kokorina, S. Alam, and P. L. Hermonat. 2000. Ubiquitous human adeno-associated virus type 2 autonomously replicates in differentiating keratinocytes of a normal skin model. Virology 272:338-46.

Mori, S., L. Wang, T. Takeuchi, and T. Kanda. 2004. Two novel adenoassociated viruses from cynomolgus monkey: pseudotyping characterization of capsid protein. Virology 330:375-83.

Mouw, M. B. and Pintel, D. J.: Adeno-associated virus RNAs appear in a temporal order and their splicing is stimulated during coinfection with adenovirus. J Virol 74 (2000) 9878-88.

Muramatsu, S., H. Mizukami, et al. (1996). "Nucleotide sequencing and generation of an infectious clone of adeno-associated virus 3." Virology 221(1): 208-17.

Myrup, A. C., Mohanty, S. B. and Hetrick, F. M.: Isolation and characterization of adeno-associated viruses from bovine adenovirus types 1 and 2. Am J Vet Res 37 (1976) 907-10.

Naz, S., Griffith, A. J., Riazuddin, S., Hampton, L. L., Battey, J. F. Jr, Khan, S. N., Riazuddin, S., Wilcox, E. R., Friedman, T. B. Mutations of ESPN cause autosomal recessive deafness and vestibular dysfunction. J Med. Genet. 2004 August, 41(8):591-5.

No D, Yao T P, Evans R M. (1996). Ecdysone-inducible gene expression in mammalian cells and transgenic mice. Proc Natl Acad Sci USA. 93(8):3346-51.

Ogston, P., K. Raj, and P. Beard. 2000. Productive replication of adenoassociated virus can occur in human papillomavirus type 16 (HPV-16) episome containing keratinocytes and is augmented by the HPV-16 E2 protein. J Virol 74:3494-504.

Opie, S. R., K. H. Warrington, Jr., et al. (2003). "Identification of amino acid residues in the capsid proteins of adeno-associated virus type 2 that contribute to heparan sulfate proteoglycan binding." J Virol 77(12): 6995-7006.

Parks, W. P., J. L. Melnick, R. Rongey, and H. D. Mayor. 1967. Physical assay and growth cycle studies of a defective adeno-satellite virus. J Virol 1:171-80.

Rabinowitz J E, Bowles D E, Faust S M, Ledford J G, Cunningham S E, Samulski R J. Cross-dressing the virion: the transcapsidation of adeno-associated virus serotypes functionally defines subgroups. J. Virol. 2004 May; 78(9):4421-32.

Reddy, V. S., P. Natarajan, B. Okerberg, K. Li, K. V. Damodaran, R. T. Morton, C. L. Brooks, 3rd, and J. E. Johnson. 2001. Virus Particle Explorer (VIPER), a website for virus capsid structures and their computational analyses. J Virol 75:11943-7.

Richardson, W. D., and H. Westphal. 1984. Requirement for either early region 1a or early region 1b adenovirus gene products in the helper effect for adenoassociated virus. J Virol 51:404-10.

Rutledge, E. A., C. L. Halbert, and D. W. Russell. 1998. Infectious clones and vectors derived from adeno-associated virus (AAV) serotypes other than AAV type 2. J Virol 72:309-19.

Rzadzinska, A. K., M. E. Schneider, et al. (2004). "An actin molecular treadmill and myosins maintain stereocilia functional architecture and self-renewal." J Cell Biol 164(6): 887-97.

Saffer, L. D., R. Gu, et al. (1996). "An RT-PCR analysis of mRNA for growth factor receptors in damaged and control sensory epithelia of rat utricles." Hear Res 94(1-2): 14-23.

Samulski, R. J., and T. Shenk. 1988. Adenovirus E1B 55-Mr polypeptide facilitates timely cytoplasmic accumulation of adeno-associated virus mRNAs. J Virol 62:206-10.

Samulski, R. J., K. I. Berns, M. Tan, and N. Muzyczka. 1982. Cloning of adeno-associated virus into pBR322: rescue of intact virus from the recombinant plasmid in human cells. Proc Natl Acad Sci USA 79:2077-81.

Sanlioglu, S., Benson, P. K., Yang, J., Atkinson, E. M., Reynolds, T. and Engelhardt, J. F.: Endocytosis and nuclear trafficking of adeno-associated virus type 2 are controlled by rac1 and phosphatidylinositol-3 kinase activation. J Virol 74 (2000) 9184-96.

Schlehofer, J. R., M. Ehrbar, and H. zur Hausen. 1986. Vaccinia virus, herpes simplex virus, and carcinogens induce DNA amplification in a human cell line and support replication of a helpervirus dependent parvovirus. Virology 152:110-7.

Schmidt, M., H. Katano, et al. (2004). "Cloning and characterization of a bovine adeno-associated virus." J Virol 78(12): 6509-16.

Schmidt, M., H. Katano, I. Bossis, and J. A. Chiorini. 2004. Cloning and characterization of a bovine adeno-associated virus. J Virol 78:6509-16.

Schneider, M. E., I. A. Belyantseva, et al. (2002). "Rapid renewal of auditory hair bundles." Nature 418(6900): 837-8.

Schwede, T., J. Kopp, N. Guex, and M. C. Peitsch. 2003. SWISS-MODEL: An automated protein homology-modeling server. Nucleic Acids Res 31:3381-5.

Seiler, M. P., C. L. Halbert, J. A. Chiorini, A. D. Miller, and J. Zabner. 2002. AAV5 and AAV6 Mediate Gene Transfer to Human Airway Epthelia Via Different Receptors. Mol. Ther. 5:540.

Shou, J., J. L. Zheng, et al. (2003). "Robust generation of new hair cells in the mature mammalian inner ear by adenoviral expression of Hath1." Mol Cell Neurosci 23(2): 169-79.

Smith, R. H., and R. M. Kotin. 2002. Adeno-associated virus as a transposable element. In R. C. Nancy L. Craig, Martin Gellert, and Alan M. Lambowitz (ed.), Mobile DNA II. ASM Press.

Smith, R. H., S. A. Afione, and R. M. Kotin. 2002. Transposase-mediated construction of an integrated adeno-associated virus type 5 helper plasmid. Biotechniques 33:204-6, 208, 210-1.

Sobkowicz, H. M., J. M. Loftus, et al. (1993). "Tissue culture of the organ of Corti." Acta Otolaryngol Suppl 502: 3-36.

Srivastava, A., E. W. Lusby, and K. I. Berns. 1983. Nucleotide sequence and organization of the adeno-associated virus 2 genome. J Virol 45:555-64.

Staecker H, Li D, O'Malley B W Jr, Van De Water T R. Gene expression in the mammalian cochlea: a study of multiple vector systems. Acta Otolaryngol. 2001 January; 121(2): 157-63.

Stracker, T. H., G. D. Cassell, P. Ward, Y. M. Loo, B. van Breukelen, S. D. Carrington-Lawrence, R. K. Hamatake, P. C. van der Vliet, S. K. Weller, T. Melendy, and M. D. Weitzman. 2004. The Rep protein of adeno-associated virus type 2 interacts with single-stranded DNA-binding proteins that enhance viral replication. J Virol 78:441-53.

Summerford, C. and R. J. Samulski (1998). "Membrane-associated heparan sulfate proteoglycan is a receptor for adeno-associated virus type 2 virions." J Virol 72(2): 1438-45.

Superti, F., M. L. Marziano, A. Tinari, and G. Donelli. 1993. Effect of polyions on the infectivity of SA-11 rotavirus in LCC-MK2 cells. Comp Immunol Microbiol Infect Dis 16:55-62.

Suzuki, H., Y. Katori, et al. (1995). "Carbohydrate distribution in the living utricular macula of the guinea pig detected by lectins." Hear Res 87(1-2): 32-40.

Tratschin, J. D., M. H. West, T. Sandbank, and B. J. Carter. 1984. A human parvovirus, adeno-associated virus, as a eucaryotic vector: transient expression and encapsidation of the procaryotic gene for chloramphenicol acetyltransferase. Mol Cell Biol 4:2072-81.

Walters, R. W., S. M. Yi, S. Keshavjee, K. E. Brown, M. J. Welsh, J. A. Chiorini, and J. Zabner. 2001. Binding of adeno-associated virus type 5 to 2,3-linked sialic acid is required for gene transfer. J Biol Chem 276:20610-6.

Walz, C., A. Deprez, T. Dupressoir, M. Durst, M. Rabreau, and J. R. Schlehofer. 1997. Interaction of human papillomavirus type 16 and adenoassociated virus type 2 co-infecting human cervical epithelium. J Gen Virol 78 (Pt 6):1441-52.

Wang, X. S., and A. Srivastava. 1998. Rescue and autonomous replication of adeno-associated virus type 2 genomes containing Rep-binding site mutations in the viral p5 promoter. J Virol 72:4811-8.

Ward, P., F. B. Dean, M. E. O'Donnell, and K. I. Berns. 1998. Role of the adenovirus DNA-binding protein in in vitro adeno-associated virus DNA replication. J Virol 72:420-7.

Weindler, F. W., and R. Heilbronn. 1991. A subset of herpes simplex virus replication genes provides helper functions for productive adeno-associated virus replication. J Virol 65:2476-83.

Xiao, W., N. Chirmule, S. C. Berta, B. McCullough, G. Gao, and J. M. Wilson. 1999. Gene therapy vectors based on adeno-associated virus type 1. J Virol 73:3994-4003.

Yakinoglu, A. 0., R. Heilbronn, A. Burkle, J. R. Schlehofer, and H. zur Hausen. 1988. DNA amplification of adeno-associated virus as a response to cellular genotoxic stress. Cancer Res 48:3123-9.

Yakobson, B., T. A. Hrynko, M. J. Peak, and E. Winocour. 1989. Replication of adeno-associated virus in cells irradiated with UV light at 254 nm. J Virol 63:1023-30.

Yamano, S., Huang, L. Y., Ding, C., Chiorini, J. A., Goldsmith, C. M., Wellner, R. B., Golding, B., Kotin, R. M., Scott, D. E. and Baum, B. J.: Recombinant adeno-associated virus serotype 2 vectors mediate stable interleukin 10 secretion from salivary glands into the bloodstream. Hum Gene Ther 13 (2002) 287-98.

Zabner, J., Seiler, M., Walters, R., Kotin, R. M., Fulgeras, W., Davidson, B. L., Chiorini, J. A. Adeno-associated virus type 5 (AAV5) but not AAV2 binds to the apical surfaces of airway epithelia and facilitates gene transfer. J. Virol. 2000 April; 74(8):3852-8.

What is claimed is:

1. An isolated nucleic acid molecule that encodes a polypeptide consisting of an amino acid sequence at least 95% identical to SEQ ID NO:30, wherein the polypeptide binds an antibody raised against a protein consisting of SEQ ID NO:30.

2. The isolated nucleic acid molecule of claim 1, wherein the nucleic acid sequence encodes a polypeptide consisting of an amino acid sequence at least 98% identical to SEQ ID NO:30, and wherein the polypeptide binds an antibody raised against a protein consisting of SEQ ID NO:30.

3. An isolated nucleic acid molecule which encodes a polypeptide consisting of at least 50 contiguous amino acids from SEQ ID NO:30.

4. The isolated nucleic acid molecule of claim 1, wherein the nucleic acid sequence encodes a protein consisting of SEQ ID NO:30.

5. The isolated nucleic acid molecule of claim 1, wherein the molecule is an AAV vector.

6. An isolated AAV particle comprising the nucleic acid molecule of claim 1.

7. An isolated nucleic acid molecule comprising a nucleic acid sequence selected from the group consisting of:
   a) a nucleic acid sequence at least 95% identical to SEQ ID NO:20;
   b) a nucleic acid sequence consisting of at least 50 contiguous nucleotides from SEQ ID NO:20; and
   c) a nucleic acid sequence fully complementary to the nucleic acid sequence of a) or b),
   wherein the polypeptide encoded by the nucleic acid sequence of a) or b) binds an antibody raised against a protein consisting of SEQ ID NO:30.

8. The isolated nucleic acid sequence of claim 7, wherein the nucleic acid sequence consists of SEQ ID NO:20.

9. The isolated nucleic acid molecule of claim 7, wherein the molecule is an AAV vector.

10. An isolated AAV particle comprising the nucleic acid molecule of claim 7.

11. An isolated protein, wherein the protein is selected from the group consisting of:
    a) a protein comprising at least 50 contiguous amino acids from SEQ ID NO:30; and
    b) a protein comprising an amino acid sequence at least 95% identical to SEQ ID NO:30,
    wherein the protein selectively binds an antibody raised against a protein consisting of SEQ ID NO:30.

12. The isolated protein of claim 11, wherein the nucleic acid sequence is at least 95% identical to SEQ ID NO:30.

13. The isolated protein of claim 11, wherein the nucleic acid sequence comprises at least 50 contiguous nucleotides from SEQ ID NO:20.

14. An isolated antibody that selectively binds the protein of claim 12.

15. An AAV particle comprising the isolated protein of claim 11.

16. Use of the isolated protein of claim 11 in detecting antibodies to AAV X26, the use comprising:
    a) obtaining an antibody-containing sample;
    b) contacting the sample with the isolated protein; and
    c) determining if an antibody-protein reaction occurred, the presence of such a reaction indicating the presence of antibodies to AAV X26 virus.

* * * * *

```
                          SEQUENCE LISTING

<160> NUMBER OF SEQ ID NOS: 54

<210> SEQ ID NO 1
<211> LENGTH: 4259
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 6
<223> OTHER INFORMATION: N can be A, C, G, or T

<400> SEQUENCE: 1
tttgcgacat tttgcgacac cacgtggcca ttcagggtat atatggccga gtgagcgagc      60
aggatcccca ttttgaccgc gaaatttgaa cgagcagcag ccatgccggg cttctacgag     120
atcgtgatca aggtgccgag cgacctggac gagcacctgc cgggcatttc tgactcgttt     180
gtgaactggg tggccgagaa ggaatgggag ctgccccgg attctgacat ggatctgaat      240
ctgattgagc aggcacccct gaccgtggcc gagaagctgc agcgcgactt cctggtccaa     300
tggcgccgcg tgagtaaggc cccggaggcc ctcttctttg ttcagttcga gaagggcgag     360
tcctacttcc acctccatat tctggtggag accacggggg tcaaatccat ggtgctgggc     420
cgcttcttga gtcagattag ggacaagctg gtgcagacca tctaccgcgg gatcgagccg     480
accctgccca actggttcgc ggtgaccaag acgcgtaatg gcgccggagg ggggaacaag     540
gtggtggacg agtgctacat ccccaactac ctcctgccca agactcagcc cgagctgcag     600
tgggcgtgga ctaacatgga ggagtatata agcgcgtgtt tgaacctggc cgagcgcaaa     660
cggctcgtgg cgcagcacct gacccacgtc agccagaccc aggagcagaa caaggagaat     720
ctgaacccca attctgacgc gcctgtcatc cggtcaaaaa cctccgcgcg ctacatggag     780
ctggtcgggt ggctggtgga ccggggcatc acctccgaga gcagtggat ccaggaggac      840 caggcctcgt acatctcctt caacgccgcc tccaactcgc ggtcccagat caaggccgct     900
ctggacaatg ccggcaagat catggcgctg accaaatccg cgcccgacta cctggtaggc     960
cccgctcctc ccgcggacat taaaccaac cgcatctacc gcatcctgga gctgaacggc    1020
tacgaccctg cctacgccgg ctccgtcttt ctcggctggg cccagaaacg gttcgggaag    1080
cgcaacacca tctggctgtt tgggccgcc accacgggca gaccaacat cgcggaagcc     1140 atcgcccacg ccgtgccctt ctacggctgc gtcaactgga ccaatgagaa ctttccccttc    1200 aacgattgcg tcgacaagat ggtgatctgg tgggaggagg gcaagatgac ggccaaggtc    1260
gtggagtccg ccaaggccat tctcggcggc agcaaggtgc gcgtggacca aaagtgcaag    1320
tcgtccgccc agatcgatcc caccccgtg atcgtcacct ccaacaccaa catgtgcgcc    1380
gtgattgacg gaacagcac caccttcgag caccagcagc cgttgcagga ccggatgttc    1440
```

```
aaatttgaac tcacccgccg tctggagcat gactttggca aggtgacaaa gcaggaagtc   1500
aaagagttct tccgctgggc gcaggatcac gtgaccgagg tggcgcatga gttctacgtc   1560
agaaagggtg gagccaacaa aagacccgcc cccgatgacg cggataaaag cgagcccaag   1620
cgggcctgcc cctcagtcgc ggatccatcg acgtcagacg cggaaggagc tccggtggac   1680
tttgccgaca ggtaccaaaa caaatgttct cgtcacgcgg gcatgcttca gatgctgttt   1740
ccctgcaaga catgcgagag aatgaatcag aatttcaaca tttgcttcac gcacgggacc   1800
agagactgtt cagaatgttt ccccggcgtg tcagaatctc aaccggtcgt cagaaaaagg   1860
acgtatcgga aactctgtgc gattcatcat ctgctggggc gggctcccga gattgcttgc   1920
tcggcctgcg atctggtcaa cgtggacctg gatgactgtg tctctgagca ataaatgact   1980
taaaccaggt atggctgccg atggttatct tccagattgg ctcgaggaca acctctctga   2040
gggcattcgc gagtggtggg acttgaaacc tggagccccg aaacccaaag ccaaccagca   2100
aaagcaggac gacggccggg gtctggtgct tcctggctac aagtacctcg gacccttcaa   2160
cggactcgac aaggggagc ccgtcaacgc ggcggacgca gcggccctcg agcacgacaa   2220
ggcctacgac cagcagctca aagcgggtga caatccgtac ctgcggtata accacgccga   2280
cgccgagttt caggagcgtc tgcaagaaga tacgtctttt gggggcaacc tcgggcgagc   2340
agtcttccag gccaagaagc gggttctcga acctttggt ctggttgagg aaggcgctaa   2400
gacggctcct ggaaagaaac gtccggtaga gcagtcgcca caagagccag actcctcctc   2460
gggcatcggc aagacaggcc agcagcccgc taaaaagaga ctcaattttg gtcagactgg   2520
cgactcagag tcagtccccg acccacaacc tctcggagaa cctccagcaa cccccgctgc   2580
tgtgggacct actacaatgg cttcaggcgg tggcgcacca atggcagaca ataacgaagg   2640
cgccgacgga gtgggtaatg cctcaggaaa ttggcattgc gattccacat ggctgggcga   2700
cagagtcatc accaccagca cccgcacctg ggccttgccc acctacaata accacctcta   2760
caagcaaatc tccagtgctt caacgggggc cagcaacgac aaccactact cggctacag   2820 caccccctgg gggtattttg atttcaacag attccactgc cacttttcac cgcgtgactg   2880
gcagcgactc atcaacaaca attggggatt ccggcccaag agactcaact tcaagctctt   2940
caacatccaa gtcaaggagg tcacgacgag tgatggcgtc acaaccatcg ctaataacct   3000
taccagcacg gttcaagtct tctcggactc ggagtaccag cttccgtacg tcctcggctc   3060
tgcgcaccag ggctgcctcc ctccgttccc ggcggacgtg ttcatgattc cgcaatacgg   3120
ctacctgacg ctcaacaatg gcagccaagc cgtgggacgt tcatccttt actgcctgga   3180 atatttccct tctcagatgc tgagaacggg caacaacttt accttcagct acaccttgga   3240
ggaagtgcct ttccacagca gctacgcgca cagccagagc ctggaccggc tgatgaatcc   3300
tctcatcgac caataccgtg attacctgaa cagaactcaa aatcagtccg gaagtgccca   3360
aaacaaggac ttgctgttta gccgtgggtc tccagctggc atgtctgttc agcccaaaaa   3420
ctggctacct ggaccctgtt atcggcagca gcgcgtttct aaaacaaaaa caggcaacaa   3480
caacagcaat tttacctgga ctggtgcttc aaaatataac ctcaatgggc atgaatccat   3540
catcaaccct ggcactgcta tggcctcaca caaagacgac gaagcaagt tctttcccat   3600 gagcggtgtc atgatttttg gaaaagagag cgccggagct tcaaacactg cattggacaa   3660
tgtcatgatt acagacgaag aggaaattaa agccactaac cctgtggcca ccgaaagatt   3720
tgggaccgtg gcagtcaatt tccagagcag cagcacacac cctgcgaccg gagatgtgca   3780
tgttatggga gcattacctg gcatggtgtg gcaagataga gacgtgtacc tgcagggtcc   3840
```

| | |
|---|---|
| catctgggcc aaaattcctc acacagatgg acactttcac ccgtctcctc ttatgggcgg | 3900 |
| ctttggactc aagcacccgc ctcctcagat cctcatcaaa acacgcctg ttcctgcgaa | 3960 |
| tcctccggcg gagttttcag ctacaaagtt tgcttcattc atcacccaat actccacagg | 4020 |
| acaagtgagt gtgaaattg aatgggagct gcagaaagaa aacagcaagc gctggaatcc | 4080 |
| cgaagtgcag tacacatcca attatgcaaa atctgccaac gttgatttta ccgtggacaa | 4140 |
| caatggactt tatactgagc ctcgccccat tggcacccgt taccttaccc gtccctgta | 4200 |
| attacgtgtt aatcaataaa ccggttgatt cgtttcagtt gaactttggt ctcctgtcc | 4259 |

<210> SEQ ID NO 2
<211> LENGTH: 4305
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 2

| | |
|---|---|
| accctcacta aagggactag tcctgcaggt ttaaacgaat tcgcccttg cgacattttg | 60 |
| cgacaccacg tggccattca gggtatatat ggccgagtga gcgagcagga tccccattt | 120 |
| gaccgcgaaa tttgaacgag cagcagccat gccgggcttc tacgagatcg tgatcaaggt | 180 |
| gccgagcgac ctgacgagc acctgccggg catttctgac tcgtttgtga actgggtggc | 240 |
| cgagaaggaa tgggagctgc ccccggattc tgacatggat ctgaatctga ttgagcaggc | 300 |
| accctgacc gtgccgaga gctgcagcg cgacttcctg gtccaatggc gccgcgtgag | 360 |
| taaggccccg gaggccctct tctttgttca gttcgagaag ggcgagtcct acttccacct | 420 |
| ccatattctg gtggagacca cggggtcaa atccatggtg ctgggccgct tcttgagtca | 480 |
| gattagggac aagctggtgc agaccatcta ccgcgggatc gagccgaccc tgcccaactg | 540 |
| gttcgcggtg accaagacgc gtaatggcgc cggagggggg aacaaggtgg tggacgagtg | 600 |
| ctacatcccc aactacctcc tgcccaagac tcagcccgag ctgcagtggg cgtggactaa | 660 |
| catggaggag tatataagcg cgtgtttgaa cctggccgag cgcaaacggc tcgtggcgca | 720 |
| gcacctgacc cacgtcagcc agacccagga gcagaacaag gagaatctga accccaattc | 780 |
| tgacgcgcct gtcatccggt caaaaacctc cgcgcgctac atggagctgg tcgggtggct | 840 |
| ggtggaccgg ggcatcacct ccgagaagca gtggatccag gaggaccagg cctcgtacat | 900 |
| ctccttcaac gccgcctcca actcgcggtc ccagatcaag gccgctctgg acaatgccgg | 960 |
| caagatcatg gcgctgacca atccgcgcc cgactacctg gtaggccccg ctcctcccgc | 1020 |
| ggacattaaa accaaccgca tctaccgcat cctggagctg aacggctacg accctgccta | 1080 |
| cgccggctcc gtcttctcg gctgggccca gaaacggttc gggaagcgca acaccatctg | 1140 |
| gctgtttggg ccggccacca cgggcaagac caacatcgcg gaagccatcg cccacgccgt | 1200 |
| gcccttctac ggctgcgtca actggaccaa tgagaacttt cccttcaacg attgcgtcga | 1260 |
| caagatggtg atctggtggg aggagggcaa gatgacggcc aaggtcgtgg agtccgccaa | 1320 |
| ggccattctc ggcggcagca aggtgcgcgt ggaccaaaag tgcaagtcgt ccgcccagat | 1380 |
| cgatccacc cccgtgatcg tcacctccaa caccaacatg tgcgccgtga ttgacgggaa | 1440 |
| cagcaccacc ttcgagcacc agcagccgtt gcaggaccgg atgttcaaat ttgaactcac | 1500 |
| ccgccgtctg gagcatgact ttggcaaggt gacaaagcag gaagtcaaag agttcttccg | 1560 |
| ctgggcgcag gatcacgtga ccgaggtggc gcatgagttc tacgtcagaa agggtggagc | 1620 |
| caacaaaaga cccgccccg atgacgcgga taaaagcgag cccaagcggg cctgcccctc | 1680 |

```
agtcgcggat ccatcgacgt cagacgcgga aggagctccg gtggactttg ccgacaggta    1740
ccaaaacaaa tgttctcgtc acgcgggcat gcttcagatg ctgtttccct gcaagacatg    1800
cgagagaatg aatcagaatt tcaacatttg cttcacgcac gggaccagag actgttcaga    1860
atgtttcccc ggcgtgtcag aatctcaacc ggtcgtcaga aaaaggacgt atcggaaact    1920
ctgtgcgatt catcatctgc tggggcgggc tcccgagatt gcttgctcgg cctgcgatct    1980
ggtcaacgtg gacctggatg actgtgtctc tgagcaataa atgacttaaa ccaggtatgg    2040
ctgccgatgg ttatcttcca gattggctcg aggacaacct ctctgagggc attcgcgagt    2100
ggtgggactt gaaacctgga gccccgaaac ccaaagccaa ccagcaaaag caggacgacg    2160
gccggggtct ggtgcttcct ggctacaagt acctcggacc cttcaacgga ctcgacaagg    2220
gggagcccgt caacgcggcg gacgcagcgg ccctcgagca cgacaaggcc tacgaccagc    2280
agctcaaagc gggtgacaat ccgtacctgc ggtataacca cgccgacgcc gagtttcagg    2340
agcgtctgca agaagatacg tcttttgggg caacctcgg gcgagcagtc ttccaggcca    2400
agaagcgggt tctcgaacct tttggtctgg ttgaggaagg cgctaagacg gctcctggaa    2460
agaaacgtcc ggtagagcag tcgccacaag agccagactc ctcctcgggc atcggcaaga    2520
caggccagca gcccgctaaa aagagactca attttggtca gactggcgac tcagagtcag    2580
tccccgaccc acaacctctc ggagaacctc cagcaacccc cgctgctgtg ggacctacta    2640
caatggcttc aggcggtggc gcaccaatgg cagacaataa cgaaggcgcc gacggagtgg    2700
gtaatgcctc aggaaaattg cattgcgatt ccacatggct gggcgacaga gtcatcacca    2760
ccagcacccg cacctgggcc ttgcccacct acaataacca cctctacaag caaatctcca    2820
gtgcttcaac gggggccagc aacgacaacc actacttcgg ctacagcacc ccctgggggt    2880
attttgattt caacagattc cactgccact tttcaccgcg tgactggcag cgactcatca    2940
acaacaattg gggattccgg cccaagagac tcaacttcaa gctcttcaac atccaagtca    3000
aggaggtcac gacgagtgat ggcgtcacaa ccatcgctaa taccttacc agcacggttc    3060
aagtcttctc ggactcggag taccagcttc cgtacgtcct cggctctgcg caccagggct    3120
gcctccctcc gttcccggcg gacgtgttca tgattccgca atacggctac ctgacgctca    3180
acaatggcag ccaagccgtg ggacgttcat ccttttactg cctggaatat ttcccttctc    3240
agatgctgag aacgggcaac aactttacct tcagctacac ctttgaggaa gtgccttttc    3300
acagcagcta cgcgcacagc cagagcctgg accggctgat gaatcctctc atcgaccaat    3360
acctgtatta cctgaacaga actcaaaatc agtccggaag tgcccaaaac aaggacttgc    3420
tgtttagccg tgggtctcca gctggcatgt ctgttcagcc caaaaactgg ctacctggac    3480
cctgttatcg gcagcagcgc gtttctaaaa caaaaacagg caacaacaac agcaatttta    3540
cctggactgg tgcttcaaaa tataacctca tgggcatga atccatcatc aaccctggca    3600
ctgctatggc ctcacacaaa gacgacgaag acaagttctt tcccatgagc ggtgtcatga    3660
ttttggaaa agagagcgcc ggagcttcaa acactgcatt ggacaatgtc atgattacag    3720
acgaagagga aattaaagcc actaaccctg tggccaccga agatttggg accgtggcag    3780
tcaatttcca gagcagcagc acacaccctg cgaccggaga tgtgcatgtt atgggagcat    3840
tacctggcat ggtgtggcaa gatagagacg tgtacctgca gggtcccatc tgggccaaaa    3900
ttcctcacac agatgacac tttcaccgt ctcctcttat gggcggcttt ggactcaagc    3960
acccgcctcc tcagatcctc atcaaaaaca cgcctgttcc tgcgaatcct ccggcggagt    4020
tttcagctac aaagtttgct tcattcatca cccaatactc cacaggacaa gtgagtgtgg    4080
```

| aaattgaatg ggagctgcag aaagaaaaca gcaagcgctg gaatcccgaa gtgcagtaca | 4140 |
| catccaatta tgcaaaatct gccaacgttg attttaccgt ggacaacaat ggactttata | 4200 |
| ctgagcctcg ccccattggc acccgttacc ttacccgtcc cctgtaatta cgtgttaatc | 4260 |
| aataaaccgg ttgattcgtt tcagttgaac tttggtctcc tgtcc | 4305 |

<210> SEQ ID NO 3
<211> LENGTH: 4196
<212> TYPE: DNA
<213> ORGANISM: Artificial Sequence
<220> FEATURE:
<223> OTHER INFORMATION: Description of Artificial Sequence: Note = synthethic construct
<220> FEATURE:
<221> NAME/KEY: misc_feature
<222> LOCATION: 745, 826, 845, 932, 960, 1003
<223> OTHER INFORMATION: N can be A, C, G, or T

<400> SEQUENCE: 3

| ccgcgagtga gcgaaccagg agctccattt tgcccgcgaa ttttgaacga gcagcagcca | 60 |
| tgccgggatt ctacgagatt gtcctgaagg tgcccagcga cctggacgag cacctgcctg | 120 |
| gcatttctga ctcttttgta aactgggtgg cggagaagga atgggagctg ccgccggatt | 180 |
| ctgacatgga tctgaatctg attgagcagg caccccctaac cgtggccgaa agctgcaac | 240 |
| gcgaattcct ggtcgagtgg cgccgcgtga gtaaggcccc ggaggccctc ttctttgttc | 300 |
| agttcgagaa gggggacagc tacttccacc tacacattct ggtggagacc gtgggcgtga | 360 |
| aatccatggt ggtgggccgc tacgtgagcc agattaaaga gaagctggtg acccgcatct | 420 |
| accgcggggt cgagccgcag cttccgaact ggttcgcggt gaccaagacg cgtaatggcg | 480 |
| ccggaggcgg gaacaaggtg gtggacgact gctacatccc caactacctg ctccccaaga | 540 |
| cccagcccga gctccagtgg gcgtggacta atatggacca gtatttaagc gcctgtttga | 600 |
| atctcgcgga gcgtaaacgg ctggtggcgc agcatctgac gcacgtgtcg cagacgcagg | 660 |
| agcagaacaa agagaaccag aaccnaattc tgacgcgccg gtgattcgat caaaacctcc | 720 |
| gcgaggtaca tggagctggt cgggtggctg gtggacccng gatcncgtc agaaaagcaa | 780 |
| tggantccag gaggaccagg cctcttacat ctccttcaac gccgcctcca actcgcggtc | 840 |
| acaaatcaag gccgcactgg acaatgcctc cnaaattatg agcctgacaa aaacggctcc | 900 |
| ggactacctg gtgggaaaca acccgccgga ggacattact canaaccgga tctacaaaat | 960 |
| cctcgagatg aacgggtacg atccgcagta cgcggcctcc gtcttcctgg gctgggcgca | 1020 |
| aaagaagttc gggaagagga acaccatctg gctctttggg ccggccacga cgggtaaaac | 1080 |
| caacatcgct gaagctatcg cccacgcccgt gccctttttac ggctgcgtga actgaccaa | 1140 |
| tgagaacttt ccgttcaacg attgcgtcga caagatggtg atctggtggg aggagggcaa | 1200 |
| gatgacggcc aaggtcgtgg agtccgccaa ggccattctg gcggaagca aggtgcgcgt | 1260 |
| ggaccaaaag tgcaagtcat cggcccagat cgacccaact cccgtcatcg tcacctccaa | 1320 |
| caccaacatg tgcgcggtca tcgacggaaa ttccaccacc ttcgagcacc aacaaccact | 1380 |
| ccaagaccgg atgttcaagt tcgagctcac caagcgcctg gagcacgact ttggcaaggt | 1440 |
| caccaagcag gaagtcaagg acttttttccg gtgggcgtca gatcacgtga ctgaggtgtc | 1500 |
| tcacgagttt acgtcagaa agggtggagc tagaaagagg cccgccccca atgacgcaga | 1560 |
| tataagtgag cccaagcggg cctgtccgtc agttgcgcag ccatcgacgt cagacgcgga | 1620 |
| agctccggtg gactacgcgg acaggtacca aaacaaatgt tctcgtcacg tgggcatgaa | 1680 |
| tctgatgctt tttccctgcc ggcaatgcga gagaatgaat cagaatgtgg acatttgctt | 1740 |

```
cacgcacggg gtcatggact gtgccgagtg cttcccgtg  tcagaatctc aacccgtgtc      1800
tgtcgtcaga aagcggacat atcagaaact gtgtccgatt catcacatca tggggagggc      1860
gcccgaggtg gcttgttcgg cctgcgatct ggccaatgtg gacttggatg actgtgacat      1920
ggagcaataa atgactcaaa ccagatatga ctgacggtta ccttccagat tggctagagg      1980
acaacctctc tgaaggcgtt cgagagtggt gggcgctgca acctggagcc cctaaaccca      2040
aggcaaatca acaacatcag gacaacgctc ggggtcttgt gcttccgggt tacaaatacc      2100
tcggacccgg caacggactt gacaagggg aacccgtcaa cgcagcggac gcggcagccc      2160
tcgaacacga caaggcctac gaccagcagc tcaaggccgg tgacaacccc tacctcaagt      2220
acaaccacgc cgacgccgag tttcaggagc gtcttcaaga agatacgtct tttgggggca      2280
acctcggacg agcagtcttc caggccaaaa agaggatcct tgagcctctg gtctggttg       2340 aggaagcggc taagacggct cctggaaaaa agagacctgt agagcaatct ccagcagaac      2400
cggactcctc ttcgggcatc ggcaaatcag gccagcagcc cgctagaaaa agactgaatt      2460
ttggtcagac tggcgacaca gagtcagtcc cagaccctca accactcgga caacctcccg      2520
cagccccctc tggtgtggga tctactacaa tggcttcagg cggtggcgca ccaatggcag      2580
acaataacga gggtgccgat ggagtgggta attcctcagg aaattggcat tgcgattccc      2640
aatggctggg cgacagagtc atcaccacca gcacccgcac ctgggccctg cccacctaca      2700
acaatcacct ctacaagcaa atctccagcc aatcaggagc caccaacgac aaccactact      2760
ttggctacag caccccctgg gggtattttg acttcaacag attccactgc cacttttcac      2820
cacgtgactg gcaaagactc atcaacaaca actgggggatt ccgacccaag agactcaact      2880
tcaagctctt taacattcaa gtcaaagagg tcacgcagaa tgacggtacg acgacgattg      2940
ccaataacct taccagcacg gttcaggtgt ttactgactc cgagtaccag ctcccgtacg      3000
tcctcggctc ggcgcatcag ggatgcctcc cgccgttccc agcagacgtc ttcatggtcc      3060
cacagtatgg atacctcacc ctgaacaacg ggagtcaggc ggtaggacgc tcttcctttt      3120
actgcctgga gtactttcct tctcagatgc tgcgtactgg aaacaacttt cagtttagct      3180
acactttgta agacgtgcct ttccacagca gctacgctca cagccaaagt ctggaccgtc      3240
tcatgaatcc tctgatcgac cagtacctgt actatctgaa caggacacaa acagccagtg      3300
gaactcagca gtctcggcta ctgtttagcc aagctggacc caccagtatg tctcttcaag      3360
ctaaaaactg gctgcctgga ccttgctaca gacagcagcg tctgtcaaag caggcaaacg      3420
acaacaacaa cagcaacttt ccctggactg gtgccaccaa atatcatctg aatggccggg      3480
actcattggt gaacccgggc cctgctatgg ccagtcacaa ggatgacaaa gaaaagtttt      3540 tcccatgca tggaacctg atatttggta aagaaggaac aaatgccaac aacgcggatt       3600
tggaaaatgt catgattaca gatgaagaag aaatccgcac caccaatccc gtggctacgg      3660
agcagtacgg gactgtgtca aataatttgc aaaactcaaa cgctggtcca actactggaa      3720
ctgtcaatca ccaaggagcg ttacctggta tggtgtggca ggatcgagac gtgtacctgc      3780
agggacccat ttgggccaag attcctcaca ccgatgaca  cttcatcct tctccactga      3840 tgggaggttt tgggctcaaa cacccgcctc ctcagatcat gatcaaaaac actcccgttc      3900
cagccaatcc tccacaaac  tttagtgcgg caaagtttgc ttccttcatc acacagtact      3960
ccacggggca ggtcagcgtg gagatcgagt gggagctgca gaaggagaac agcaaacgct      4020
ggaatcccga aattcagtac acttccaact acaacaaatc tgttaatgtg gactttactg      4080
```

```
tggacactaa tggtgtgtat tcagagcctc gccccattgg caccagatac ctgactcgta    4140
atctgtaatt gcttgttaat caataaaccg gttgattcgt ttcagttgaa ctttgg        4196

<210> SEQ ID NO 4
<211> LENGTH: 3005
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 4
tggtgggagg agggcaagat gacggccaag gtcgtggagt ccgccaaggc cattctcggc      60
ggcagcaagg tgcgcgtgga ccaaaagtgc aagtcgtccg cccagatcga tcccaccccc    120
gtgatcgtca cctccaacac caacatgtgc gccgtgattg acgggaacag caccaccttc    180
gagcaccagc agccgttgca ggaccggatg ttcaaatttg aactcacccg ccgtctggag    240
catgactttg gcaaggtgac aaagcaggaa gtcaaagagt tcttccgctg ggcgcaggat    300
cacgtgaccg aggtggcgca tgagttctac gtcagaaagg gtggagccaa caaagacccc   360
gcccccgatg acgcggataa aagcgagccc aagcgggcct gcccctcagt cgcggatcca    420
tcgacgtcag acgcggaagg agctccggtg gactttgccg acaggtacca aaacaaatgt    480
tctcgtcacg cgggcatgct tcagatgctg tttccctgca agacatgcga gagaatgaat    540
cagaatttca acatttgctt cacgcacggg accagagact gttcagaatg tttccccggc    600
gtgtcagaat ctcaaccggt cgtcagaaaa aggacgtatc ggaaactctg tgcgattcat    660
catctgctgg ggcgggctcc cgagattgct tgctcggcct gcgatctggt caacgtggac    720
ctggatgact gtgtctctga gcaataaatg acttaaacca ggtatggctg ccgatggtta    780
tcttccagat tggctcgagg acaacctctc tgagggcatt cgcgagtggt gggacttgaa    840
acctggagcc cgaaacccaa agccaacca gcaaaagcag gacgacgcc ggggtctggt      900 gcttcctggc tacaagtacc tcggaccctt caacggactc gacaagggg agcccgtcaa     960 cgcggcggac gcagcggccc tcgagcacga caaggcctac gaccagcagc tcaaagcggg   1020
tgacaatccg tacctgcggt ataaccacgc cgacgccgag tttcaggagc gtctgcaaga   1080
agatacgtct tttggggggca acctcgggcg agcagtcttc caggccaaga gcgggttct    1140 cgaaccttt ggtctggttg aggaaggcgc taagacggct cctggaaaga acgtccggt     1200 agagcagtcg ccacaagagc cagactcctc ctcgggcatc ggcaagacag gccagcagcc   1260
cgctaaaaag agactcaatt ttggtcagac tggcgactca gagtcagtcc ccgacccaca   1320
acctctcgga gaacctccag caaccccgc tgctgtggga cctactacaa tggcttcagg    1380
cggtggcgca ccaatggcag acaataacga aggcgccgac ggagtgggta atgcctcagg   1440
aaattggcat tgcgattcca catggctggg cgacagagtc atcaccacca gcacccgcac   1500
ctgggccttg cccacctaca ataaccacct ctacaagcaa atctccagtg cttcaacggg   1560
ggccagcaac gacaaccact acttcggcta cagcacccccc tgggggtatt tgatttcaa    1620 cagattccac tgccactttt caccacgtga ctggcagcga ctcatcaaca caattgggg     1680 attccggccc aagagactca acttcaagct cttcaacatc caagtcaagg aggtcacgac   1740
gaatgatggc gtcacaacca tcgctaataa ccttaccagc acggttcaag tcttctcgga   1800
ctcggagtac cagcttccgt acgtcctcgg ctctgcgcac caggggctgcc tccctccgtt   1860 cccggcggac gtgttcatga ttccgcaata cggctacctg acgctcaaca atggcagcca   1920
agccgtggga cgttcatcct tttactgcct ggaatatttc ccttctcaga tgctgagaac   1980
```

-continued

```
gggcaacaac tttaccttca gctacacctt tgaggaagtg cctttccaca gcagctacgc   2040
gcacagccag agcctggacc ggctgatgaa tcctctcatc gaccaatacc tgtattacct   2100
gaacagaact caaaatcagt ccggaagtgc ccaaaacaag gacttgctgt ttagccgtgg   2160
gtctccagct ggcatgtctg ttcagcccaa aaactggcta cctggaccct gttatcggca   2220
gcagcgcgtt tctaaaacaa aaacagacaa caacaacagc aattttacct ggactggtgc   2280
ttcaaaatat aacctcaatg ggcgtgaatc catcatcaac cctggcactg ctatggcctc   2340
acacaaagac gacgaagaca agttctttcc catgagcggt gtcatgattt ttggaaaaga   2400
gagcgccgga gcttcaaaca ctgcattgga caatgtcatg attacagacg aagaggaaat   2460
taaagccact aaccctgtgg ccaccgaaag atttgggacc gtggcagtca atttccagag   2520
cagcagcaca gaccctgcga ccggagatgt gcatgttatg ggagcattac ctggcatggt   2580
gtggcaagat agagacgtgt acctgcaggg tcccatctgg gccaaaattc ctcacacaga   2640
tggacacttt cacccgtctc ctcttatggg cggctttgga ctcaagcacc cgcctcctca   2700
gatcctcatc aaaaacacgc ctgttcctgc gaatcctccg gcggagtttt cagctacaaa   2760
gtttgcttca ttcatcaccc aatactccac aggacaagtg agtgtggaaa ttgaatggga   2820
gctgcagaaa gaaaacagca gcgctggaa tcccgaagtg cagtacacat ccaattatgc   2880
aaaatctgcc aacgttgatt ttaccgtgga caacaatgga ctttatactg agcctcgccc   2940
cattggcacc cgttacctta cccgtcccct gtaattacgt gttaatcaat aaaccgtttm   3000
attcg                                                                3005
```

<210> SEQ ID NO 5
<211> LENGTH: 3014
<212> TYPE: DNA
<213> ORGANISM: Artificial Sequence
<220> FEATURE:
<223> OTHER INFORMATION: Description of Artificial Sequence: Note = synthethic construct
<220> FEATURE:
<221> NAME/KEY: misc_feature
<222> LOCATION: 6
<223> OTHER INFORMATION: N can be A, C, G, or T (U)

<400> SEQUENCE: 5

```
atgctnatgt ggtgggagga gggcaagatg acggccaagg tcgtggagtc cgccaaggcc     60
attctcggcg gcagcaaagt gcgcgtggac caaaagtgca agtcgtccgc ccagatcgat    120 cccaccccg tgatcgtcac ctccaacacc aacatgtgcg ccgtgattga cgggaacagc    180
accaccttcg agcaccagca gccgttgcag gaccggatgt tcaaatttga actcacccgc    240
cgtctggagc atgactttgg caaggtgaca aaacaggaag tcaaagagtt cttccgctgg    300
gcgcaggatc acgtgaccga ggtggcgcat gagttctacg tcagaaaggg tggagccaac    360
aagagacccg ccccgatga cgcggataaa gcgagccca gcgggtctg cccctcagtc     420 gcggatccat cgacgtcaga gcggaagga gctccggtgg actttgccga caggtaccaa    480
aacaaatgtt ctcgtcacgc gggcatgctt cagatgctgt ttccctgcaa acatgcgag    540 agaatgaatc agaatttcaa catttgcttc acgcacggga ccagagactg ttcagaatgt    600
ttccccggcg tgtcagaatc tcaaccggtc gtcagaaaaa ggacgtatcg gaaactctgt    660
gccattcatc atctgctggg gcgggctccc gagattgctt gctcggcctg cgatctggtc    720
aacgtggacc tggatgactg tgtttctgag caataaatga cttaaaccag gtatggctgc    780
cgatggttat cttccagatt ggctcgagga caacctctct gagggcattc gcaagtggtg    840
ggacttgaaa cctggagccc cgaaacccaa agccaaccag caaaagcagg acgacggccg    900
```

```
gggtctggtg cttcctggct acaagtacct cggacccttc aacggactcg acaaggggga    960
gcccgtcaac gcggcggacg cagcggccct cgagcacgac aaggcctacg accagcagct   1020
caaagcgggt gacaatccgt acctgcggta taaccacgcc gacgccgagt tcaggagcg    1080 tctgcaagaa gatacgtctt ttgggggcaa cctcgggaga gcagtcttcc aggccaagaa   1140
gcgggttctc gaaccttttg gtctggttga ggaaggcgct aagacggctc ctggaaagaa   1200
acgtccggta gagcagtcgc cacaagagcc agactcctcc tcgggcatcg gcaagacagg   1260
ccagcagccc gctaaaaaga gactcaattt tggtcagact ggcgactcag agtcagtccc   1320
cgacccacaa cctctcggag aacctccagc aaccccgct gctgtgggac ctactacaat    1380
ggcttcaggc ggtggcgcac caatggcaga caataacgaa ggcgccgacg gagtgggtaa   1440
tgcctcagga aattggcatt gcgattccac atggctgggc gacagagtca tcaccaccag   1500
cacccgcacc tgggccttgc ccacctacaa taaccacctc tacaagcaaa tctccagtgc   1560
ttcaacgggg gccagcaacg acaaccacta cttcggctac agcaccccct gggggtattt   1620
tgatttcaac agattccact gccactttt accacgtgac tggcagcgac tcatcaacaa    1680
caattgggga ttccggccca agagactcaa cttcaagctc ttcaacatcc aagtcaagga   1740
ggtcacgacg aatgatggcg tcacaaccat cgctaataac cttaccagca cggttcaagt   1800
cttctcggac tcggagtacc agcttccgta cgtcctcggc tctgcgcacc agggctgcct   1860
ccctccgttc ccggcggacg tgttcatgat tccgcaatac ggctacctga cgctcaacaa   1920
tggcagccaa gccgtgggac gttcatcctt ttactgcctg gaatatttcc cttctcagat   1980
gctgagaacg ggcaacaact ttaccttcag ctacaccttt gaggaagtgc ctttccacag   2040
cagctacgcg cacagccaga gcctggaccg gctgatgaat cctctcatcg accaataacct   2100 gtattacctg aacagaactc aaaatcagtc cggaagtgcc caaacaagg acttgctgtt    2160 tagccgtggg tctccagctg gcatgtctgt tcagcccaaa aactggctac ctggaccctg   2220
ttatcggcag cagcgcgttt ctaaaacaaa aacagacaac aacaacagca attttacctg   2280
gactggtgct tcaaaatata acctcaatgg gcgtgaatcc atcatcaacc ctggcactgc   2340 tatgcctca cacaaagacg acaaagacaa gttcttcc atgagcggtg tcatgatttt     2400
tggaaaagag agcgccggag cttcaaacac tgcattggac aatgtcatga ttacagacga   2460
agaggaaatt aaagccacta accctgtggc caccgaaaga tttgggaccg tggcagtcaa   2520
tttccagagc agcagcacag accctgcgac cggagatgtg catgttatgg gagcattacc   2580
tggcatggtg tggcaagata gagacgtgta cctgcagggt cccatttggg ccaaaattcc   2640
tcacacagat ggacactttc acccgtctcc tcttatgggc ggctttggac tcaagcaccc   2700
gcctcctcag atcctcatca aaacacacc tgttcctgcg aatcctccgg cggagttttc    2760
agctacaaag tttgcttcat tcatcaccca atactccaca ggacaagtga gtgtggaaat   2820
tgaatgggag ctgcagaaag aaaacagcaa gcgctgaat  cccgaagtgc agtacacatc    2880
caattatgca aaatctgcca acgttgattt taccgtggac aacaatggac tttatactga   2940
gcctcgcccc attggcaccc gttaccttac ccgtccctg taattacgtg ttaatcaata    3000 aaccgktha ttcg                                                      3014
```

<210> SEQ ID NO 6
<211> LENGTH: 3010
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 6

```
tgatttggtg ggaggagggc aagatgacgg ccaaggtcgt ggagtccgcc aaagccattc      60
tcggcggcag caaggtgcgc gtggaccaaa agtgcaagtc gtccgcccrg atcgatccca     120
cccccgtgat cgtcacctcc aacaccaaca tgtgcgccgt gattgacggg aacagcacca     180
ccttcgagca ccagcagccg ttgcaggacc ggatgttcaa atttgaactc acccgccgtc     240
tggagcatga ctttggcaag gtgacaaagc aggaagtcaa agagttcttc cgctgggcgc     300
aggatcacgt gaccgaggtg gcgcatgagt tctacgtcag aaagggtgga gccaacaaaa     360
gacccgcccc cgatgacgcg gataaaagcg agcccaagcg ggcctgcccc tcagtcgcgg     420
atccatcgac gtcagacgcg gaaggagctc cggtggactt tgccgacagg taccaaaaca     480
aatgttctcg tcacgcgggc atgcttcaga tgctgtttcc ctgcaagaca tgcgagagaa     540
tgaatcagaa tttcaacatt tgcttcacgc acgggaccag agactgttca gaatgtttcc     600
ccggcgtgtc agaatctcaa ccggtcgtca gaaaaaggac gtatcggaaa ctctgtgcga     660
ttcatcatct gctggggcgg gctcccgaga ttgcttgctc ggcctgcgat ctggtcaacg     720
tggacctgga tgactgtgtc tctgagcaat aaatgactta aaccaggtat ggctgccgat     780
ggttatcttc cagattggct cgaggacaac ctctctgagg gcattcgcga gtggtgggac     840
ttgaaacctg gagccccgaa acccaaagcc aaccagcaaa gcaggacaa cggccggggt     900
ctggtgcttc ctggctacaa gtacctcgga cccttcaacg gactcgacaa ggggggagccc     960
gtcaacgcgg cggacgcagc ggccctcgag cacgacaagg cctacgacca gcagctcaaa    1020
gcgggtgaca atccgtacct gcggtataac cacgccgacg ccgagtttca ggagcgtctg    1080
caagaagata cgtctttggg gggcaaccte gggcgagcag tcttccaggc caagaagcgg    1140
gttctcgaac cttttggtct ggttgaggaa ggcgctaaga cggctcctgg aaagaaacgt    1200
ccggtagagc agtcgccaca agagccgac tcctcctcgg gcatcggcaa acaggccag    1260
cagcccgcta aaagagact caattttggt cagactggcg actcagagtc agtccccgac    1320
ccacaacctc tcggagaacc tccagcaacc ccgctgctg tgggacctac tacaatggct    1380
tcaggcggtg gcgcaccaat ggcagacaat aacgaaggcg ccgacggagt gggtaatgcc    1440
tcaggaaatt ggcattgcga ttccacatgg ctgggcgaca gagtcatcac caccagcacc    1500
cgcacctggg ccttgcccac ctacaataac cacctctaca gcaaatctc cagtgcttca    1560
acggggggcca gcaacgacaa ccactacttc ggctacagca cccctgggg gtattttgat    1620
ttcaacagat tccactgcca cttttcacca cgtgactggc agcgactcat caacaacaat    1680
tggggattcc ggcccaagag actcaacttc aagctcttca acatccaagt caaggaggtc    1740
acgacgaatg atggcgtcac aaccatcgct aataaccta ccagcacggt tcaagtcttc    1800
tcggactcgg agtaccagct tccgtacgtc ctcggctctg cgcaccaggg ctgcctccct    1860
ccgttcccgg cggacgtgtt catgattccg caatacggct acctgacgct caacaatggc    1920
agccaagccg tgggacgttc atcctttac tgcctggaat atttcccttc tcagatgctg    1980
agaacgggca caactttac cttcagctac acctttgagg aagtgccttt ccacagcagc    2040
tacgcgcaca gccagagcct ggaccggctg atgaatcctc tcatcgacca ataccctgtat    2100
tacctgaaca gaactcaaaa tcagtccgga agtgcccaaa acaaggactt gctgtttagc    2160
cgtgggtctc cagctggcat gtctgttcag cccaaaaact ggctacctgg accctgttat    2220
cggcagcagc gcgtttctaa aacaaaaaca gacaacaaca acagcaattt tacctggact    2280
ggtgcttcaa aatataacct caatgggcgt gaatccatca tcaaccctgg cactgctatg    2340
```

-continued

| | |
|---|---|
| gcctcacaca aagacgacga agacaagttc tttcccatga gcggtgtcat gattttgga | 2400 |
| aaagagagcg ccggagcttc aaacactgca ttggacaatg tcatgattac agacgaagag | 2460 |
| gaaattaaag ccactaaccc tgtggccacc gaaagatttg ggaccgtggc agtcaatttc | 2520 |
| cagagcagca gcacacaccc tgcgaccgga gatgtgcatg ttatgggagc attacctggc | 2580 |
| atggtgtggc aagatagaga cgtgtacctg cagggtccca tctgggccaa aattcctcac | 2640 |
| acagatggac actttcaccc gtctcctctt atgggcggct ttggactcaa gcacccgcct | 2700 |
| cctcagatcc tcatcaaaaa cacgcctgtt cctgcgaatc ctccggcgga ttttcagct | 2760 |
| acaaagtttg cttcattcat cacccaatac tccacaggac aagtgagtgt ggaaattgaa | 2820 |
| tgggagctgc agaaagaaaa cagcaagcgc tggaatcccg aagtgcagta cacatccaat | 2880 |
| tatgcaaaat ctgccaacgt tgattttacc gtggacaaca atggacttta tactgagcct | 2940 |
| cgccccattg gcacccgtta ccttacccgt ccctgtaat tacgtgttaa tcaataaacc | 3000 |
| gtttyattcg | 3010 |

<210> SEQ ID NO 7
<211> LENGTH: 3008
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 7

| | |
|---|---|
| atytggtggg aggagggcaa gatgacggcc aaggtcgtgg agtccgccaa ggccattctc | 60 |
| ggcggcagca aggtgcgcgt ggaccaaaag tgcaagtcgt ccgcccagat cgatcccacc | 120 |
| cccgtgatcg tcacctccaa caccaacatg tgcgccgtga ttgacgggaa cagcaccacc | 180 |
| ttcgagcacc agcagccgtt gcaggaccgg atgttcaaat ttgaactcac ccgccgtctg | 240 |
| gagcacgact ttggcaaggt gacaaagcag gaagtcaaag agttcttccg ctgggcgcag | 300 |
| gatcacgtga ccgaggtggc gcatgagttc tacgtcagaa agggtggagc caacaagaga | 360 |
| cccgcccccg atgacgcgga taaaagcgag cccaagcggg cctgcccctc agtcgcggat | 420 |
| ccatcgacgt cagacgcgga aggagctccg gtggactttg ccgacaggta ccaaaacaaa | 480 |
| tgttctcgtc acgcgggcat gcttcagatg ctgtttccct gcaaaacatg cgagagaatg | 540 |
| aatcagaatt caacatttg cttcacgcac gggaccagag actgttcaga gtgctttccc | 600 |
| ggcgtgtcag aatctcaacc ggtcgtcaga aaaaggacgt atcggaaact ctgtgccatt | 660 |
| catcatctgc tggggcgggc tcccgagatt gcttgctcgg cctgcgatct ggtcaacgtg | 720 |
| gacatggatg rctgtgtttc tgagcaataa atgacttaaa ccaggtatgg ctgccgatgg | 780 |
| ttatcttcca gattggctcg aggacaacct ctctgagggc attcgcgagt ggtgggactt | 840 |
| gaaacctgga gccccgaaac ccaaagccaa ccagcaaaag caggacgacg gccgggtct | 900 |
| ggtgcttcct ggctacaagt acctcggacc cttcaacgga ctcgacaagg gggagcccgt | 960 |
| caacgcggcg gacgcagcgg ccctcgagca cgacaaggcc tacgaccagc agctcaaagc | 1020 |
| gggtgacaat ccgtacctgc ggtataacca cgccgacgcc gagtttcagg agcgtctgca | 1080 |
| agaagatacg tctttttgggg gcaacctcgg gcgagcagtc ttccaggcca aaaagcgggt | 1140 |
| tctcgaacct tttggtctgg ttgaggaagg cgctaagacg gctcctggaa agaaacgtcc | 1200 |
| ggtagagcag tcgccacaag agccagactc tcctcgggc atcggcaaga caggccagca | 1260 |
| gccccgctaaa aagagactca attttggtca gactggcgac tcagagtcag tccccgaccc | 1320 |
| acaacctctc ggagaacctc cagcaacccc cgctgctgtg ggacctacta caatggcttc | 1380 |

| | |
|---|---:|
| aggcggtggc gcaccaatgg cagacaataa cgaaggcgcc gacggagtgg gtaatgcctc | 1440 |
| aggaaattgg cattgcgatt ccacatggct gggcgacaga gtcatcacca ccagcacccg | 1500 |
| cacctgggcc ttgcccacct acaataacca cctctacaag caaatctcca gtgcttcaac | 1560 |
| gggggccagc aacgacaacc actacttcgg ctacagcacc ccctgggggt attttgattt | 1620 |
| caacagattc cactgccact tttcaccacg tgactggcag cgactcatca acaacaattg | 1680 |
| gggattccgg cccaagagac tcaacttcaa gctcttcaac atccaagtca aggaggtcac | 1740 |
| gacgaatgat ggcgtcacaa ccatcgctaa taaccttacc agcacggttc aagtcttctc | 1800 |
| ggactcggag taccagcttc cgtacgtcct cggctctgcg caccagggct gcctccctcc | 1860 |
| gttcccggcg gacgtgttca tgattccgca atacggctac ctgacgctca caatggcag | 1920 |
| ccaagccgtg ggacgttcat ccttttattg cctggaatat ttcccatcgc agatgctgag | 1980 |
| aacgggcaat aactttacct tcagctacac ctttgaggac gtgcctttcc acagcagcta | 2040 |
| cgcgcacagc cagagcctgg accggctgat gaatcctctc atcgaccagt acctgtatta | 2100 |
| cctgaacaga actcagaacc agtccggaag tgcccaaaac aaggacttgc tgtttagccg | 2160 |
| ggggtctcca gctggcatgt ctgttcagct caaaaactgg ctacctggac cctgttatcg | 2220 |
| gcagcagcgc gtttctaaaa caaaaacaga caacaacaac agcaattta cctggactgg | 2280 |
| tgcttcaaaa tataacctta atgggcgtga atccatcatc aaccctggca ctgctatggc | 2340 |
| ctcacacaaa gacgacgaag acaagttctt tcccatgagc ggtgtcatga tttttggaaa | 2400 |
| agagagcgcc ggagcttcaa acactgcatt ggacaatgtc atgattacag acgaagagga | 2460 |
| aattaaagcc actaaccctg tggccaccga agatttggg accgtggcag tcaatttcca | 2520 |
| gagcagcagc acagaccctg cgaccggaga tgtgcatgtt atgggagcat acctggcat | 2580 |
| ggtgtggcaa gatagagacg tgtacctgca gggtcccatt tgggccaaaa ttcctcacac | 2640 |
| agatggacac tttcacccgt ctcctcttat gggcggcttt ggactcaaac acccgcctcc | 2700 |
| tcagatcctc atcaaaaaca cacctgttcc tgcgaatcct ccggcggagt tttcagctac | 2760 |
| aaagtttgct tcattcatca cccaatactc cacaggacaa gtgagcgtgg aaattgaatg | 2820 |
| ggagctgcag aaagaaaaca gcaagcgctg gaatcccgaa gtgcagtaca catccaatta | 2880 |
| tgcaaaatct gccaacgttg atttaccgt ggacaacaat ggactttata ctgagcctcg | 2940 |
| ccccattggc acccgttacc ttacccgtcc cctgtaatta cgtgttaatc aataaaccgk | 3000 |
| ttaattcg | 3008 |

<210> SEQ ID NO 8
<211> LENGTH: 3021
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 8

| | |
|---|---:|
| atgctdatgt ggtgggagga gggcaagatg acggccaagg tcgtggagtc cgccaaggcc | 60 |
| attctcggcg gcagcaaagt gcgcgtggac caaaagtgca gtcgtccgc ccagatcgac | 120 |
| cccaccccg tcatcgtcac ctccaacacc aacatgtgcg ccgtgattga cgggaacagc | 180 |
| accaccttcg agcaccagca gccgttcag gaccggatgt tcaaatttga actcaccccgc | 240 |
| cgtctggagc acgactttgg caaggtgaca aagcaggaag tcaaagagtt cttccactgg | 300 |
| gcgcaggatc acgtgaccga ggtggcgcat gagttctacg tcagaaaggg tggagccaac | 360 |
| aagagacccg ccccgatga cgcggataaa agcgagccca gcgggcctg cccctcagtc | 420 |

-continued

| | |
|---|---|
| gcggatccat cgacgtcaga cgcggaagga gctccggtgg actttgccga caggtaccaa | 480 |
| aacaaatgtt ctcgtcacgc gggcatgctt cagatgctgt ttccctgcaa acatgcgag | 540 |
| agaatgaatc agaatttcaa catttgcttc acgcacggga ccagagactg ttcagaatgt | 600 |
| ttccccggcg tgtcagaatc tcaaccggtc gtcagaaaaa agacgtatcg gaaactctgt | 660 |
| gccattcatc atctgctggg gcgggctccc gagattgctt gctcggcctg cgatctggtc | 720 |
| aatgtggacc tggatgactg tgtttctgag caataaatga cttaaaccag gtatggctgc | 780 |
| cgatggttat cttccagatt ggctcgagga caacctctct gagggcattc gcgagtggtg | 840 |
| ggacttgaaa cctggagccc cgaaacccaa agccaaccag caaaagcagg acgacggccg | 900 |
| gggtctggtg cttcctggct acaagtacct cggacccttc aacggactcg acaaggggga | 960 |
| gcccgtcaac gcggcggacg cagcggccct cgagcacgac aaggcctacg accagcagct | 1020 |
| caaagcgggt gacaatccgt acctgcggta taaccacgcc gacgccgagt tcaggagcg | 1080 |
| tctgcaagaa gatacgtctt ttgggggcaa cctcggcga gcagtcttcc aggccaagaa | 1140 |
| gcgggttctc gaaccttttg gtctggttga ggaaggtgct aagacggctc ctggaaagaa | 1200 |
| gagaccggta gagcagtcgc cccaagaacc agactcctca tcgggcatcg gcaaatcagg | 1260 |
| ccagcagccc gctaaaaaga gactcaattt tggtcagact ggcgactcag agtcagtccc | 1320 |
| cgacccacaa cctctcggag aacctccagc aaccccgct gctgtgggac ctactacaat | 1380 |
| ggcttcaggc ggtggcgcac caatggcaga caataacgaa ggcgccgacg gagtgggtaa | 1440 |
| tgcctcagga aattggcatt gcgattccac atggctgggc gacagagtca ttaccaccag | 1500 |
| caccccgaacc tgggccctgc ccacctataa caaccacctc tacaaacaaa tctccagcgc | 1560 |
| ttcaacgggg gccagcaacg acaaccacta cttcggctac agcacccct gggggtattt | 1620 |
| tgattttaac agattccact gccacttctc accacgtgac tggcagcgac tcatcaacaa | 1680 |
| caattgggga ttccggccca agagactcaa cttcaagctc ttcaacatcc aagtcaagga | 1740 |
| ggtcacgacg aacgatggcg tcacgaccat cgctaataac cttaccagca cggttcaagt | 1800 |
| cttctcggac tcggagtacc agttgccgta cgtcctcggc tctgcgcacc agggctgcct | 1860 |
| ccctccgttc ccggcggacg tgttcatgat tccgcagtac ggctacctaa cactcaacaa | 1920 |
| tggcagccag gccgtgggac gttcatcctt ttactgcctg gaatatttcc catcgcagat | 1980 |
| gctgagaacg ggcaataact ttaccttcag ctacacattc gaggacgtgc ctttccacag | 2040 |
| cagctacgcg cacagccaaa gcctggaccg gctgatgaat cctctcatcg accagtactt | 2100 |
| gtattaccta aacagaactc aaaatcagtc cggaagtgcc caaacaagg acttgctgtt | 2160 |
| tagccggggg tctccagctg gcatgtctgt tcagcccaaa aactggctac ctggaccctg | 2220 |
| ttatcggcag cagcgcgttt ctaaaacaaa aacagacaac aacaacagca actttacctg | 2280 |
| gactggtgct tcaaaatata accttaatgg gcgtgaatct ataatcaacc ctggcactgc | 2340 |
| tatggcttca cacaaagacg acgaagacaa gttctttcca atgagcggtg tcatgatttt | 2400 |
| tggcaaggag agcgccggag cttcaaacac tgcattggac aatgtcatga ttacagacga | 2460 |
| agaggaaatt aaagccacta accctgtggc caccgaaaga tttgggaccg tggcagtcaa | 2520 |
| tttccagagc agcagcacag accctgcgac cggagatgtg catgttatgg agcattacc | 2580 |
| tggcatggtg tggcaagata gagacgtgta cctgcagggt ccaatttggg ccaaaattcc | 2640 |
| tcacacagat ggcacttttc accgtctctc tcttatgggc ggctttggac ttaagcaccc | 2700 |
| gcctcctcag atcctcatca aaaacacgcc tgttcctgcg aatcctccgg cagagttttc | 2760 |
| ggctacaaag tttgcttcat tcatcaccca gtattccaca ggacaagtga gtgtggaaat | 2820 |

```
tgaatgggag ttgcagaaag aaaacagcaa gcgttggaat cccgaagtgc agtacacatc    2880
taattatgca aaatctgcca acgttgattt cactgtggac aacaatggac tttatactga    2940
gcctcgcccc attggcaccc gttacctcac ccgtcccctg taattacttg ttaatcaata    3000
aaccgtgtha ttcgtgtcag t                                              3021

<210> SEQ ID NO 9
<211> LENGTH: 4222
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 9
ttgcgacatt ttgcgacacc atgtggccat tcagggtata tatggccgag tgagcgagca      60
ggatctccat tttgaccgcg aaatttgaac gagcagcagc catgccgggc ttctacgaga     120
tcgtgatcaa ggtgccgagc gacctggacg agcacctgcc gggcatttct gactcgtttg     180
tgaactgggt ggccgagaag gaatgggagc tgccccgga ttctgacatg gatctgaatc      240
tgattgagca ggcaccctg accgtggccg agaagctgca gcgcgacttc ctggtccaat      300
ggcgccgcgt gagtaaggcc ccggaggccc tcttctttgt tcagttcgag aagggcgagt     360
cctacttcca cctccatatt ctggtggaga ccacgggggt caaatccatg gtgctgggcc     420
gcttcctgag tcagattagg acaagctgg tgcagaccat ctaccgcggg atcgagccga      480
ccctgcccaa ctggttcgcg gtgaccaaga cgcgtaatgg cgccggaggg gggaacaagg     540
tggtggacga gtgctacatc cccaactacc tcctgcccaa gactcagccc gagctgcagt     600
gggcgtggac taacatggag gagtatataa gcgcgtgttt gaacctggcc gagcgcaaac     660
ggctcgtggc gcagcacctg acccacgtca gccagaccca ggagcagaac aaggagaatc     720
tgaacccgaa ttctgacgcg cctgtcatcc ggtcaaaaac ctccgcgcgc tacatggagc     780
tggtcgggtg gctggtggac cggggcatca cctccgagaa gcagtggatc caggaggacc     840
aggcctcgta catctccttc aacgccgcct ccaactcgcg gtcccagatc aaggccgctc     900
tggacaatgc cggcaagatc atggcgctaa ccaaatccgc gcccgactac ctggtaggcc     960
ccgctccgcc cgcggacatt aaaaccaacc gcatttaccg catcctggag ctgaacggct    1020
acgaccctgc ctacgccggc tccgtctttc tcggctgggc ccagaaaagg ttcgggaagc    1080
gcaacaccat ctggctgttt gggcggcca ccacgggcaa gaccaacatc gcggaagcca     1140
tcgcacacgc cgtgcccttc tacggctgcg tcaactggac caatgaaaac tttcccttca    1200
acgactgcgt cgacaagatg gtgatctggt gggaggaggg caagatgacg gccaaggtcg    1260
tggagtccgc caaggccatt ctcggcggca gcaaggtgcg cgtggaccaa aagtgcaagt    1320
cgtccgccca gatcgatccc accccgtga tcgtcacctc caacaccaac atgtgcgccg     1380
tgattgacgg gaacagcacc accttcgagc accagcagcg gttgcaggac cggatgttca    1440
aatttgaact caccccgccg tctggagcacg actttggcaa ggtgacaaag caggaagtca    1500
aagagttctt ccgctgggcg caggatcacg tgaccgaggt ggcgcatgag ttctacgtca    1560
gaaagggtgg agccaacaag agacccgccc ccgatgacgc ggataaaagc gagcccaagc    1620
gggtctgccc ctcagtcgcg gatccatcga cgtcagacgc ggaaggagct ccggtggact    1680 tgccgacag gtaccaaaac aaatgttctc gtcacgcggg catgcttcag atgctgtttc     1740
cctgcaaaac atgcgagaga atgaatcaga atttcaacat ttgcttcacg cacgggacca    1800
gagactgttc agaatgtttc cccggcgtgt cagaatctca accggtcgtc agaaaaagga    1860
```

```
cgtatcggaa actctgtgcc attcatcatc tgctggggcg ggctcccgag attgcttgct    1920
cggcctgcga tctggtcaac gtggacctgg atgactgtgt ttctgagcaa taaatgactt    1980
aaaccaggta tggctgccga tggttatctt ccagattggc tcgaggacaa cctctctgag    2040
ggcattcgcg agtggtggga cttgaaacct ggagccccga aacccaaagc caaccagcaa    2100
aagcaggacg acggccgggg tctggtgctt cctggctaca agtacctcgg acccttcaac    2160
ggactcgaca agggggagcc cgtcaacgcg gcggacgcag cggccctcga gcacgacaag    2220
gcctacgacc agcagctcaa agcgggtgac aatccgtacc tgcggtataa ccacgccgac    2280
gccgagtttc aggagcgtct gcaagaagat acgtcttttg ggggcaacct cgggcgagca    2340
gtcttccagg ccaagaagag ggttctcgaa ccttttggtc tggttgagga aggtgctaag    2400
acggctcctg gaaagaaacg tccggtagag cagtcacccc aagaaccaga ctcctcctcg    2460
ggcattggca aatcaggcca gcagcccgct aaaaagagac tcaattttgg tcagactggc    2520
gactcagagt cagtccccga cccacaacct ctcggagaac ctccagcaac cccgctgct    2580 ttgggaccta ctacaatggc ttcaggcggt ggcgcaccaa tggcagacaa taacgaaggc    2640
gccgacggag tgggtaatgc ctcaggaaat tggcattgcg attccacatg ctgggcgac    2700 agagtcatca ccaccagcac ccgcacctgg gccttgccca cctacaataa ccacctctac    2760
aagcaaatct ccagtgcttc aacgggggcc agcaacgaca ccactactt cggctacagc    2820 acccccctggg ggtattttga tttcaacaga ttccactgcc atttctcacc acgtgactgg    2880
cagcgactca tcaacaacaa ctggggattc cggcccaaga gactcaactt caagctcttc    2940
aacatccaag tcaaggaggt cacgacgaac gatggcgtca cgaccatcgc taataacctt    3000
accagcacgg ttcaagtctt ctcggactcg gagtaccagc ttccgtacgt cctcggctct    3060
gcgcaccagg gctgcctccc tccgttcccg gcggacgtgt tcatgattcc gcagtacggc    3120
tacctgacgc tcaacaatgg cagcaaagcc gtgggacgtt catccttta ctgcctggaa    3180 tatttccctt ctcagatgct gagaacgggc aacaacttta ccttcagcta caccttgag    3240 gaagtgcctt tccacagcag ctacgcgcac agccagagcc tggaccggct gatgaatcct    3300
ctcatcgacc aatacctgta ttacctgaac agaactcaaa atcagtccgg aagtgcccaa    3360
aacaaggact gctgtttag ccgtgggtct ccagctggca tgtctgttca gcccaaaaac    3420
tggctacctg gaccctgtta tcggcagcag cgcgtttcta aaacaaaaac agacaacaac    3480
aacagcaatt ttacctggac tggtgcttca aaatataacc tcaatgggcg tgaatccatc    3540
atcaaccctg gcactgctat ggcctcacac aaagacgacg aagacaagtt ctttcccatg    3600
agcggtgtca tgattttggg aaaagagagc gccggagctt caaacactgc attggacaat    3660
gtcatgatta cagacgaaga ggaaattaaa gccactaacc ctgtggccac cgaaagattt    3720
gggaccgtgg cagtcaattt ccagagcagc agcacagacc ctgcgaccgg agatgtgcat    3780
gttatgggag cattacctgg catggtgtgg caagatagag acgtgtacct gcagggtccc    3840
atttgggcca aaattcctca cacgatgga cactttcacc cgtctcctct tatgggcggc    3900
tttggactca gcaccccgcc tcctcagatc ctcatcaaaa acacacctgt tcctgcgaat    3960
cctccggcag agttttcggc tacaaagttt gcttcattca tcacccagta ctccacagga    4020
caagtgagcg tggaaattga atgggagttg cagaaagaaa acagtaagcg ctggaatccc    4080
gaagtgcagt acacatctaa ttatgcaaaa tctgccaacg ttgacttcac tgtggacaac    4140 aatggactt atactgagcc tcgccccatt ggcacccgtt acctcacccg tccctgtaa    4200 ttacttgtta atcaataaac cg                                               4222
```

<210> SEQ ID NO 10
<211> LENGTH: 4213
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 10

| | | | | | |
|---|---|---|---|---|---|
| ttgcgacagt | ttgcgacacc | atgtggtcac | aagaggtata | taaccgcgag | tgagccagcg | 60 |
| aggagctcca | ttttgcccgc | gaagtttgaa | cgagcagcag | ccatgccggg | gttctacgag | 120 |
| gtggtgatca | aggtgcccag | cgacctggac | gagcacctgc | ccggcatttc | tgactccttt | 180 |
| gtgaactggg | tggccgagaa | ggaatgggag | ttgcccccgg | attctgacat | ggatcagaat | 240 |
| ctgattgagc | aggcacccct | gaccgtggcc | gagaagctgc | agcgcgagtt | cctggtggaa | 300 |
| tggcgccgag | tgagtaaatt | tctggaggcc | aagttttttg | tgcagtttga | aaaggggac | 360 |
| tcgtactttc | atttgcatat | tctgattgaa | attaccggcg | tgaaatccat | ggtggtgggc | 420 |
| cgctacgtga | gtcagattag | ggataaactg | atccagcgca | tctaccgcgg | ggtcgagccc | 480 |
| cagctgccca | actggttcgc | ggtcacaaag | acccgaaatg | cgccggagg | cgggaacaag | 540 |
| gtggtggacg | agtgctacat | ccccaactac | ctgctcccca | aggtccagcc | cgagcttcag | 600 |
| tgggcgtgga | ctaacatgga | ggagtatata | agcgcctgtt | tgaacctcgc | ggagcgtaaa | 660 |
| cggctcgtgg | cgcagcacct | gacgcacgtc | tcccagaccc | aggagggcga | caaggagaat | 720 |
| ctgaacccga | attctgacgc | gccggtgatc | cggtcaaaaa | cctccgccag | gtacatggag | 780 |
| ctggtcgggt | ggctggtgga | caagggcatc | acgtccgaga | agcagtggat | ccaggaggac | 840 |
| caggcctcgt | acatctcctt | caacgcggcc | tccaactccc | ggtcgcagat | caaggcggcc | 900 |
| ctggacaatg | cctccaaaat | catgagcctc | accaaaacgg | ctccggacta | tctcatcggg | 960 |
| cagcagcccg | tgggggacat | taccaccaac | cggatctaca | aaatcctgga | actgaacggg | 1020 |
| tacgaccccc | agtacgccgc | ctccgtcttt | ctcggctggg | cccagaaaaa | gtttggaaag | 1080 |
| cgcaacacca | tctggctgtt | tgggcccgcc | accaccggca | agaccaacat | cgcggaagcc | 1140 |
| atcgcccacg | cggtcccctt | ctacggctgc | gtcaactgga | ccaatgagaa | ctttcccttc | 1200 |
| aacgactgcg | tcgacaaaat | ggtgatttgg | tgggaggagg | gcaagatgac | cgccaaggtc | 1260 |
| gtagagtccg | ccaaggccat | tctgggcggc | agcaaggtgc | gcgtggacca | aaaatgcaag | 1320 |
| gcctctgcgc | agatcgaccc | cacccccgtg | atcgtcacct | ccaacaccaa | catgtgcgcc | 1380 |
| gtgattgacg | gaacagcac | caccttcgag | caccagcagc | cctgcagga | ccggatgttc | 1440 |
| aagtttgaac | tcacccgccg | cctcgaccac | gactttggca | aggtcaccaa | gcaggaagtc | 1500 |
| aaggactttt | tccggtgggc | ggctgatcac | gtgactgacg | tggctcatga | gttttacgtc | 1560 |
| acaaagggtg | gagctaagaa | aaggcccgcc | ccctctgacg | aggatataag | cgagcccaag | 1620 |
| cggccgcgcg | tgtcatttgc | gcagccgag | acgtcgacg | cggaagctcc | cggagacttc | 1680 |
| gccgacaggt | accaaaacaa | atgttctcgt | cacgcgggta | tgctgcagat | gctctttccc | 1740 |
| tgcaagacgt | gcgagagaat | gaatcagaat | tccaacgtct | gcttcacgca | cggtcagaaa | 1800 |
| gattgcgggg | agtgctttcc | cggtcagaa | tctcaaccgg | tttctgtcgt | cagaaaaacg | 1860 |
| tatcagaaac | tgtgcatcct | tcatcagctc | cgggggcac | ccgagatcgc | ctgctctgct | 1920 |
| tgcgaccaac | tcaaccccga | tttggacgat | tgccaatttg | agcaataaat | gactgaaatc | 1980 |
| aggtatggct | gctgacggtt | atcttccaga | ttggctcgag | gacaacctct | ctgaaggcat | 2040 |
| tcgcgagtgg | tgggcgctga | aacctggagc | tccacaaccc | aaggccaacc | aacagcatca | 2100 |

| | |
|---|---|
| ggacaacggc agggggtcttg tgcttcctgg gtacaagtac ctcggaccct tcaacggact | 2160 |
| cgacaaggga gagccggtca acgaggcaga cgccgcggcc ctcgagcacg acaaggccta | 2220 |
| cgacaagcag ctcgagcagg gggacaaccc gtatctcaag tacaaccacg ccgacgccga | 2280 |
| gttccagcag cgcttggcga ccgacacctc ttttggggggc aacctcgggc gagcagtctt | 2340 |
| ccaggccaaa aagaggattc tcgagcctct gggtctggtt gaagagggcg ttaaaacggc | 2400 |
| tcctggaaag aaacgcccat tagaaaagac tccaaatcgg ccgaccaacc cggactctgg | 2460 |
| gaaggccccg gccaagaaaa agcaaaaaga cggcgaacca gccgactctg ctagaaggac | 2520 |
| actcgacttt gaagactctg gagcaggaga cggacccccct gagggatcat cttccggaga | 2580 |
| aatgtctcat gatgctgaga tgcgtgcggc gccaggcgga aatgctgtcg aggcgggaca | 2640 |
| aggtgccgat ggagtgggta atgcctccgg tgattggcat tgcgattcca cctggtcaga | 2700 |
| gggccgagtc accaccacca gcacccgaac ctgggtccta cccacgtaca caaccacct | 2760 |
| gtacctgcga atcggaacaa cggccaacag caacacctac aacggattct ccacccccctg | 2820 |
| gggatacttt gactttaacc gcttccactg ccacttttcc ccacgcgact ggcagcgact | 2880 |
| catcaacaac aactggggac tcaggccgaa atcgatgcgt gttaaaatct tcaacataca | 2940 |
| ggtcaaggag gtcacgacgt caaacggcga gactacggtc gctaataacc ttaccagcac | 3000 |
| ggttcagatc tttgcggatt cgacgtatga actcccatac gtgatggacg ccggtcagga | 3060 |
| ggggagcttt cctccgtttc ccaacgacgt ctttatggtt ccccaatacg gatactgcgg | 3120 |
| agttgtcact ggaaaaaacc agaaccgac agacagaaat gcctttact gcctggaata | 3180 |
| cttttccatcc caaatgctaa gaactggcaa caattttgaa gtcagttacc aatttgaaaa | 3240 |
| agttcctttc cattcaatgt acgcgcacag ccagagcctg gacagaatga tgaatccttt | 3300 |
| actggatcag tacctgtggc atctgcaatc gaccactacc ggaaattccc ttaatcaagg | 3360 |
| aacagctacc accacgtacg ggaaaattac cactggagac tttgcctact acaggaaaaa | 3420 |
| ctggttgcct ggagcctgca ttaaacaaca aaaattttca aagaatgcca atcaaaacta | 3480 |
| caagattccc gccagcgggg gagacgcccct tttaaagtat gacacgcata ccactctaaa | 3540 |
| tgggcgatgg agtaacatgg ctcctggacc tccaatggca accgcaggtg ccggggactc | 3600 |
| ggatttttagc aacagccagc tgatctttgc cggacccaat ccgagcggta acacgaccac | 3660 |
| atcttcaaac aatttgttgt ttaccctcaga agaggagatt gccacaacaa acccacgaga | 3720 |
| cacggacatg tttggacaga ttgcagataa taatcaaaat gccaccaccg cccctcacat | 3780 |
| cgctaacctg gacgctatgg gaattgttcc cggaatggtc tggcaaaaca gagacatcta | 3840 |
| ctaccagggc cctatttggg ccaaggtccc tcacacggac ggacactttc acccttcgcc | 3900 |
| gctgatggga ggattttggac tgaaacaccc gcctccacag attttcatca aaaacacccc | 3960 |
| cgtacccgcc aatcccaata ctacctttag cgctgcaagg attaattctt ttctgacgca | 4020 |
| gtacagcacc ggcaaagttg ccgttcagat cgactgggaa attcagaagg agcattccaa | 4080 |
| acgctggaat cccgaagttc aatttacttc aaactacggc actcaaaatt ctatgctgtg | 4140 |
| ggctcccgac aatgctggca actaccacga actccgggct attgggtccc gtttcctcac | 4200 |
| ccaccacttg taa | 4213 |

<210> SEQ ID NO 11
<211> LENGTH: 2211
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 11

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg accccttcaa cggactcgac     180
aagggggagc ccgtcaacgc ggcggacgca gcggccctcg agcacgacaa ggcctacgac     240
cagcagctca agcgggtga caatccgtac ctgcggtata ccacgccga cgccgagttt      300
caggagcgtc tgcaagaaga tacgtctttt gggggcaacc tcgggcgagc agtcttccag     360
gccaagaagc gggttctcga accttttggt ctggttgagg aaggcgctaa gacggctcct     420
ggaaagaaac gtccggtaga gcagtcgcca caagagccag actcctcctc gggcatcggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct     600
actacaatgg cttcaggcgg tggcgcacca atggcagaca taacgaagg cgccgacgga     660
gtgggtaatg cctcaggaaa ttggcattgc gattccacat ggctgggcga cagagtcatc     720
accaccagca cccgcacctg ggccttgccc acctacaata accacctcta caagcaaatc     780
tccagtgctt caacggggc cagcaacgac aaccactact tcggctacag cacccccctgg    840
gggtattttg atttcaacag attccactgc cacttttcac cgcgtgactg cagcgactc     900
atcaacaaca attggggatt ccggcccaag agactcaact tcaagctctt caacatccaa     960
gtcaaggagg tcacgacgag tgatggcgtc acaaccatcg ctaataacct taccagcacg    1020
gttcaagtct tctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg gcagccaagc cgtgggacgt tcatcctttt actgcctgga atatttccct    1200
tctcagatgc tgagaacggg caacaacttt accttcagct acacctttga ggaagtgcct    1260
ttccacagca gctacgcgca cagccagagc ctggaccggc tgatgaatcc tctcatcgac    1320
caatacctgt attacctgaa cagaactcaa aatcagtccg gaagtgccca aaacaaggac    1380
ttgctgttta ccgtgggtc tccagctggc atgtctgttc agcccaaaaa ctggctacct    1440
ggaccctgtt atcggcagca gcgcgtttct aaaacaaaaa caggcaacaa caacagcaat    1500
tttacctgga ctggtgcttc aaaatataac ctcaatgggc atgaatccat catcaaccct    1560
ggcactgcta tggcctcaca caagacgac gaagacaagt tctttcccat gagcggtgtc    1620
atgattttg gaaagagag cgccggagct tcaaacactg cattggacaa tgtcatgatt    1680
acagacgaag aggaaattaa agccactaac cctgtggcca ccgaaagatt tgggaccgtg    1740
gcagtcaatt tccagagcag cagcacacac cctgcgaccg gagatgtgca tgttatggga    1800
gcattacctg gcatggtgtg gcaagataga gacgtgtacc tgcagggtcc catctgggcc    1860
aaaattcctc acagatgg acactttcac ccgtctcctc ttatgggcgg ctttggactc    1920
aagcaccgc ctcctcagat cctcatcaaa aacacgcctg ttcctgcgaa tcctccggcg    1980
gagttttcag ctacaaagtt tgcttcattc atcacccaat actccacagg acaagtgagt    2040
gtggaaattg aatgggagct gcagaaagaa acagcaagc gctggaatcc gaagtgcag    2100
tacacatcca attatgcaaa atctgccaac gttgatttta ccgtggacaa caatggactt    2160
tatactgagc ctcgccccat tggcacccgt taccttaccc gtccctgta a             2211
```

<210> SEQ ID NO 12
<211> LENGTH: 2211
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 12

| | | | | | |
|---|---|---|---|---|---|
| atggctgccg | atggttatct | tccagattgg | ctcgaggaca | acctctctga | gggcattcgc | 60 |
| gagtggtggg | acttgaaacc | tggagccccg | aaacccaaag | ccaaccagca | aaagcaggac | 120 |
| gacggccggg | gtctggtgct | tcctggctac | aagtacctcg | acccttcaa | cggactcgac | 180 |
| aagggggagc | ccgtcaacgc | ggcggacgca | gcggccctcg | agcacgacaa | ggcctacgac | 240 |
| cagcagctca | aagcgggtga | caatccgtac | ctgcggtata | accacgccga | cgccgagttt | 300 |
| caggagcgtc | tgcaagaaga | tacgtctttt | gggggcaacc | tcgggcgagc | agtcttccag | 360 |
| gccaagaagc | gggttctcga | accttttggt | ctggttgagg | aaggcgctaa | gacggctcct | 420 |
| ggaaagaaac | gtccggtaga | gcagtcgcca | caagagccag | actcctcctc | gggcatcggc | 480 |
| aagacaggcc | agcagcccgc | taaaaagaga | ctcaattttg | gtcagactgg | cgactcagag | 540 |
| tcagtccccg | acccacaacc | tctcggagaa | cctccagcaa | ccccgctgc | tgtgggacct | 600 |
| actacaatgg | cttcaggcgg | tggcgcacca | atggcagaca | taacgaagg | cgccgacgga | 660 |
| gtgggtaatg | cctcaggaaa | ttggcattgc | gattccacat | ggctgggcga | cagagtcatc | 720 |
| accaccagca | cccgcacctg | gccttgccc | acctacaata | accacctcta | caagcaaatc | 780 |
| tccagtgctt | caacgggggc | cagcaacgac | aaccactact | tcggctacag | cacccctgg | 840 |
| gggtattttg | atttcaacag | attccactgc | cacttttcac | cgcgtgactg | gcagcgactc | 900 |
| atcaacaaca | attggggatt | ccggcccaag | agactcaact | tcaagctctt | caacatccaa | 960 |
| gtcaaggagg | tcacgacgag | tgatggcgtc | acaaccatcg | ctaataacct | taccagcacg | 1020 |
| gttcaagtct | tctcggactc | ggagtaccag | cttccgtacg | tcctcggctc | tgcgcaccag | 1080 |
| ggctgcctcc | ctccgttccc | ggcggacgtg | ttcatgattc | cgcaatacgg | ctacctgacg | 1140 |
| ctcaacaatg | gcagccaagc | cgtgggacgt | tcatcctttt | actgcctgga | atatttccct | 1200 |
| tctcagatgc | tgagaacggg | caacaacttt | accttcagct | acacctttga | ggaagtgcct | 1260 |
| ttccacagca | gctacgcgca | cagccagagc | ctggaccggc | tgatgaatcc | tctcatcgac | 1320 |
| caatacctgt | attacctgaa | cagaactcaa | aatcagtccg | gaagtgccca | aaacaaggac | 1380 |
| ttgctgttta | gccgtgggtc | tccagctggc | atgtctgttc | agcccaaaaa | ctggctacct | 1440 |
| ggaccctgtt | atcggcagca | gcgcgtttct | aaaacaaaaa | caggcaacaa | caacagcaat | 1500 |
| tttacctgga | ctggtgcttc | aaaatataac | ctcaatgggc | atgaatccat | catcaaccct | 1560 |
| ggcactgcta | tggcctcaca | caaagacgac | gaagacaagt | tctttcccat | gagcggtgtc | 1620 |
| atgattttg | gaaagagag | cgccggagct | tcaaacactg | cattggacaa | tgtcatgatt | 1680 |
| acagacgaag | aggaaattaa | agccactaac | cctgtggcca | ccgaaagatt | tgggaccgtg | 1740 |
| gcagtcaatt | tccagagcag | cagcacacac | cctgcgaccg | agatgtgca | tgttatggga | 1800 |
| gcattacctg | gcatggtgtg | gcaagataga | gacgtgtacc | tgcagggtcc | catctgggcc | 1860 |
| aaaattcctc | acacagatgg | cacttttcac | ccgtctcctc | ttatgggcgg | ctttggactc | 1920 |
| aagcaccccgc | ctcctcagat | cctcatcaaa | aacacgcctg | ttcctgcgaa | tcctccggcg | 1980 |
| gagttttcag | ctacaaagtt | tgcttcattc | atcacccaat | actccacagg | acaagtgagt | 2040 |
| gtggaaattg | aatgggagct | gcagaaagaa | aacagcaagc | gctggaatcc | cgaagtgcag | 2100 |

| | |
|---|---|
| tacacatcca attatgcaaa atctgccaac gttgatttta ccgtggacaa caatggactt | 2160 |
| tatactgagc ctcgccccat tggcacccgt taccttaccc gtcccctgta a | 2211 |

<210> SEQ ID NO 13
<211> LENGTH: 2202
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 13

| | |
|---|---|
| atgactgacg gttaccttcc agattggcta gaggacaacc tctctgaagg cgttcgagag | 60 |
| tggtgggcgc tgcaacctgg agcccctaaa cccaaggcaa atcaacaaca tcaggacaac | 120 |
| gctcggggtc ttgtgcttcc gggttacaaa tacctcggac ccggcaacgg acttgacaag | 180 |
| ggggaacccg tcaacgcagc ggacgcggca gccctcgaac acgacaaggc ctacgaccag | 240 |
| cagctcaagg ccggtgacaa cccctacctc aagtacaacc acgccgacgc cgagtttcag | 300 |
| gagcgtcttc aagaagatac gtcttttggg ggcaacctcg gacgagcagt cttccaggcc | 360 |
| aaaaagagga tccttgagcc tctgggtctg gttgaggaag cggctaagac ggctcctgga | 420 |
| aaaaagagac ctgtagagca atctccagca gaaccggact cctcttcggg catcggcaaa | 480 |
| tcaggccagc agcccgctag aaaaagactg aatttggtc agactggcga cacagagtca | 540 |
| gtcccagacc ctcaaccact cggacaacct cccgcagccc cctctggtgt gggatctact | 600 |
| acaatggctt caggcggtgg cgcaccaatg gcagacaata cgagggtgc cgatggagtg | 660 |
| ggtaattcct caggaaattg gcattgcgat tcccaatggc tgggcgacag agtcatcacc | 720 |
| accagcaccc gcacctgggc cctgcccacc tacaacaatc acctctacaa gcaaatctcc | 780 |
| agccaatcag gagccaccaa cgacaaccac tactttggct acagcacccc ctgggggtat | 840 |
| tttgacttca acagattcca ctgccacttt tcaccacgtg actggcaaag actcatcaac | 900 |
| aacaactggg gattccgacc caagagactc aacttcaagc tctttaacat tcaagtcaaa | 960 |
| gaggtcacgc agaatgacgg tacgacgacg attgccaata accttaccag cacggttcag | 1020 |
| gtgtttactg actccgagta ccagctcccg tacgtcctcg gctcggcgca tcagggatgc | 1080 |
| ctcccgccgt tcccagcaga cgtcttcatg gtcccacagt atggataccc caccctgaac | 1140 |
| aacgggagtc aggcggtagg acgctcttcc ttttactgcc tggagtactt tccttctcag | 1200 |
| atgctgcgta ctggaaacaa ctttcagttt agctacactt ttgaagacgt gccttttcac | 1260 |
| agcagctacg ctcacagcca aagtctggac cgtctcatga atcctctgat cgaccagtac | 1320 |
| ctgtactatc tgaacaggac acaaacagcc agtggaactc agcagtctcg gctactgttt | 1380 |
| agccaagctg gacccaccag tatgtctctt caagctaaaa actggctgcc tggaccttgc | 1440 |
| tacagacagc agcgtctgtc aaagcaggca acgacaacac acaacagcaa ctttccctgg | 1500 |
| actggtgcca ccaaatatca tctgaatggc cgggactcat ggtgaaccc gggccctgct | 1560 |
| atggccagtc acaaggatga caaagaaaag ttttccccca tgcatggaac cctgatattt | 1620 |
| ggtaaagaag aacaaatgc caacaacgcg gatttggaaa atgtcatgat tacagatgaa | 1680 |
| gaagaaatcc gcaccaccaa tcccgtggct acggagcagt acgggactgt gtcaaataat | 1740 |
| ttgcaaaact caaacgctgg tccaactact ggaactgtca atcaccaagg agcgttacct | 1800 |
| ggtatggtgt ggcaggatcg agacgtgtac ctgcagggac ccatttgggc caagattcct | 1860 |
| cacaccgatg gacactttca tccttctcca ctgatgggag gttttgggct caaacacccg | 1920 |
| cctcctcaga tcatgatcaa aaacactccc gttccagcca atcctccac aaactttagt | 1980 |

```
gcggcaaagt tgcttccttt catcacacag tactccacgg ggcaggtcag cgtggagatc    2040
gagtgggagc tgcagaagga gaacagcaaa cgctggaatc ccgaaattca gtacacttcc    2100
aactacaaca aatctgttaa tgtggacttt actgtggaca ctaatggtgt gtattcagag    2160
cctcgcccca ttggcaccag atacctgact cgtaatctgt aa                       2202

<210> SEQ ID NO 14
<211> LENGTH: 2211
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 14
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac      180 aaggggagc ccgtcaacgc ggcggacgca gcggccctcg agcacgacaa ggcctacgac      240
cagcagctca aagcgggtga caatccgtac ctgcggtata ccacgccga cgccgagttt     300 caggagcgtc tgcaagaaga tacgtctttt gggggcaacc tcgggcgagc agtcttccag     360
gccaagaagc gggttctcga accttttggt ctggttgagg aaggcgctaa gacggctcct     420
ggaaagaaac gtccggtaga gcagtcgcca caagagccag actcctcctc gggcatcggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
accaccagca cccgcacctg gccttgccc acctacaata ccacctcta caagcaaatc     780 tccagtgctt caacgggggc cagcaacgac aaccactact cggctacag cacccctgg     840 gggtattttg atttcaacag attccactgc cacttttcac cacgtgactg gcagcgactc     900
atcaacaaca ttggggatt ccggcccaag agactcaact tcaagctctt caacatccaa     960
gtcaaggagg tcacgacgaa tgatggcgtc acaaccatcg ctaataacct taccagcacg    1020
gttcaagtct tctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg gcagccaagc cgtgggacgt tcatccttt actgcctgga atatttccct    1200
tctcagatgc tgagaacggg caacaacttt accttcagct acacctttga ggaagtgcct    1260
ttccacagca gctacgcgca gccagcgagc ctggaccggc tgatgaatcc tctcatcgac    1320
caatacctgt attacctgaa cagaactcaa aatcagtccg gaagtgccca aaacaaggac    1380
ttgctgttta gccgtgggtc tccagctggc atgtctgttc agccaaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac gaagacaagt tctttcccat gagcggtgtc    1620 atgattttg aaaagagag cgccggagct tcaaacactg cattggacaa tgtcatgatt    1680
acagacgaag aggaaattaa agccactaac cctgtggcca ccgaaagatt gggaccgtg    1740 gcagtcaatt tccagagcag cagcacagac cctgcgaccg gagatgtgca tgttatggaa    1800
gcattacctg gcatggtgtg gcaagataga gacgtgtacc tgcagggtcc catctgggcc    1860
```

```
aaaattcctc acacagatgg acactttcac ccgtctcctc ttatgggcgg ctttggactc    1920
aagcacccgc ctcctcagat cctcatcaaa aacacgcctg ttcctgcgaa tcctccggcg    1980
gagttttcag ctacaaagtt tgcttcattc atcacccaat actccacagg acaagtgagt    2040
gtggaaattg aatgggagct gcagaaagaa aacagcaagc gctggaatcc cgaagtgcag    2100
tacacatcca attatgcaaa atctgccaac gttgatttta ccgtggacaa caatggactt    2160
tatactgagc ctcgccccat tggcacccgt taccttaccc gtcccctgta a             2211
```

<210> SEQ ID NO 15
<211> LENGTH: 2211
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 15

```
atggctgccg atggttatct tccagattgg ctcgaggaca acctctctga gggcattcgc      60
aagtggtggg acttgaaacc tggagccccg aaacccaaag ccaaccagca aaagcaggac     120
gacggccggg gtctggtgct tcctggctac aagtacctcg gacccttcaa cggactcgac     180 aaggggagc ccgtcaacgc ggcggacgca gcggccctcg agcacgacaa ggcctacgac      240
cagcagctca aagcgggtga caatccgtac ctgcggtata accacgccga cgccgagttt     300
caggagcgtc tgcaagaaga tacgtctttt ggggcaacc tcgggagagc agtcttccag      360
gccaagaagc gggttctcga accttttggt ctggttgagg aaggcgctaa gacggctcct     420
ggaaagaaac gtccggtaga gcagtcgcca caagagccag actcctcctc gggcatcggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct      600 actacaatgg cttcaggcgg tggcgcacca atggcagaca taacgaagg cgccgacgga      660 gtgggtaatg cctcaggaaa ttggcattgc gattccacat ggctgggcga cagagtcatc     720
accaccagca cccgcacctg gccttgccc cctacaata accacctcta caagcaaatc       780
tccagtgctt caacgggggc cagcaacgac aaccactact cggctacag cacccctgg       840 gggtattttg atttcaacag attccactgc cacttttcac cacgtgactg gcagcgactc     900
atcaacaaca attggggatt ccggcccaag agactcaact tcaagctctt caacatccaa     960
gtcaaggagg tcacgacgaa tgatggcgtc acaaccatcg ctaataacct taccagcacg    1020
gttcaagtct ctcggactc ggagtaccag cttccgtacg tcctcggctc tgcgcaccag     1080
ggctgcctcc ctccgttccc ggcggacgtg ttcatgattc cgcaatacgg ctacctgacg    1140
ctcaacaatg gcagccaagc cgtgggacgt tcatcctttt actgcctgga atatttccct    1200
tctcagatgc tgagaacggg caacaacttt accttcagct acaccttga ggaagtgcct     1260 ttccacagca gctacgcgca cagccagagc ctggaccggc tgatgaatcc tctcatcgac    1320
caatacctgt attacctgaa cagaactcaa aatcagtccg aagtgccca aaacaaggac     1380 ttgctgttta gccgtgggtc tccagctggc atgtctgttc agcccaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac aaagacaagt ctttccccat gagcggtgtc    1620 atgattttg gaaagagag cgccggagct tcaaacactg cattggacaa tgtcatgatt    1680
acagacgaag aggaaattaa agccactaac cctgtggcca ccgaaagatt tgggaccgtg    1740
```

```
gcagtcaatt tccagagcag cagcacagac cctgcgaccg agatgtgca tgttatggga   1800 gcattacctg gcatggtgtg gcaagataga gacgtgtacc tgcagggtcc catttgggcc   1860
aaaattcctc acacagatgg acactttcac ccgtctcctc ttatgggcgg ctttggactc   1920
aagcacccgc ctcctcagat cctcatcaaa aacacacctg ttcctgcgaa tcctccggcg   1980
gagttttcag ctacaaagtt tgcttcattc atcacccaat actccacagg acaagtgagt   2040
gtggaaattg aatgggagct gcagaaagaa acagcaagc gctggaatcc cgaagtgcag    2100
tacacatcca attatgcaaa atctgccaac gttgatttta ccgtggacaa caatggactt   2160
tatactgagc ctcgcccat tggcacccgt taccttaccc gtccctgta a              2211

<210> SEQ ID NO 16
<211> LENGTH: 2211
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 16
atggctgccg atggttatct tccagattgg ctcgaggaca acctctctga gggcattcgc     60
gagtggtggg acttgaaacc tggagccccg aaacccaaag ccaaccagca aaagcaggac    120
aacggccggg tctggtgct tcctggctac aagtacctcg acccttcaa cggactcgac      180 aaggggagc ccgtcaacgc ggcggacgca gcggccctcg agcacgacaa ggcctacgac     240
cagcagctca aagcgggtga caatcctac ctgcggtata ccacgccga cgccgagttt     300 caggagcgtc tgcaagaaga tacgtctttt gggggcaacc tcgggcgagc agtcttccag    360
gccaagaagc gggttctcga accttttggt ctggttgagg aaggcgctaa gacggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg acccacaacc tctcggagaa cctccagcaa cccccgctgc tgtgggacct    600
actacaatgg cttcaggcgg tggcgcacca atggcagaca taacgaagg cgccgacgga    660 gtgggtaatg cctcaggaaa ttggcattgc gattccacat ggctgggcga cagagtcatc    720
accaccagca cccgcacctg gccttgccc acctacaata accacctcta caagcaaatc    780
tccagtgctt caacgggggc cagcaacgac aaccactact cggctacag cacccctgg    840 gggtattttg atttcaacag attccactgc cacttttcac cacgtgactg gcagcgactc    900
atcaacaaca attggggatt ccggcccaag agactcaact tcaagctctt caacatccaa    960
gtcaaggagg tcacgacgaa tgatggcgtc acaaccatcg ctaataacct taccagcacg   1020
gttcaagtct tctcggactc ggagtaccag cttccgtacg tcctcggctc tgcgcaccag   1080
ggctgcctcc ctccgttccc ggcggacgtg ttcatgattc cgcaatacgg ctacctgacg   1140
ctcaacaatg gcagccaagc cgtgggacgt tcatccttt actgcctgga atatttccct   1200
tctcagatgc tgagaacggg caacaacttt accttcagct acaccttga ggaagtgcct    1260 ttccacagca gctacgcgca cagccagagc ctggaccggc tgatgaatcc tctcatcgac   1320
caatacctgt attacctgaa cagaactcaa aatcagtccg gaagtgccca aaacaaggac   1380
ttgctgttta gccgtgggtc tccagctggc atgtctgttc agcccaaaaa ctggctacct   1440
ggaccctgtt atcggcagca gcgcgttttct aaaacaaaaa cagacaacaa caacagcaat   1500
tttacctgga ctggtgcttc aaaatataac ctcaatgggc gtgaatccat catcaaccct   1560
ggcactgcta tggcctcaca caaagacgac gaagacaagt tctttcccat gagcggtgtc   1620
```

```
atgattttg gaaaagagag cgccggagct tcaaacactg cattggacaa tgtcatgatt    1680
acagacgaag aggaaattaa agccactaac cctgtggcca ccgaaagatt tgggaccgtg   1740
gcagtcaatt tccagagcag cagcacacac cctgcgaccg gagatgtgca tgttatggga   1800
gcattacctg gcatggtgtg gcaagataga gacgtgtacc tgcagggtcc catctgggcc   1860
aaaattcctc acacagatgg acactttcac ccgtctcctc ttatgggcgg ctttggactc   1920
aagcacccgc ctcctcagat cctcatcaaa aacacgcctg ttcctgcgaa tcctccggcg   1980
gagttttcag ctacaaagtt tgcttcattc atcacccaat actccacagg acaagtgagt   2040
gtggaaattg aatgggagct gcagaaagaa aacagcaagc gctggaatcc cgaagtgcag   2100
tacacatcca attatgcaaa atctgccaac gttgatttta ccgtggacaa caatggactt   2160
tatactgagc ctcgccccat ggcacccgt taccttaccc gtcccctgta a              2211
```

<210> SEQ ID NO 17
<211> LENGTH: 2211
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 17

```
atggctgccg atggttatct tccagattgg ctcgaggaca acctctctga gggcattcgc    60
gagtggtggg acttgaaacc tggagccccg aaacccaaag ccaaccagca aaagcaggac   120
gacggccggg gtctggtgct tcctggctac aagtacctcg gacccttcaa cggactcgac   180
aagggggagc ccgtcaacgc ggcggacgca gcggccctcg agcacgacaa ggcctacgac   240
cagcagctca aagcgggtga caatccgtac ctgcggtata accacgccga cgccgagttt   300
caggagcgtc tgcaagaaga tacgtctttt gggggcaacc tcgggcgagc agtcttccag   360
gccaaaaagc gggttctcga accttttggt ctggttgagg aaggcgctaa gacggctcct   420
ggaaagaaac gtccggtaga gcagtcgcca caagagccag actcctcctc gggcatcggc   480
aagacaggcc agcagcccgc taaaaagaga ctcaattttg gtcagactgg cgactcagag   540
tcagtccccg acccacaacc tctcggagaa cctccagcaa ccccgctgc tgtgggacct   600
actacaatgg cttcaggcgg tggcgcacca atggcagaca taacgaagg cgccgacgga   660
gtgggtaatg cctcaggaaa ttggcattgc gattccacat ggctgggcga cagagtcatc   720
accaccagca cccgcacctg gccttgccc acctacaata accacctcta aagcaaatc   780
tccagtgctt caacgggggc cagcaacgac aaccactact cggctacag cacccctgg   840
gggtattttg atttcaacag attccactgc cacttttcac cacgtgactg gcagcgactc   900
atcaacaaca attggggatt ccggcccaag agactcaact tcaagctctt caacatccaa   960
gtcaaggagg tcacgacgaa tgatggcgtc acaaccatcg ctaataacct taccagcacg  1020
gttcaagtct tctcggactc ggagtaccag cttccgtacg tcctcggctc tgcgcaccag  1080
ggctgcctcc ctccgttccc ggcggacgtg ttcatgattc cgcaatacgg ctacctgacg  1140
ctcaacaatg gcagccaagc cgtgggacgt tcatccttt attgcctgga atatttccca  1200
tcgcagatgc tgagaacggg caataacttt accttcagct acaccttga ggacgtgcct  1260
ttccacagca gctacgcgca cagccagagc ctggaccggc tgatgaatcc tctcatcgac  1320
cagtacctgt attacctgaa cagaactcag aaccagtccg gaagtgccca aaacaaggac  1380
ttgctgtttta gccgggggtc tccagctggc atgtctgttc agctcaaaaa ctggctacct  1440
ggaccctgtt atcggcagca gcgcgttct aaaaacaaaaa cagacaacaa caacagcaat  1500
```

| | |
|---|---|
| tttacctgga ctggtgcttc aaaatataac cttaatgggc gtgaatccat catcaaccct | 1560 |
| ggcactgcta tggcctcaca caaagacgac gaagacaagt tctttcccat gagcggtgtc | 1620 |
| atgattttg gaaaagagag cgccggagct tcaaacactg cattggacaa tgtcatgatt | 1680 |
| acagacgaag aggaaattaa agccactaac cctgtggcca ccgaaagatt tgggaccgtg | 1740 |
| gcagtcaatt tccagagcag cagcacagac cctgcgaccg agatgtgca tgttatggga | 1800 |
| gcattacctg gcatggtgtg gcaagataga gacgtgtacc tgcagggtcc catttgggcc | 1860 |
| aaaattcctc acacagatgg acactttcac ccgtctcctc ttatgggcgg ctttggactc | 1920 |
| aaacacccgc ctcctcagat cctcatcaaa aacacacctg ttcctgcgaa tcctccggcg | 1980 |
| gagttttcag ctacaaagtt tgcttcattc atcacccaat actccacagg acaagtgagc | 2040 |
| gtggaaattg aatgggagct gcagaaagaa acagcaagc gctggaatcc cgaagtgcag | 2100 |
| tacacatcca attatgcaaa atctgccaac gttgatttta ccgtggacaa caatggactt | 2160 |
| tatactgagc ctcgccccat tggcacccgt taccttaccc gtccctgta a | 2211 |

<210> SEQ ID NO 18
<211> LENGTH: 2211
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 18

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aaggggagc ccgtcaacgc ggcggacgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaagc gggttctcga accttttggt ctggttgagg aaggtgctaa gacggctcct | 420 |
| ggaaagaaga gaccggtaga gcagtcgccc caagaaccag actcctcatc gggcatcggc | 480 |
| aaatcaggcc agcagcccgc taaaaagaga ctcaattttg gtcagactgg cgactcagag | 540 |
| tcagtccccg acccacaacc tctcggagaa cctccagcaa ccccgctgc tgtgggacct | 600 |
| actacaatgg cttcaggcgg tggcgcacca atggcagaca taacgaagg cgccgacgga | 660 |
| gtgggtaatg cctcaggaaa ttggcattgc gattccacat ggctgggcga cagagtcatt | 720 |
| accaccagca cccgaacctg ggcctgccc acctataaca accacctcta caaacaaatc | 780 |
| tccagcgctt caacgggggc cagcaacgac aaccactact cggctacag cacccctgg | 840 |
| gggtattttg attttaacag attccactgc cacttctcac cacgtgactg gcagcgactc | 900 |
| atcaacaaca ttggggatt ccggcccaag agactcaact tcaagctctt caacatccaa | 960 |
| gtcaaggagg tcacgacgaa cgatggcgtc acgaccatcg ctaataacct taccagcacg | 1020 |
| gttcaagtct tctcggactc ggagtaccag ttgccgtacg tcctcggctc tgcgcaccag | 1080 |
| ggctgcctcc ctccgttccc ggcggacgtg ttcatgattc cgcagtacgg ctacctaaca | 1140 |
| ctcaacaatg gagccaggc cgtggacgt tcatccttt actgcctgga atatttccca | 1200 |
| tcgcagatgc tgagaacggg caataacttt accttcagct acacattcga ggacgtgcct | 1260 |
| ttccacagca gctacgcgca cagccaaagc ctggaccggc tgatgaatcc tctcatcgac | 1320 |
| cagtacttgt attacctaaa cagaactcaa aatcagtccg gaagtgccca aaacaaggac | 1380 |

-continued

| | |
|---|---|
| ttgctgttta gccggggggtc tccagctggc atgtctgttc agcccaaaaa ctggctacct | 1440 |
| ggaccctgtt atcggcagca gcgcgtttct aaaacaaaaa cagacaacaa caacagcaac | 1500 |
| tttacctgga ctggtgcttc aaaatataac cttaatgggc gtgaatctat aatcaaccct | 1560 |
| ggcactgcta tggcttcaca caaagacgac gaagacaagt tctttccaat gagcggtgtc | 1620 |
| atgattttg gcaaggagag cgccggagct tcaaacactg cattggacaa tgtcatgatt | 1680 |
| acagacgaag aggaaattaa agccactaac cctgtggcca ccgaaagatt tgggaccgtg | 1740 |
| gcagtcaatt tccagagcag cagcacagac cctgcgaccg agatgtgca tgttatggga | 1800 |
| gcattacctg catggtgtg gcaagataga acgtgtacc tgcagggtcc aatttgggcc | 1860 |
| aaaattcctc acacagatgg acactttcac ccgtctcctc ttatgggcgg ctttggactt | 1920 |
| aagcacccgc ctcctcagat cctcatcaaa aacacgcctg ttcctgcgaa tcctccggca | 1980 |
| gagttttcgg ctacaaagtt tgcttcattc atcacccagt attccacagg acaagtgagt | 2040 |
| gtggaaattg aatgggagtt gcagaaagaa acagcaagc gttggaatcc cgaagtgcag | 2100 |
| tacacatcta attatgcaaa atctgccaac gttgatttca ctgtggacaa caatggactt | 2160 |
| tatactgagc ctcgcccat ggcacccgt tacctcaccc gtccctgta a | 2211 |

<210> SEQ ID NO 19
<211> LENGTH: 2211
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 19

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aaggggggagc ccgtcaacgc ggcggacgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcagtcaccc caagaaccag actcctcctc gggcattggc | 480 |
| aaatcaggcc agcagcccgc taaaaagaga ctcaattttg gtcagactgg cgactcagag | 540 |
| tcagtccccg acccacaacc tctcggagaa cctccagcaa cccccgctgc tttgggacct | 600 |
| actacaatgg cttcaggcgg tggcgcacca atggcagaca ataacgaagg cgccgacgga | 660 |
| gtgggtaatg cctcaggaaa ttggcattgc gattccacat ggctgggcga cagagtcatc | 720 |
| accaccagca cccgcacctg gccttgccc acctacaata accacctcta caagcaaatc | 780 |
| tccagtgctt caacggggc cagcaacgac aaccactact tcggctacag cacccctgg | 840 |
| gggtattttg atttcaacag attccactgc catttctcac acgtgactgg cagcgactc | 900 |
| atcaacaaca ctggggatt ccggcccaag agactcaact tcaagctctt caacatccaa | 960 |
| gtcaaggagg tcacgacgaa cgatggcgtc acgaccatcg ctaataacct taccagcacg | 1020 |
| gttcaagtct tctcggactc ggagtaccag cttccgtacg tcctcggctc tgcgcaccag | 1080 |
| ggctgcctcc ctccgttccc ggcggacgtg ttcatgattc cgcagtacgg ctacctgacg | 1140 |
| ctcaacaatg gcagcaaagc cgtgggacgt tcatccttt actgcctgga atatttccct | 1200 |
| tctcagatgc tgagaacggg caacaacttt accttcagct acaccttga ggaagtgcct | 1260 |

-continued

| | |
|---|---|
| ttccacagca gctacgcgca cagccagagc ctggaccggc tgatgaatcc tctcatcgac | 1320 |
| caatacctgt attacctgaa cagaactcaa atcagtccg gaagtgccca aaacaaggac | 1380 |
| ttgctgttta gccgtgggtc tccagctggc atgtctgttc agcccaaaaa ctggctacct | 1440 |
| ggaccctgtt atcggcagca gcgcgtttct aaaacaaaaa cagacaacaa caacagcaat | 1500 |
| tttacctgga ctggtgcttc aaaatataac ctcaatgggc gtgaatccat catcaaccct | 1560 |
| ggcactgcta tggcctcaca caaagacgac gaagacaagt tctttcccat gagcggtgtc | 1620 |
| atgattttg gaaagagag cgccggagct tcaaacactg cattggacaa tgtcatgatt | 1680 |
| acagacgaag aggaaattaa agccactaac cctgtggcca ccgaaagatt tgggaccgtg | 1740 |
| gcagtcaatt tccagagcag cagcacagac cctgcgaccg gagatgtgca tgttatggga | 1800 |
| gcattacctg gcatggtgtg gcaagataga gacgtgtacc tgcagggtcc catttgggcc | 1860 |
| aaaattcctc acacggatgg acactttcac ccgtctcctc ttatgggcgg ctttggactc | 1920 |
| aagcaccgc ctcctcagat cctcatcaaa aacacacctg ttcctgcgaa tcctccggca | 1980 |
| gagttttcgg ctacaaagtt tgcttcattc atcacccagt actccacagg acaagtgagc | 2040 |
| gtggaaattg aatgggagtt gcagaaagaa aacagtaagc gctggaatcc cgaagtgcag | 2100 |
| tacacatcta attatgcaaa atctgccaac gttgacttca ctgtggacaa caatggactt | 2160 |
| tatactgagc ctcgccccat ggcacccgt tacctcaccc gtcccctgta a | 2211 |

<210> SEQ ID NO 20
<211> LENGTH: 2970
<212> TYPE: DNA
<213> ORGANISM: Artificial Sequence
<220> FEATURE:
<223> OTHER INFORMATION: Description of Artificial Sequence: Note =
  synthethic construct

<400> SEQUENCE: 20

| | |
|---|---|
| agatgaccgc caaggtcgta gagtccgcca aggccattct gggcggcagc aaggtgcgcg | 60 |
| tggaccaaaa atgcaaggcc tctgcgcaga tcgaccccac ccccgtgatc gtcacctcca | 120 |
| acaccaacat gtgcgccgtg attgacggga acagcaccac cttcgagcac cagcagcccc | 180 |
| tgcaggaccg gatgttcaag tttgaactca cccgccgcct cgactacgac tttggcaagg | 240 |
| tcaccaagca ggaagtcaag gactttttcc ggtgggcggc tgatcacgtg actgacgtgg | 300 |
| ctcatgagtt ttacgtcaca aagggtggag ctaagaaaag gcccgccccc tctgacgagg | 360 |
| atataagcga gccaagcgg ccgcgcgtgt catttgcgca gccggagacg tcagacgcgg | 420 |
| aagctcccgg agacttcgcc gacaggtacc aaaacaaatg ttctcgtcac gcgggtatgc | 480 |
| tgcagatgct ctttccctgc aagacgtgcg agagaatgaa tcagaattcc aacgtctgct | 540 |
| tcacgcacgg tcagaaagat tgcggggagt gcttttccgg gtcagaatct caaccggttt | 600 |
| ctgtcgtcag aaaaacgtat cagaaactgt gcatccttca tcagctccgg ggggcacccg | 660 |
| agatcgcctg ctctgcttgc gaccaactca accccgattt ggacgattgc caatttgagc | 720 |
| aataaatgac tgaaatcagg tatgctgct gacggttatc ttccagattg gctcgaggac | 780 |
| aacctctctg aaggcattcg cgagtggtgg gcgctgaaac ctggagctcc acaacccaag | 840 |
| gccaaccaac agcatcagga caacggcagg ggtcttgtgc ttcctgggta caagtacctc | 900 |
| ggaccctcca acggactcga caaggagag ccggtcaacg aggcagacgc cgcggccctc | 960 |
| gagcacgaca aggcctacga caagcagctc gagcagggg acaacccgta tctcaagtac | 1020 |
| aaccacggcc acgccgagtt ccagcagcgc ttggcgaccg acacctcttt tggggcaac | 1080 |
| ctcgggcgag cagtcttcca ggccaaaaag aggattctcg agcctctggg tctggttgaa | 1140 |

-continued

```
gagggcgtta aaacggctcc tggaaagaaa cgcccattag aaaagactcc aaatcggccg   1200
accaacccgg actctgggaa ggccccggcc aagaaaaagc aaaagacgg cgaaccagcc    1260 gactctgcta aaggacact cgactttgaa actctggag caggagacgg acccctgag      1320 ggatcatctt ccgagaaat gtctcatgat gctgagatgc gtgcggcgcc aggcggaaat    1380
gctgtcgagg cgggacaagg tgccgatgga gtgggtaatg cctccggtga ttggcattgc   1440
gattccacct ggtcagaggg ccgagtcacc accaccagca cccgaacctg ggtcctaccc   1500
acgtacaaca accacctgta cctgcgaatc ggaacaacgg ccaacagcaa cacctacaac   1560
ggattctcca cccctgggg atactttgac tttaaccgct tccactgcca cttttcccca    1620
cgcgactggc agcgactcat caacaacaac tggggactca ggccgaaatc gatgcgtgtt   1680
aaaatcttca acatacaggt caaggaggtc acgacgtcaa acggcgagac tacggtcgct   1740 aataaccta ccagcacggt tcagatcttt gcggattcga cgtatgaact cccatacgtg    1800
atggacgccg gtcaggaggg gagctttcct ccgtttccca acgacgtctt tatggttccc    1860
caatacggat actgcggagt tgtcactgga aaaaaccaga accagacaga cagaaatgcc   1920
ttttactgcc tggaatactt tccatcccaa atgctaagaa ctggcaacaa ttttgaagtc   1980
agttaccaat ttgaaaaagt tcctttccat tcaatgtacg cgcacagcca gagcctggac   2040
agaatgatga atcctttact ggatcagtac ctgtggcatc tgcaatcgac cactaccgga    2100 aattcccta atcaaggaac agctaccacc acgtacggga aaattaccac tggagacttt    2160
gcctactaca ggaaaaactg gttgcctgga gcctgcatta acaacaaaa attttcaaag    2220 aatgccaatc aaaactacaa gattcccgcc agcggggag acgccctttt aaagtatgac    2280
acgcatacca ctctaaatgg gcgatggagt aacatggctc ctggacctcc aatggcaacc   2340
gcaggtgccg gggactcgga ttttagcaac agccagctga tctttgccgg acccaatccg   2400
agcggtaaca cgaccacatc ttcaaacaat ttgttgttta cctcagaaga ggagattgcc   2460
acaacaaacc cacgagacac ggacatgttt ggacagatg cagataataa tcaaaatgcc    2520
accaccgccc ctcacatcgc taacctggac gctatgggaa ttgttccgg aatggtctgg    2580 caaaacagag acatctacta ccagggcccct atttgggcca aggtccctca cacgacggaa   2640
cactttcacc cttcgccgct gatgggagga tttggactga acacccgcc tccacagatt   2700 ttcatcaaaa acacccccgt acccgccaat cccaatacta cctttagcgc tgcaaggatt    2760
aattcttttc tgacgcagta cagcaccgga caagttgccg ttcagatcga ctgggaaatt   2820
cagaaggagc attccaaacg ctggaatccc gaagttcaat ttacttcaaa ctacggcact   2880
caaaattcta tgctgtgggc tcccgacaat gctggcaact accacgaact ccgggctatt   2940
gggtcccgtt tcctcaccca ccacttgtaa                                    2970
```

<210> SEQ ID NO 21
<211> LENGTH: 736
<212> TYPE: PRT
<213> ORGANISM: Artificial Sequence
<220> FEATURE:
<223> OTHER INFORMATION: Description of Artificial Sequence: Note = synthethic construct

<400> SEQUENCE: 21

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asp Gly Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Ser Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460
```

```
Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Gly Asn
                485                 490                 495

Asn Asn Ser Asn Phe Thr Trp Thr Gly Ala Ser Lys Tyr Asn Leu Asn
            500                 505                 510

Gly His Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr His Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 22
<211> LENGTH: 736
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Glu Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Ser Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Gly Asn
                485                 490                 495

Asn Asn Ser Asn Phe Thr Trp Thr Gly Ala Ser Lys Tyr Asn Leu Asn
            500                 505                 510

Gly His Glu Ser Ile Ile Asn Pro Gly Thr Ala Met Ala Ser His Lys
        515                 520                 525
```

```
Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr His Pro Ala
                580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 23
<211> LENGTH: 733
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 23

Met Thr Asp Gly Tyr Leu Pro Asp Trp Leu Glu Asp Asn Leu Ser Glu
 1               5                  10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Ala Glu Pro Asp Ser Ser Ser Gly Ile Gly Lys
145                 150                 155                 160
```

```
Ser Gly Gln Gln Pro Ala Arg Lys Arg Leu Asn Phe Gly Gln Thr Gly
            165                 170                 175
Asp Thr Glu Ser Val Pro Asp Pro Gln Pro Leu Gly Gln Pro Pro Ala
            180                 185                 190
Ala Pro Ser Gly Val Gly Ser Thr Thr Met Ala Ser Gly Gly Gly Ala
            195                 200                 205
Pro Met Ala Asp Asn Asn Glu Gly Ala Asp Gly Val Gly Asn Ser Ser
210                 215                 220
Gly Asn Trp His Cys Asp Ser Gln Trp Leu Gly Asp Arg Val Ile Thr
225                 230                 235                 240
Thr Ser Thr Arg Thr Trp Ala Leu Pro Thr Tyr Asn Asn His Leu Tyr
            245                 250                 255
Lys Gln Ile Ser Ser Gln Ser Gly Ala Thr Asn Asp Asn His Tyr Phe
            260                 265                 270
Gly Tyr Ser Thr Pro Trp Gly Tyr Phe Asp Phe Asn Arg Phe His Cys
            275                 280                 285
His Phe Ser Pro Arg Asp Trp Gln Arg Leu Ile Asn Asn Asn Trp Gly
            290                 295                 300
Phe Arg Pro Lys Arg Leu Asn Phe Lys Leu Phe Asn Ile Gln Val Lys
305                 310                 315                 320
Glu Val Thr Gln Asn Asp Gly Thr Thr Thr Ile Ala Asn Asn Leu Thr
            325                 330                 335
Ser Thr Val Gln Val Phe Thr Asp Ser Glu Tyr Gln Leu Pro Tyr Val
            340                 345                 350
Leu Gly Ser Ala His Gln Gly Cys Leu Pro Pro Phe Pro Ala Asp Val
            355                 360                 365
Phe Met Val Pro Gln Tyr Gly Tyr Leu Thr Leu Asn Asn Gly Ser Gln
            370                 375                 380
Ala Val Gly Arg Ser Ser Phe Tyr Cys Leu Glu Tyr Phe Pro Ser Gln
385                 390                 395                 400
Met Leu Arg Thr Gly Asn Asn Phe Gln Phe Ser Tyr Thr Phe Glu Asp
            405                 410                 415
Val Pro Phe His Ser Ser Tyr Ala His Ser Gln Ser Leu Asp Arg Leu
            420                 425                 430
Met Asn Pro Leu Ile Asp Gln Tyr Leu Tyr Tyr Leu Asn Arg Thr Gln
            435                 440                 445
Thr Ala Ser Gly Thr Gln Gln Ser Arg Leu Leu Phe Ser Gln Ala Gly
            450                 455                 460
Pro Thr Ser Met Ser Leu Gln Ala Lys Asn Trp Leu Pro Gly Pro Cys
465                 470                 475                 480
Tyr Arg Gln Gln Arg Leu Ser Lys Gln Ala Asn Asp Asn Asn Asn Ser
            485                 490                 495
Asn Phe Pro Trp Thr Gly Ala Thr Lys Tyr His Leu Asn Gly Arg Asp
            500                 505                 510
Ser Leu Val Asn Pro Gly Pro Ala Met Ala Ser His Lys Asp Asp Lys
            515                 520                 525
Glu Lys Phe Phe Pro Met His Gly Thr Leu Ile Phe Gly Lys Glu Gly
            530                 535                 540
Thr Asn Ala Asn Asn Ala Asp Leu Glu Asn Val Met Ile Thr Asp Glu
545                 550                 555                 560
Glu Glu Ile Arg Thr Thr Asn Pro Val Ala Thr Glu Gln Tyr Gly Thr
            565                 570                 575
Val Ser Asn Asn Leu Gln Asn Ser Asn Ala Gly Pro Thr Thr Gly Thr
            580                 585                 590
```

```
Val Asn His Gln Gly Ala Leu Pro Gly Met Val Trp Gln Asp Arg Asp
        595                 600                 605

Val Tyr Leu Gln Gly Pro Ile Trp Ala Lys Ile Pro His Thr Asp Gly
610                 615                 620

His Phe His Pro Ser Pro Leu Met Gly Gly Phe Gly Leu Lys His Pro
625                 630                 635                 640

Pro Pro Gln Ile Met Ile Lys Asn Thr Pro Val Pro Ala Asn Pro Pro
                645                 650                 655

Thr Asn Phe Ser Ala Ala Lys Phe Ala Ser Phe Ile Thr Gln Tyr Ser
                660                 665                 670

Thr Gly Gln Val Ser Val Glu Ile Glu Trp Glu Leu Lys Glu Asn
                675                 680                 685

Ser Lys Arg Trp Asn Pro Glu Ile Gln Tyr Thr Ser Asn Tyr Asn Lys
        690                 695                 700

Ser Val Asn Val Asp Phe Thr Val Asp Thr Asn Gly Val Tyr Ser Glu
705                 710                 715                 720

Pro Arg Pro Ile Gly Thr Arg Tyr Leu Thr Arg Asn Leu
                725                 730

<210> SEQ ID NO 24
<211> LENGTH: 736
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 24

Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220
```

-continued

```
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
        260                 265                 270

Tyr Phe Gly Tyr Ser Thr Pro Trp Gly Tyr Phe Asp Phe Asn Arg Phe
    275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
        340                 345                 350

Tyr Val Leu Gly Ser Ala His Gln Gly Cys Leu Pro Pro Phe Pro Ala
    355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Asn Arg
    435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
    515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
        580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655
```

```
Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 25
<211> LENGTH: 736
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 25

Met Ala Ala Asp Gly Tyr Leu Pro Asp Trp Leu Glu Asp Asn Leu Ser
1               5                   10                  15

Glu Gly Ile Arg Lys Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285
```

```
His Cys His Phe Ser Pro Arg Asp Trp Gln Arg Leu Ile Asn Asn Asn
        290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
        370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
            435                 440                 445
Thr Gln Asn Gln Ser Gly Ser Ala Gln Asn Lys Asp Leu Leu Phe Ser
        450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Lys Asp Lys Phe Phe Pro Met Ser Gly Val Met Ile Phe Gly
        530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
                580                 585                 590
Thr Gly Asp Val His Val Met Gly Ala Leu Pro Gly Met Val Trp Gln
            595                 600                 605
Asp Arg Asp Val Tyr Leu Gln Gly Pro Ile Trp Ala Lys Ile Pro His
        610                 615                 620
Thr Asp Gly His Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Val Gln Tyr Thr Ser Asn
        690                 695                 700
```

```
Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735
```

<210> SEQ ID NO 26
<211> LENGTH: 736
<212> TYPE: PRT
<213> ORGANISM: Artificial Sequence
<220> FEATURE:
<223> OTHER INFORMATION: Description of Artificial Sequence: Note = synthethic construct

<400> SEQUENCE: 26

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335
```

```
Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr His Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 27
<211> LENGTH: 736
<212> TYPE: PRT
<213> ORGANISM: Artificial Sequence
```

```
<220> FEATURE:
<223> OTHER INFORMATION: Description of Artificial Sequence: Note =
      synthethic construct

<400> SEQUENCE: 27

Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400
```

```
Ser Gln Met Leu Arg Thr Gly Asn Asn Phe Thr Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Leu Lys Asn Trp Leu Pro
465                 470                 475                 480

Gly Pro Cys Tyr Arg Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 28
<211> LENGTH: 736
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asp Gly Arg Gly Leu Val Leu Pro
         35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65              70                  75                  80
Gln Gln Leu Lys Ala Gly Asp Asn Pro Tyr Leu Arg Tyr Asn His Ala
             85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Phe Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Ser Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
    450                 455                 460
```

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540

Lys Gly Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 29
<211> LENGTH: 736
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 29

Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Leu Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Lys Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525
```

```
Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 30
<211> LENGTH: 742
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 30

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160
```

```
Ala Pro Ala Lys Lys Lys Gln Lys Asp Gly Glu Pro Ala Asp Ser Ala
            165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
            195                 200                 205

Ala Pro Gly Gly Asn Ala Val Glu Ala Gly Gln Gly Ala Asp Gly Val
            210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
            245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
            325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
            355                 360                 365

Val Phe Met Val Pro Gln Tyr Gly Tyr Cys Gly Val Val Thr Gly Lys
            370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
            405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
            450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
            485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
            530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
            565                 570                 575

Pro Arg Asp Thr Asp Met Phe Gly Gln Ile Ala Asp Asn Asn Gln Asn
            580                 585                 590
```

-continued

```
Ala Thr Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
            740

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 31
gcgacakttt gcgacaccay gtgg                                          24

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 4-6
<223> OTHER INFORMATION: N can be a, g, c, or t (u)

<400> SEQUENCE: 32
ccannnggaa tcgcaatgcc aat                                           23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 4, 6, 9
<223> OTHER INFORMATION: N can be a, g, c, or t (u)

<400> SEQUENCE: 33
atgntnatnt ggtgggagga ggg                                           23
```

```
<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 6
<223> OTHER INFORMATION: N can be a, g, c, or t (u)

<400> SEQUENCE: 34
cgaatnaamc ggtttattga ttaac                                          25

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 35

Asn Gly Arg Ala His Ala
 1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 36

Ser Ile Gly Tyr Pro Leu Pro
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 37

Lys Phe Asn Lys Pro Phe Val Phe Leu Ile
 1               5                  10

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Note =
      synthethic construct

<400> SEQUENCE: 38

Asn Ile Ser Leu Asp Asn Pro Leu Glu Asn Pro Ser Ser Leu Phe Asp
 1               5                  10                  15

Leu Val Ala Arg Ile Lys
            20

<210> SEQ ID NO 39
<211> LENGTH: 26
<212> TYPE: DNA
<213> ORGANISM: Artificial Sequence
```

```
<220> FEATURE:
<223> OTHER INFORMATION: Description of Artificial Sequence: Note =
      synthethic construct
<220> FEATURE:
<221> NAME/KEY: misc_feature
<222> LOCATION: 14
<223> OTHER INFORMATION: N can be a, g, c, or t (u)

<400> SEQUENCE: 39
caataaaccg kktnattcgt ktcagt                                          26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 4-5, 21
<223> OTHER INFORMATION: N can be a, g, c, or t (u)

<400> SEQUENCE: 40
acannwgagt cagaaatkcc nggcag                                          26

<210> SEQ ID NO 41
<211> LENGTH: 640
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 608, 624
<223> OTHER INFORMATION: N can be a, g, c, or t (u)

<400> SEQUENCE: 41
gcgaattgaa tttagcggcc gcgaattcgc ccttcaataa accgtttgat tcgtgtcagt     60
tgatctttgg cctacttgtc cttcttatct tatctggtcg ccatggctgc gtagataagc   120
agcttggtat gcgcttcgcg gttaatcatc aactacgcca aaccctagat gatggagttg   180
gccactccct ctatgcgcgc tcgctcgctc ggtggggccg gactgcccgg catttctgac   240
tcctttgtga actgggtggc cctccgggct attgggtccc gtttcctcac ccaccacttg   300
taacccttcc tggttaatca atgaaccgtt taattcgttt cagttgatct ttggcctact   360
tgtccttctt atcttatctg gttgccatgg ctgcgtagat aagcagcttg gtatgcgctt   420
cgcggttaat catcaactac gccaaaccct agatgatgga gttggccact ccctctatgc   480
gcgctcgctc gctcggtggg gccggactgc cgggcatttc tgactcactt gtaagggcga   540
aattcgttta aacctgcagg actagtccct ttagtgaggg ttaattctga gcttggcgta   600
atcatggnca tagctgtttc ctgnggaaaa tgttatccgc                         640

<210> SEQ ID NO 42
<211> LENGTH: 248
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 42
tggaggggtg gagtcgtgrc gtgaattacg tcatagggtt agggaggtcc tgtattagag     60
gtcacgtgag tgttttgcga cattttgcga caccatgtgg tcacgctggg tatttaagcc   120
```

```
cgagtgwgca cgcagggtct ccatttgaa gcgggaggtt tgaacgcgca gccgccatgc      180
cggggtttta cgagattgtg attaaggtcc ccagcgacct tgacgagcat ctgccaggaa    240
tttctgac                                                              248
```

<210> SEQ ID NO 43
<211> LENGTH: 317
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 43

```
gcccgggcgg cctcagtgag cgagcgagcg cgcagagagg gagtggccaa ctccatcact    60
aggggttcct ggagggtgg agtcgtgacg tgaattacgt catagggtta gggaggtcct    120
gtattagagg tcacgtgagt gttttgcgac attttgcgac accatgtggt cacgctgggt    180
atttaagccc gagtgagcac gcaggtctc cattttgaag cgggaggttt gaacgcgcag    240
ccgccatgcc ggggttttac gagattgtga ttaaggtccc cagcgacctt gacgagcatc   300
tgcctggaat ttctgac                                                   317
```

<210> SEQ ID NO 44
<211> LENGTH: 157
<212> TYPE: DNA
<213> ORGANISM: Artificial Sequence
<220> FEATURE:
<223> OTHER INFORMATION: Description of Artificial Sequence: Note = synthethic construct
<220> FEATURE:
<221> NAME/KEY: misc_feature
<222> LOCATION: 33, 105, 141
<223> OTHER INFORMATION: N can be a, g, c, or t (u)

<400> SEQUENCE: 44

```
gagtgagcga gcagggtctc cattttgacc gcnaaatttg aacgagcagc atccatgccg    60
ggcttctacg agatcgtgat caaggtgccg agcgacctgg acgancacct gcctggcatt   120
tctgactcaa ttgtaagggc naattcgttt aaacctg                             157
```

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Note = synthethic construct

<400> SEQUENCE: 45

```
gcgacakttt gcgacaccay gtgg                                           24
```

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Note = synthethic construct
<220> FEATURE:
<221> NAME/KEY: misc_feature
<222> LOCATION: 4-6
<223> OTHER INFORMATION: N can be a, g, c, or t (u)

<400> SEQUENCE: 46

```
ccannnggaa tcgcaatgcc aat                                            23
```

```
<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 4, 6, 9
<223> OTHER INFORMATION: N can be a, g, c, or t (u)

<400> SEQUENCE: 47
atgntnatnt ggtgggagga ggg                                            23

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Note =
      synthethic construct
<220> FEATURE:
<221> NAME/KEY: misc_feature
<222> LOCATION: 6
<223> OTHER INFORMATION: N can be a, g, c, or t (u)

<400> SEQUENCE: 48
cgaatnaamc ggtttattga ttaac                                          25

<210> SEQ ID NO 49
<211> LENGTH: 1872
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 49
atgccgggct tctacgagat cgtgatcaag gtgccgagcg acctggacga gcacctgccg      60
ggcatttctg actcgtttgt gaactgggtg gccgagaagg aatgggagct gccccgggat     120
tctgacatgg atctgaatct gattgagcag gcacccctga ccgtggccga aagctgcag      180 cgcgacttcc tggtccaatg cgccgcgtg agtaaggccc cggaggccct cttctttgtt      240
cagttcgaga agggcgagtc ctacttccac ctccatattc tggtggagac cacggggtc      300 aaatccatgg tgctgggccg cttcttgagt cagattaggg acaagctggt gcagaccatc     360
taccgcggga tcgagccgac cctgcccaac tggttcgcgg tgaccaagac gcgtaatggc     420
gccggagggg ggaacaaggt ggtggacgag tgctacatcc ccaactacct cctgcccaag     480
actcagcccg agctgcagtg ggcgtggact aacatggagg agtatataag cgcgtgtttg     540
aacctggccg agcgcaaacg gctcgtggcg cagcacctga cccacgtcag ccagacccag     600
gagcagaaca aggagaatct gaaccccaat tctgacgcgc ctgtcatccg gtcaaaaacc     660
tccgcgcgct acatggagct ggtcgggtgg ctggtggacc ggggcatcac ctccgagaag     720
cagtggatcc aggaggacca ggcctcgtac atctccttca cgccgcctc caactcgcgg     780 tcccagatca aggccgctct ggacaatgcc ggcaagatca tggcgctgac caaatccgcg     840
cccgactacc tggtaggccc cgctcctccc gcggacatta aaccaaccg catctaccgc     900 atcctggagc tgaacggcta cgaccctgcc tacgccggct ccgtctttct cggctgggcc     960
cagaaacggt tcgggaagcg caacaccatc tggctgtttg gccggccac cacgggcaag    1020 accaacatcg cggaagccat cgcccacgcc gtgccttct acggctgcgt caactggacc    1080
```

```
aatgagaact ttcccttcaa cgattgcgtc gacaagatgg tgatctggtg ggaggagggc  1140
aagatgacgg ccaaggtcgt ggagtccgcc aaggccattc tcggcggcag caaggtcgcg  1200
gtggaccaaa agtgcaagtc gtccgcccag atcgatccca ccccgtgat cgtcacctcc   1260 aacaccaaca tgtgcgccgt gattgacggg aacagcacca ccttcgagca ccagcagccg  1320
ttgcaggacc ggatgttcaa atttgaactc acccgccgtc tggagcatga ctttggcaag  1380
gtgacaaagc aggaagtcaa agagttcttc cgctgggcgc aggatcacgt gaccgaggtg  1440
gcgcatgagt tctacgtcag aaagggtgga gccaacaaaa gacccgcccc cgatgacgcg  1500
gataaaagcg agcccaagcg ggcctgcccc tcagtcgcgg atccatcgac gtcagacgcg  1560
gaaggagctc cggtggactt tgccgacagg taccaaaaca aatgttctcg tcacgcgggc  1620
atgcttcaga tgctgtttcc ctgcaagaca tgcgagagaa tgaatcagaa tttcaacatt  1680
tgcttcacgc acgggaccag agactgttca gaatgtttcc ccggcgtgtc agaatctcaa  1740
ccggtcgtca gaaaaggac gtatcggaaa ctctgtgcga ttcatcatct gctgggggcgg  1800 gctcccgaga ttgcttgctc ggcctgcgat ctggtcaacg tggacctgga tgactgtgtc  1860
tctgagcaat aa                                                      1872
```

<210> SEQ ID NO 50
<211> LENGTH: 623
<212> TYPE: PRT
<213> ORGANISM: Artificial Sequence
<220> FEATURE:
<223> OTHER INFORMATION: Description of Artificial Sequence: Note = synthethic construct

<400> SEQUENCE: 50

```
Met Pro Gly Phe Tyr Glu Ile Val Ile Lys Val Pro Ser Asp Leu Asp
 1               5                  10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220
```

```
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
        260                 265                 270

Ile Met Ala Leu Thr Lys Ser Ala Pro Asp Tyr Leu Val Gly Pro Ala
    275                 280                 285

Pro Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
        340                 345                 350

Phe Tyr Gly Cys Val Asn Trp Thr Asn Glu Asn Phe Pro Phe Asn Asp
    355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
    435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
            485                 490                 495

Pro Asp Asp Ala Asp Lys Ser Glu Pro Lys Arg Ala Cys Pro Ser Val
        500                 505                 510

Ala Asp Pro Ser Thr Ser Asp Ala Glu Gly Ala Pro Val Asp Phe Ala
    515                 520                 525

Asp Arg Tyr Gln Asn Lys Cys Ser Arg His Ala Gly Met Leu Gln Met
530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
            565                 570                 575

Ser Glu Ser Gln Pro Val Val Arg Lys Arg Thr Tyr Arg Lys Leu Cys
        580                 585                 590

Ala Ile His His Leu Leu Gly Arg Ala Pro Glu Ile Ala Cys Ser Ala
    595                 600                 605

Cys Asp Leu Val Asn Val Asp Leu Asp Asp Cys Val Ser Glu Gln
610                 615                 620

<210> SEQ ID NO 51
<211> LENGTH: 1872
<212> TYPE: DNA
<213> ORGANISM: Artificial Sequence
```

<220> FEATURE:
<223> OTHER INFORMATION: Description of Artificial Sequence: Note = synthethic construct

<400> SEQUENCE: 51

| | | | | | |
|---|---|---|---|---|---|
| atgccgggct | tctacgagat | cgtgatcaag | gtgccgagcg | acctggacga | gcacctgccg | 60 |
| ggcatttctg | actcgtttgt | gaactgggtg | gccgagaagg | aatgggagct | gccccggat | 120 |
| tctgacatgg | atctgaatct | gattgagcag | gcaccctga | ccgtggccga | gaagctgcag | 180 |
| cgcgacttcc | tggtccaatg | gcgccgcgtg | agtaaggccc | cggaggccct | cttctttgtt | 240 |
| cagttcgaga | agggcgagtc | ctacttccac | ctccatattc | tggtggagac | cacggggggtc | 300 |
| aaatccatgg | tgctgggccg | cttcctgagt | cagattaggg | acaagctggt | gcagaccatc | 360 |
| taccgcggga | tcgagccgac | cctgcccaac | tggttcgcgg | tgaccaagac | gcgtaatggc | 420 |
| gccggagggg | ggaacaaggt | ggtggacgag | tgctacatcc | ccaactacct | cctgcccaag | 480 |
| actcagcccg | agctgcagtg | ggcgtggact | aacatggagg | agtatataag | cgcgtgtttg | 540 |
| aacctggccg | agcgcaaacg | gctcgtggcg | cagcacctga | cccacgtcag | ccagacccag | 600 |
| gagcagaaca | aggagaatct | gaacccgaat | tctgacgcgc | ctgtcatccg | gtcaaaaacc | 660 |
| tccgcgcgct | acatggagct | ggtcgggtgg | ctggtggacc | ggggcatcac | ctccgagaag | 720 |
| cagtggatcc | aggaggacca | ggcctcgtac | atctccttca | acgccgcctc | caactcgcgg | 780 |
| tcccagatca | aggccgctct | ggacaatgcc | ggcaagatca | tggcgctaac | caaatccgcg | 840 |
| cccgactacc | tggtaggccc | cgctccgccc | gcggacatta | aaaccaaccg | catttaccgc | 900 |
| atcctggagc | tgaacggcta | cgaccctgcc | tacgccggct | ccgtctttct | cggctgggcc | 960 |
| cagaaaaggt | tcgggaagcg | caacaccatc | tggctgtttg | ggccggccac | cacgggcaag | 1020 |
| accaacatcg | cggaagccat | cgcacacgcc | gtgcccttct | acggctgcgt | caactggacc | 1080 |
| aatgaaaact | ttcccttcaa | cgactgcgtc | gacaagatgg | tgatctggtg | ggaggagggc | 1140 |
| aagatgacgc | ccaaggtcgt | ggagtccgcc | aaggccattc | tcggcggcag | caaggtgcgc | 1200 |
| gtggaccaaa | agtgcaagtc | gtccgcccag | atcgatccca | ccccgtgat | cgtcacctcc | 1260 |
| aacaccaaca | tgtgcgccgt | gattgacggg | aacagcacca | ccttcgagca | ccagcagccg | 1320 |
| ttgcaggacc | ggatgttcaa | atttgaactc | acccgccgtc | tggagcacga | ctttggcaag | 1380 |
| gtgacaaagc | aggaagtcaa | agagttcttc | cgctgggcgc | aggatcacgt | gaccgaggtg | 1440 |
| gcgcatgagt | tctacgtcag | aaagggtgga | gccaacaaga | gacccgcccc | cgatgacgcg | 1500 |
| gataaaagcg | agcccaagcg | ggtctgcccc | tcagtcgcgg | atccatcgac | gtcagacgcg | 1560 |
| gaaggagctc | cggtggactt | tgccgacagg | taccaaaaca | aatgttctcg | tcacgcgggc | 1620 |
| atgcttcaga | tgctgtttcc | ctgcaaaaca | tgcgagagaa | tgaatcagaa | tttcaacatt | 1680 |
| tgcttcacgc | acgggaccag | agactgttca | gaatgtttcc | ccggcgtgtc | agaatctcaa | 1740 |
| ccggtcgtca | gaaaaaggac | gtatcggaaa | ctctgtgcca | ttcatcatct | gctggggcgg | 1800 |
| gctcccgaga | ttgcttgctc | ggcctgcgat | ctggtcaacg | tggacctgga | tgactgtgtt | 1860 |
| tctgagcaat | aa | | | | | 1872 |

<210> SEQ ID NO 52
<211> LENGTH: 623
<212> TYPE: PRT
<213> ORGANISM: Artificial Sequence
<220> FEATURE:
<223> OTHER INFORMATION: Description of Artificial Sequence: Note = synthethic construct

```
<400> SEQUENCE: 52

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415
```

```
Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Val Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
        610                 615                 620

<210> SEQ ID NO 53
<211> LENGTH: 2689
<212> TYPE: DNA
<213> ORGANISM: Artificial Sequence
<220> FEATURE:
<223> OTHER INFORMATION: Description of Artificial Sequence: Note =
      synthethic construct

<400> SEQUENCE: 53
ttgcgacagt ttgcgacacc atgtggtcac aagaggtata taaccgcgag tgagccagcg     60
aggagctcca ttttgcccgc gaagtttgaa cgagcagcag ccatgccggg gttctacgag    120
gtggtgatca aggtgcccag cgacctggac gagcacctgc ccggcatttc tgactccttt    180
gtgaactggg tggccgagaa ggaatgggag ttgcccccgg attctgacat ggatcagaat    240
ctgattgagc aggcacccct gaccgtggcc gagaagctgc agcgcgagtt cctggtggaa    300
tggcgccgag tgagtaaatt tctggaggcc aagttttttg tgcagtttga aaaggggggac    360 tcgtactttc atttgcatat tctgattgaa attaccggcg tgaaatccat ggtggtgggc    420
cgctacgtga gtcagattag ggataaactg atccagcgca tctaccgcgg ggtcgagccc    480
cagctgccca actggttcgc ggtcacaaag acccgaaatg cgccggagg cgggaacaag    540 gtggtggacg agtgctacat ccccaactac ctgctcccca aggtccagcc cgagcttcag    600
tgggcgtgga ctaacatgga ggagtatata agcgcctgtt tgaacctcgc ggagcgtaaa    660
cggctcgtgg cgcagcacct gacgcacgtc tcccagaccc aggagggcga caaggagaat    720
ctgaacccga attctgacgc gccggtgatc cggtcaaaaa cctccgccag gtacatggag    780
ctggtcgggt ggctggtgga caagggcatc acgtccgaga agcagtggat ccaggaggac    840
caggcctcgt acatctcctt caacgcggcc tccaactccc ggtcgcagat caaggcggcc    900
```

```
ctggacaatg cctccaaaat catgagcctc accaaaacgg ctccggacta tctcatcggg    960
cagcagcccg tggggacat taccaccaac cggatctaca aaatcctgga actgaacggg   1020
tacgaccccc agtacgccgc ctccgtcttt ctcggctggg cccagaaaaa gtttggaaag   1080
cgcaacacca tctggctgtt tgggcccgcc accaccggca agaccaacat cgcggaagcc   1140
atcgcccacg cggtcccctt ctacggctgc gtcaactgga ccaatgagaa ctttcccttc   1200
aacgactgcg tcgacaaaat ggtgatttgg tgggaggagg gcaagatgac cgccaaggtc   1260
gtagagtccg ccaaggccat tctgggcggc agcaaggtgc gcgtggacca aaaatgcaag   1320
gcctctgcgc agatcgaccc cacccccgtg atcgtcacct ccaacaccaa catgtgcgcc   1380
gtgattgacg ggaacagcac caccttcgag caccagcagc cctgcagga ccggatgttc   1440
aagtttgaac tcacccgccg cctcgaccac gactttggca aggtcaccaa gcaggaagtc   1500
aaggactttt tccggtgggc ggctgatcac gtgactgacg tggctcatga gttttacgtc   1560
acaaagggtg gagctaagaa aaggcccgcc ccctctgacg aggatataag cgagcccaag   1620
cggccgcgcg tgtcatttgc gcagccggag acgtcagacg cggaagctcc cggagacttc   1680
gccgacaggt accaaaacaa atgttctcgt cacgcgggta tgctgcagat gctctttccc   1740
tgcaagacgt gcgagagaat gaatcagaat tccaacgtct gcttcacgca cggtcagaaa   1800
gattgcgggg agtgctttcc cgggtcagaa tctcaaccgg tttctgtcgt cagaaaaacg   1860
tatcagaaac tgtgcatcct tcatcagctc cgggggcac ccgagatcgc ctgctctgct   1920
tgcgaccaac tcaaccccga tttggacgat tgccaatttg agcaataaat gactgaaatc   1980
aggtatggct gctgacggtt atcttccaga ttggctcgag acaacctcct ctgaaggcat   2040
tcgcgagtgg tgggcgctga aacctggagc tccacaaccc aaggccaacc aacagcatca   2100
ggacaacggc aggggtcttg tgcttcctgg gtacaagtac ctcggaccct tcaacggact   2160
cgacaaggga gagccggtca acgaggcaga cgccgcggcc ctcgagcacg acaaggccta   2220
cgacaagcag ctcgagcagg gggacaaccc gtatctcaag tacaaccacg ccgacgccga   2280
gttccagcag cgcttggcga ccgacacctc ttttgggggc aacctcgggc gagcagtctt   2340
ccaggccaaa aagaggattc tcgagcctct gggtctggtt gaagagggcg ttaaaacggc   2400
tcctggaaag aaacgcccat tagaaaagac tccaaatcgg ccgaccaacc cggactctgg   2460
gaaggccccg gccaagaaaa agcaaaaaga cggcgaacca gccgactctg ctagaaggac   2520
actcgacttt gaagactctg gagcaggaga cggacccccct gagggatcat cttccggaga   2580
aatgtctcat gatgctgaga tgcgtgcggc gccaggcgga aatgctgtcg aggcgggaca   2640
aggtgccgat ggagtgggta atgcctccgg tgattggcat tgcgattcc                2689
```

<210> SEQ ID NO 54
<211> LENGTH: 621
<212> TYPE: PRT
<213> ORGANISM: Artificial Sequence
<220> FEATURE:
<223> OTHER INFORMATION: Description of Artificial Sequence: Note =
    synthethic construct

<400> SEQUENCE: 54

Met Pro Gly Phe Tyr Glu Val Val Ile Lys Val Pro Ser Asp Leu Asp
 1               5                  10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Gln Asn Leu Ile
            35                  40                  45

```
Glu Gln Ala Pro Leu Thr Val Ala Glu Lys Leu Gln Arg Glu Phe Leu
    50                  55                  60

Val Glu Trp Arg Arg Val Ser Lys Phe Leu Glu Ala Lys Phe Phe Val
65                  70                  75                  80

Gln Phe Glu Lys Gly Asp Ser Tyr Phe His Leu His Ile Leu Ile Glu
                85                  90                  95

Ile Thr Gly Val Lys Ser Met Val Val Gly Arg Tyr Val Ser Gln Ile
                100                 105                 110

Arg Asp Lys Leu Ile Gln Arg Ile Tyr Arg Gly Val Glu Pro Gln Leu
            115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Val Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gly Asp Lys Glu Asn Leu Asn
                195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Ile Gly Gln Gln
                275                 280                 285

Pro Val Gly Asp Ile Thr Thr Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ala Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ala Asp His Val Thr Asp Val
465                 470                 475                 480
```

```
Ala His Glu Phe Tyr Val Thr Lys Gly Gly Ala Lys Lys Arg Pro Ala
            485                 490                 495

Pro Ser Asp Glu Asp Ile Ser Glu Pro Lys Arg Pro Arg Val Ser Phe
            500                 505                 510

Ala Gln Pro Glu Thr Ser Asp Ala Glu Ala Pro Gly Asp Phe Ala Asp
        515                 520                 525

Arg Tyr Gln Asn Lys Cys Ser Arg His Ala Gly Met Leu Gln Met Leu
    530                 535                 540

Phe Pro Cys Lys Thr Cys Glu Arg Met Asn Gln Asn Ser Asn Val Cys
545                 550                 555                 560

Phe Thr His Gly Gln Lys Asp Cys Gly Glu Cys Phe Pro Gly Ser Glu
            565                 570                 575

Ser Gln Pro Val Ser Val Val Arg Lys Thr Tyr Gln Lys Leu Cys Ile
            580                 585                 590

Leu His Gln Leu Arg Gly Ala Pro Glu Ile Ala Cys Ser Ala Cys Asp
        595                 600                 605

Gln Leu Asn Pro Asp Leu Asp Asp Cys Gln Phe Glu Gln
    610                 615                 620
```